United States Patent [19]
Lonberg et al.

[11] Patent Number: 5,661,016
[45] Date of Patent: Aug. 26, 1997

[54] TRANSGENIC NON-HUMAN ANIMALS CAPABLE OF PRODUCING HETEROLOGOUS ANTIBODIES OF VARIOUS ISOTYPES

[75] Inventors: Nils Lonberg; Robert M. Kay, both of San Francisco, Calif.

[73] Assignee: GenPharm International Inc., Palo Alto, Calif.

[21] Appl. No.: 53,131

[22] Filed: Apr. 26, 1993

Related U.S. Application Data

[63] Continuation-in-part of Ser. No. 990,860, Dec. 16, 1992, Pat. No. 5,454,806, which is a continuation-in-part of Ser. No. 904,068, Jun. 23, 1992, which is a continuation-in-part of Ser. No. 853,408, Mar. 18, 1992, which is a continuation-in-part of Ser. No. 834,539, Feb. 5, 1992, which is a continuation-in-part of Ser. No. 810,279, Dec. 17, 1991, Pat. No. 5,569,825, which is a continuation-in-part of Ser. No. 575,962, Aug. 31, 1990, abandoned, which is a continuation-in-part of Ser. No. 574,748, Aug. 29, 1990, abandoned.

[30] Foreign Application Priority Data

Aug. 28, 1991 [WO] WIPO ............ PCT/US92/06185
Dec. 17, 1992 [WO] WIPO ............ PCT/US92/10983

[51] Int. Cl.$^6$ .................... C12N 15/00; A61K 39/00; C12P 19/34; C07K 16/00
[52] U.S. Cl. ................... 435/172.3; 424/184.1; 435/91.1; 435/172.1; 530/387.1; 536/23.1; 536/23.53; 800/2; 935/19; 935/89; 935/93; 935/103
[58] Field of Search ............ 800/2; 435/172.2, 435/240.2; 530/388.1

[56] References Cited

U.S. PATENT DOCUMENTS

| | | | |
|---|---|---|---|
| 4,643,234 | 2/1987 | Moore | 530/388 |
| 4,683,195 | 7/1987 | Mullis | 435/6 |
| 4,965,188 | 10/1990 | Mullis | 435/6 |
| 5,047,507 | 9/1991 | Buchegger | 530/387 |
| 5,175,384 | 12/1992 | Krimpenfort et al. | 800/2 |
| 5,416,260 | 5/1995 | Koller | 800/2 |
| 5,434,340 | 7/1995 | Krimpenfort et al. | 800/2 |

FOREIGN PATENT DOCUMENTS

| | | |
|---|---|---|
| 0 315 062 | 5/1989 | European Pat. Off. . |
| WO 90/04036 | 4/1990 | WIPO . |
| 901443 | 11/1990 | WIPO . |
| WO 90/12878 | 11/1990 | WIPO . |
| WO 91/00906 | 1/1991 | WIPO . |
| WO 91/10741 | 7/1991 | WIPO . |
| WO 92/03918 | 3/1992 | WIPO . |

OTHER PUBLICATIONS

James et al Journal of Immunological Methods 100:5–40, 1987.
Breggenam et al PNAS 86: 6709, 1989.
Miller et al Nature 295: 428, 1982.
Berman et al EMBO J 7: 727, 1988.
Sideras et al International Amweg 1(6); 631, 1989.
Rothman et al International Immunology 2(7):621, 1990.
Nihoido et al nature 292: 843, 1981.
Nihaudo et al. JBC 257: 7322, 1982.
Yamamura et al PNAS 83 2152, 1986.
Ward et al Nature 341: 544, 1989.
Orlandi et al PNAS 86: 3833, 1989.
Larrick et al BBNC 160(3): 1250, 1989.
Larrick et al In Virto Immuniakia . . . 1988, pp. 231–246.
Marks et al J. Mol. Biol. 222: 581, 1991.
Clackson et al Nature 352: 624, 1991.
Sasty et al PNAS 86: 5728, 1989.
Winter et al Nature 349: 293, 1991.
Marx Science 246: 1250, 1989.
Alt et al., Immunoglobulin genes in transgenic mice, TIG—Aug. 1985.
Berman et. al., Content and organization of the human Ig $V_H$ locus: definition of three new $V_H$ families and linkage to the Ig $C_H$ locus, The EMBO J. 7:727–738 (1988).
Berton et. al., Synthesis of germ–line γ1 immunoglobulin heavy–chain transcripts in resting B cells: Induction by interleukin 4 and inhibition by interferon γ, Proc. Natl. Acad. Sci. (U.S.A.) 86:2829–2833 (1989).
Bollag et al., Homologous recombination in mammalian cells, Annu. Rev. Genet. 23:199–225 (1989).
Bruggemann et al., Human antibody production in transgenic mice: expression from 100 kb of the human IgH locus, Eur. J. Immunol. 21:1323–1326 (1991).
Bruggemann et al., A repertoire of monoclonal antibodies with human heavy chains from transgenic mice, Proc. Natl. Acad. Sci. USA 86:6709–6713 (1989).

(List continued on next page.)

*Primary Examiner*—Suzanne E. Ziska
*Attorney, Agent, or Firm*—Townsend and Townsend and Crew LLP

[57] ABSTRACT

The invention relates to transgenic non-human animals capable of producing heterologous antibodies and transgenic non-human animals having inactivated endogenous immunoglobulin genes. In one aspect of the invention, endogenous immunoglobulin genes are suppressed by antisense polynucleotides and/or by antiserum directed against endogenous immunoglobulins. Heterologous antibodies are encoded by immunoglobulin genes not normally found in the genome of that species of non-human animal. In one aspect of the invention, one or more transgenes containing sequences of unrearranged heterologous human immunoglobulin heavy chains are introduced into a non-human animal thereby forming a transgenic animal capable of functionally rearranging transgenic immunoglobulin sequences and producing a repertoire of antibodies of various isotypes encoded by human immunoglobulin genes. Such heterologous human antibodies are produced in B-cells which are thereafter immortalized, e.g., by fusing with an immortalizing cell line such as a myeloma or by manipulating such B-cells by other techniques to perpetuate a cell line capable of producing a monoclonal heterologous antibody. The invention also relates to heavy and light chain immunoglobulin transgenes for making such transgenic non-human animals as well as methods and vectors for disrupting endogenous immunoglobulin loci in the transgenic animal.

21 Claims, 46 Drawing Sheets

OTHER PUBLICATIONS

Bucchini et al., Rearrangement of a chicken immunoglobulin gene occurs in the lymphoid lineage of transgenic mice, Nature 326:409–411 (1987).

Capecchi, The new mouse genetics: Altering the genome by gene targeting, TIG 5:70–76 (1989).

Capecchi, Altering the genome by homologous recombination, Science 244:1288–1292 (1989).

Coffman et. al., T cell activity that enhances polyclonal IgE production and its inhibition by interferon–γ, J. Immunol. 136:949–954 (1986).

Coffman et al., A mouse T cell product that preferentially enhances IgA production, J. Immunol. 139:3685–3690 (1987).

Doetschman et al., Targetted correction of a mutant HPRT gene in mouse embryonic stem cells, Nature 330:576–578 (1987).

Durdik et al., Isotype switching by a microinjected μ immunoglobulin heavy chain gene in transgenic mice, Proc. Natl. Acad. Sci. USA 86:2346–2350 (1989).

Esser and Radbruch, Rapid induction of transcription of unrearranged Sγ1 switch regions in activated murine B cells by interleukin 4, The EMBO J. 8:483–488 (1989).

Ferrier et al., Separate elements control DJ and VDJ rearrangement in a transgenic recombination substrate, The EMBO J. 9:117–125 (1990).

Forni, extensive splenic B cell activation in IgM–transgenic mice, Eur. J. Immunol. 20:983–989 (1990).

Gerstein et al., Isotype switching of an immunoglobulin heavy chain transgene occurs by dna recombination between different chromosomes, Cell 63:537–548 (1990).

Goodhardt et al., Rearrangement and expression of rabbit immunoglobulin κ light chain gene in transgenic mice, Proc. Natl. Acad. Sci. (U.S.A.) 84:4229–4233 (1987).

Gordon, Transgenic mice in immunology, The Mount Sinai Journal of Medicine 53:223–231 (1986).

Hagman et al, Inhibition of immunoglobulin gene rearrangement by the expression of a λ2 transgene, J. Exp. Med. 169:1911–1929 (1989).

Ichihara et al., Organization of human immunoglobulin heavy chain diversity gene loci, The EMBO J. 7:4141–4150 (1988).

Iglesias et al., Expression of immunoglobulin delta chain causes allelic exclusion in transgenic mice, Nature 330:482–484 (1987).

James and Bell, Human monoclonal antibody production current status and future prospects, J. of Immunol. Methods 100:5–40 (1987).

Jasin and Berg, Homologous integration in mammalian cells without target gene selection, Genes & Development 2:1353–1363 (1988).

Kenny et al., Alternation of the B cell surface phenotype, immune response to phosphocholine and the B cell repertoire in M167 α plus κ transgenic mice, J. of Immunol. 142:4466–4474 (1989).

Jung et al., Shutdown of class switching recombination by deletion of a switch region control element, Science 259:984–987 (1993).

Kitamura et al., A B cell–deficient mouse by targeted disruption of the membrane exon of the immunoglobulin μ chain gene, Nature 350:423–426 (1991).

Koller and Smithies, Inactivating the $β_2$–microglobulin locus in mouse embryonic stem cells by homologous recombination, Proc. Natl. Acad. Sci. USA 86:8932–8935 (1989).

Lin et al., Recombination in mouse L cells between DNA introduced into cells and homologous chromosomal sequences, Proc. Natl. Acad. Sci. USA 82:1391–1395 (1985).

Linton et al., Primary antibody–forming cells secondary B cells are generated from separate precursor cell subpopulations, Cell 59:1049–1059 (1989).

Lo et al., Expression of mouse IgA by transgenic mice, pigs and sheep, Eur. J. Immunol. 21:1001–1006 (1991).

Lorenz et al., Physical map of the human immunoglobulin k locus and its implications for the mechanisms of $V_K$–$J_K$ rearrangement, Nucl. Acids Res. 15:9667–9676 (1987).

Lutzker and Alt, Structure and expression of germ line immunoglobulin γ2b transcripts, Mol. Cell. Biol. 8:1849–1852 (1988).

Mansour et al., Disruption of the proto–oncogene int–2 in mouse embryo–derived stem cells: a general strategy for targeting mutations to non–selectable genes, Nature 336:348–352 (1988).

Mills et.al., Sequences of human immunoglobulin switch regions: implications for recombination and transcription, Nucl. Acids. Res. 18:7305–7316 (1991).

Mills et al. DNase I hypersensitive sites in the chromatin of human μ immunoglobulin heavy–chain genes, Nature 306:809–812 (1983).

Mowatt et. al., DNA sequence of the murine δ1 switch segment reveals novel structural elements, J.Immunol. 136:2674–2683 (1986).

Muller et al., Membrane–bound IgM Obstructs B cell development in transgenic mice, Eur. J. Immunol. 19:923–928 (1989).

Murray & Szostack, Construction of artificial chromosomes in yeast, Nature 305:189–193 (1983).

Neuberger et al., Isotype exclusion and transgene down–regulation in immungloublin–λ transgenic mice, Nature 338:350–352 (1989).

Nikaido et al., Nucleotide sequences of switch regions of immunoglobulin C and C genes and their comparison, J. Biol. Chem. 257:7322–7329 (1982).

Nikaido et al., Switch region of immunoglobulin Cμ gene is composed of simple tandem repetitive sequences, Nature 292:845–848 (1981).

Nussenzweig et al., A human immunoglobulin gene reduces the incidence of lymphomas in c–Myc–bearing transgenic mice, Nature 336:446–450 (1988).

Nussenzweig et al., Allelic exclusion in transgenic mice carrying mutant human IgM genesJ Exp. Med. 167:1969 (1988).

Oettinger et al., RAG–1 and RAG–2, adjacent genes that synergistically activate V(D)J recombination, Science 248:1517–1523 (1990).

Petters, transgenic mice in immunological research, Vet. Immunol. Immunopath. 17:267–278 (1987).

Rabbits et. al., Human immunoglobulin heavy chain genes: evolutionary comparisons of Cμ, Cδ and Cγ genes and associated switch sequences, Nucl. Acids Res. 9:4509–4524 (1981).

Rath et al., Quantitative analysis of idiotypic mimicry and allelic exclusion in mice with a μ Ig Transgene, J. of Immunol. 143:2074–2080 (1989).

Rath et al., B cell abnormalities induced by a μ ig transgene extend to L chain isotype usage, J. of Immunol. 146:2841 (1991).

Ravetch et al., Evolutionary approach to the question of immunoglobulin heavy chain switching: Evidence from cloned human and mouse genes, Proc. Natl. Acad. Sci. (U.S.A.) 77:6734–6738 (1980).

Reid et al., A single DNA response element can confer inducibility by both α–and γ–interferons, Proc. Natl. Acad. Sci. (U.S.A.) 86:840–844 (1989).

Ritchie et al., Allelic exclusion and control of endogenous immunoglobulin gene rearrangement in κ transgenic mice, Nature 312:517–520 (1984).

Rothman et al., Structure and expression of germline immunoglobulin γ3 heavy chain gene transcripts: implications for mitogen and lymphokine directed class–switching, Intl. Immunol. 2:621–627 (1990).

Rusconi et al., Transmission and expression of a specific pair of rearranged immunoglobulin μ and κ genes in a transgenic mouse line, Nature 314:330–334 (1985).

Sato et al., Physical linkage of a variable region segment and the joining region segment of the human immunoglobulin heavy chain locus, Biochem. Biophys. Res. Comm. 154:264–271 (1988).

Sevidy and Sharp, Positive genetic selection for gene disruption in mammalian cells by homologous recombination, Proc. Natl. Acad. Sci. USA 86:227–231 (1989).

Shimizu et al., Trans–splicing as a possible molecular mechanism for the multiple isotype expression of the immunoglobulin gene, J. Exp. Med. 173:1385–1393 (1991).

Shimizu et al., Immunoglobulin double–isotype expression by trans–mRNA in a human immunoglobulin transgenic mouse, Proc. Natl. Acad. Sci. USA 86:8020–8023 (1989).

Sideras et. al., Production of sterile transcripts of Cγ genes in an IgM–producing human neoplastic B cell line that switches to IgG–producing cells, Intl. Immunol. 1: 631–642 (1989).

Siebenlist et al., Human immunoglobulin D segments encoded in tandem multigenic families, Nature 294:631–635 (1981).

Smithies et al., Insertion of DNA sequences into the human chromosomal β–globulin locus by homologous recombination, Nature 317:230–234 (1985).

Snapper et. al., Interferon–γ and B cell stimulatory factor–1 reciprocally regulate Ig isotype production, Science 236:944–947 (1987).

Song et al., Accurate modification of a chromosomal plasmid by homologous recombination in human cells, Proc. Natl. Acad. Sci. USA 84:6820–6824 (1987).

Soriano et al., Targeted disruption of the c–src protooncogene leads to osteopetrosis in mice, Cell 64:693–702 (1991).

Stavnezer et al., Immunoglobulin heavy–chain switching may be directed by prior induction of transcripts from constant–region genes, Proc. Natl. Acad Sci. (U.S.A.) 85:7704–7708 (1988).

Storb, Immunoglobulin gene analysis in transgenic mice, in Immunoglobulin Genes, Academic Press Limited, pp. 303–326 (1989).

Storb et al., Expression, allelic exclusion and somatic mutation of mouse immunoglobulin kappa genes, Immunological Reviews 89:85–102 (1986).

Szurek et al., Complete nucleotide sequence of the murine γ3 switch region and analysis of switch recombinant ion in two γ3–expressing hybridomas, J. Immunol. 135:620–626 (1985).

Tahara et al., HLA antibody responses in HLA class I transgenic mice, Immunogenetics 32:351–360 (1990).

Taussig et al., Regulation of immunoglobulin gene rearrangement and expresion, immunology today 10:143–146 (1989).

Thomas and Capecchi, Site–directed mutagenesis by gene targeting in mouse embryo–derived stem cells, Cell 51:503–512 (1987).

Thomas et al., High frequency targeting of genes to specific sites in the mammalian genome, Cell 44:419–428 (1986).

Uhlmann and Peyman, Antisense Oligonucleotides: A new therapeutic principle, Chemical Reviews 90:544–584 (1990).

Weaver et al., A transgenic immunoglobulin Mu gene prevents rearrangement of endogenous genes, Cell 42:117–127 (1985).

Yamamura et al., Cell–type–specific and regulated expression of a human λ1 heavy–chain immunoglobulin gene in transgenic mice, Proc. Natl. Acad. Sci. USA 83:2152–2156 (1986).

Yancopoulos and Alt, Regulation of the assembly and expression of variable–region genes, Ann. Rev. Immunol. 4;339–368 (1986).

Yancopoulos and Alt, Developmentally controlled and tissue–specific expression of unrearranged $V_H$ gene segments, Cell 40:271–281 (1985).

Yasui et al., Class switch from μ to δ is mediated by homologous recombination between $\sigma_\mu$ and $\epsilon_\mu$ sequences in human immunoglobulin gene loci, Eur. J. Immunol. 19:1399–1403 (1989).

Zijlstra et al., Germ–line transmission of a disrupted $\beta_2$–microglobulin gene produced by homologous recombination in embryonic stem cells, Nature 342:435–438 (1989).

Zimmer and Gruss, Production of chimaeric mice containing embryonic stem (ES) cells carrying a homoeobox Hox 1.1 allele mutated by homologous recombination, Nature 338:150–153 (1989).

Buttin, Exogenous Ig gene rearrangement in transgenic mice: a new strategy for human monoclonal antibody production? TIG—vol. 3, No. 8 (Aug. 1987).

Green et al., Antigen–specific human monoclonal antibodies from mice engineered with human Ig heavy and light chain YACs, Nature Genetics 7:13–21 (1994).

Hofker et al., Complete physical map of the human immunoglobulin heavy chain constant region gene complex, Proc. Natl. Acad. Sci. USA 86:5567–5571 (1989).

Humphries et al., A new human immunoglobulin $V_H$ family preferentially rearranged in immature B–cell tumours, Nature 331:446–449 (1988).

Jaenisch, Transgenic Animals, Science 240:1468–1474 (1988).

Jakobovits et al., Analysis of homozygous mutant chimeric mice: Deletion of the immunoglobulin heavy–chain joining region blocks B–cell development and antibody production, Proc. Natl. Acad. Sci. USA 909:2551–2555 (1993).

Lonberg et al., Antigen–specific human antibodies from mice comprising four distinct genetic modifications, Nature 368:856–859 (1994).

Miller et al., Structural alterations in J regions of mouse immunoglobulin λ genes are associated with differnetial gene expression, Nature 295:428–430 (1982).

Morrison, Success in specification, Nature 368:812–813 (1994).

Pettersson et al., A second B cell–specific enhancer 3' of the immunoglobulin heavy–chain locus, Nature 344:165–168 (1990).

Scangos and Bieberich, Gene transfer into mice, Advances in Genetics 24: 285–322 (1987).

Stites et al., *Basic & Clinical Immunology*, p. 50 (1984).

Tanaka et al., An antisense oligonucleotide complementary to a sequence in Iγ2b Increase γ2b germline transcrips, stimulates B cell DNA synthesis, and inhibits immunoglobulin secretion, The Journal of Experimental Medicine 175:597–607 (1992).

Taki et al., Targeted insertion of a variable region gene into the immunoglobulin heavy chain locus, Science 262:1268–1271 (1993).

Taylor et al., Human immunoglobulin transgenes undergo rearrangement, somatic mutation and class switching in mice that lack endogenous IgM, International Immunology 6:579–591 (1994).

Vlasov et al., Arrest of immunoglobulin G mRNA translation in vitro with an alkylating antisense oligonucleotide derivative, Chemical Abstracts, p. 28, 112:229433X (1990).

Weiss, Mice making human–like antibodies, The Washington Post, Apr. 28, 1994.

|  OLIGO-1  |  OLIGO-2  |  OLIGO-3  |
|-----------|-----------|-----------|
|  OLIGO-4  |  OLIGO-5  |  OLIGO-6  |

```
                           82 Xba I
                        78 EcoR V              115 Kpn I
                  60 Sty I                  111 Sma I
                  60 Nco I         94 Sph I        127 Mlu I
               56 BamH I      89 Xho I      121 HinD III
          42 Sfi I        75 Cla I     106 EcoR I    139 Not I
          40 Not I    65 BssH II    100 Bgl II    133 Spe I
```

147 BASE PAIRS pGP1 POLYLINKER

FIG. 8

HUMAN μ LOCUS

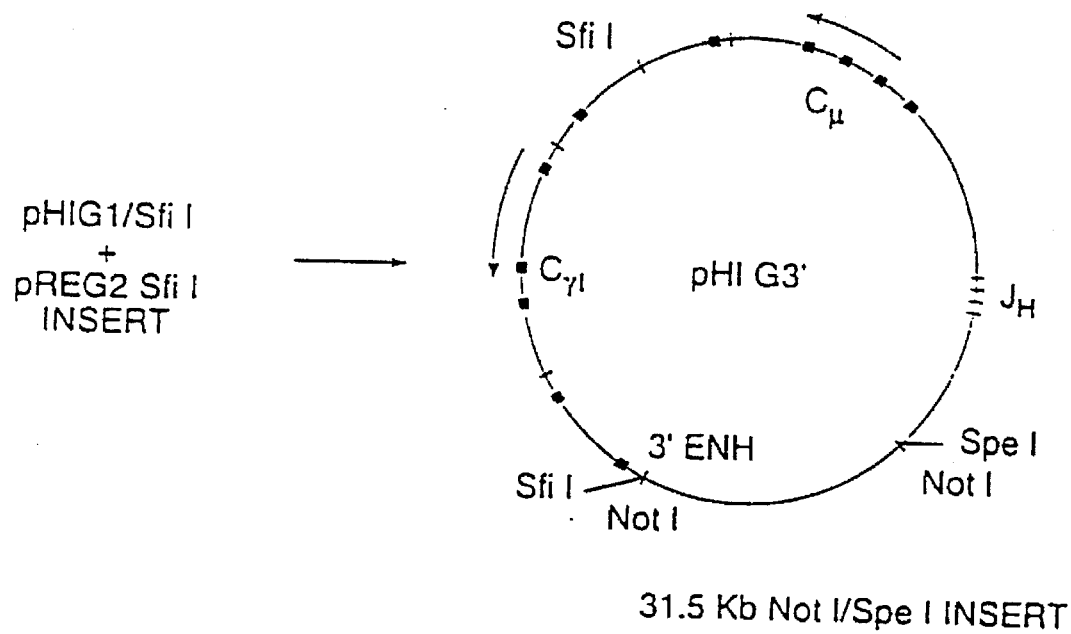
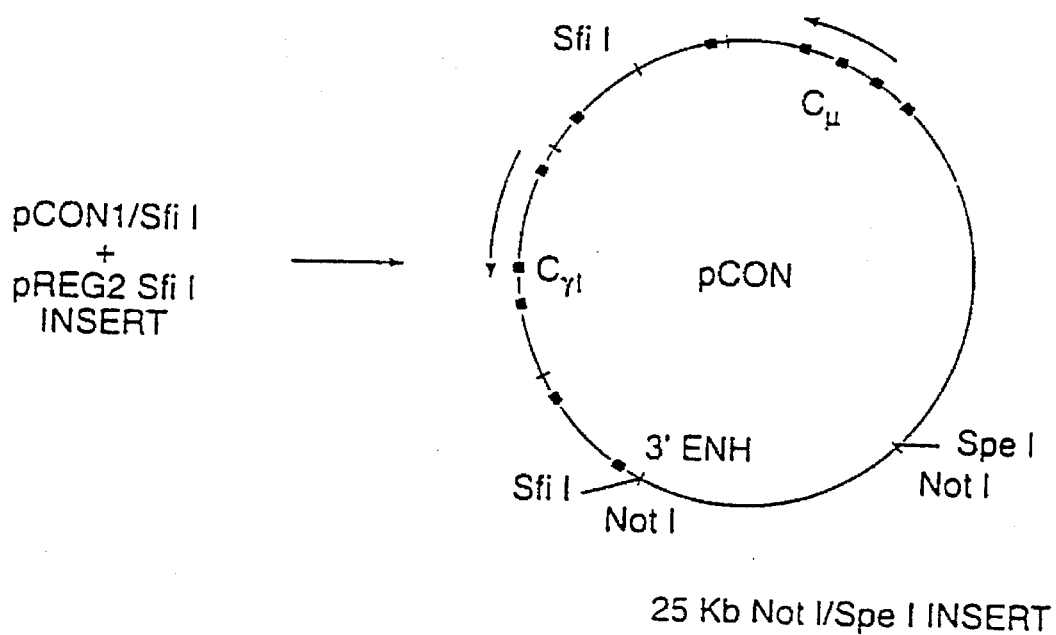
FIG. 12

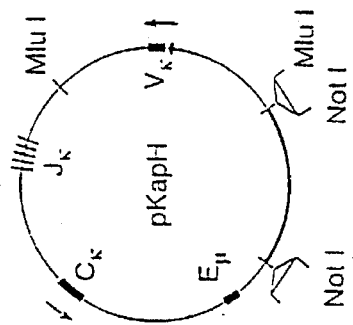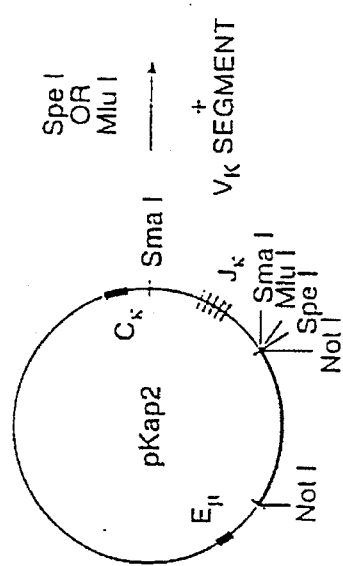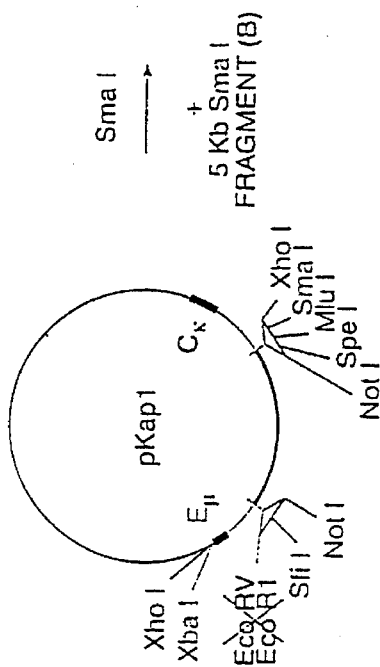
FIG. 17

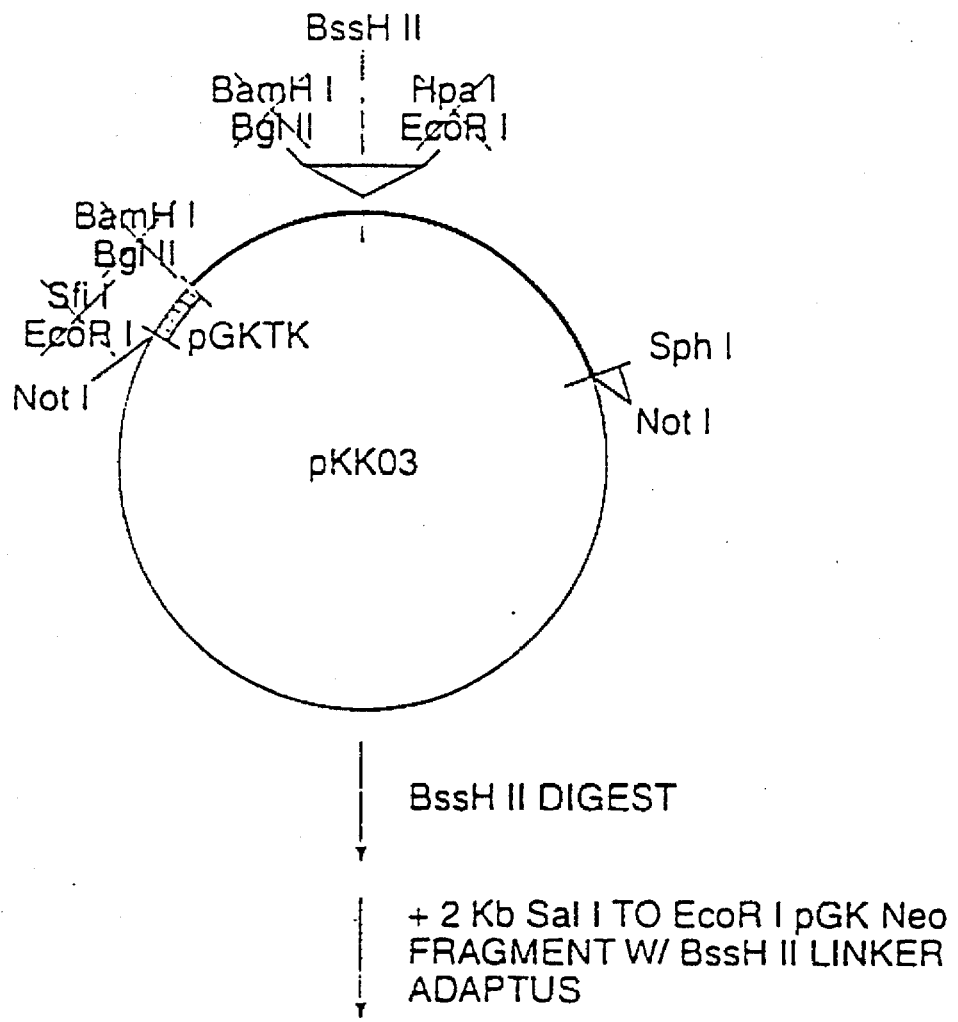
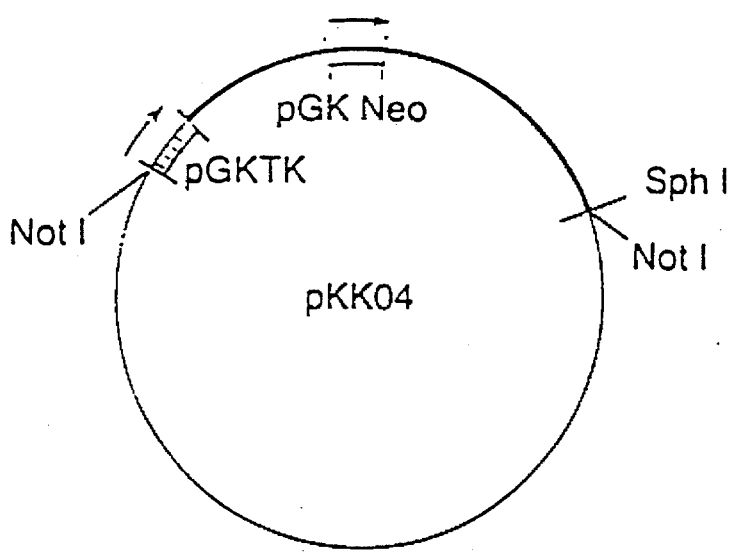
FIG. 19C

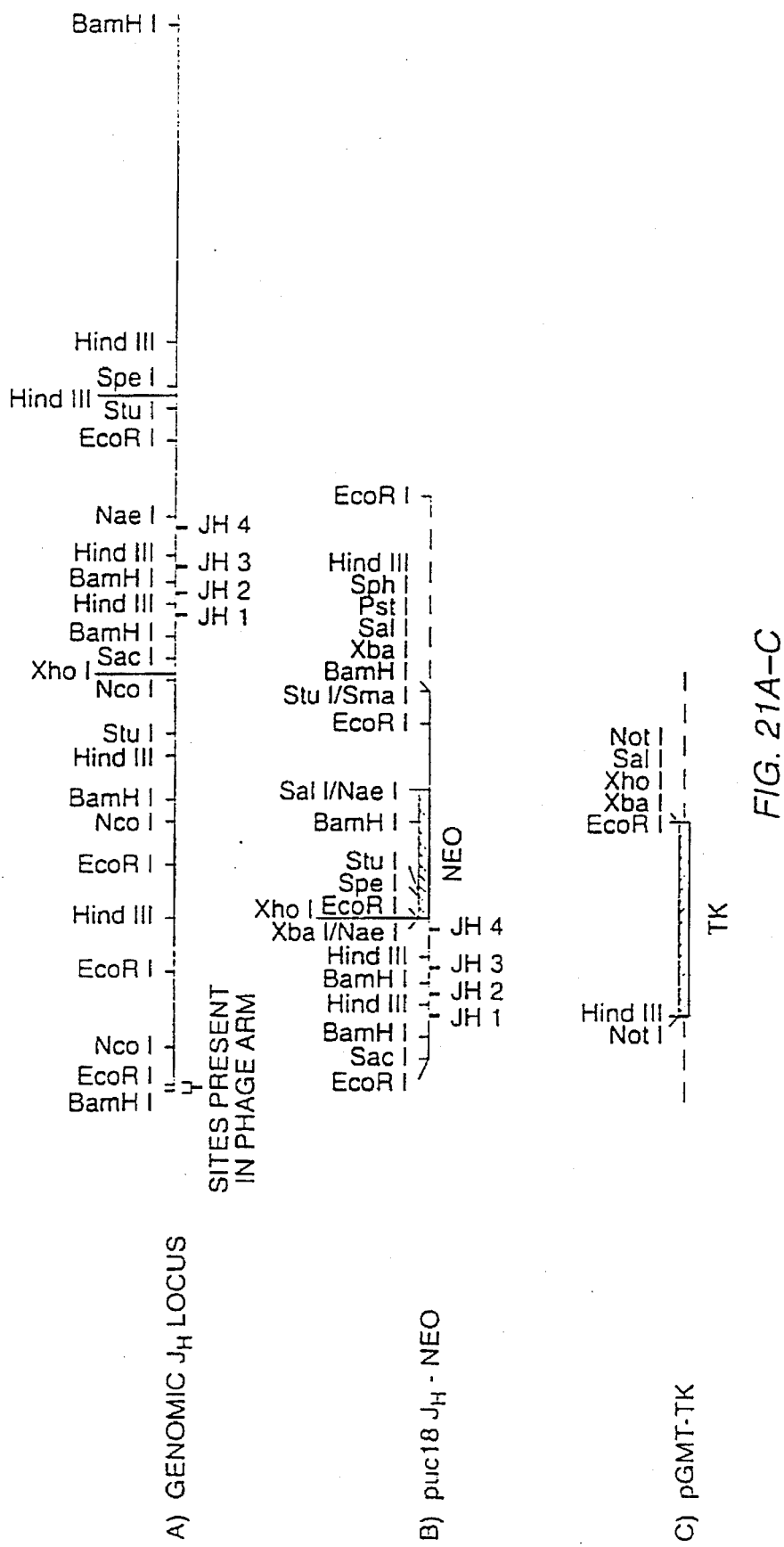
FIG. 21A-C

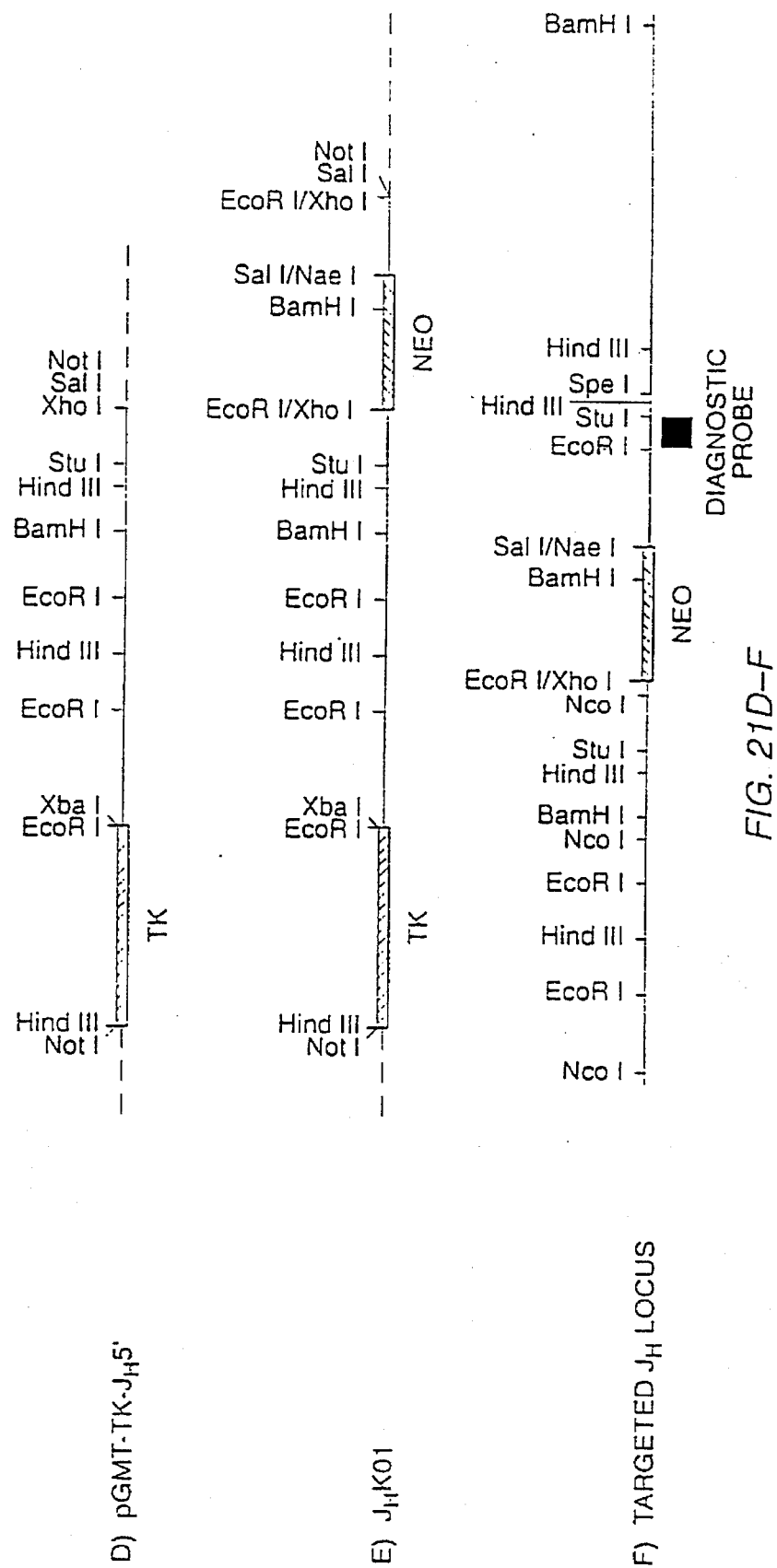
FIG. 21D-F

SYNTHETIC HEAVY CHAIN VARIABLE REGION

FIG. 40

```
TTTTCTGGCC  TGACAACCAG  GGTGGCGCAG  GATGCTCAGT  GCAGAGAGGA    50

AGAAGCAGGT  GGTCTCTGCA  GCTGGAAGCT  CAGCTCCCAC  CCAGCTGCTT   100

TGCATGTCCC  TCCCAGCTGC  CCTACCTTCC  AGAGCCATA TCAATGCCTG    150

TGTCAGAGCC  CTGGGGAGGA  ACTGCTCAGT  TAGGACCCAG  AGGGAACCAT   200
                                                Me
GGAAGCCCCA  GCTCAGCTTC  TCTTCCTCCT  GCTACTCTGG  CTCCCAGgtg   250
tGluAlaPro  AlaGlnLeuL  euPheLeuLe  uLeuLeuTrp  LeuPro aggggggaacc  atgaggtggt  tttgcacatt  agtgaaaact  cttgccacct   300
ctgctcagca  agaaatataa  ttaaaattca  aagtatatca  acaattttgg   350
ctctactcaa  agacagttgg  tttgatcttg  attacatgag  tgcatttctg   400
ttttatttcc  aatttcagAT  ACCACCGGAG  AAATTGTGTT  GACACAGTCT   450
            Asp ThrThrGlyG luIleValLe uThrGlnSer
CCAGCCACCC  TGTCTTTGTC  TCCAGGGGAA  AGAGCCACCC  TCTCCTGCAG   500
ProAlaThrL  euSerLeuSe  rProGlyGlu  ArgAlaThrL  euSerCysAr
GGCCAGTCAG  AGTGTTAGCA  GCTACTTAGC  CTGGTACCAA  CAGAAACCTG   550
gAlaSerGln  SerValSerS  erTyrLeuAl  aTrpTyrGln  GlnLysProG
GCCAGGCTCC  CAGGCTCCTC  ATCTATGATG  CATCCAACAG  GGCCACTGGC   600
lyGlnAlaPr  oArgLeuLeu  IleTyrAspA  laSerAsnAr  gAlaThrGly
ATCCCAGCCA  GGTTCAGTGG  CAGTGGGTCT  GGGACAGACT  TCACTCTCAC   650
IleProAlaA  rgPheSerGl  ySerGlySer  GlyThrAspP  heThrLeuTh
CATCAGCAGC  CTAGAGCCTG  AAGATTTTGC  AGTTTATTAC  TGTCAGCAGC   700
rIleSerSer  LeuGluProG  luAspPheAl  aValTyrTyr  CysGlnGlnA
GTAGCAACTG  GCCTCCCACA  GTGATTCCAC  ATGAAACAAA  AACCCCAACA   750
rgSerAsnTr  pPro
AGACCATCAG  TGTTTACTAG  ATTATTATAC  CAGCTGCTTC  CTTTACAGAC   800

AGCTAGTGGG  GT                                               812
```

FIG. 41

```
AGGGCGGCGC AGATGCTCAG TGCAGAGAGA AGAAACAGGT GGTCTCTGCA    50

GCTGGAAGCT CAGCTCCCAC CCCAGCTGCT TTGCATGTCC CTCCCAGCTG   100

CCCTACCTTC CAGAGCCAT ATCAATGCCT GGGTCAGAGC TCTGGGGAGG    150

AACTGCTCAG TTAGGACCCA GACGGAACCA TGGAAGCCCC AGCGCAGCTT   200
                                 M etGluAlaPr oAlaGlnLeu
CTCTTCCTCC TGCTACTCTG GCTCACAGgt gaggggaata tgaggtgtct   250
LeuPheLeuL euLeuLeuTr pLeuThr
ttgcacatca gtgaaaactc ctgccacctc tgctcagcaa gaaatataat   300
taaaattcaa aatagatcaa caattttggc tctactcaaa gacagtgggt   350
ttgattttga ttacatgagt gcatttctgt tttatttcca atttcagATA   400
                                                 AspT
CCACCGGAGA AATTGTGTTG ACACAGTCTC CAGCCACCCT GTCTTTGTCT   450
hrThrGlyGl uIleValLeu ThrGlnSerP roAlaThrLe uSerLeuSer
CCAGGGGAAA GAGCCACCCT CTCCTGCAGG GCCAGTCAGG GTGTTAGCAG   500
ProGlyGluA rgAlaThrLe uSerCysArg AlaSerGlnG lyValSerSe
CTACTTAGCC TGGTACCAGC AGAAACCTGG CCAGGCTCCC AGGCTCCTCA   550
rTyrLeuAla TrpTyrGlnG lnLysProGl yGlnAlaPro ArgLeuLeuI
TCTATGATGC ATCCAACAGG GCCACTGGCA TCCCAGCCAG GTTCAGTGGC   600
leTyrAspAl aSerAsnArg AlaThrGlyI leProAlaAr gPheSerGly
AGTGGGCCTG GGACAGACTT CACTCTCACC ATCAGCAGCC TAGAGCCTGA   650
SerGlyProG lyThrAspPh eThrLeuThr IleSerSerL euGluProGl
AGATTTTGCA GTTTATTACT GTCAGCAGCG TAGCAACTGG CATCCCACAG   700
uAspPheAla ValTyrTyrC ysGlnGlnAr gSerAsnTrp His
TGATTCCACA TGAAACAAAA ACCCCAACAA GACCATCAGT GTTTACTAGA   750

TTATTATACC AGCTGCTTCC TTTACAGACA GCTAGTGGGG TGGCCACTCA   800

GTGTTAGCAT CTCAGCTCTA TTTGGCCATT TTGGAGTTCA AGTTGTCAAG   850

TCCAAAATTA CTTATGTTAG TCCATTGCAT CATACCATTT CAGTGTGGCT   900
```

*FIG. 42*

```
CCGCCCCAGC  TGCTTTGCAT  GTCCCTCCCA  GCCGCCCTGC  AGTCCAGAGC   50

CCATATCAAT  GCCTGGGTCA  GAGCTCTGGA  GAAGAGCTGC  TCAGTTAGGA  100

ACCCCAGAGG  GAACCATGGA  AACCCCAGCG  CAGCTTCTCT  TCCTCCTGCT  150
            MetGl  uThrProAla  GlnLeuLeuP  heLeuLeuLe
ACTCTGGCTC  CCAGgtgagg  ggaacatggg  atggttttgc  atgtcagtga  200
uLeuTrpLeu  Pro
aaaccctctc  aagtcctgtt  acctggcaac  tctgctcagt  caatacaata  250
attaaagctc  aatataaagc  aataattctg  gctcttctgg  gaagacaatg  300
ggtttgattt  agattacatg  ggtgacttttt  ctgttttatt  tccaatctca  350
gATACCACCG  GAGAAATTGT  GTTGACGCAG  TCTCCAGGCA  CCCTGTCTTT  400
AspThrThrG  lyGluIleVa  lLeuThrGln  SerProGlyT  hrLeuSerLe
GTCTCCAGGG  GAAAGAGCCA  CCCTCTCCTG  CAGGGCCAGT  CAGAGTGTTA  450
uSerProGly  GluArgAlaT  hrLeuSerCy  sArgAlaSer  GlnSerValS
GCAGCAGCTA  CTTAGCCTGG  TACCAGCAGA  AACCTGGCCA  GGCTCCCAGG  500
erSerSerTy  rLeuAlaTrp  TyrGlnGlnL  ysProGlyGl  nAlaProArg
CTCCTCATCT  ATGGTGCATC  CAGCAGGGCC  ACTGGCATCC  CAGACAGGTT  550
LeuLeuIleT  yrGlyAlaSe  rSerArgAla  ThrGlyIleP  roAspArgPh
CAGTGGCAGT  GGGTCTGGGA  CAGACTTCAC  TCTCACCATC  AGCAGACTGG  600
eSerGlySer  GlySerGlyT  hrAspPheTh  rLeuThrIle  SerArgLeuG
AGCCTGAAGA  TTTTGCAGTG  TATTACTGTC  AGCAGTATGG  TAGCTCACCT  650
luProGluAs  pPheAlaVal  TyrTyrCysG  lnGlnTyrGl  ySerSerPro
CCCACAGTGA  TTCAGCTTGA  AACAAAAACC  TCTGCAAGAC  CTTCATTGTT  700

TACTAGATTA  TACCAGCTGC  TTCCTTTACA  GATAGCTGCT  GCAATGACAA  750

CTCAATTTAG  CATCTCTCTC  TGCTTGGGCA  TTTTGGGGAT  CTTAAAAAAG  800

TAATCCCTTG  ATATATTTTT  GACTCTGATT  CCTGCATTTT  TCCTCAGACC  850

AAGATGGACA  GCCAGGTTTA  AGCACAGTTT  CACAGTAATG  GCCACTGGAT  900
```

FIG. 43

```
AAACACATTC  TCTGCAGACA  AATTTGAGCT  ACCTTGATCT  TACCTGGACA   50

GGTGGGGACA  CTGAGCTGGT  GCTGAGTTAC  TCAGATGCGC  CAGCTCTGCA  100

GCTGTGCCCA  GCCTGCCCCA  TCCCCTGCTC  ATTTGCATGT  TCCCAGAGCA  150

CAACCTCCTG  CCCTGAAGCC  TTATTAATAG  GCTGGTCAGA  CTTTGTGCAG  200

GAATCAGACC  CAGTCAGGAC  ACAGCATGGA  CATGAGGGTC  CTCGCTCAGC  250
                                    MetAs pMetArgVal LeuAlaGlnL
TCCTGGGGCT  CCTGCTGCTC  TGTTTCCCAG  gtaaggatgg  agaacactag  300
euLeuGlyLe  uLeuLeuLeu  CysPhePro
cagtttactc  agcccagggt  gctcagtact  gctttactat  tcagggaaat  350
tctcttacaa  catgattaat  tgtgtggaca  tttgttttta  tgtttccaat  400
ctcagGTGCC  AGATGTGACA  TCCAGATGAC  CCAGTCTCCA  TCCTCACTGT  450
     GlyAla ArgCysAspI  leGlnMetTh  rGlnSerPro  SerSerLeuS
CTGCATCTGT  AGGAGACAGA  GTCACCATCA  CTTGTCGGGC  GAGTCAGGGT  500
erAlaSerVa  lGlyAspArg  ValThrIleT  hrCysArgAl  aSerGlnGly
ATTAGCAGCT  GGTTAGCCTG  GTATCAGCAG  AAACCAGAGA  AAGCCCCTAA  550
IleSerSerT  rpLeuAlaTr  pTyrGlnGln  LysProGluL  ysAlaProLy
GTCCCTGATC  TATGCTGCAT  CCAGTTTGCA  AAGTGGGGTC  CCATCAAGGT  600
sSerLeuIle  TyrAlaAlaS  erSerLeuGl  nSerGlyVal  ProSerArgP
TCAGCGGCAG  TGGATCTGGG  ACAGATTTCA  CTCTCACCAT  CAGCAGCCTG  650
heSerGlySe  rGlySerGly  ThrAspPheT  hrLeuThrIl  eSerSerLeu
CAGCCTGAAG  ATTTTGCAAC  TTATTACTGC  CAACAGTATA  ATAGTTACCC  700
GlnProGluA  spPheAlaTh  rTyrTyrCys  GlnGlnTyrA  snSerTyrPr
ACCCACAGTG  TTACACACCC  AAACATAAAC  CCCCAGGGAA  GCAGATGTGT  750
o
GAGGCTGGGC  TGCCCCAGCT  GCTTCTCCTG  ATGCCTCCAT  CAGCTGAGAG  800

TGTTCCTCAG  ATGCAGCCAC  ACTCTGATGG  TGTTGGTAGA  TGGGGAC     847
```

FIG. 44

SEQUENCE LISTING ( 1 ) GENERAL INFORMATION:

( i i i ) NUMBER OF SEQUENCES: 197

( 2 ) INFORMATION FOR SEQ ID NO:1:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:1:

C T A A D T G G G G         10

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Asp Ala Phe Asp Ile
1               5

( 2 ) INFORMATION FOR SEQ ID NO:3:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

Asp Tyr Phe Asp Tyr
1               5

( 2 ) INFORMATION FOR SEQ ID NO:4:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:4:

Gly Ala Phe Asp Ile
1               5

( 2 ) INFORMATION FOR SEQ ID NO:5:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:5:

Lys Gly Arg Val
1

( 2 ) INFORMATION FOR SEQ ID NO:6:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:6:

Asn Asp Ser Val
1

( 2 ) INFORMATION FOR SEQ ID NO:7:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: RNA ( x i ) SEQUENCE DESCRIPTION: SEQ ID NO:7:

AAAGAAAGAG UU  12

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: RNA ( x i ) SEQUENCE DESCRIPTION: SEQ ID NO:8:

AACGACAGCG UU  12

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:9:

AATTGCGGCC GC  12

( 2 ) INFORMATION FOR SEQ ID NO:10:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:10:

CTTGAGCCCG CCTAATGAGC GGGCTTTTTT TTGCATACTG CGGCC  45

( 2 ) INFORMATION FOR SEQ ID NO:11:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:11:

GCAATGGCCT GGATCCATGG CGCGCTAGCA TCGATATCTA GAGCTCGAGC A  51

( 2 ) INFORMATION FOR SEQ ID NO:12:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:12:

TGCAGATCTG AATTCCCGGG TACCAAGCTT ACGCGTACTA GTGCGGCCGC T  51

( 2 ) INFORMATION FOR SEQ ID NO:13:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:13:

AATTAGCGGC CGCACTAGTA CGCGTAAGCT TGGTACCCGG GAATT    45

( 2 ) INFORMATION FOR SEQ ID NO:14:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:14:

CAGATCTGCA TGCTCGAGCT CTAGATATCG ATGCTAGCGC GCCATGGATC C    51

( 2 ) INFORMATION FOR SEQ ID NO:15:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:15:

AGGCCATTGC GGCCGCAGTA TGCAAAAAAA AGCCCGCTCA TTAGGCGGGC T    51

( 2 ) INFORMATION FOR SEQ ID NO:16:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:16:

CGCGTGGCCG CAATGGCCA    19

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:17:

CTAGTGGCCA TTGCGGCCA    19

( 2 ) INFORMATION FOR SEQ ID NO:18:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:18:

CAGGATCCAG ATATCAGTAC CTGAAACAGG GCTTGC  36

( 2 ) INFORMATION FOR SEQ ID NO:19:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:19:

GAGCATGCAC AGGACCTGGA GCACACACAG CCTTCC  36

( 2 ) INFORMATION FOR SEQ ID NO:20:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:20:

GGACTGTGTC CCTGTGTCAT GCTTTTGATG TCTGGGGCCA AG  42

( 2 ) INFORMATION FOR SEQ ID NO:21:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:21:

CACCAAGTTG ACCTGCCTGG TCACAGACCT GACCACCTAT GA  42

( 2 ) INFORMATION FOR SEQ ID NO:22:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:22:

CCTGTGGACC ACCGCCTCCA CCTTCATCGT CCTCTTCCTC CT  42

( 2 ) INFORMATION FOR SEQ ID NO:23:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:23:

TGAGCCACGA AGACCCTGAG GTCAAGTTCA AGTTCAACTG GTACGTGG    48

(2) INFORMATION FOR SEQ ID NO:24:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:24:

TGGTATTACT ATGGTTCGGG GAGTTATTAT AACCACAGTG TC    42

(2) INFORMATION FOR SEQ ID NO:25:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:25:

GCCTGAAATG GAGCCTCAGG GCACAGTGGG CACGGACACT GT    42

(2) INFORMATION FOR SEQ ID NO:26:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:26:

GCAGGGAGGA CATGTTTAGG ATCTGAGGCC GCACCTGACA CC    42

(2) INFORMATION FOR SEQ ID NO:27:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:27:

GATCCTGGTT TAGTTAAAGA GGATTTTATT CACCCCTGTG TC    42

(2) INFORMATION FOR SEQ ID NO:28:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:28:

GATCCAAGCA GT    12

(2) INFORMATION FOR SEQ ID NO:29:

( i ) SEQUENCE CHARACTERISTICS:
  ( A ) LENGTH: 12 base pairs
  ( B ) TYPE: nucleic acid
  ( C ) STRANDEDNESS: single
  ( D ) TOPOLOGY: linear ( i i ) MOLECULE TYPE: DNA (primer)

( x i ) SEQUENCE DESCRIPTION: SEQ ID NO:29:

CTAGACTGCT TG    12

( 2 ) INFORMATION FOR SEQ ID NO:30:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:30:

CGCGTCGAAC TA    12

( 2 ) INFORMATION FOR SEQ ID NO:31:

( i ) SEQUENCE CHARACTERISTICS:
    ( A ) LENGTH: 12 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:31:

AGCTTAGTTC GA    12

( 2 ) INFORMATION FOR SEQ ID NO:32:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:32:

GAATGGGAGT GAGGCTCTCT CATACCCTAT TCAGAACTGA CT    42

( 2 ) INFORMATION FOR SEQ ID NO:33:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:33:

GAACTGTGGC TGCACCATCT GTCTTCATCT TCCCGCCATC TG    42

( 2 ) INFORMATION FOR SEQ ID NO:34:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:34:

GAGGTACACT GACATACTGG CATGCCCCCC CCCCCC          36

( 2 ) INFORMATION FOR SEQ ID NO:35:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:35:

GTACGCCATA TCAGCTGGAT GAAGTCATCA GATGGCGGGA AGATGAAGAC AGATGGTGCA          60

( 2 ) INFORMATION FOR SEQ ID NO:36:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:36:

TCATCAGATG GCGGGAAGAT GAAGACAGAT GGTGCA          36

( 2 ) INFORMATION FOR SEQ ID NO:37:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:37:

GTACGCCATA TCAGCTGGAT GAAG          24

( 2 ) INFORMATION FOR SEQ ID NO:38:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:38:

GAGGTACACT GACATACTGG CATG          24

( 2 ) INFORMATION FOR SEQ ID NO:39:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:39:

GTACGCCATA TCAGCTGGAT GAAG                                                              24

(2) INFORMATION FOR SEQ ID NO:40:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:40:

GAGGTACACT GACATACTGG CATG                                                              24

(2) INFORMATION FOR SEQ ID NO:41:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:41:

GTACGCCATA TCAGCTGGAT GAAGACAGGA GACGAGGGGG AAAAGGGTTG GGGCGGATGC                        60

(2) INFORMATION FOR SEQ ID NO:42:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:42:

ACAGGAGACG AGGGGAAAA GGGTTGGGGC GGATGC                                                  36

(2) INFORMATION FOR SEQ ID NO:43:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:43:

GTACGCCATA TCAGCTGGAT GAAG                                                              24

(2) INFORMATION FOR SEQ ID NO:44:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:44:

GAGGTACACT GACATACTGG CATG                                                              24

(2) INFORMATION FOR SEQ ID NO:45:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (primer)

( x i ) SEQUENCE DESCRIPTION: SEQ ID NO:45:

GTACTCCATA TCAGCTGGAT GAAG      24

( 2 ) INFORMATION FOR SEQ ID NO:46:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:46:

GAGGTACACT GACATACTGG CATG      24

( 2 ) INFORMATION FOR SEQ ID NO:47:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:47:

GGCTGATGCT GCACCAACTG TATCCATCTT CCCACCATCC AG      42

( 2 ) INFORMATION FOR SEQ ID NO:48:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:48:

CTCACGTTCG GTGCTGGGAC CAAGCTGGAG CTGAAACGTA AG      42

( 2 ) INFORMATION FOR SEQ ID NO:49:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:49:

ACTATGCTAT GGACTACTGG GGTCAAGGAA CCTCAGTCAC CG      42

( 2 ) INFORMATION FOR SEQ ID NO:50:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:50:

GGCCGCTCGA CGATAGCCTC GAGGCTATAA ATCTAGAAGA ATTCCAGCAA AGCTTTGGC      59

( 2 ) INFORMATION FOR SEQ ID NO:51:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:51:

CAAGAGCCCG CCTAATGAGC GGGCTTTTTT TTGCATACTG CGGCCGCT      48

( 2 ) INFORMATION FOR SEQ ID NO:52:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:52:

AATTAGCGGC CGCAGTATGC AAAAAAAAGC CCGCTCATTA GGCGGGCT      48

( 2 ) INFORMATION FOR SEQ ID NO:53:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:53:

GCGGCCGCCT CGAGATCACT ATCGATTAAT TAAGGATCCA GCAGTAAGCT TGCGGCCGC      59

( 2 ) INFORMATION FOR SEQ ID NO:54:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:54:

GCGGCCGCAT CCCGGGTCTC GAGGTCGACA AGCTTTCGAG GATCCGCGGC CGC      53

( 2 ) INFORMATION FOR SEQ ID NO:55:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:55:

```
GCGGCCGCTG  TCGACAAGCT  TATCGATGGA  TCCTCGAGTG  CGGCCGC                47
```

(2) INFORMATION FOR SEQ ID NO:56:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:56:

```
GCGGCCGCTG  TCGACAAGCT  TCGAATTCAG  ATCGATGTGG  TACCTGGATC  CTCGAGTGCG    60
GCCGC                                                                     65
```

(2) INFORMATION FOR SEQ ID NO:57:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:57:

```
GGCCGCAAGC  TTACTGCTGG  ATCCTTAATT  AATCGATAGT  GATCTCGAGG  C             51
```

(2) INFORMATION FOR SEQ ID NO:58:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:58:

```
GGCCGCCTCG  AGATCACTAT  CGATTAATTA  AGGATCCAGC  AGTAAGCTTG  C             51
```

(2) INFORMATION FOR SEQ ID NO:59:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:59:

```
CTCCAGGATC  CAGATATCAG  TACCTGAAAC  AGGGCTTGC                             39
```

(2) INFORMATION FOR SEQ ID NO:60:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:60:

```
CTCGAGCATG  CACAGGACCT  GGAGCACACA  CAGCCTTCC                             39
```

( 2 ) INFORMATION FOR SEQ ID NO:61:

( i ) SEQUENCE CHARACTERISTICS:
        ( A ) LENGTH: 813 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 241..285

( i x ) FEATURE:
        ( A ) NAME/KEY: CDS
        ( B ) LOCATION: 373..678

( x i ) SEQUENCE DESCRIPTION: SEQ ID NO:61:

```
TTCCTCAGGC AGGATTTAGG GCTTGGTCTC TCAGCATCCC ACACTTGTAC AGCTGATGTG    60

GCATCTGTGT TTTCTTTCTC ATCCTAGATC AAGCTTTGAG CTGTGAAATA CCCTGCCTCA   120

TGAATATGCA AATAATCTGA GGTCTTCTGA GATAAATATA GATATATTGG TGCCCTGAGA   180

GCATCACATA ACAACCAGAT TCCTCCTCTA AGAAGCCCC  TGGGAGCACA GCTCATCACC   240

ATG GAC TGG ACC TGG AGG TTC CTC TTT GTG GTG GCA GCA GCT ACA         285
Met Asp Trp Thr Trp Arg Phe Leu Phe Val Val Ala Ala Ala Thr
 1               5                  10                  15

GGTAAGGGGC TTCCTAGTCC CTAAGGCTGA GGAAGGGATC CTGGTTTAGT TAAAGAGGAT   345

TTTATTCACC CCTGTGTCCT CTCCACA GGT GTC CAG TCC CAG GTC CAG CTG       396
                                Gly Val Gln Ser Gln Val Gln Leu
                                 1               5

GTG CAG TCT GGG GCT GAG GTG AAG AAG CCT GGG TCC TCG GTG AAG GTC     444
Val Gln Ser Gly Ala Glu Val Lys Lys Pro Gly Ser Ser Val Lys Val
         10                  15                  20

TCC TGC AAG GCT TCT GGA GGC ACC TTC AGC AGC TAT GCT ATC AGC TGG     492
Ser Cys Lys Ala Ser Gly Gly Thr Phe Ser Ser Tyr Ala Ile Ser Trp
 25                  30                  35                  40

GTG CGA CAG GCC CCT GGA CAA GGG CTT GAG TGG ATG GGA AGG ATC ATC     540
Val Arg Gln Ala Pro Gly Gln Gly Leu Glu Trp Met Gly Arg Ile Ile
                 45                  50                  55

CCT ATC CTT GGT ATA GCA AAC TAC GCA CAG AAG TTC CAG GGC AGA GTC     588
Pro Ile Leu Gly Ile Ala Asn Tyr Ala Gln Lys Phe Gln Gly Arg Val
             60                  65                  70

ACG ATT ACC GCG GAC AAA TCC ACG AGC ACA GCC TAC ATG GAG CTG AGC     636
Thr Ile Thr Ala Asp Lys Ser Thr Ser Thr Ala Tyr Met Glu Leu Ser
         75                  80                  85

AGC CTG AGA TCT GAG GAC ACG GCC GTG TAT TAC TGT GCG AGA             678
Ser Leu Arg Ser Glu Asp Thr Ala Val Tyr Tyr Cys Ala Arg
     90                  95                 100

GACACAGTGT GAAAACCCAC ATCCTGAGAG TGTCAGAAAC CCTGAGGGAG AAGGCAGCTG   738

TGCCGGGCTG AGGAGATGAC AGGGTTTATT AGGTTTAAGG CTGTTTACAA AATGGGTTAT   798

ATATTTGAGA AAAAA                                                    813
```

( 2 ) INFORMATION FOR SEQ ID NO:62:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

| Met | Asp | Trp | Thr | Trp | Arg | Phe | Leu | Phe | Val | Val | Ala | Ala | Ala | Thr |
|---|---|---|---|---|---|---|---|---|---|---|---|---|---|---|
| 1 | | | | 5 | | | | | 10 | | | | | 15 |

(2) INFORMATION FOR SEQ ID NO:63:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO:63:

| Gly | Val | Gln | Ser | Gln | Val | Gln | Leu | Val | Gln | Ser | Gly | Ala | Glu | Val | Lys |
|---|---|---|---|---|---|---|---|---|---|---|---|---|---|---|---|
| 1 | | | | 5 | | | | | 10 | | | | | 15 | |

| Lys | Pro | Gly | Ser | Ser | Val | Lys | Val | Ser | Cys | Lys | Ala | Ser | Gly | Gly | Thr |
|---|---|---|---|---|---|---|---|---|---|---|---|---|---|---|---|
| | | | 20 | | | | 25 | | | | | | 30 | | |

| Phe | Ser | Ser | Tyr | Ala | Ile | Ser | Trp | Val | Arg | Gln | Ala | Pro | Gly | Gln | Gly |
|---|---|---|---|---|---|---|---|---|---|---|---|---|---|---|---|
| | | 35 | | | | | 40 | | | | | 45 | | | |

| Leu | Glu | Trp | Met | Gly | Arg | Ile | Ile | Pro | Ile | Leu | Gly | Ile | Ala | Asn | Tyr |
|---|---|---|---|---|---|---|---|---|---|---|---|---|---|---|---|
| | 50 | | | | | 55 | | | | | 60 | | | | |

| Ala | Gln | Lys | Phe | Gln | Gly | Arg | Val | Thr | Ile | Thr | Ala | Asp | Lys | Ser | Thr |
|---|---|---|---|---|---|---|---|---|---|---|---|---|---|---|---|
| 65 | | | | | 70 | | | | | 75 | | | | | 80 |

| Ser | Thr | Ala | Tyr | Met | Glu | Leu | Ser | Ser | Leu | Arg | Ser | Glu | Asp | Thr | Ala |
|---|---|---|---|---|---|---|---|---|---|---|---|---|---|---|---|
| | | | | 85 | | | | | 90 | | | | | 95 | |

| Val | Tyr | Tyr | Cys | Ala | Arg |
|---|---|---|---|---|---|
| | | | 100 | | |

(2) INFORMATION FOR SEQ ID NO:64:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:64:

GGACTGTGTC CCTGTGTGAT GCTTTTGATG TCTGGGGCCA AG    42

(2) INFORMATION FOR SEQ ID NO:65:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:65:

CACCAAGTTG ACCTGCCTGG TCACAGACCT GACCACCTAT GA    42

(2) INFORMATION FOR SEQ ID NO:66:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:66:

TGGTATTACT ATGGTTCGGG GAGTTATTAT AACCACAGTG TC    42

( 2 ) INFORMATION FOR SEQ ID NO:67:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:67:

CAGCAGGTGC ACACCCAATG CCCATGAGCC CAGACACTGG AC    42

( 2 ) INFORMATION FOR SEQ ID NO:68:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:68:

TGAGCCCAGA CACTGGAC    18

( 2 ) INFORMATION FOR SEQ ID NO:69:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:69:

GTTAAAGAGG ATTTTATTCA CCCCTGTGTC CTCTCCACAG GTGTC    45

( 2 ) INFORMATION FOR SEQ ID NO:70:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:70:

CCGGTCGACC GG    12

( 2 ) INFORMATION FOR SEQ ID NO:71:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:71:

Tyr Cys Ala Arg Arg Leu Thr Gly Val Asp Ala Phe Asp Ile Trp Gly
 1              5                   10                 15

Gln Gly Thr Met Val Thr Val Ser Ser Ala Ser Thr Lys
         20                   25

( 2 ) INFORMATION FOR SEQ ID NO:72:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:72:

```
Tyr Cys Ala Arg His Arg Ile Ala Ala Ala Gly Phe Asp Tyr Trp Gly
 1               5                  10                      15

Gln Gly Thr Leu Val Thr Val Ser Ser Ala Ser Thr Lys
            20                  25
```

( 2 ) INFORMATION FOR SEQ ID NO:73:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:73:

```
Tyr Cys Ala Arg Tyr Tyr Tyr Tyr Tyr Gly Met Asp Val Trp Gly
 1               5                  10                      15

Gln Gly Thr Thr Val Thr Val Ser Ser Ala Ser Thr Lys
            20                  25
```

( 2 ) INFORMATION FOR SEQ ID NO:74:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:74:

```
Tyr Cys Ala Arg His Tyr Asp Ile Leu Thr Gly Pro Thr Thr Thr Thr
 1               5                  10                      15

Val Trp Thr Ser Gly Ala Lys Gly Pro Arg Ser Pro Ser Pro Gln Pro
            20                  25                      30

Pro Pro
```

( 2 ) INFORMATION FOR SEQ ID NO:75:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:75:

```
Tyr Cys Ala Arg Arg Arg Tyr Tyr Gly Ser Gly Ser Tyr Tyr Asn Val
 1               5                  10                      15

Phe Asp Tyr Trp Gly Gln Gly Thr Leu Val Thr Val Ser Ser Ala Ser
            20                  25                      30

Thr Lys
```

( 2 ) INFORMATION FOR SEQ ID NO:76:

( i ) SEQUENCE CHARACTERISTICS:
        ( A ) LENGTH: 28 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:76:

```
Tyr Cys Ala Arg Arg Gly Val Ser Asp Ala Phe Asp Ile Trp Gly Gln
1               5                   10                  15
Gly Thr Met Val Thr Val Ser Ser Ala Ser Thr Lys
            20                  25
```

( 2 ) INFORMATION FOR SEQ ID NO:77:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:77:

```
Tyr Cys Ala Arg Ala Thr Gly Ala Phe Asp Ile Trp Gly Gln Gly Thr
1               5                   10                  15
Met Val Thr Val Ser Ser Gly Ser Ala Ser
            20                  25
```

( 2 ) INFORMATION FOR SEQ ID NO:78:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:78:

```
Tyr Cys Ala Arg Ser Ala Asn Trp Gly Ser Tyr Tyr Tyr Tyr Gly Met
1               5                   10                  15
Asp Val Trp Gly Gln Gly Thr Met Val Thr Val Ser Ser Gly Ser Ala
            20                  25                  30
Ser
```

( 2 ) INFORMATION FOR SEQ ID NO:79:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:79:

```
Tyr Cys Ala Arg Tyr Phe Gly His Trp Gly Gln Gly Thr Leu Val Thr
1               5                   10                  15
Val Ser Ser Gly Ser Ala Ser
            20
```

( 2 ) INFORMATION FOR SEQ ID NO:80:

(i) SEQUENCE CHARACTERISTICS:
   (A) LENGTH: 27 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:80:

Tyr Cys Ala Arg His Val Ala Asn Ser Phe Asp Tyr Trp Gly Gln Gly
1               5                   10                  15

Thr Leu Val Thr Val Ser Ser Gly Ser Ala Ser
            20              25

(2) INFORMATION FOR SEQ ID NO:81:

(i) SEQUENCE CHARACTERISTICS:
   (A) LENGTH: 31 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:81:

Tyr Cys Ala Arg Gln Ile Thr Met Val Arg Gly Val Pro Phe Asp Tyr
1               5                   10                  15

Trp Gly Gln Gly Thr Leu Val Thr Val Ser Ser Gly Ser Ala Ser
            20                  25                  30

(2) INFORMATION FOR SEQ ID NO:82:

(i) SEQUENCE CHARACTERISTICS:
   (A) LENGTH: 24 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:82:

Tyr Cys Ala Arg Gln Tyr Phe Gln His Trp Gly Gln Gly Thr Leu Val
1               5                   10                  15

Thr Val Ser Ser Gly Ser Ala Ser
            20

(2) INFORMATION FOR SEQ ID NO:83:

(i) SEQUENCE CHARACTERISTICS:
   (A) LENGTH: 31 amino acids
   (B) TYPE: amino acid
   (C) STRANDEDNESS: single
   (D) TOPOLOGY: linear (ii) MOLECULE TYPE: peptide (xi) SEQUENCE DESCRIPTION: SEQ ID NO:83:

Tyr Cys Ala Arg Gln Thr Gly Asp Tyr Tyr Tyr Gly Met Asp Val
1               5                   10                  15

Trp Gly Gln Gly Thr Thr Val Thr Val Ser Ser Gly Ser Ala Ser
            20                  25                  30

(2) INFORMATION FOR SEQ ID NO:84:

(i) SEQUENCE CHARACTERISTICS:
   (A) LENGTH: 36 amino acids
   (B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:84:

```
Tyr Cys Ala Arg His Tyr Tyr Gly Ser Gly Ser Tyr Asp Tyr Tyr Tyr
1               5                   10                  15

Tyr Gly Met Asp Val Trp Gly Gln Gly Thr Thr Val Thr Val Ser Ser
            20                  25                  30

Gly Ser Ala Ser
            35
```

( 2 ) INFORMATION FOR SEQ ID NO:85:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:85:

```
Tyr Cys Ala Arg Gln Gly Val Gly Pro Gly Asn Pro Gly His Arg Leu
1               5                   10                  15

Leu Ser Leu His Gln
            20
```

( 2 ) INFORMATION FOR SEQ ID NO:86:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:86:

```
Tyr Cys Ala Arg Phe Thr Glu Thr Gly Ser Thr Pro Gly Ala Arg Glu
1               5                   10                  15

Pro Trp Ser Pro Ser Pro Gln Gly Val His
            20                  25
```

( 2 ) INFORMATION FOR SEQ ID NO:87:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:87:

```
Tyr Cys Ala Arg Arg Arg Tyr Tyr Gly Ser Gly Ser Tyr Tyr Asn Val
1               5                   10                  15

Phe Asp Tyr Trp Gly Gln Gly Thr Leu Val Thr Val Ser Ser Ala Ser
            20                  25                  30

Thr Lys
```

( 2 ) INFORMATION FOR SEQ ID NO:88:

( i ) SEQUENCE CHARACTERISTICS:
        ( A ) LENGTH: 26 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:88:

```
Tyr Cys Ala Arg Gln Thr Trp Gly Gly Asp Tyr Trp Gly Gln Gly Thr
1               5                   10                  15
Leu Val Thr Val Ser Ser Ala Ser Thr Lys
            20                  25
```

(2) INFORMATION FOR SEQ ID NO:89:

(i) SEQUENCE CHARACTERISTICS:
(A) LENGTH: 33 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:89:

```
Tyr Cys Ala Arg Gly Tyr Ser Gly Tyr Asp Asn Tyr Tyr Tyr Gly Ile
1               5                   10                  15
His Val Trp Gly Gln Gly Thr Thr Val Thr Val Ser Ser Ala Ser Thr
            20                  25                  30
Lys
```

(2) INFORMATION FOR SEQ ID NO:90:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:90:

```
Tyr Cys Ala Arg Gln Thr Gly Glu Asp Tyr Phe Asp Tyr Trp Gly Gln
1               5                   10                  15
Gly Thr Leu Val Thr Val Ser Ser Gly Ser Ala Ser
            20                  25
```

(2) INFORMATION FOR SEQ ID NO:91:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:91:

```
Tyr Cys Ala Arg Tyr Ser Gly Tyr Asp Tyr Leu Leu Val Leu Arg Ser
1               5                   10                  15
Leu Gly Pro Trp His Pro Gly His Cys Leu Leu Ser Leu His Arg
            20                  25                  30
```

(2) INFORMATION FOR SEQ ID NO:92:

(i) SEQUENCE CHARACTERISTICS:
(A) LENGTH: 32 amino acids
(B) TYPE: amino acid
(C) STRANDEDNESS: single ( D ) TOPOLOGY: linear ( i i ) MOLECULE TYPE: peptide ( x i ) SEQUENCE DESCRIPTION: SEQ ID NO:92:

```
Tyr Cys Ala Arg Ala Ser Leu Pro Ser Phe Asp Tyr Tyr Gly Met Asp
1               5                   10                  15
Val Trp Gly Gln Gly Thr Thr Val Thr Val Ser Ser Ala Ser Thr Lys
            20                  25                  30
```

( 2 ) INFORMATION FOR SEQ ID NO:93:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:93:

```
Tyr Cys Ala Arg Arg Gly Gly Gly Leu Thr Thr Gly Ala Arg Glu Pro
1               5                   10                  15
Trp Ser Pro Ser Pro Gln Gly Val His
            20                  25
```

( 2 ) INFORMATION FOR SEQ ID NO:94:

( i ) SEQUENCE CHARACTERISTICS:
    ( A ) LENGTH: 31 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:94:

```
Tyr Cys Val Pro Val Glu Thr Leu Leu Leu Leu Arg Tyr Gly Arg
1               5                   10                  15
Leu Gly Pro Arg Asp His Gly His Arg Leu leu Arg Glu Cys Ile
            20                  25                  30
```

( 2 ) INFORMATION FOR SEQ ID NO:95:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:95:

```
Tyr Cys Val Arg Asp Ile Leu Thr Gly Glx Arg Asp Tyr Trp Gly Gln
1               5                   10                  15
Gly Thr Leu Val Thr Val Ser Ser Gly Ser Ala Ser
            20                  25
```

( 2 ) INFORMATION FOR SEQ ID NO:96:

( i ) SEQUENCE CHARACTERISTICS:
    ( A ) LENGTH: 31 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:96:

Tyr Cys Ala Arg His Gly Ile Ala Ala Ala Gly Thr Ala Phe Asp Ile
1               5                   10                  15

Trp Gly Gln Gly Thr Met Val Thr Val Ser Ser Gly Ser Ala Ser
            20                  25                  30

( 2 ) INFORMATION FOR SEQ ID NO:97:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:97:

Tyr Cys Val Arg Ser Thr Gly Val Asp Ala Phe Asp Ile Trp Gly Gln
1               5                   10                  15

Gly Thr Met Val Thr Val Ser Ser Gly Ser Ala Ser
            20                  25

( 2 ) INFORMATION FOR SEQ ID NO:98:

( i ) SEQUENCE CHARACTERISTICS:
    ( A ) LENGTH: 28 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:98:

Tyr Cys Ala Glu Ile Ala Ala Ala Ala Leu Leu Glx Leu Leu Gly Pro
1               5                   10                  15

Gly Met Pro Gly His Arg Leu Leu Arg Glu Cys Ile
            20                  25

( 2 ) INFORMATION FOR SEQ ID NO:99:

( i ) SEQUENCE CHARACTERISTICS:
    ( A ) LENGTH: 30 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:99:

Tyr Cys Val Cys Ser Ile Ala Ala Ala Gly Asn Gly Asn Gly Tyr Trp
1               5                   10                  15

Gly Gln Gly Thr Leu Val Thr Val Ser Ser Gly Ser Ala Ser
            20                  25                  30

( 2 ) INFORMATION FOR SEQ ID NO:100:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:100:

Tyr Cys Ala Arg Gln Met Met Gly Asp Tyr Trp Gly Gln Gly Thr Leu
1               5                   10                  15

```
    Val Thr Val Ser Ser Gly Ser Ala Ser
             20                  25
```

( 2 ) INFORMATION FOR SEQ ID NO:101:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:101:

CTAGCTCGAG TCCAAGGAGT CTGTGCCGAG GTGCAGCTG    39

( 2 ) INFORMATION FOR SEQ ID NO:102:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:102:

GTTGCTCGAG TGAAAGGTGT CCAGTGTGAG GTGCAGCTG    39

( 2 ) INFORMATION FOR SEQ ID NO:103:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:103:

GGCGCTCGAG TTCCACGACA CCGTCACCGG TTC    33

( 2 ) INFORMATION FOR SEQ ID NO:104:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:104:

CCTGCTCGAG GCAGCCAACG GCCACGCTGC TCG    33

( 2 ) INFORMATION FOR SEQ ID NO:105:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:105:

TCAGTGAAGG TTTCCTGCAA GGCATCTGGA TACACCTTCA CC    42

( 2 ) INFORMATION FOR SEQ ID NO:106:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:106:

TCCCTGAGAC TCTCCTGTGC AGCCTCTGGA TTCACCTTCA GT      42

( 2 ) INFORMATION FOR SEQ ID NO:107:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:107:

GGCCGCATCC CGGGTCTCGA GGTCGACAAG CTTTCGAGGA TCCGC      45

( 2 ) INFORMATION FOR SEQ ID NO:108:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:108:

GGCCGCGGAT CCTCGAAAGC TTGTCGACCT CGAGACCCGG GATGC      45

( 2 ) INFORMATION FOR SEQ ID NO:109:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:109:

GGCCGCTGTC GACAAGCTTA TCGATGGATC CTCGAGTGC      39

( 2 ) INFORMATION FOR SEQ ID NO:110:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:110:

GGCCGCACTC GAGGATCCAT CGATAAGCTT GTCGACAGC      39

( 2 ) INFORMATION FOR SEQ ID NO:111:

( i ) SEQUENCE CHARACTERISTICS:
        ( A ) LENGTH: 42 base pairs
        ( B ) TYPE: nucleic acid (C) STRANDEDNESS: single
(D) TOPOLOGY: linear (ii) MOLECULE TYPE: DNA (primer)

(xi) SEQUENCE DESCRIPTION: SEQ ID NO:111:

CACCTTCGGC CAAGGGACAC GACTGGAGAT TAAACGTAAG CA    42

(2) INFORMATION FOR SEQ ID NO:112:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:112:

AGGTTCAGTG GCAGTGGGTC TGGACAGAC TTCACTCTCA CCATCAGC    48

(2) INFORMATION FOR SEQ ID NO:113:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:113:

AATTGCGGCC GC    12

(2) INFORMATION FOR SEQ ID NO:114:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:114:

GATCCTCGAG ACCAGGTACC AGATCTTGTG AATTCG    36

(2) INFORMATION FOR SEQ ID NO:115:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:115:

TCGACGAATT CACAAGATCT GGTACCTGGT CTCGAG    36

(2) INFORMATION FOR SEQ ID NO:116:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (primer)

( x i ) SEQUENCE DESCRIPTION: SEQ ID NO:116:

CGCGGTACCG AGAGTCAGTC CTTCCCAAAT GTC 33

( 2 ) INFORMATION FOR SEQ ID NO:117:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:117:

CGCCTCGAGA CAGCTGGAAT GGGCACATGC AGA 33

( 2 ) INFORMATION FOR SEQ ID NO:118:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:118:

CGCGGTACCG CTGATGCTGC ACCAACTGTA TCC 33

( 2 ) INFORMATION FOR SEQ ID NO:119:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:119:

CGCCTCGAGC TAACACTCAT TCCTGTTGAA GCT 33

( 2 ) INFORMATION FOR SEQ ID NO:120:

( i ) SEQUENCE CHARACTERISTICS:
        ( A ) LENGTH: 3699 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:120:

```
AATTAGCGGC CGCCTCGAGA TCACTATCGA TTAATTAAGG ATCCAGATAT CAGTACCTGA      60
AACAGGGCTT GCTCACAACA TCTCTCTCTC TGTCTCTCTG TCTCTGTGTG TGTGTCTCTC     120
TCTGTCTCTG TCTCTCTCTG TCTCTCTGTC TCTGTGTGTG TCTCTCTCTG TCTCTCTCTC     180
TGTCTCTCTG TCTCTCTGTC TGTCTCTGTC TCTGTCTCTG TCTCTCTCTC TCTCTCTCTC     240
TCTCTCTCTC TCTCTCTCAC ACACACACAC ACACACACAC ACACCTGC CGAGTGACTC       300
ACTCTGTGCA GGGTTGGCCC TCGGGCACA TGCAAATGGA TGTTTGTTCC ATGCAGAAAA      360
ACATGTTTCT CATTCTCTGA GCCAAAAATA GCATCAATGA TTCCCCCACC CTGCAGCTGC     420
AGGTTCACCC CACCTGGCCA GGTTGACCAG CTTTGGGGAT GGGGCTGGGG GTTCCATGAC     480
CCCTAACGGT GACATTGAAT TCAGTGTTTT CCCATTTATC GACACTGCTG GAATCTGACC     540
```

| | | | | | |
|---|---|---|---|---|---|
|CTAGGAGGGA|ATGACAGGAG|ATAGGCAAGG|TCCAAACACC|CCAGGGAAGT|GGGAGAGACA|600|
|GGAAGGCTGT|GTGTGCTCCA|GGTCCTGTGC|ATGCTGCAGA|TCTGAATTCC|CGGGTACCAA|660|
|GCTTGCGGCC|GCAGTATGCA|AAAAAAGCC|CGCTCATTAG|GCGGGCTCTT|GGCAGAACAT|720|
|ATCCATCGCG|TCCGCCATCT|CCAGCAGCCG|CACGCGGCGC|ATCTCGGGCA|GCGTTGGGTC|780|
|CTGGCCACGG|GTGCGCATGA|TCGTGCTCCT|GTCGTTGAGG|ACCCGGCTAG|GCTGGCGGGG|840|
|TTGCCTTACT|GGTTAGCAGA|ATGAATCACC|GATACGCGAG|CGAACGTGAA|GCGACTGCTG|900|
|CTGCAAAACG|TCTGCGACCT|GAGCAACAAC|ATGAATGGTC|TTCGGTTTCC|GTGTTTCGTA|960|
|AAGTCTGGAA|ACGCGGAAGT|CAGCGCCCTG|CACCATTATG|TTCCGGATCT|GCATCGCAGG|1020|
|ATGCTGCTGG|CTACCCTGTG|AACACCTAC|ATCTGTATTA|ACGAAGCGCT|GGCATTGACC|1080|
|CTGAGTGATT|TTTCTCTGGT|CCCGCCGCAT|CCATACCGCC|AGTTGTTTAC|CCTCACAACG|1140|
|TTCCAGTAAC|CGGGCATGTT|CATCATCAGT|AACCCGTATC|GTGAGCATCC|TCTCTCGTTT|1200|
|CATCGGTATC|ATTACCCCCA|TGAACAGAAA|TTCCCCCTTA|CACGGAGGCA|TCAAGTGACC|1260|
|AAACAGGAAA|AAACCGCCCT|TAACATGGCC|CGCTTTATCA|GAAGCCAGAC|ATTAACGCTT|1320|
|CTGGAGAAAC|TCAACGAGCT|GGACGCGGAT|GAACAGGCAG|ACATCTGTGA|ATCGCTTCAC|1380|
|GACCACGCTG|ATGAGCTTTA|CCGCAGCTGC|CTCGCGCGTT|TCGGTGATGA|CGGTGAAAAC|1440|
|CTCTGACACA|TGCAGCTCCC|GGAGACGGTC|ACAGCTTGTC|TGTAAGCGGA|TGCCGGGAGC|1500|
|AGACAAGCCC|GTCAGGGCGC|GTCAGCGGGT|GTTGGCGGGT|GTCGGGCGC|AGCCATGACC|1560|
|CAGTCACGTA|GCGATAGCGG|AGTGTATACT|GGCTTAACTA|TGCGGCATCA|GAGCAGATTG|1620|
|TACTGAGAGT|GCACCATATG|CGGTGTGAAA|TACCGCACAG|ATGCGTAAGG|AGAAAATACC|1680|
|GCATCAGGCG|CTCTTCCGCT|TCCTCGCTCA|CTGACTCGCT|GCGCTCGGTC|GTTCGGCTGC|1740|
|GGCGAGCGGT|ATCAGCTCAC|TCAAAGGCGG|TAATACGGTT|ATCCACAGAA|TCAGGGGATA|1800|
|ACGCAGGAAA|GAACATGTGA|GCAAAAGGCC|AGCAAAAGGC|CAGGAACCGT|AAAAAGGCCG|1860|
|CGTTGCTGGC|GTTTTCCAT|AGGCTCCGCC|CCCTGACGA|GCATCACAAA|AATCGACGCT|1920|
|CAAGTCAGAG|GTGGCGAAAC|CCGACAGGAC|TATAAAGATA|CCAGGCGTTT|CCCCCTGGAA|1980|
|GCTCCCTCGT|GCGCTCTCCT|GTTCCGACCC|TGCCGCTTAC|CGGATACCTG|TCCGCCTTTC|2040|
|TCCCTTCGGG|AAGCGTGGCG|CTTTCTCATA|GCTCACGCTG|TAGGTATCTC|AGTTCGGTGT|2100|
|AGGTCGTTCG|CTCCAAGCTG|GGCTGTGTGC|ACGAACCCCC|CGTTCAGCCC|GACCGCTGCG|2160|
|CCTTATCCGG|TAACTATCGT|CTTGAGTCCA|ACCCGGTAAG|ACACGACTTA|TCGCCACTGG|2220|
|CAGCAGCCAC|TGGTAACAGG|ATTAGCAGAG|CGAGGTATGT|AGGCGGTGCT|ACAGAGTTCT|2280|
|TGAAGTGGTG|GCCTAACTAC|GGCTACACTA|GAAGGACAGT|ATTTGGTATC|TGCGCTCTGC|2340|
|TGAAGCCAGT|TACCTTCGGA|AAAAGAGTTG|GTAGCTCTTG|ATCCGGCAAA|CAAACCACCG|2400|
|CTGGTAGCGG|TGGTTTTTTT|GTTTGCAAGC|AGCAGATTAC|GCGCAGAAAA|AAAGGATCTC|2460|
|AAGAAGATCC|TTTGATCTTT|TCTACGGGGT|CTGACGCTCA|GTGGAACGAA|AACTCACGTT|2520|
|AAGGGATTTT|GGTCATGAGA|TTATCAAAAA|GGATCTTCAC|CTAGATCCTT|TTAAATTAAA|2580|
|AATGAAGTTT|TAAATCAATC|TAAAGTATAT|ATGAGTAAAC|TTGGTCTGAC|AGTTACCAAT|2640|
|GCTTAATCAG|TGAGGCACCT|ATCTCAGCGA|TCTGTCTATT|TCGTTCATCC|ATAGTTGCCT|2700|
|GACTCCCCGT|CGTGTAGATA|ACTACGATAC|GGGAGGGCTT|ACCATCTGGC|CCCAGTGCTG|2760|
|CAATGATACC|GCGAGACCCA|CGCTCACCGG|CTCCAGATTT|ATCAGCAATA|AACCAGCCAG|2820|
|CCGGAAGGGC|CGAGCGCAGA|AGTGGTCCTG|CAACTTTATC|CGCCTCCATC|CAGTCTATTA|2880|
|ATTGTTGCCG|GGAAGCTAGA|GTAAGTAGTT|CGCCAGTTAA|TAGTTTGCGC|AACGTTGTTG|2940|

```
CCATTGCTGC   AGGCATCGTG   GTGTCACGCT   CGTCGTTTGG   TATGGCTTCA   TTCAGCTCCG        3000

GTTCCCAACG   ATCAAGGCGA   GTTACATGAT   CCCCCATGTT   GTGCAAAAAA   GCGGTTAGCT        3060

CCTTCGGTCC   TCCGATCGTT   GTCAGAAGTA   AGTTGGCCGC   AGTGTTATCA   CTCATGGTTA        3120

TGGCAGCACT   GCATAATTCT   CTTACTGTCA   TGCCATCCGT   AAGATGCTTT   TCTGTGACTG        3180

GTGAGTACTC   AACCAAGTCA   TTCTGAGAAT   AGTGTATGCG   GCGACCGAGT   TGCTCTTGCC        3240

CGGCGTCAAC   ACGGGATAAT   ACCGCGCCAC   ATAGCAGAAC   TTTAAAAGTG   CTCATCATTG        3300

GAAAACGTTC   TTCGGGGCGA   AAACTCTCAA   GGATCTTACC   GCTGTTGAGA   TCCAGTTCGA        3360

TGTAACCCAC   TCGTGCACCC   AACTGATCTT   CAGCATCTTT   TACTTTCACC   AGCGTTTCTG        3420

GGTGAGCAAA   AACAGGAAGG   CAAAATGCCG   CAAAAAAGGG   AATAAGGGCG   ACACGGAAAT        3480

GTTGAATACT   CATACTCTTC   CTTTTTCAAT   ATTATTGAAG   CATTTATCAG   GGTTATTGTC        3540

TCATGAGCGG   ATACATATTT   GAATGTATTT   AGAAAAATAA   ACAATAGGG    GTTCCGCGCA        3600

CATTTCCCCG   AAAAGTGCCA   CCTGACGTCT   AAGAAACCAT   TATTATCATG   ACATTAACCT        3660

ATAAAAATAG   GCGTATCACG   AGGCCCTTTC   GTCTTCAAG                                  3699
```

( 2 ) INFORMATION FOR SEQ ID NO:121:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:121:

```
TACTGTGCGA   GACGGCTAAC   TGGGGTTGAT   GCTTTTGATA   TCTGGGGCCA   AGGGACAATG        60

GTCACCGTCT   CTTCAGCCTC   CACCAAG                                                 87
```

( 2 ) INFORMATION FOR SEQ ID NO:122:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:122:

```
TACTGTGCGA   GACACCGTAT   AGCAGCAGCT   GGCTTTGACT   ACTGGGGCCA   GGGAACCCTG        60

GTCACCGTCT   CCTCAGCCTC   CACCAAG                                                 87
```

( 2 ) INFORMATION FOR SEQ ID NO:123:

( i ) SEQUENCE CHARACTERISTICS:
        ( A ) LENGTH: 86 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:123:

```
TACTGTGCGA   GAATTACTAC   TACTACTACG   GTATGGACGT   CTGGGGCCAA   GGGACCACGG        60

TCACCGTCTC   CTCAGCCTCC   ACCAAG                                                  86
```

( 2 ) INFORMATION FOR SEQ ID NO:124:

( i ) SEQUENCE CHARACTERISTICS:
  ( A ) LENGTH: 102 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:124:

```
TACTGTGCGA GAATTACGAT ATTTTGACTG GTCTACTACT ACTACGGTAT GGACGTCTGG      60
GGCCAAGGGA CCACGGTCAC CGTCTCCTCA GCCTCCACCA AG                        102
```

( 2 ) INFORMATION FOR SEQ ID NO:125:

( i ) SEQUENCE CHARACTERISTICS:
    ( A ) LENGTH: 84 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:125:

```
TACTATGGTT CGGGGAGTTA TTATAACGTC TTTGACTACT GGGGCCAGGG AACCCTGGTC      60
ACCGTCTCCT CAGCCTCCAC CAAG                                            84
```

( 2 ) INFORMATION FOR SEQ ID NO:126:

( i ) SEQUENCE CHARACTERISTICS:
    ( A ) LENGTH: 85 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:126:

```
TACTATGGTT CGCGGGGGGT GTCTGATGCT TTTGATATCT GGGGCCAAGG GACAATGGTC      60
ACCGTCTCTT CAGGCCTCCA CCAAG                                           85
```

( 2 ) INFORMATION FOR SEQ ID NO:127:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:127:

```
TACTATGGTT CGGCAACTGG CGCTTTTGAT ATCTGGGGCC AAGGGACAAT GGTCACCGTC      60
TCTTCAGGGG AGTGCATCC                                                  79
```

( 2 ) INFORMATION FOR SEQ ID NO:128:

( i ) SEQUENCE CHARACTERISTICS:
    ( A ) LENGTH: 95 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:128:

```
TACTATGGTT CGTCGGCTAA CTGGGGATCC TACTACTACT ACGGACGTCT GGGGCCAAGG      60
```

GACCACGGTC ACCGTCTCCT CAGCGGAGTG CATCC                                     95

( 2 ) INFORMATION FOR SEQ ID NO:129:

( i ) SEQUENCE CHARACTERISTICS:
    ( A ) LENGTH: 69 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:129:

TACTATGGTT CGTACTTCCA GCACTGGGGC CAGGGCACCC TGGTCACCGT CTCCTCAGGG         60

AGTGCATCC                                                                 69

( 2 ) INFORMATION FOR SEQ ID NO:130:

( i ) SEQUENCE CHARACTERISTICS:
    ( A ) LENGTH: 81 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:130:

TACTATGGTT CGCACGTAGC TAACTCTTTT GACTACTGGG GCCAGGGAAC CTGGTCACC          60

GTCTCCTCAG GGAGTGCATC C                                                   81

( 2 ) INFORMATION FOR SEQ ID NO:131:

( i ) SEQUENCE CHARACTERISTICS:
    ( A ) LENGTH: 90 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:131:

TACTGTGCGA GAATTACTAT GGTTCGGGGA GTTCCCTTTG ACTACTGGGG CCAGGGAACC         60

CTGGTCACCG TCTCCTCAGG GAGTGCATCC                                          90

( 2 ) INFORMATION FOR SEQ ID NO:132:

( i ) SEQUENCE CHARACTERISTICS:
    ( A ) LENGTH: 72 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:132:

TACTGTGCGA GCAAATACTT CCAGCACTGG GGCCAGGGCA CCCTGGTCAC CGTCTCCTCA         60

GGGAGTGCAT CC                                                             72

( 2 ) INFORMATION FOR SEQ ID NO:133:

( i ) SEQUENCE CHARACTERISTICS:
    ( A ) LENGTH: 93 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:133:

TACTGTGCGA GACAAACTGG GGACTACTAC TACTACGGTA TGGACGTCTG GGGCCAAGGG    60

ACCACGGTCA CCGTCTCCTC AGGGAGTGCA TCC    93

( 2 ) INFORMATION FOR SEQ ID NO:134:

( i ) SEQUENCE CHARACTERISTICS:
        ( A ) LENGTH: 108 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:134:

TACTGTGCGA GACATTACTA TGGTTCGGGG AGTTATGACT ACTACTACTA CGGTATGGAC    60

GTCTGGGGCC AAGGGACCAC GGTCACCGTC TCCTCAGGGA GTGCATCC    108

( 2 ) INFORMATION FOR SEQ ID NO:135:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:135:

TACTGTGCGA GACAGGGAGT GGGGCCAGGG AACCCTGGTC ACCGTCTCCT CAGCCTCCAC    60

CAAG    64

( 2 ) INFORMATION FOR SEQ ID NO:136:

( i ) SEQUENCE CHARACTERISTICS:
        ( A ) LENGTH: 80 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:136:

TACTGTGTGA GATTCTGGGA GACTGGTTCG ACCCCTGGGG CCAGGGAACC CTGGTCACCG    60

TCTCCTCAGG GAGTGCATCC    80

( 2 ) INFORMATION FOR SEQ ID NO:137:

( i ) SEQUENCE CHARACTERISTICS:
        ( A ) LENGTH: 102 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:137:

TACTGTGCGA GACGGAGGTA CTATGGTTCG GGGAGTTATT ATAACGTCTT TGACTACTGG    60

GGCCAGGGAA CCCTGGTCAC CGTCTCCTCA GCCTCCACCA AG    102

( 2 ) INFORMATION FOR SEQ ID NO:138:

( i ) SEQUENCE CHARACTERISTICS:
        ( A ) LENGTH: 78 base pairs ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:138:

TACTGTGCGA GACAAACCTG GGGAGGAGAC TACTGGGGCC AGGGAACCCT GGTCACCGTC        60

TCCTCAGCCT CCACCAAG        78

( 2 ) INFORMATION FOR SEQ ID NO:139:

( i ) SEQUENCE CHARACTERISTICS:
( A ) LENGTH: 99 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:139:

TACTGTGCGA GAGGATATAG TGGCTACGAT AACTACTACT ACGGTATGGA CGTCTGGGGC        60

CAAGGGACCA CGGTCACCGT CTCCTCAGCC TCCACCAAG        99

( 2 ) INFORMATION FOR SEQ ID NO:140:

( i ) SEQUENCE CHARACTERISTICS:
( A ) LENGTH: 84 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:140:

TACTGTGCGA GACAAACTGG GGAGGACTAC TTTGACTACT GGGGCCAGGG AACCCTGGTC        60

ACCGTCTCCT CAGGGAGTGC ATCC        84

( 2 ) INFORMATION FOR SEQ ID NO:141:

( i ) SEQUENCE CHARACTERISTICS:
( A ) LENGTH: 94 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:141:

TACTGTGCGA GATATAGTGG CTACGATTAC CTACTGGTAC TTCGATCTCT GGGGCCGTGG        60

CACCCTGGTC ACTGTCTCCT CAGCCTCCAC CGAG        94

( 2 ) INFORMATION FOR SEQ ID NO:142:

( i ) SEQUENCE CHARACTERISTICS:
( A ) LENGTH: 96 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:142:

TACTGTGCGA GAGCATCCCT CCCCTCCTTT GACTACTACG GTATGGACGT CTGGGGCCAA        60

GGGACCACGG TCACCGTCTC CTCAGCCTCC ACCAAG        96

( 2 ) INFORMATION FOR SEQ ID NO:143:

( i ) SEQUENCE CHARACTERISTICS:
      ( A ) LENGTH: 77 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:143:

```
TACTGTGCGA GACGGGGTGG GGGTTTGACT ACTGGGGCCA GGGAACCCTG GTCACCGTCT      60

CCTCAGGGAG TGCATCC                                                     77
```

( 2 ) INFORMATION FOR SEQ ID NO:144:

( i ) SEQUENCE CHARACTERISTICS:
      ( A ) LENGTH: 94 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:144:

```
TACTGTGTGC CGGTCGAAAC TTTACTACTA CTACTACGGT ATGGACGTCT GGGGCCAAGG      60

GACCACGGTC ACCGTCTCCT CAGGGAGTGC ATCC                                  94
```

( 2 ) INFORMATION FOR SEQ ID NO:145:

( i ) SEQUENCE CHARACTERISTICS:
      ( A ) LENGTH: 84 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:145:

```
TACTGTGTGA GAGATATTTT GACTGGTTAA CGTGACTACT GGGGCCAGGG AACCCTGGTC      60

ACCGTCTCCT CAGGGAGTGC ATCC                                             84
```

( 2 ) INFORMATION FOR SEQ ID NO:146:

( i ) SEQUENCE CHARACTERISTICS:
      ( A ) LENGTH: 93 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:146:

```
TACTGTGCGA GACATGGTAT AGCAGCAGCT GGTACTGCTT TTGATATCTG GGGCCAAGGG      60

ACAATGGTCA CCGTCTCTTC AGGGAGTGCA TCC                                   93
```

( 2 ) INFORMATION FOR SEQ ID NO:147:

( i ) SEQUENCE CHARACTERISTICS:
      ( A ) LENGTH: 84 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:147:

```
TACTGTGTGA GATCAACTGG GGTTGATGCT TTTGATATCT GGGGCCAAGG GACAATGGTC      60

ACCGTCTCTT CAGGGAGTGC ATCC                                            84
```

( 2 ) INFORMATION FOR SEQ ID NO:148:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:148:

```
TACTGTGCGG AAATAGCAGC AGCTGCCCTA CTTTGACTAC TGGGGCCAGG GAACCCTGGT      60

CACCGTCTCC TCAGGGAGTG CATCC                                           85
```

( 2 ) INFORMATION FOR SEQ ID NO:149:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:149:

```
TACTGTGTGT GTATAGCAGC AGCTGGTAAA GGAAACGGCT ACTGGGGCCA GGGAACCCTG      60

GTCACCGTCT CCTCAGGGAG TGCATCC                                         87
```

( 2 ) INFORMATION FOR SEQ ID NO:150:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:150:

```
TACTGTGCGA GACAAAACTG GGGTGACTAC TGGGGCCAGG GAACCCTGGT CACCGTCTCC      60

TCAGGGAGTG CATCC                                                      75
```

( 2 ) INFORMATION FOR SEQ ID NO:151:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:151:

```
CTAGCTCGAG TCCAAGGAGT CTGTGCCGAG GTGCAGCTGN                           40
```

( 2 ) INFORMATION FOR SEQ ID NO:152:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:152:

GGCGCTCGAG TTCCACGACA CCGTCACCGG TTC         33

( 2 ) INFORMATION FOR SEQ ID NO:153:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:153:

GGCGCTCGAG CTGGACAGGG MTCCAKAGTT CCA         33

( 2 ) INFORMATION FOR SEQ ID NO:154:

( i ) SEQUENCE CHARACTERISTICS:
        ( A ) LENGTH: 246 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:154:

```
TCTCTGAAGA TCTCCTGTAA GGGTTCTGGA TACAGCTTTA CCAGCTACTG GATCGGCTGG    60
GTGCGCCAGA TGCCCGGGAA AGGCCTGGAG TGGATGGGGA TCATCTATCC TGGTGACTCT   120
GATACCAGAT ACAGCCCGTC CTTCCAAGGC CAGGTCACCA TCTCAGCCGA CAAGTCCATC   180
AGCACCGCCT ACCTGCAGTG GAGCAGCCTG AAGGCCTCGG ACACCGCCAT GTATTACTGT   240
GCGAGA                                                             246
```

( 2 ) INFORMATION FOR SEQ ID NO:155:

( i ) SEQUENCE CHARACTERISTICS:
        ( A ) LENGTH: 381 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:155:

```
TCTCTGAAGA TCTCCTGTAA GGGTTCTGGA TACAGTTTTT CCGACTACTG GATCGGCTGG    60
GTGCGCCAGA TGCCCGGGAA AGGCCTGGAG TGGATGGGGA TCATCTATCC TGGTGACTCT   120
GACACCAGAT ACAGCCCGTC CTTCCAGGGC CAGGTCTCCA TCTCAGTCGA CAAGTCCATC   180
AACACCGCCT TCCTGCAGTG GAACACCCTG GAGGCTTCGG ACACCGCCAT GTATTACTGT   240
GCGAGAGGGT ATTATTATGA TTCGGGGACT TATTATAAGT CTACCCCCTT TGACTATTGG   300
GGCCAGGGAA CCCTGGTCAC CGTCTCCTCA GCCTCCACCA AGGGCCCATC GGTCTTCCCC   360
CTGGCACCCT CCTCCAAGAG C                                            381
```

( 2 ) INFORMATION FOR SEQ ID NO:156:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:156:

| | | | | | |
|---|---|---|---|---|---|
| TCTCTGAAGA | TCTCCTGTAA | GGGTTCTGGA | TACAGCTTTA | CCAGCTACTG | GATCGGCTGG | 60 |
| GTGCGCCAGA | TGCCCGGGAA | AGGCCTGGAG | TGGATGGGGA | TCATCTATCC | TGGTGACTCT | 120 |
| GATACCAGAT | ACAGCCCGTC | CTTCCAAGGC | CAGGTCACCA | TCTCAGCCGA | CAAGTCCATC | 180 |
| AGCACCGCCT | ACCTGCAGTG | GAGCAGCCTG | AAGGCCTCGG | ACACCGCCAT | GTATTACTGT | 240 |
| GCGAGACATG | AGCTAACTGG | CCTCTTTAAC | TACTGGGGCC | AGGGAACCCT | GGTCACCGTC | 300 |
| TCCTCAGCCT | CCACCAAGGG | CCCATCGGTC | TTCCCCCTGG | CACCCTCCTC | CAAGAGC | 357 |

( 2 ) INFORMATION FOR SEQ ID NO:157:

( i ) SEQUENCE CHARACTERISTICS:
       ( A ) LENGTH: 348 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:157:

| | | | | | |
|---|---|---|---|---|---|
| TCTCTGAAGA | TCTCCTGTAA | GGGTTCTGGA | TACAGCTTTA | CCAGCTACTG | GATCGGCTGG | 60 |
| GTGCGCCAGA | TGCCCGGGAA | AGGCCTGGAG | TGGATGGGGA | TCATCTATCC | TGGTGACTCT | 120 |
| GATACCAGAT | ACAGCCCGTC | CTTCCAAGGC | CAGGTCACCA | TCTCAGCCGA | CAAGTCCATC | 180 |
| AGCACCGCCT | ACCTGCAGTG | GAGCAGCCTG | AAGGCCTCGG | ACACCGCCAT | GTATTACTGT | 240 |
| GCGAGACATC | TTTACTTTGA | CTACTGGGGC | CAGGGAACCC | AGGTCACCGT | CTCCTCAGCC | 300 |
| TCCACCAAGG | GCCCATCGGT | CTTCCCCCTG | GCACCCTCCT | CCAAGAGC | | 348 |

( 2 ) INFORMATION FOR SEQ ID NO:158:

( i ) SEQUENCE CHARACTERISTICS:
       ( A ) LENGTH: 345 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:158:

| | | | | | |
|---|---|---|---|---|---|
| TCTCTGAAGA | TCTCCTGTAA | GGGTTCTGGA | TACAGCTTTA | CCAGCCAATG | GATCGGCTGG | 60 |
| GTGCGCCAGA | TGCCCGGGAA | AGGCCTGGAG | TGGATGGGGA | TCATCTGGCC | TGGTGACTCT | 120 |
| GATACCAGAT | ACAGCCCGTC | CTTCCAAGGC | CAGGTCACCA | TCTCAGCCGA | CAAGTCCATC | 180 |
| AGTACCGCCT | ACCTGCAGTG | GAGCAGCCTG | AAGGCCTCGG | ACACCGCCAT | GTATTACTGT | 240 |
| GCGAGACAAG | GGTTTGACTA | CTGGGGCCAG | GGAACCCTGG | TCACCGTCTC | CTCAGCCTCC | 300 |
| ACCAAGGGCC | CATCGGTCTT | CCCCCTGGCA | CCCTCCTCCA | AGAGC | | 345 |

( 2 ) INFORMATION FOR SEQ ID NO:159:

( i ) SEQUENCE CHARACTERISTICS:
       ( A ) LENGTH: 357 base pairs
       ( B ) TYPE: nucleic acid
       ( C ) STRANDEDNESS: single
       ( D ) TOPOLOGY: linear ( i i ) MOLECULE TYPE: DNA (genomic)

( x i ) SEQUENCE DESCRIPTION: SEQ ID NO:159:

| | | | | | |
|---|---|---|---|---|---|
| TCTCTGAAGA | TCTCCTGTAA | GGGCTCTGGA | TACAGCTTTA | CCAGCTACTG | GATCGGCTGG | 60 |

```
GTGCGCCAGA  TGCCCGGGAA  AGGCCTGGAG  TGGATGGGGA  TCATCTATCC  TGGTGACTCT    120

GATACCAGAT  ACAGCCCGTC  CTTCCGAGGC  CAGGTCACCA  TCTCAGCCGA  CAAGTCCATC    180

AGCACCGCCT  ACCTCGAGTG  GAGCAGCCTG  AAGGCCTCGG  ACACCGCCAT  GTATTACTGT    240

GCGAGACAGG  GGGGGGATAG  GTACTTCGAT  CTCTGGGGCC  GTGGCACCCT  GGTCACTGTC    300

TCCTCAGCCT  CCACCAAGGG  CCCATCGGTC  TTCCCCCTGG  CACCCTCCTC  CAAGAGC       357
```

( 2 ) INFORMATION FOR SEQ ID NO:160:

( i ) SEQUENCE CHARACTERISTICS:
        ( A ) LENGTH: 348 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:160:

```
TCTCTGAAGA  TCTCCTGTAA  GGGTTCTGGA  TACAGTTTTA  GCAGCTACTG  GATCGGCTGG    60

GTGCGCCAGA  TGCCCGGGAA  AGGCCTGGAG  TGGATGGGGA  TCATCTATCC  TGGTGACTCT    120

GATACCAGAT  ACAGCCCGTC  CTTCCAAGGC  CAGGTCACCA  TCTCAGCCGA  CAAGTCCATC    180

AGCACCGCCT  ACCTGCAGTG  GAGCAGCCTG  AAGGCCTCGG  ACACCGCCAT  GTATTACTGT    240

GCGAGACATC  TTTACTTTGA  CTACTGGGGC  CAGGGAACCC  AGGTCACCGT  CTCCTCAGCC    300

TCCACCAAGG  GCCCATCGGT  CTTCCCCCTG  GCACCCTCCT  CCAAGAGC                  348
```

( 2 ) INFORMATION FOR SEQ ID NO:161:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:161:

```
TCTCTGAAGA  TCTCCTGTAA  GGGTTCTGGA  TACAGCTTTA  CCAGCTACTG  GATCGGCTGG    60

GTGCGCCAGA  TGCCCGGGAA  AGGCCTGGAG  TGGATGGGGA  TCATCTATCC  TGGTGACTCT    120

GATACCAGAT  ACAGCCCGTC  CTTCCAAGGC  CAGGTCACCA  TCTCAGCCGA  CAAGTCCATC    180

AGCACCGCCT  ACCTGCAGTG  GAGCAGCCTG  AAGGCCTCGG  ACACCGCCAT  GTATTACTGT    240

GCGAGACATT  GGCTAAATGG  GGATGCTTTT  GATATCTGGG  GCCAAGGGAC  AATGGTCACC    300

GTCTCTTCAG  CCTCCACCAA  GGGCCCATCG  GTCTTCCCCC  TGGCACCCTC  CTCCAAGAGC    360
```

( 2 ) INFORMATION FOR SEQ ID NO:162:

( i ) SEQUENCE CHARACTERISTICS:
        ( A ) LENGTH: 325 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:162:

```
TCTCTGAAGA  TCTCCTGTAA  GGGTTCTGGA  TACAGCTTTA  CCAACTACTG  GATCGGCTGG    60

GTGCGCCAGA  TGCCCGGGAA  AGGCCTGGAG  TGGATGGGGA  TCATCTATCC  TGGTGACTCT    120

GATACCAGAT  ACAGCCCGTC  CTTCCAAGGC  CAGGTCACCA  TCTCAGCCGA  CAAGTCCATC    180
```

```
AGCACCGCCT   ACCTGCAGTG   GAGCAGCCTG   AAGGCCTCGG   ACACCGCCAT   GTATTACTGT        240

GCGAGACAAA   CTTTTGACTA   CTGGGGCCAG   GGAACCCTGG   TCACCGTCTC   CTCAGCCTCC        300

ACCAAGGGCC   CATCGGTCTT   CCCCC                                                    325
```

( 2 ) INFORMATION FOR SEQ ID NO:163:

( i ) SEQUENCE CHARACTERISTICS:
        ( A ) LENGTH: 366 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:163:

```
TCTCTGAAGA   TCTCCTGTAA   GGGTTCTGGA   TACAGCTTTA   CCAGCTACTG   GATCGGCTGG         60

GTGCGCCAGA   TGCCCGGGAA   AGGCCTGGAG   TGGATGGGGA   TCATCTATCC   TGGTGACTCT        120

GATACCAGAT   ACAGCCCGTC   CTTCCAAGGC   CAGGTCACCA   TCTCAGCCGA   CAAGTCCATC        180

AGGACCGCCT   ACCTGCAGTG   GAGCAGCCTG   AAGGCCTCGG   ACACCGCCAT   GTATTACTGT        240

GCGAGACATG   GTATAGCAGC   AGCTGGTACG   TGGTTCGACC   CCTGGGGCCA   GGGAACCCTG        300

GTCACCGTCT   CCTCAGCCTC   CACCAAGGGC   CCATCGGTCT   TCCCCCTGGC   ACCCTCCTCC        360

AAGAGC                                                                             366
```

( 2 ) INFORMATION FOR SEQ ID NO:164:

( i ) SEQUENCE CHARACTERISTICS:
        ( A ) LENGTH: 375 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:164:

```
TCTCTGAAGA   TCTCCTGTAA   GGGTTCTGGA   TACAACTTTA   TCACCTACTG   GATCGGCTGG         60

GTGCGCCAGA   TACCCGGGAA   AGGCCTGGAG   TGGATGGGGA   TCATCTATCC   TGGTGACTCT        120

GATACCAGAT   ACAGCCCGTC   CTTCCAAGGC   CAGGTCACCA   TCTCAGCCGA   CAAGTCCATC        180

AGCACCGCCT   ACCTGCAGTG   GAGCAGCCTG   AAGGCCTCGG   ACACCGCCAT   GTATTACTGT        240

GCGAGACATG   AGCAGCTGGT   ACAGGGTTAC   TACTACTACG   GTATGGACGT   CTGGGGCCAA        300

GGGACCACGG   TCACCGTCTC   CTCAGCCTCC   ACCAAGGGCC   CATCGGTCTT   CCCCCTGGCA        360

CCCTCCTCCA   AGAGC                                                                 375
```

( 2 ) INFORMATION FOR SEQ ID NO:165:

( i ) SEQUENCE CHARACTERISTICS:
        ( A ) LENGTH: 349 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:165:

```
TCTCTGAAGA   TCTCCTGTAG   GGGTTCTGGA   TACAGCTTTT   CCAGTTACTG   GATCGCCTGG         60

GTGCGCCAGA   TGCCCGGGAA   AGGCCTGGAG   TGGATGGGGA   TCATCTATCC   TGGTGACTCT        120

GAAACCAGAT   ACAGTCCGTC   CTTCCAAGGC   CAGGTCACCA   TCTCAGCCGA   CAAGTCCATC        180

AGCACCGCCT   ACCTGCAGTG   GAGCAGCCTG   AAGGCCTCGG   ACACCGCCAT   GTATTACTGT        240
```

```
GCGAGACAGG  GCTACTTTGA  CTACTGGGGC  CAGGGAACCC  TGGTCACCGT  CTCCTCAGCC   300

TCCACCAAGG  GCCCATCGGT  CTTCCCCCTG  GCACCCTCCT  CCAAGAGCA                349
```

( 2 ) INFORMATION FOR SEQ ID NO:166:

( i ) SEQUENCE CHARACTERISTICS:
        ( A ) LENGTH: 375 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:166:

```
TCTCTGAAGA  TCTCCTGTAA  GGGTTCTGGA  TACACCTTTA  CCAGTTACTG  GATCGCCTGG   60

GTGCGCCAGA  TGCCCGGGAA  AGGCCTGGAG  TGGATGGGGA  TCATCTATCC  TGGTGACTCT  120

GATACCAGAT  ACAGCCCGTC  CTTCCAAGGC  CAGGTCACCA  TCTCAGCCGA  CAAGTCCATC  180

AGCACCGCCT  ACCTGCAGTG  GAGCAGCCTG  AAGGCCTCGG  ACACCGCCAT  GTATTACTGT  240

GCGAGAGATA  TGGGGGGGGC  CTCCTACTTC  TACTTCGGTA  TGGACGTCTG  GGGCCAAGGG  300

ACCACGGTCA  CCGTCTCCTC  AGCCTCCACC  AAGGGCCCAT  CGGTCTTCCC  CCTGGCACCC  360

TCCTCCAAGA  GCACC                                                       375
```

( 2 ) INFORMATION FOR SEQ ID NO:167:

( i ) SEQUENCE CHARACTERISTICS:
        ( A ) LENGTH: 326 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:167:

```
TCTCTGAAGA  TCTCCTGTAA  GGGTTCTGGA  TACAGCTTTA  CCAGCTACTG  GATCGGCTGG   60

GTGCGCCAGA  TGCCCGGGAA  AGGCCTGGAG  TGGATGGGGA  TCATCTATCC  TGGTGACTCT  120

GATACCAGAT  ACAGCCCGTC  CTTCCAAGGC  CAGGTCACCA  TCTCAGCCGA  CAAGTCCATC  180

AGTACCGCCT  ACCTGCAGTG  GAGCAGCCTG  AGGGCCTCGG  ACACCGCCAT  TTATTACTGT  240

GCGAGACATC  TTTACTTTGA  CTACTGGGGC  CAGGGAACCC  AGGTCACCGT  CTCCTCAGCC  300

TCCACCAAGG  GCCCATCGGT  CTTCCC                                          326
```

( 2 ) INFORMATION FOR SEQ ID NO:168:

( i ) SEQUENCE CHARACTERISTICS:
        ( A ) LENGTH: 384 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:168:

```
TCTCTGAAGA  TCTCCTGTAA  GGGTTCTGGA  TACAGCTTTA  CCAGCTACTG  GATCGGCTGG   60

GTGCGCCAGA  TGCCCGGGAA  AGGCCTGGAG  TGGATGGGGA  TCATCTATCC  TGGTGACTCT  120

GATACCAGAT  ACAGCCCGTC  CTTCCAAGGC  CAGGTCACCA  TCTCAGCCGA  CAAGTCCATC  180

AGCACCGCCT  ACCTGCAGTG  GAGCAGCCTG  AGGGCCTCGG  ACAGTGTCAT  GTATTACTGT  240

GCGAGACGGG  ATTACGATAT  TTTGACTGGT  TATTATGCGG  CTTTTGATAT  CTGGGGCCAA  300
```

| GGGACAATGG | TCACCGTCTC | TTCAGCCTCC | ACCAAGGGCC | CATCGGTCTT | CCCCCTGGCA | 360 |
| CCCTCCTCCA | AGAGCACCTC | TGGG | | | | 384 |

( 2 ) INFORMATION FOR SEQ ID NO:169:

( i ) SEQUENCE CHARACTERISTICS:
        ( A ) LENGTH: 360 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:169:

| TCTCTGAAGA | TCTCCTGTAA | GGGTTCTGGA | TACAACTTTA | CCACCTACTG | GATCGGCTGG | 60 |
| GTGCGCCAGA | TGCCCGGGAA | AGGCCTGGAG | TGGATGGGGA | TCATCTATCC | TGGTGACTCT | 120 |
| GATACCAGAT | ACAGCCCGTC | CTTCCAAGGC | CAGGTCACCA | TCTCAGCCGA | CAAGTCCGTC | 180 |
| AGCACCGCCT | ACCTGCAGTG | GAGCAGCCTG | AAGGCCTCGG | ACACCGCCAT | GTATTACTGT | 240 |
| GCGAGACTCC | CCAATGACAG | TTGGTTCGAC | CCCTGGGGCC | AGGGAACCCT | GGTCACCGTC | 300 |
| TCCTCAGCCT | CCACCAAGGG | CCCATCGGTC | TTCCCCCTGG | CACCCTCCTC | CAAGAGCACC | 360 |

( 2 ) INFORMATION FOR SEQ ID NO:170:

( i ) SEQUENCE CHARACTERISTICS:
        ( A ) LENGTH: 362 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:170:

| TCTCTGAAGA | TCTCCTGTAA | GGGTTCTGGA | TACAGCTTTA | CCAGCTACTG | GATCGGCTGG | 60 |
| GTGCGCCAGA | TGCCCGGGAA | AGGCCTGGAG | TGGATGGGGA | TCATCTATCC | TGGTGACTCT | 120 |
| GATACCAGAT | ACAGCCCGTC | CTTCCAAGGC | CAGGTCACCA | TCTCAGCCGA | CAAGTCCATC | 180 |
| AGCACCGCCT | ACCTGCAGTG | GAGCAGCCTG | AAGGCCTCGG | ACACCGCCAT | GTATTACTGT | 240 |
| GCGGCCGGGT | ATACCAGCAG | CTGGTTCTTT | GACTTCTGGG | GCCAGGGAAC | CCTGGTCACC | 300 |
| GTCTCCTCAG | CCTCCACCAA | GGGCCCATCG | GTCTTCCCCC | TGGCACCCTC | CTCCAAGAGC | 360 |
| AC | | | | | | 362 |

( 2 ) INFORMATION FOR SEQ ID NO:171:

( i ) SEQUENCE CHARACTERISTICS:
        ( A ) LENGTH: 361 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:171:

| TCTCTGAAGA | TCTCCTGTAA | GGGTTCTGGA | TACAGCTTTG | CCAACTACTG | GATCGGCTGG | 60 |
| GTGCGCCAGA | TGCCCGGGAA | AGGCCTGGAG | TGGATGGGGA | TCATCTTTCC | TGGTGACTCT | 120 |
| GATACCAGAT | ACAGCCCGTC | CTTCCAAGGC | CAGGTCACCA | TCTCAGCCGA | CAACTCCATC | 180 |
| AGCACCGCCT | ACCTGCAGTG | GAGCAGCCTG | AAGGCCTCGG | ACACCGCCAT | GTATTACTGT | 240 |
| GCGAGACACC | ACGACTACTA | CGGTATGGAC | GTCTGGGGCC | AAGGGACCAC | GGTCACCGTC | 300 |
| TCCTCAGCCT | CCACCAAGGG | CCCATCGGTC | TTCCCCCTGG | CACCCTCCTC | CAAGAGCACC | 360 |

T                                                                                      361

(2) INFORMATION FOR SEQ ID NO:172:

(i) SEQUENCE CHARACTERISTICS:
       (A) LENGTH: 358 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:172:

| TCTCTGAAGA | TCTCCTGTAA | GGGTTCTGGA | TACAGCTTTA | CCAGCTACTG | GATCGGCTGG | 60 |
| GTGCGCCAGA | TGCCCGGGAA | AGGCCTGGAG | TGGATGGGGA | TCATCTATCC | TGGTGACTCT | 120 |
| GATACCAGAT | ACAGCCCGTC | CTTCCAAGGC | CAGGTCACCA | TCTCAGCCGA | CAAGTCCATC | 180 |
| AGCACCGCCT | ACCTGCAGTG | GAGCAGCCTG | AAGGCCTCGG | ACACCGCCAT | GTATCGCTGT | 240 |
| GCGAGACATC | TTTACTTTGA | CTACTGGGGC | CAGGGAACCC | AGGTCACCGT | CTCCTCAGCC | 300 |
| TCCACCAAGG | GCCCATCGGT | CTTCCCCCTG | GCACCCTCCT | CCAAGAGCAC | CTCTGGGG  | 358 |

(2) INFORMATION FOR SEQ ID NO:173:

(i) SEQUENCE CHARACTERISTICS:
       (A) LENGTH: 370 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:173:

| TCTCTGAAGA | TCTCCTGTAA | GGGTTCTGGA | TACAGCTTTC | CCATCTACTG | GATCGGCTGG | 60 |
| GTGCGCCAGA | TGCCCGGGAA | AGGCCTGGAG | TGGATGGGGA | TCATCTATCC | TGGTGACTCT | 120 |
| GATACCAGAT | ACAGCCCGTC | CTTCCAAGGC | CAGGTCACCA | TCTCAGCCGA | CAAGTCCATC | 180 |
| AGCACCGCCT | ACCTGCAGTG | GAGCAGCCTG | AAGGCCTCGG | ACACCGCCAT | GTATTACTGT | 240 |
| GCGAGAGTGG | TTCGGGGATT | TATTATTTAC | TTTGACTACT | GGGGCCAGGG | AACCCTGGTC | 300 |
| ACCGTCTCCT | CAGCCTCCAC | CAAGGGCCCA | TCGGTCTTCC | CCCTGGCACC | CTCCTCCAAG | 360 |
| AGCACCTCTG |            |            |            |            |            | 370 |

(2) INFORMATION FOR SEQ ID NO:174:

(i) SEQUENCE CHARACTERISTICS:
       (A) LENGTH: 358 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:174:

| TCTCTGAAGA | TCTCCTGTAA | GGGTTCTGGA | TACAGCTTTA | CCAGCTACTG | GATCGGCTGG | 60 |
| GTGCGCCAGA | TGCCCGGGAA | AGGCCTGGAG | TGGATGGGGA | TCATCTTTCC | TGGTGACTCT | 120 |
| GATACCAGAT | ACAGCCCGCC | CTTCCAAGGC | CAGGTCACCA | TCTCAGCCGA | CAAGTCCATC | 180 |
| AACACCGCCT | ACCTGCAGTG | GAGCAGCCTG | AAGGCCTCGG | ACACCGCCAT | GTATTACTGT | 240 |
| GCGAGACGCT | ACTACGGTAT | GGACGTCTGG | GGCCAAGGGA | CCACGGTCAC | CGTCTCCTCA | 300 |
| GCCTCCACCA | AGGGCCCATC | GGTCTTCCCC | CTGGCACCCT | CCTCCAAGAG | CACCTCTG  | 358 |

( 2 ) INFORMATION FOR SEQ ID NO:175:

( i ) SEQUENCE CHARACTERISTICS:
        ( A ) LENGTH: 352 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:175:

```
TCTCTGAAGA TCTCCTGTAA GGTTTCTGGA TACAGCTTAA CCAGTTATTG GATCGGCTGG      60
GTGCGCCAGA TGCCCGGGAA AGGCCTGGAG TGGATGGGGA TCATCTATCC TGGTGACTCT     120
GATACCAGAT ACAGCCCGTC CTTCCAAGGC CAGGTCACCA TCTCAGCCGA CAAGTCCATC     180
AGCACCGCCT ACCTGCAGTG GAGCAGCCTG AAGGCCTCGG ACACCGCCAT GTATTACTGT     240
GCGAGACAAA GGGGTACTTT GACTACTGGG GCCAGGGAAC CCTGGTCACC GTCTCCTCAG     300
CCTCCACCAA GGGCCCATCG GTCTTCCCCC TGGCACCCTC CTCCAAGAGC AC             352
```

( 2 ) INFORMATION FOR SEQ ID NO:176:

( i ) SEQUENCE CHARACTERISTICS:
        ( A ) LENGTH: 383 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:176:

```
TCTCTGAAGA TCTCCTGTAA GGGTTCTGGA TACAGCTTTA CCAGCTACTG GATCGGCTGG      60
GTGCGCCAGA TGCCCGGGAA AGGCCTGGAG TGGATGGGGA TCATCTATCC TGGTGACTCT     120
GATACCAGAT ACAGCCGTC CTTCCAAGGC CAGGTCACCA TCTCAGCCGA CAAGTCCATC      180
AGCACCGCCT ACCTGCAGTG GAGCAGCCTG AAGGCCTCGG ACACCGCCAT GTATTACTGT     240
GCGAGACGGG GGTACTATGG TTCGGGGAGT TATTATAACT GGTTCGACCC CTGGGGCCAG     300
GGAACCCTGG TCACCGTCTC CTCAGCCTCC ACCAAGGGCC CATCGGTCTT CCCCCTGGCA     360
CCCTCCTCCA AGAGCACCTC TGG                                             383
```

( 2 ) INFORMATION FOR SEQ ID NO:177:

( i ) SEQUENCE CHARACTERISTICS:
        ( A ) LENGTH: 361 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:177:

```
TCTCTGAAGA TCTCCTGTAA GGGTTCTGGA TACAGCTTTA CCAGCTACTG GATCGGCTGG      60
GTGCGCCAGA TGCCCGGGAA AGGCCTGGAG TGGATGGGGA TCATCTATCC TGGTGACTCT     120
GATACCAGAT ACAGCCCGTC CTTCCAAGGC CAGGTCACCA TCTCAGCCGA CAAGTCCATC     180
AGCACCGCCT ACCTGCAGTG GAGCAGCCTG AAGGCCTCGG ACACCGCCAT GTATTACTGT     240
GCGAGGGGAT CGTGGTACTT TGACTACTGG GGCCAGGGAA CCCTGGTCAC CGTCTCCTCA     300
GCCTCCACCA AGGGCCCATC GGTCTTCCCC CTGGCACCCT CCTCCAAGAG CACCTCTGGG     360
G                                                                     361
```

( 2 ) INFORMATION FOR SEQ ID NO:178:

( i ) SEQUENCE CHARACTERISTICS:
        ( A ) LENGTH: 812 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(199..246, 418..714)

( x i ) SEQUENCE DESCRIPTION: SEQ ID NO:178:

```
TTTTCTGGCC TGACAACCAG GGTGGCGCAG GATGCTCAGT GCAGAGAGGA AGAAGCAGGT              60

GGTCTCTGCA GCTGGAAGCT CAGCTCCCAC CCAGCTGCTT TGCATGTCCC TCCCAGCTGC             120

CCTACCTTCC AGAGCCCATA TCAATGCCTG TGTCAGAGCC CTGGGGAGGA ACTGCTCAGT             180

TAGGACCCAG AGGGAACC ATG GAA GCC CCA GCT CAG CTT CTC TTC CTC CTG              231
                    Met Glu Ala Pro Ala Gln Leu Leu Phe Leu Leu
                     1               5                  10

CTA CTC TGG CTC CCA GGTGAGGGGG AACCATGAGG TGGTTTTGCA CATTAGTGAA              286
Leu Leu Trp Leu Pro
              15

AACTCTTGCC ACCTCTGCTC AGCAAGAAAT ATAATTAAAA TTCAAAGTAT ATCAACAATT             346

TTGGCTCTAC TCAAAGACAG TTGGTTTGAT CTTGATTACA TGAGTGCATT TCTGTTTTAT             406

TTCCAATTTC A GAT ACC ACC GGA GAA ATT GTG TTG ACA CAG TCT CCA GCC              456
             Asp Thr Thr Gly Glu Ile Val Leu Thr Gln Ser Pro Ala
                              20                  25

ACC CTG TCT TTG TCT CCA GGG GAA AGA GCC ACC CTC TCC TGC AGG GCC              504
Thr Leu Ser Leu Ser Pro Gly Glu Arg Ala Thr Leu Ser Cys Arg Ala
 30                  35                  40                  45

AGT CAG AGT GTT AGC AGC TAC TTA GCC TGG TAC CAA CAG AAA CCT GGC              552
Ser Gln Ser Val Ser Ser Tyr Leu Ala Trp Tyr Gln Gln Lys Pro Gly
                 50                  55                  60

CAG GCT CCC AGG CTC CTC ATC TAT GAT GCA TCC AAC AGG GCC ACT GGC              600
Gln Ala Pro Arg Leu Leu Ile Tyr Asp Ala Ser Asn Arg Ala Thr Gly
             65                  70                  75

ATC CCA GCC AGG TTC AGT GGC AGT GGG TCT GGG ACA GAC TTC ACT CTC              648
Ile Pro Ala Arg Phe Ser Gly Ser Gly Ser Gly Thr Asp Phe Thr Leu
         80                  85                  90

ACC ATC AGC AGC CTA GAG CCT GAA GAT TTT GCA GTT TAT TAC TGT CAG              696
Thr Ile Ser Ser Leu Glu Pro Glu Asp Phe Ala Val Tyr Tyr Cys Gln
     95                  100                 105

CAG CGT AGC AAC TGG CCT CCCACAGTGA TTCCACATGA AACAAAAACC              744
Gln Arg Ser Asn Trp Pro
110                 115

CCAACAAGAC CATCAGTGTT TACTAGATTA TTATACCAGC TGCTTCCTTT ACAGACAGCT             804

AGTGGGGT                                                                     812
```

( 2 ) INFORMATION FOR SEQ ID NO:179:

( i ) SEQUENCE CHARACTERISTICS:
        ( A ) LENGTH: 115 amino acids
        ( B ) TYPE: amino acid
        ( D ) TOPOLOGY: linear ( i i ) MOLECULE TYPE: protein ( x i ) SEQUENCE DESCRIPTION: SEQ ID NO:179:

```
Met Glu Ala Pro Ala Gln Leu Leu Phe Leu Leu Leu Leu Trp Leu Pro
 1               5                  10                  15
```

```
Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro
        115
```

( 2 ) INFORMATION FOR SEQ ID NO:180:

( i ) SEQUENCE CHARACTERISTICS:
        ( A ) LENGTH: 900 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: join(180..227, 397..693)

( x i ) SEQUENCE DESCRIPTION: SEQ ID NO:180:

```
AGGGCGGCGC AGATGCTCAG TGCAGAGAGA AGAAACAGGT GGTCTCTGCA GCTGGAAGCT        60

CAGCTCCCAC CCCAGCTGCT TTGCATGTCC CTCCCAGCTG CCCTACCTTC CAGAGCCCAT       120

ATCAATGCCT GGGTCAGAGC TCTGGGGAGG AACTGCTCAG TTAGGACCCA GACGGAACC        179

ATG GAA GCC CCA GCG CAG CTT CTC TTC CTC CTG CTA CTC TGG CTC ACA         227
Met Glu Ala Pro Ala Gln Leu Leu Phe Leu Leu Leu Leu Trp Leu Thr
 1               5                  10                  15

GGTGAGGGGA ATATGAGGTG TCTTTGCACA TCAGTGAAAA CTCCTGCCAC CTCTGCTCAG       287

CAAGAAATAT AATTAAAATT CAAAATAGAT CAACAATTTT GGCTCTACTC AAAGACAGTG       347

GGTTTGATTT TGATTACATG AGTGCATTTC TGTTTATTT CCAATTTCA GAT ACC            402
                                                      Asp Thr

ACC GGA GAA ATT GTG TTG ACA CAG TCT CCA GCC ACC CTG TCT TTG TCT         450
Thr Gly Glu Ile Val Leu Thr Gln Ser Pro Ala Thr Leu Ser Leu Ser
        20                  25                  30

CCA GGG GAA AGA GCC ACC CTC TCC TGC AGG GCC AGT CAG GGT GTT AGC         498
Pro Gly Glu Arg Ala Thr Leu Ser Cys Arg Ala Ser Gln Gly Val Ser
35                  40                  45                  50

AGC TAC TTA GCC TGG TAC CAG CAG AAA CCT GGC CAG GCT CCC AGG CTC         546
Ser Tyr Leu Ala Trp Tyr Gln Gln Lys Pro Gly Gln Ala Pro Arg Leu
                55                  60                  65

CTC ATC TAT GAT GCA TCC AAC AGG GCC ACT GGC ATC CCA GCC AGG TTC         594
Leu Ile Tyr Asp Ala Ser Asn Arg Ala Thr Gly Ile Pro Ala Arg Phe
            70                  75                  80

AGT GGC AGT GGG CCT GGG ACA GAC TTC ACT CTC ACC ATC AGC AGC CTA         642
Ser Gly Ser Gly Pro Gly Thr Asp Phe Thr Leu Thr Ile Ser Ser Leu
        85                  90                  95

GAG CCT GAA GAT TTT GCA GTT TAT TAC TGT CAG CAG CGT AGC AAC TGG         690
Glu Pro Glu Asp Phe Ala Val Tyr Tyr Cys Gln Gln Arg Ser Asn Trp
    100                 105                 110
```

```
CAT CCCACAGTGA TTCCACATGA AACAAAAACC CCAACAAGAC CATCAGTGTT          743
His
115

TACTAGATTA TTATACCAGC TGCTTCCTTT ACAGACAGCT AGTGGGGTGG CCACTCAGTG    803

TTAGCATCTC AGCTCTATTT GGCCATTTTG GAGTTCAAGT TGTCAAGTCC AAAATTACTT    863

ATGTTAGTCC ATTGCATCAT ACCATTTCAG TGTGGCT                             900
```

(2) INFORMATION FOR SEQ ID NO:181:

(i) SEQUENCE CHARACTERISTICS:
        (A) LENGTH: 115 amino acids
        (B) TYPE: amino acid
        (D) TOPOLOGY: linear (ii) MOLECULE TYPE: protein (xi) SEQUENCE DESCRIPTION: SEQ ID NO:181:

```
Met Glu Ala Pro Ala Gln Leu Leu Phe Leu Leu Leu Leu Trp Leu Thr
 1               5                  10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Gly
            35                  40                  45

Val Ser Ser Tyr Leu Ala Trp Tyr Gln Gln Lys Pro Gly Gln Ala Pro
        50                  55                  60

Arg Leu Leu Ile Tyr Asp Ala Ser Asn Arg Ala Thr Gly Ile Pro Ala
 65                  70                  75                  80

Arg Phe Ser Gly Ser Gly Pro Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp His
        115
```

(2) INFORMATION FOR SEQ ID NO:182:

(i) SEQUENCE CHARACTERISTICS:
        (A) LENGTH: 900 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(116..163, 351..650)

(xi) SEQUENCE DESCRIPTION: SEQ ID NO:182:

```
CCGCCCCAGC TGCTTTGCAT GTCCCTCCCA GCCGCCCTGC AGTCCAGAGC CCATATCAAT    60

GCCTGGGTCA GAGCTCTGGA GAAGAGCTGC TCAGTTAGGA ACCCCAGAGG GAACC ATG    118
                                                              Met
                                                                1

GAA ACC CCA GCG CAG CTT CTC TTC CTC CTG CTA CTC TGG CTC CCA          163
Glu Thr Pro Ala Gln Leu Leu Phe Leu Leu Leu Leu Trp Leu Pro
         5                  10                  15

GGTGAGGGGA ACATGGGATG GTTTTGCATG TCAGTGAAAA CCCTCTCAAG TCCTGTTACC    223

TGGCAACTCT GCTCAGTCAA TACAATAATT AAAGCTCAAT ATAAAGCAAT AATTCTGGCT    283

CTTCTGGGAA GACAATGGGT TTGATTTAGA TTACATGGGT GACTTTCTG TTTTATTTCC     343

AATCTCA GAT ACC ACC GGA GAA ATT GTG TTG ACG CAG TCT CCA GGC ACC      392
```

```
                Asp  Thr  Thr  Gly  Glu  Ile  Val  Leu  Thr  Gln  Ser  Pro  Gly  Thr
                               20                       25                       30

CTG  TCT  TTG  TCT  CCA  GGG  GAA  AGA  GCC  ACC  CTC  TCC  TGC  AGG  GCC  AGT         440
Leu  Ser  Leu  Ser  Pro  Gly  Glu  Arg  Ala  Thr  Leu  Ser  Cys  Arg  Ala  Ser
                    35                       40                       45

CAG  AGT  GTT  AGC  AGC  AGC  TAC  TTA  GCC  TGG  TAC  CAG  CAG  AAA  CCT  GGC         488
Gln  Ser  Val  Ser  Ser  Ser  Tyr  Leu  Ala  Trp  Tyr  Gln  Gln  Lys  Pro  Gly
               50                       55                       60

CAG  GCT  CCC  AGG  CTC  CTC  ATC  TAT  GGT  GCA  TCC  AGC  AGG  GCC  ACT  GGC         536
Gln  Ala  Pro  Arg  Leu  Leu  Ile  Tyr  Gly  Ala  Ser  Ser  Arg  Ala  Thr  Gly
          65                       70                       75

ATC  CCA  GAC  AGG  TTC  AGT  GGC  AGT  GGG  TCT  GGG  ACA  GAC  TTC  ACT  CTC         584
Ile  Pro  Asp  Arg  Phe  Ser  Gly  Ser  Gly  Ser  Gly  Thr  Asp  Phe  Thr  Leu
     80                       85                       90

ACC  ATC  AGC  AGA  CTG  GAG  CCT  GAA  GAT  TTT  GCA  GTG  TAT  TAC  TGT  CAG         632
Thr  Ile  Ser  Arg  Leu  Glu  Pro  Glu  Asp  Phe  Ala  Val  Tyr  Tyr  Cys  Gln
95                       100                      105                      110

CAG  TAT  GGT  AGC  TCA  CCT  CCCACAGTGA  TTCAGCTTGA  AACAAAAACC                       680
Gln  Tyr  Gly  Ser  Ser  Pro
                    115

TCTGCAAGAC  CTTCATTGTT  TACTAGATTA  TACCAGCTGC  TTCCTTTACA  GATAGCTGCT                 740

GCAATGACAA  CTCAATTTAG  CATCTCTCTC  TGCTTGGGCA  TTTTGGGGAT  CTTAAAAAAG                 800

TAATCCCTTG  ATATATTTTT  GACTCTGATT  CCTGCATTTT  TCCTCAGACC  AAGATGGACA                 860

GCCAGGTTTA  AGCACAGTTT  CACAGTAATG  GCCACTGGAT                                         900
```

( 2 ) INFORMATION FOR SEQ ID NO:183:

( i ) SEQUENCE CHARACTERISTICS:
        ( A ) LENGTH: 116 amino acids
        ( B ) TYPE: amino acid
        ( D ) TOPOLOGY: linear ( i i ) MOLECULE TYPE: protein ( x i ) SEQUENCE DESCRIPTION: SEQ ID NO:183:

```
Met  Glu  Thr  Pro  Ala  Gln  Leu  Leu  Phe  Leu  Leu  Leu  Leu  Trp  Leu  Pro
1                   5                        10                       15

Asp  Thr  Thr  Gly  Glu  Ile  Val  Leu  Thr  Gln  Ser  Pro  Gly  Thr  Leu  Ser
                    20                       25                       30

Leu  Ser  Pro  Gly  Glu  Arg  Ala  Thr  Leu  Ser  Cys  Arg  Ala  Ser  Gln  Ser
               35                       40                       45

Val  Ser  Ser  Ser  Tyr  Leu  Ala  Trp  Tyr  Gln  Gln  Lys  Pro  Gly  Gln  Ala
     50                       55                       60

Pro  Arg  Leu  Leu  Ile  Tyr  Gly  Ala  Ser  Ser  Arg  Ala  Thr  Gly  Ile  Pro
65                       70                       75                       80

Asp  Arg  Phe  Ser  Gly  Ser  Gly  Ser  Gly  Thr  Asp  Phe  Thr  Leu  Thr  Ile
                    85                       90                       95

Ser  Arg  Leu  Glu  Pro  Glu  Asp  Phe  Ala  Val  Tyr  Tyr  Cys  Gln  Gln  Tyr
               100                      105                      110

Gly  Ser  Ser  Pro
               115
```

( 2 ) INFORMATION FOR SEQ ID NO:184:

( i ) SEQUENCE CHARACTERISTICS:
        ( A ) LENGTH: 847 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: CDS
    ( B ) LOCATION: join(226..279, 405..700)

( x i ) SEQUENCE DESCRIPTION: SEQ ID NO:184:

```
AAACACATTC TCTGCAGACA AATTTGAGCT ACCTTGATCT TACCTGGACA GGTGGGGACA        60

CTGAGCTGGT GCTGAGTTAC TCAGATGCGC CAGCTCTGCA GCTGTGCCCA GCCTGCCCCA       120

TCCCCTGCTC ATTTGCATGT TCCCAGAGCA CAACCTCCTG CCCTGAAGCC TTATTAATAG       180

GCTGGTCAGA CTTTGTGCAG GAATCAGACC CAGTCAGGAC ACAGC ATG GAC ATG          234
                                                Met Asp Met
                                                  1

AGG GTC CTC GCT CAG CTC CTG GGG CTC CTG CTG CTC TGT TTC CCA              279
Arg Val Leu Ala Gln Leu Leu Gly Leu Leu Leu Leu Cys Phe Pro
      5              10                  15

GGTAAGGATG GAGAACACTA GCAGTTACT CAGCCCAGGG TGCTCAGTAC TGCTTTACTA        339

TTCAGGGAAA TTCTCTTACA ACATGATTAA TTGTGTGGAC ATTTGTTTTT ATGTTTCCAA       399

TCTCA GGT GCC AGA TGT GAC ATC CAG ATG ACC CAG TCT CCA TCC TCA           446
      Gly Ala Arg Cys Asp Ile Gln Met Thr Gln Ser Pro Ser Ser
            20                  25                  30

CTG TCT GCA TCT GTA GGA GAC AGA GTC ACC ATC ACT TGT CGG GCG AGT          494
Leu Ser Ala Ser Val Gly Asp Arg Val Thr Ile Thr Cys Arg Ala Ser
          35                  40                  45

CAG GGT ATT AGC AGC TGG TTA GCC TGG TAT CAG CAG AAA CCA GAG AAA          542
Gln Gly Ile Ser Ser Trp Leu Ala Trp Tyr Gln Gln Lys Pro Glu Lys
      50                  55                  60

GCC CCT AAG TCC CTG ATC TAT GCT GCA TCC AGT TTG CAA AGT GGG GTC          590
Ala Pro Lys Ser Leu Ile Tyr Ala Ala Ser Ser Leu Gln Ser Gly Val
65                  70                  75                  80

CCA TCA AGG TTC AGC GGC AGT GGA TCT GGG ACA GAT TTC ACT CTC ACC          638
Pro Ser Arg Phe Ser Gly Ser Gly Ser Gly Thr Asp Phe Thr Leu Thr
              85                  90                  95

ATC AGC AGC CTG CAG CCT GAA GAT TTT GCA ACT TAT TAC TGC CAA CAG          686
Ile Ser Ser Leu Gln Pro Glu Asp Phe Ala Thr Tyr Tyr Cys Gln Gln
          100                 105                 110

TAT AAT AGT TACCCACCCA CAGTGTTACA CACCCAAACA TAAACCCCCA                  735
Tyr Asn Ser Tyr
          115

GGGAAGCAGA TGTGTGAGGC TGGGCTGCCC CAGCTGCTTC TCCTGATGCC TCCATCAGCT       795

GAGAGTGTTC CTCAGATGCA GCCACACTCT GATGGTGTTG GTAGATGGGG AC              847
```

( 2 ) INFORMATION FOR SEQ ID NO:185:

( i ) SEQUENCE CHARACTERISTICS:
        ( A ) LENGTH: 116 amino acids
        ( B ) TYPE: amino acid
        ( D ) TOPOLOGY: linear ( i i ) MOLECULE TYPE: protein ( x i ) SEQUENCE DESCRIPTION: SEQ ID NO:185:

```
Met Asp Met Arg Val Leu Ala Gln Leu Leu Gly Leu Leu Leu Leu Cys
  1               5                  10                  15

Phe Pro Gly Ala Arg Cys Asp Ile Gln Met Thr Gln Ser Pro Ser Ser
              20                  25                  30

Leu Ser Ala Ser Val Gly Asp Arg Val Thr Ile Thr Cys Arg Ala Ser
          35                  40                  45

Gln Gly Ile Ser Ser Trp Leu Ala Trp Tyr Gln Gln Lys Pro Glu Lys
```

|  | 50 |  |  |  | 55 |  |  |  | 60 |  |  |  |
|---|---|---|---|---|---|---|---|---|---|---|---|---|

Ala Pro Lys Ser Leu Ile Tyr Ala Ala Ser Ser Leu Gln Ser Gly Val
65              70              75              80

Pro Ser Arg Phe Ser Gly Ser Gly Ser Gly Thr Asp Phe Thr Leu Thr
            85              90              95

Ile Ser Ser Leu Gln Pro Glu Asp Phe Ala Thr Tyr Tyr Cys Gln Gln
            100             105             110

Tyr Asn Ser Tyr
        115

( 2 ) INFORMATION FOR SEQ ID NO:186:

( i ) SEQUENCE CHARACTERISTICS:
        ( A ) LENGTH: 134 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:186:

GCCTCGGACA CCGCCATGTA TTACTGTGTG AGACATTTAT GGTTCGGGGA GTTACGCGGT 60

GTGAACGTCT GGGGCCAAGG GACCACGGTC ACCGTCTCCT CAGCCAAAAC GACACCCCCA 120

TCTGTCTATC CACT 134

( 2 ) INFORMATION FOR SEQ ID NO:187:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:187:

GCCTCGGACA CCGCCATGTA TTACTGTGCG AGACACTGGG CATTGGATGC TCTTGATGTC 60

TGGGGCCAAG GGACAATGCT CACCGTCTCT TCAGCCAAAA CGACACCCCC ATCTGTCTAT 120

CCACT 125

( 2 ) INFORMATION FOR SEQ ID NO:188:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:188:

GCCTCGGACA CCGCCATGTA TTACTGTGCG AGAACTGGGG ATGATGCTTT TGATATCTGG 60

GGCCAAGGGA CAATGGTCAC CGTCTCTTCA GCCAAAACAA CACCCCCATC AGTCTATCCA 120

CT 122

( 2 ) INFORMATION FOR SEQ ID NO:189:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:189:

| GACTCGGACA | CCGCCATGTA | TTACTGTGCG | AGACAGGGGA | GAGATGCTTT | AGATATCTGG | 60 |
| GGCCAAGGGA | CAATGGTCAC | CGTCTCTTCA | GCCAAAACAA | CACCCCATC | AGTCTATCCA | 120 |
| CT | | | | | | 122 |

( 2 ) INFORMATION FOR SEQ ID NO:190:

( i ) SEQUENCE CHARACTERISTICS:
        ( A ) LENGTH: 137 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:190:

| GCCTCGGACA | CCGCCATGTA | TTATTGTGTG | AGACATAGGG | ACTATATTTC | GGGGAGTTAT | 60 |
| TTTCCTGACT | ACTGGGGCCA | GGGAACCCTG | GTCACCGTCT | CCTCAGCCAA | AACAACACCC | 120 |
| CCATCAGTCT | ATCCACT | | | | | 137 |

( 2 ) INFORMATION FOR SEQ ID NO:191:

( i ) SEQUENCE CHARACTERISTICS:
        ( A ) LENGTH: 122 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:191:

| GCCTCGGACA | CCGCCATGTA | TTACTGTGCG | AGAACTGGGG | ATGATGCTTT | TGATATCTGG | 60 |
| GGCCAAGGGA | CAATGGTCAC | CGTCTCTTCA | GCCAAAACAA | CACCCCATC | AGTCTATCCA | 120 |
| CT | | | | | | 122 |

( 2 ) INFORMATION FOR SEQ ID NO:192:

( i ) SEQUENCE CHARACTERISTICS:
        ( A ) LENGTH: 116 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:192:

| GCCTCGGACA | CCGCCATGTA | TTACTGTGCG | AGACATGGGT | CTATGGATAT | CTGGGGCCAA | 60 |
| GGGACAATGG | TCACCGTCTC | TTCAGCTACA | ACAACAGCCC | CATCTGTCTA | TCCCTT | 116 |

( 2 ) INFORMATION FOR SEQ ID NO:193:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:193:

| GCCTCGGACA | CCGCCATGTA | TTACTGTGCG | AGAGAGAGCG | GTCACTGGGG | ATCGTTTGAC | 60 |

( 2 ) INFORMATION FOR SEQ ID NO:194:

( i ) SEQUENCE CHARACTERISTICS:
        ( A ) LENGTH: 125 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:194:

```
GCCTCGGACA CCGCCATGTA TTACTGTGCG AGAAGGGACC CCCCTGATGC TTTTGATATC      60
TGGGGCCAAG GGACAATGGT CACCGTCTCT TCAGCTACAA CAACAGCCCC ATCTGTCTAT     120
CCCTT                                                                 125
```

( 2 ) INFORMATION FOR SEQ ID NO:195:

( i ) SEQUENCE CHARACTERISTICS:
        ( A ) LENGTH: 131 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:195:

```
GCCTCGGACA CCGCCATGTA TTACTGTGCG AGACGGGGGC CTTACTACTA CTACGGTATG      60
GACGTCTGGG GCCAAGGGAC CACGGTCACC GTCTCCTCAG CTACAACAAC AGCCCCATCT     120
GTCTATCCCT T                                                          131
```

( 2 ) INFORMATION FOR SEQ ID NO:196:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:196:

```
GGACCCAGAS GGAACCATGG AARN                                             24
```

( 2 ) INFORMATION FOR SEQ ID NO:197:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (oligonucleotide)

( x i ) SEQUENCE DESCRIPTION: SEQ ID NO:197:

```
GTGCAATCAA TTCTCGAGTT TGACTACAGA C                                     31
```

TRANSGENIC NON-HUMAN ANIMALS CAPABLE OF PRODUCING HETEROLOGOUS ANTIBODIES OF VARIOUS ISOTYPES

CROSS-REFERENCE TO RELATED APPLICATION

This application is a continuation-in-part of U.S. Ser. No. 07/990,860 filed Dec. 16, 1992 now U.S. Pat. No. 5,545,806 which is a continuation-in-part of U.S. Ser. No. 07/904,068 filed 23 Jun. 1992, which is a continuation-in-part of U.S. Ser. No. 07/853,408 filed 18 Mar. 1992, which is a continuation in part of U.S. Ser. No. 07/834,539, filed Feb. 5, 1992, which is a continuation-in-part of U.S. Ser. No. 07/810,279 filed Dec. 17, 1991, now U.S. Pat. No. 5,569,825 which is a continuation-in-part of U.S. Ser. No. 07/575,962 filed Aug. 31, 1990, now abandoned, which is a continuation-in-part of U.S. Ser. No. 07/574,748 filed Aug. 29, 1990, now abandoned. This application claims foreign priority benefits under Title 35, United States Code, Section 119, to PCT Application No. PCT/US91/06185 which corresponds to U.S. Ser. No. 07/834,539 filed Feb. 5, 1992 and PCT Application No. PCT/US92/10983.

TECHNICAL FIELD

The invention relates to transgenic non-human animals capable of producing heterologous antibodies, transgenes used to produce such transgenic animals, transgenes capable of functionally rearranging a heterologous D gene in V-D-J recombination, immortalized B-cells capable of producing heterologous antibodies, methods and transgenes for producing heterologous antibodies of multiple isotypes, methods and transgenes for producing heterologous antibodies wherein a variable region sequence comprises somatic mutation as compared to germline rearranged variable region sequences, transgenic nonhuman animals which produce antibodies having a human primary sequence and which bind to human antigens, hybridomas made from B cells of such transgenic animals, and monclonal antibodies expressed by such hybridomas.

BACKGROUND OF THE INVENTION

One of the major impediments facing the development of in vivo therapeutic and diagnostic applications for monoclonal antibodies in humans is the intrinsic immunogenicity of non-human immunoglobulins. For example, when immunocompetent human patients are administered therapeutic doses of rodent monoclonal antibodies, the patients produce antibodies against the rodent immunoglobulin sequences; these human anti-mouse antibodies (HAMA) neutralize the therapeutic antibodies and can cause acute toxicity. Hence, it is desirable to produce human immunoglobulins that are reactive with specific human antigens that are promising therapeutic and/or diagnostic targets. However, producing human immunoglobulins that bind specifically with human antigens is problematic.

The present technology for generating monoclonal antibodies involves pre-exposing, or priming, an animal (usually a rat or mouse) with antigen, harvesting B-cells from that animal, and generating a library of hybridoma clones. By screening a hybridoma population for antigen binding specificity (idiotype) and also screening for immunoglobulin class (isotype), it is possible to select hybridoma clones that secrete the desired antibody.

However, when present methods for generating monoclonal antibodies are applied for the purpose of generating human antibodies that have binding specificities for human antigens, obtaining B-lymphocytes which produce human immunoglobulins a serious obstacle, since humans will typically not make immune responses against self-antigens.

Hence, present methods of generating human monoclonal antibodies that are specifically reactive with human antigens are clearly insufficient. It is evident that the same limitations on generating monoclonal antibodies to authentic self antigens apply where non-human species are used as the source of B-cells for making the hybridoma.

The construction of transgenic animals harboring a functional heterologous immunoglobulin transgene are a method by which antibodies reactive with self antigens may be produced. However, in order to obtain expression of therapeutically useful antibodies, or hybridoma clones producing such antibodies, the transgenic animal must produce transgenic B cells that are capable of maturing through the B lymphocyte development pathway. Such maturation requires the presence of surface IgM on the transgenic B cells, however isotypes other than IgM are desired for therapeutic uses. Thus, there is a need for transgenes and animals harboring such transgenes that are able to undergo functional V-D-J rearrangement to generate recombinational diversity and junctional diversity. Further, such transgenes and transgenic animals preferably include cis-acting sequences that facilitate isotype switching from a first isotype that is required for B cell maturation to a subsequent isotype that has superior therapeutic utility.

A number of experiments have reported the use of transfected cell lines to determine the specific DNA sequences required for Ig gene rearrangement (reviewed by Lewis and Gellert (1989), *Cell*, 59, 585–588). Such reports have identified putative sequences and concluded that the accessibility of these sequences to the recombinase enzymes used for rearrangement is modulated by transcription (Yancopoulos and Alt (1985), *Cell*, 40, 271–281). The sequences for V(D)J joining are reportedly a highly conserved, near-palindromic heptamer and a less well conserved AT-rich nanomer separated by a spacer of either 12 or 23 bp (Tonegawa (1983), *Nature*, 302, 575–581; Hesse, et al. (1989), *Genes in Dev.*, 3, 1053–1061). Efficient recombination reportedly occurs only between sites containing recombination signal sequences with different length spacer regions.

Ig gene rearrangement, though studied in tissue culture cells, has not been extensively examined in transgenic mice. Only a handful of reports have been published describing rearrangement test constructs introduced into mice [Buchini, et al. (1987), *Nature*, 326, 409–411 (unrearranged chicken λ transgene); Goodhart, et al. (1987) , *Proc. Natl. Acad. Sci. USA*, 84, 4229–4233) (unrearranged rabbit κ gene); and Bruggemann, et al. (1989), *Proc. Natl. Acad. Sci. USA*, 86, 6709–6713 (hybrid mouse-human heavy chain)]. The results of such experiments, however, have been variable, in some cases, producing incomplete or minimal rearrangement of the transgene.

Further, a variety of biological functions of antibody molecules are exerted by the Fc portion of molecules, such as the interaction with mast cells or basophils through Fcε, and binding of complement by Fcμ or Fcγ, it further is desirable to generate a functional diversity of antibodies of a given specificity by variation of isotype.

Although transgenic animals have been generated that incorporate transgenes encoding one or more chains of a heterologous antibody, there have been no reports of heterologous transgenes that undergo successful isotype switching. Transgenic animals that cannot switch isotypes are limited to producing heterologous antibodies of a single isotype, and more specifically are limited to producing an isotype that is essential for B cell maturation, such as IgM and possibly IgD, which may be of limited therapeutic utility. Thus, there is a need for heterologous immunoglobulin transgenes and transgenic animals that are capable of switching from an isotype needed for B cell development to an isotype that has a desired characteristic for therapeutic use.

Based on the foregoing, it is clear that a need exists for methods of efficiently producing heterologous antibodies, e.g. antibodies encoded by genetic sequences of a first species that are produced in a second species. More particularly, there is a need in the art for heterologous immunoglobulin transgenes and transgenic animals that are capable of undergoing functional V-D-J gene rearrangement that incorporates all or a portion of a D gene segment which contributes to recombinational diversity. Further, there is a need in the art for transgenes and transgenic animals that can support V-D-J recombination and isotype switching so that (1) functional B cell development may occur, and (2) therapeutically useful heterologous antibodies may be produced. There is also a need for a source of B cells which can be used to make hybridomas that produce monoclonal antibodies for therapeutic or diagnostic use in the particular species for which they are designed. A heterologous immunoglobulin transgene capable of functional V-D-J recombination and/or capable of isotype switching could fulfill these needs.

In accordance with the foregoing object transgenic non-human animals are provided which are capable of producing a heterologous antibody, such as a human antibody.

Further, it is an object to provide B-cells from such transgenic animals which are capable of expressing heterologous antibodies wherein such B-cells are immortalized to provide a source of a monoclonal antibody specific for a particular antigen.

In accordance with this foregoing object, it is a further object of the invention to provide hybridoma cells that are capable of producing such heterologous monoclonal antibodies.

Still further, it is an object herein to provide heterologous unrearranged and rearranged immunoglobulin heavy and light chain transgenes useful for producing the aforementioned non-human transgenic animals.

Still further, it is an object herein to provide methods to disrupt endogenous immunoglobulin loci in the transgenic animals.

Still further, it is an object herein to provide methods to induce heterologous antibody production in the aforementioned transgenic non-human animal.

A further object of the invention is to provide methods to generate an immunoglobulin variable region gene segment repertoire that is used to construct one or more transgenes of the invention.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

Transgenic nonhuman animals are provided which are capable of producing a heterologous antibody, such as a human antibody. Such heterologous antibodies may be of various isotypes, including: IgG1, IgG2, IgG3, IgG4, IgM, IgA1, IgA2, IgA$_{sec}$, IgD, of IgE. In order for such transgenic nonhuman animals to make an immune response, it is necessary for the transgenic B cells and pre-B cells to produce surface-bound immunoglobulin, particularly of the IgM (or possibly IgD) isotype, in order to effectuate B cell development and antigen-stimulated maturation. Such expression of an IgM (or IgD) surface-bound immunoglobulin is only required during the antigen-stimulated maturation phase of B cell development, and mature B cells may produce other isotypes, although only a single switched isotype may be produced at a time.

Typically, a cell of the B-cell lineage will produce only a single isotype at a time, although cis or trans alternative RNA splicing, such as occurs naturally with the $\mu_s$ (secreted $\mu$) and $\mu_M$ (membrane-bound $\mu$) forms, and the $\mu$ and $\delta$ immunoglobulin chains, may lead to the contemporaneous expression of multiple isotypes by a single cell. Therefore, in order to produce heterologous antibodies of multiple isotypes, specifically the therapeutically useful IgG, IgA, and IgE isotypes, it is necessary that isotype switching occur. Such isotype switching may be classical class-switching or may result from one or more non-classical isotype switching mechanisms.

The invention provides heterologous immunoglobulin transgenes and transgenic nonhuman animals harboring such transgenes, wherein the transgenic animal is capable of producing heterologous antibodies of multiple isotypes by undergoing isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ sequences ($\delta$-associated deletion). Alternative non-classical switching mechanisms, such as intertransgene and/or interchromosomal recombination, among others, may occur and effectuate isotype switching. Such transgenes and transgenic nonhuman animals produce a first immunoglobulin isotype that is necessary for antigen-stimulated B cell maturation and can switch to encode and produce one or more subsequent heterologous isotypes that have therapeutic and/or diagnostic utility. Transgenic nonhuman animals of the invention are thus able to produce, in one embodiment, IgG, IgA, and/or IgE antibodies that are encoded by human immunoglobulin genetic sequences and which also bind specific human antigens with high affinity.

The invention also encompasses B-cells from such transgenic animals that are capable of expressing heterologous antibodies of various isotypes, wherein such B-cells are immortalized to provide a source of a monoclonal antibody specific for a particular antigen. Hybridoma cells that are derived from such B-cells can serve as one source of such heterologous monoclonal antibodies.

The invention provides heterologous unrearranged and rearranged immunoglobulin heavy and light chain transgenes capable of undergoing isotype switching in vivo in the aforementioned non-human transgenic animals or in explanted lymphocytes of the B-cell lineage from such transgenic animals. Such isotype switching may occur spontaneously or be induced by treatment of the transgenic animal or explanted B-lineage lymphocytes with agents that promote isotype switching, such as T-cell-derived lymphokines (e.g., IL-4 and IFN$_\gamma$).

Still further, the invention includes methods to induce heterologous antibody production in the aforementioned transgenic non-human animal, wherein such antibodies may be of various isotypes. These methods include producing an antigen-stimulated immune response in a transgenic nonhuman animal for the generation of heterologous antibodies, particularly heterologous antibodies of a switched isotype (i.e., IgG, IgA, and IgE).

This invention provides methods whereby the transgene contains sequences that effectuate isotype switching, so that the heterologous immunoglobulins produced in the transgenic animal and monoclonal antibody clones derived from the B-cells of said animal may be of various isotypes.

This invention further provides methods that facilitate isotype switching of the transgene, so that switching between particular isotypes may occur at much higher or lower frequencies or in different temporal orders than typically occurs in germline immunoglobulin loci. Switch regions may be grafted from various $C_H$ genes and ligated to other $C_H$ genes in a transgene construct; such grafted switch sequences will typically function independently of the associated $C_H$ gene so that switching in the transgene construct will typically be a function of the origin of the associated switch regions. Alternatively, or in combination with switch sequences, δ-associated deletion sequences may be linked to various $C_H$ genes to effect non-classical switching by deletion of sequences between two δ-associated deletion sequences. Thus, a transgene may be constructed so that a particular $C_H$ gene is linked to a different switch sequence and thereby is switched to more frequently than occurs when the naturally associated switch region is used.

This invention also provides methods to determine whether isotype switching of transgene sequences has occurred in a transgenic animal containing an immunoglobulin transgene.

The invention provides immunoglobulin transgene constructs and methods for producing immunoglobulin transgene constructs, some of which contain a subset of germline immunoglobulin loci sequences (which may include deletions). The invention includes a specific method for facilitated cloning and construction of immunoglobulin transgenes, involving a vector that employs unique XhoI and SalI restriction sites flanked by two unique NotI sites. This method exploits the complementary termini of XhoI and SalI restrictions sites and is useful for creating large constructs by ordered concatemerization of restriction fragments in a vector.

The transgenes of the invention include a heavy chain transgene comprising DNA encoding at least one variable gene segment, one diversity gene segment, one joining gene segment and one constant region gene segment. The immunoglobulin light chain transgene comprises DNA encoding at least one variable gene segment, one joining gene segment and one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes permit recombination of the gene segments (functional rearrangement) and expression of the resultant rearranged immunoglobulin heavy and/or light chains within the transgenic non-human animal when said animal is exposed to antigen.

In one aspect of the invention, heterologous heavy and light immunoglobulin transgenes comprise relatively large fragments of unrearranged heterologous DNA. Such fragments typically comprise a substantial portion of the C, J (and in the case of heavy chain, D) segments from a heterologous immunoglobulin locus. In addition, such fragments also comprise a substantial portion of the variable gene segments.

In one embodiment, such transgene constructs comprise regulatory sequences, e.g. promoters, enhancers, class switch regions, recombination signals and the like, corresponding to sequences derived from the heterologous DNA. Alternatively, such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse.

In a method of the invention, a transgenic non-human animal containing germline unrearranged light and heavy immunoglobulin transgenes—that undergo VDJ joining during D-cell differentiation—is contacted with an antigen to induce production of a heterologous antibody in a secondary repertoire B-cell.

Also included in the invention are vectors and methods to disrupt the endogenous immunoglobulin loci in the non-human animal to be used in the invention. Such vectors and methods utilize a transgene, preferably positive-negative selection vector, which is constructed such that it targets the functional disruption of a class of gene segments encoding a heavy and/or light immunoglobulin chain endogenous to the non-human animal used in the invention. Such endogenous gene segments include diversity, joining and constant region gene segments. In this aspect of the invention, the positive-negative selection vector is contacted with at least one embryonic stem cell of a non-human animal after which cells are selected wherein the positive-negative selection vector has integrated into the genome of the non-human animal by way of homologous recombination. After transplantation, the resultant transgenic non-human animal is substantially incapable of mounting an immunoglobulin-mediated immune response as a result of homologous integration of the vector into chromosomal DNA. Such immune deficient non-human animals may thereafter be used for study of immune deficiencies or used as the recipient of heterologous immunoglobulin heavy and light chain transgenes.

The invention also provides vectors, methods, and compositions useful for suppressing the expression of one or more species of immunoglobulin chain(s), without disrupting an endogenous immunoglobulin locus. Such methods are useful for suppressing expression of one or more endogenous immunoglobulin chains while permitting the expression of one or more transgene-encoded immunoglobulin chains. Unlike genetic disruption of an endogenous immunoglobulin chain locus, suppression of immunoglobulin chain expression does not require the time-consuming breeding that is needed to establish transgenic animals homozygous for a disrupted endogenous Ig locus. An additional advantage of suppression as compared to engognous Ig gene disruption is that, in certain embodiments, chain suppression is reversible within an individual animal. For example, Ig chain suppression may be accomplished with: (1) transgenes encoding and expressing antisense RNA that specifically hybridizes to an endogenous Ig chain gene sequence, (2) antisense oligonucleotides that specifically hybridize to an endogenous Ig chain gene sequence, and (3) immunoglobulins that bind specifically to an endogenous Ig chain polypeptide.

The references discussed herein are provided solely for their disclosure prior to the filing date of the present application. Nothing herein is to be construed as an admission that the inventors are not entitled to antedate such disclosure by virtue of prior invention.

BRIEF DESCRIPTION OF THE FIGURES

FIG. 8 depicts the construction of the polylinker contained in pGP1.

FIG. 12 depicts the construction of pHIG3' and PCON.

FIG. 17 depicts the construction of pKapH.

FIGS. 19A through 19C depict the construction of a positive-negative selection vector for functionally disrupting the endogenous immunoglobulin light chain loci in mouse.

FIGS. 21 a through f depict the structure of a mouse heavy chain targeting vector.

FIG. 40 shows aligned variable region sequences of 23 randomly-chosen cDNAs generated from mRNA obtained from lymphoid tissue of HC1 transgenic mice immunized with human carcinoembryonic antigen (CEA) as compared to the germline transgene sequence (top line); on each line nucleotide changes relative to germline sequence are shown above the alteration in deduced amino acid sequence (if any); the regions corresponding to heavy chain CDR1, CDR2, and CDR3 are indicated. Non-germline encoded nucleotides are shown in capital letters. Germline $V_H 251$ and $J_H$ are shown in lower case letters. Deduced amino acid changes are given beneath nucleotide sequences using the conventional single-letter notation.

FIG. 41 show the nucleotide sequence of a human DNA fragment, designated vk65.3, containing a $V_\kappa$ gene segment; the deduced amino acid sequences of the $V_\kappa$ coding regions are also shown; splicing and recombination signal sequences (heptamer/nonamer) are shown boxed.

FIG. 42 show the nucleotide sequence of a human DNA fragment, designated vk65.5, containing a $V_\kappa$ gene segment; the deduced amino acid sequences of the $V_\kappa$ coding regions are also shown; splicing and recombination signal sequences (heptamer/nonamer) are shown boxed.

FIG. 43 show the nucleotide sequence of a human DNA fragment, designated vk65.8, containing a $V_\kappa$ gene segment; the deduced amino acid sequences of the $V_\kappa$ coding regions are also shown; splicing and recombination signal sequences (heptamer/nonamer) are shown boxed.

FIG. 44 show the nucleotide sequence of a human DNA fragment, designated vk65.15, containing a $V_\kappa$ gene segment; the deduced amino acid sequences of the $V_\kappa$ coding regions are also shown; splicing and recombination signal sequences (heptamer/nonamer) are shown boxed.

FIG. 46 shows ELISA results for monoclonal antibodies reactive with CEA and non-CEA antigens showing the specificity of antigen binding.

FIG. 47 shows the DNA sequences of 10 cDNAs amplified by PCR to amplify transcripts having a human VDJ and a murine constant region sequence.

FIG. 48 shows ELISA results for various dilutions of serum obtained from mice bearing both a human heavy chain minilocus transgene and a human κ minilocus transgene; the mouse was immunized with human CD4 and the data shown represents antibodies reactive with human CD4 and possessing human κ, human μ, or human γ epitopes, respectively.

Figure 1:
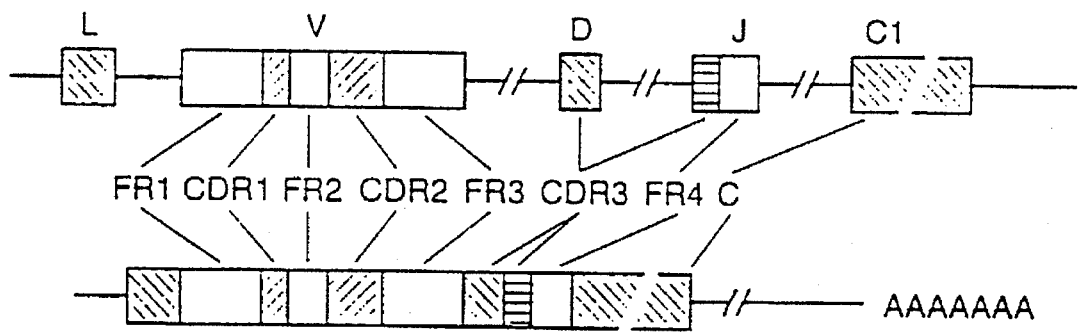
FIG. 1 depicts the complementarity determining regions CDR1, CDR2 and CDR3 and framework regions FR1, FR2, FR3 and FR4 in unrearranged genomic DNA and mRNA expressed from a rearranged immunoglobulin heavy chain gene.
Figure 2:
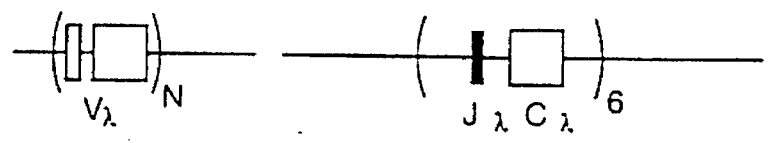
FIG. 2 depicts the human λ chain locus.
Figure 3:
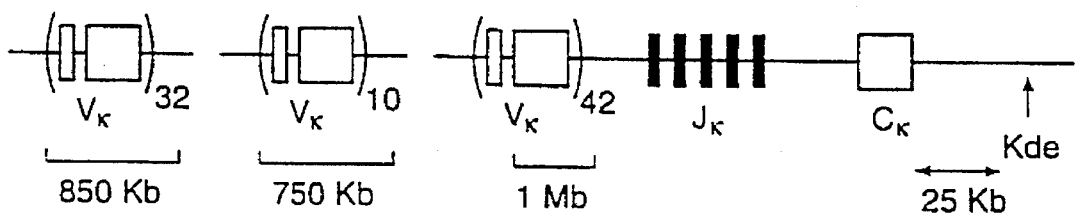
FIG. 3 depicts the human κ chain locus.

Table 1 depicts the sequence of vector pGPe.

Table 2 depicts the sequence of gene $V_H49.8$.

Table 3 depicts the detection of human IgM and IgG in the serum of transgenic mice of this invention.

Table 4 depicts sequences of VDJ joints.

Table 5 depicts the distribution of J segments incorporated into pHC1 transgene encoded transcripts to J segments found in adult human peripheral blood lymphocytes (PBL).

Table 6 depicts the distribution of D segments incorporated into pHC1 transgene encoded transcripts to D segments found in adult human peripheral blood lymphocytes (PBL).

Table 7 depicts the length of the CDR3 peptides from transcripts with in-frame VDJ joints in the pHC1 transgenic mouse and in human PBL.

Table 8 depicts the predicted amino acid sequences of the VDJ regions from 30 clones analyzed from a pHC1 transgenic.

Table 9 shows transgenic mice of line 112 that were used in the indicated experiments; (+) indicates the presence of the respective transgene, (++) indicates that the animal is homozygous for the $J_HD$ knockout transgene.

DETAILED DESCRIPTION

As has been discussed supra, it is desirable to produce human immunoglobulins that are reactive with specific human antigens that are promising therapeutic and/or diagnostic targets. However, producing human immunoglobulins that bind specifically with human antigens is problematic.

First, the immunized animal that serves as the source of B cells must make an immune response against the presented antigen. In order for an animal to make an immune response, the antigen presented must be foreign and the animal must not be tolerant to the antigen. Thus, for example, if it is desired to produce a human monoclonal antibody with an idiotype that binds to a human protein, self-tolerance will prevent an immunized human from making a substantial immune response to the human protein, since the only epitopes of the antigen that may be immunogenic will be those that result from polymorphism of the protein within the human population (allogeneic epitopes).

Second, if the animal that serves as the source of B-cells for forming a hybridoma (a human in the illustrative given example) does make an immune response against an authentic self antigen, a severe autoimmune disease may result in the animal. Where humans would be used as a source of B-cells for a hybridoma, such autoimmunization would be considered unethical by contemporary standards. Thus, developing hybridomas secreting human immunoglobulin chains specifically reactive with predetermined human antigens is problematic, since a reliable source of human antibody-secreting B cells that can evoke an antibody response against predetermined human antigens is needed.

One methodology that can be used to obtain human antibodies that are specifically reactive with human antigens is the production of a transgenic mouse harboring the human immunoglobulin transgene constructs of this invention. Briefly, transgenes containing all or portions of the human immunoglobulin heavy and light chain loci, or transgenes containing synthetic "miniloci" (described infra, and in copending applications U.S. Ser. No. 07/990,860, filed 16 Dec. 1992 now U.S. Pat. No. 5,545,806, U.S. Ser. No. 07/810,279 filed 17 Dec. 1991 now U.S. Pat. No. 5,569,825, U.S. Ser. No. 07/904,068 filed 23 Jun. 1992; U.S. Ser. No. 07/853,408, filed 18 Mar. 1992 U.S. Ser. No. 07/834,539 filed 05 Feb. 1992; U.S. Ser. No. 07/574,748 filed Aug. 29, 1990, U.S. Ser. No. 07/575,962 filed Aug. 31, 1990 abandoned, and PCT/US91/06185 filed Aug. 28, 1991, each incorporated herein by reference) which comprise essential functional elements of the human heavy and light chain loci, are employed to produce a transgenic nonhuman animal. Such a transgenic nonhuman animal will have the capacity to produce immunoglobulin chains that are encoded by human immunoglobulin genes, and additionally will be capable of making an immune response against human antigens. Thus, such transgenic animals can serve as a source of immune sera reactive with specified human antigens, and B-cells from such transgenic animals can be fused with myeloma cells to produce hybridomas that secrete monoclonal antibodies that are encoded by human immunoglobulin genes and which are specifically reactive with human antigens.

The production of transgenic mice containing various forms of immunoglobulin genes has been reported previously. Rearranged mouse immunoglobulin heavy or light chain genes have been used to produce transgenic mice. In addition, functionally rearranged human Ig genes including the μ or γ1 constant region have been expressed in transgenic mice. However, experiments in which the transgene comprises unrearranged (V-D-J or V-J not rearranged) immunoglobulin genes have been variable, in some cases, producing incomplete or minimal rearrangement of the transgene. However, there are no published examples of either rearranged or unrearranged immunoglobulin transgenes which undergo successful isotype switching between $C_H$ genes within a transgene.

The invention also provides a method for identifying candidate hybridomas which secrete a monoclonal antibody comprising a human immunoglobulin chain consisting essentially of a human VDJ sequence in polypeptide linkage to a human constant region sequence. Such candidate hybridomas are identified from a pool of hybridoma clones comprising: (1) hybridoma clones that express immunoglobulin chains consisting essentially of a human VDJ region and a human constant region, and (2) trans-switched hybridomas that express heterohybrid immunoglobulin chains consisting essentially of a human VDJ region and a murine constant region. The supernatant(s) of individual or pooled hybridoma clones is contacted with a predetermined antigen, typically an antigen which is immobilized by adsoption onto a solid substrate (e.g., a microtitre well), under binding conditions to select antibodies having the predetermined antigen binding specificity. An antibody that specifically binds to human constant regions is also contacted with the hybridoma supernatant and predetermined antigen under binding conditions so that the antibody selectively binds to at least one human constant region epitope but substantially does not bind to murine constant region epitopes; thus forming complexes consisting essentially of hybridoma supernatant (transgenic monoclonal antibody) bound to a predetermined antigen and to an antibody that specifically binds human constant regions (and which may be labeled with a detectable label or reporter). Detection of the formation of such complexes indicates hybridoma clones or pools which express a human immunoglobulin chain.

Definitions

As used herein, the term "antibody" refers to a glycoprotein comprising at least two light polypeptide chains and two heavy polypeptide chains. Each of the heavy and light polypeptide chains contains a variable region (generally the amino terminal portion of the polypeptide chain) which contains a binding domain which interacts with antigen. Each of the heavy and light polypeptide chains also comprises a constant region of the polypeptide chains (generally the carboxyl terminal portion) which may mediate the binding of the immunoglobulin to host tissues or factors including various cells of the immune system, some phagocytic cells and the first component (C1q) of the classical complement system.

As used herein, a "heterologous antibody" is defined in relation to the transgenic non-human organism producing such an antibody. It is defined as an antibody having an amino acid sequence or an encoding DNA sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody.

As used herein, "isotype" refers to the antibody class (e.g., IgM or IgG$_1$) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the $C_H$ gene encoding the non-switched isotype is typically the first $C_H$ gene immediately downstream from the functionally rearranged VDJ gene.

As used herein, the term "switch sequence" refers to those DNA sequences responsible for switch recombination. A "switch donor" sequence, typically a µ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the $C_H$ genes of the transgene were derived.

As used herein, "specific binding" refers to the property of the antibody: (1) to bind to a predetermined antigen with an affinity of at least $1 \times 10^7 M^{-1}$, and (2) to preferentially bind to the predetermined antigen with an affinity that is at least two-fold greater than its affinity for binding to a non-specific antigen (e.g., BSA, casein) other than the predetermined antigen or a closely-related antigen.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98 to 99.5% of the nucleotides. Alternatively, substantial homology exists when the segments will hybridize under selective hybridization conditions, to the complement of the strand. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. *Current Protocols in Molecular Biology*, Greene Publishing and Wiley-Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

Transgenic Nonhuman Animals Capable of Producing Heterologous Antibodies

The design of a transgenic non-human animal that responds to foreign antigen stimulation with a heterologous antibody repertoire, requires that the heterologous immunoglobulin transgenes contained within the transgenic animal function correctly throughout the pathway of B-cell development. In a preferred embodiment, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

As will be apparent from the following disclosure, not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology*, 2nd edition (1989), Paul William E., ed. Raven Press, N.Y., which is incorporated herein by reference.

In one aspect of the invention, transgenic non-human animals are provided that contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgeneic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences made be isolated and cloned by conventional cloning methods, or may be synthesized de novo from overlapping synthetic oligonucleotides designed on the basis of published sequence information relating to immunoglobulin switch region sequences (Mills et al., *Nucl. Acids Res.* 18:7305–7316 (1991); Sideras et al., *Intl. Immunol.* 1:631–642 (1989), which are incorporated herein by reference).

For each of the foregoing transgenic animals, functionally rearranged heterologous heavy and light chain immunoglobulin transgenes are found in a significant fraction of the B-cells of the transgenic animal (at least 10 percent).

The transgenes of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment.

The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to antigen.

In an alternate embodiment, the transgenes comprise an unrearranged "mini-locus". Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif.

The invention also includes transgenic animals containing germ line cells having a heavy and light transgene wherein one of the said transgenes contains rearranged gene segments with the other containing unrearranged gene segments. In the preferred embodiments, the rearranged transgene is a light chain immunoglobulin transgene and the unrearranged transgene is a heavy chain immunoglobulin transgene.

The Structure and Generation of Antibodies

The basic structure of all immunoglobulins is based upon a unit consisting of two light polypeptide chains and two heavy polypeptide chains. Each light chain comprises two regions known as the variable light chain region and the constant light chain region. Similarly, the immunoglobulin heavy chain comprises two regions designated the variable heavy chain region and the constant heavy chain region.

The constant region for the heavy or light chain is encoded by genomic sequences referred to as heavy or light constant region gene ($C_H$) segments. The use of a particular heavy chain gene segment defines the class of immunoglobulin. For example, in humans, the μ constant region gene segments define the IgM class of antibody whereas the use of a γ, γ2, γ3 or γ4 constant region gene segment defines the IgG class of antibodies as well as the IgG subclasses IgG1 through IgG4. Similarly, the use of a $\alpha_1$ or $\alpha_2$ constant region gene segment defines the IgA class of antibodies as well as the subclasses IgA1 and IgA2. The δ and ε constant region gene segments define the IgD and IgE antibody classes, respectively.

The variable regions of the heavy and light immunoglobulin chains together contain the antigen binding domain of the antibody. Because of the need for diversity in this region of the antibody to permit binding to a wide range of antigens, the DNA encoding the initial or primary repertoire variable region comprises a number of different DNA segments derived from families of specific variable region gene segments. In the case of the light chain variable region, such families comprise variable (V) gene segments and joining (J) gene segments. Thus, the initial variable region of the light chain is encoded by one V gene segment and one J gene segment each selected from the family of V and J gene segments contained in the genomic DNA of the organism. In the case of the heavy chain variable region, the DNA encoding the initial or primary repertoire variable region of the heavy chain comprises one heavy chain V gene segment, one heavy chain diversity (D) gene segment and one J gene segment, each selected from the appropriate V, D and J families of immunoglobulin gene segments in genomic DNA.

In order to increase the diversity of sequences that contribute to forming antibody binding sites, it is preferable that a heavy chain transgene include cis-acting sequences that support functional V-D-J rearrangement that can incorporate all or part of a D region gene sequence in a rearranged V-D-J gene sequence. Typically, at least about 1 percent of expressed transgene-encoded heavy chains (or mRNAs) include recognizable D region sequences in the V region. Preferably, at least about 10 percent of transgene-encoded V regions include recognizable D region sequences, more preferably at least about 30 percent, and most preferably more than 50 percent include recognizable D region sequences.

A recognizable D region sequence is generally at least about eight consecutive nucleotides corresponding to a sequence present in a D region gene segment of a heavy chain transgene and/or the amino acid sequence encoded by such D region nucleotide sequence. For example, if a transgene includes the D region gene DHQ52, a transgene-encoded mRNA containing the sequence 5'-TAACTGGG-3' located in the V region between a V gene segment sequence and a J gene segment sequence is recognizable as containing a D region sequence, specifically a DHQ52 sequence. Similarly, for example, if a transgene includes the D region gene DHQ52, a transgene-encoded heavy chain polypeptide containing the amino acid sequence -DAF- located in the V region between a V gene segment amino acid sequence and a J gene segment amino acid sequence may be recognizable as containing a D region sequence, specifically a DHQ52 sequence. However, since D region segments may be incorporated in VDJ joining to various extents and in various reading frames, a comparison of the D region area of a heavy chain variable region to the D region segments present in the transgene is necessary to determine the incorporation of particular D segments. Moreover, potential exonuclease digestion during recombination may lead to imprecise V-D and D-J joints during V-D-J recombination.

However, because of somatic mutation and N-region addition, some D region sequences may be recognizable but may not correspond identically to a consecutive D region sequence in the transgene. For example, a nucleotide sequence 5'-CTAAXTGGGG-3', where X is A, T, or G, and which is located in a heavy chain V region and flanked by a V region gene sequence and a J region gene sequence, can be recognized as corresponding to the DHQ52 sequence 5'-CTAACTGGG-3'. Similarly, for example, the polypeptide sequences -DAFDI-, -DYFDY-, or -GAFDI- located in a V region and flanked on the amino-terminal side by an amino acid sequence encoded by a transgene V gene sequence and flanked on the carboxyterminal side by an amino acid sequence encoded by a transgene J gene sequence is recognizable as a D region sequence.

Therefore, because somatic mutation and N-region addition can produce mutations in sequences derived from a transgene D region, the following definition is provided as a guide for determining the presence of a recognizable D region sequence. An amino acid sequence or nucleotide sequence is recognizable as a D region sequence if: (1) the sequence is located in a V region and is flanked on one side by a V gene sequence (nucleotide sequence or deduced amino acid sequence) and on the other side by a J gene sequence (nucleotide sequence or deduced amino acid sequence) and (2) the sequence is substantially identical or substantially similar to a known D gene sequence (nucleotide sequence or encoded amino acid sequence).

The term "substantial identity" as used herein denotes a characteristic of a polypeptide sequence or nucleic acid sequence, wherein the polypeptide sequence has at least 50 percent sequence identity compared to a reference sequence, and the nucleic acid sequence has at least 70 percent sequence identity compared to a reference sequence. The percentage of sequence identity is calculated excluding small deletions or additions which total less than 35 percent of the reference sequence. The reference sequence may be a subset of a larger sequence, such as an entire D gene; however, the reference sequence is at least 8 nucleotides long in the case of polynucleotides, and at least 3 amino residues long in the case of a polypeptide. Typically, the reference sequence is at least 8 to 12 nucleotides or at least 3 to 4 amino acids, and preferably the reference sequence is 12 to 15 nucleotides or more, or at least 5 amino acids.

The term "substantial similarity" denotes a characteristic of an polypeptide sequence, wherein the polypeptide sequence has at least 80 percent similarity to a reference sequence. The percentage of sequence similarity is calculated by scoring identical amino acids or positional conservative amino acid substitutions as similar. A positional conservative amino acid substitution is one that can result from a single nucleotide substitution; a first amino acid is replaced by a second amino acid where a codon for the first amino acid and a codon for the second amino acid can differ by a single nucleotide substitution. Thus, for example, the sequence -Lys-Glu-Arg-Val- is substantially similar to the sequence -Asn-Asp-Ser-Val-, since the codon sequence -AAA-GAA-AGA-GUU- can be mutated to -AAC-GAC-AGC-GUU- by introducing only 3 substitution mutations, single nucleotide substitutions in three of the four original codons. The reference sequence may be a subset of a larger sequence, such as an entire D gene; however, the reference sequence is at least 4 amino residues long. Typically, the reference sequence is at least 5 amino acids, and preferably the reference sequence is 6 amino acids or more.

The Primary Repertoire

The process for generating DNA encoding the heavy and light chain immunoglobulin genes occurs primarily in developing B-cells. Prior to the joining of various immunoglobulin gene segments, the V, D, J and constant (C) gene segments are found, for the most part, in clusters of V, D, J and C gene segments in the precursors of primary repertoire B-cells. Generally, all of the gene segments for a heavy or light chain are located in relatively close proximity on a single chromosome. Such genomic DNA prior to recombination of the various immunoglobulin gene segments is referred to herein as "unrearranged" genomic DNA. During B-cell differentiation, one of each of the appropriate family members of the V, D, J (or only V and J in the case of light chain genes) gene segments are recombined to form functionally rearranged heavy and light immunoglobulin genes. Such functional rearrangement is of the variable region segments to form DNA encoding a functional variable region. This gene segment rearrangement process appears to be sequential. First, heavy chain D-to-J joints are made, followed by heavy chain V-to-DJ joints and light chain V-to-J joints. The DNA encoding this initial form of a functional variable region in a light and/or heavy chain is referred to as "functionally rearranged DNA" or "rearranged DNA". In the case of the heavy chain, such DNA is referred to as "rearranged heavy chain DNA" and in the case of the light chain, such DNA is referred to as "rearranged light chain DNA". Similar language is used to describe the functional rearrangement of the transgenes of the invention.

The recombination of variable region gene segments to form functional heavy and light chain variable regions is mediated by recombination signal sequences (RSS's) that flank recombinationally competent V, D and J segments. RSS's necessary and sufficient to direct recombination, comprise a dyad-symmetric heptamer, an AT-rich nonamer and an intervening spacer region of either 12 or 23 base pairs. These signals are conserved among the different loci and species that carry out D-J (or V-J) recombination and are functionally interchangeable. See Oettinger, et al. (1990), *Science*, 248, 1517–1523 and references cited therein. The heptamer comprises the sequence CACAGTG or its analogue followed by a spacer of unconserved sequence and then a nonamer having the sequence ACAAAAACC or its analogue. These sequences are found on the J, or downstream side, of each V and D gene segment. Immediately preceding the germline D and J segments are again two recombination signal sequences, first the nonamer and then the heptamer again separated by an unconserved sequence. The heptameric and nonameric sequences following a $V_L$, $V_H$ or D segment are complementary to those preceding the $J_L$, D or $J_H$ segments with which they recombine. The spacers between the heptameric and nonameric sequences are either 12 base pairs long or between 22 and 24 base pairs long.

In addition to the rearrangement of V, D and J segments, further diversity is generated in the primary repertoire of immunoglobulin heavy and light chain by way of variable recombination between the V and J segments in the light chain and between the D and J segments of the heavy chain. Such variable recombination is generated by variation in the exact place at which such segments are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity.

After VJ and/or VDJ rearrangement, transcription of the rearranged variable region and one or more constant region gene segments located downstream from the rearranged variable region produces a primary RNA transcript which upon appropriate RNA splicing results in an mRNA which encodes a full length heavy or light immunoglobulin chain. Such heavy and light chains include a leader signal sequence to effect secretion through and/or insertion of the immunoglobulin into the transmembrane region of the B-cell. The DNA encoding this signal sequence is contained within the first exon of the V segment used to form the variable region of the heavy or light immunoglobulin chain. Appropriate regulatory sequences are also present in the mRNA to control translation of the mRNA to produce the encoded heavy and light immunoglobulin polypeptides which upon proper association with each other form an antibody molecule.

The net effect of such rearrangements in the variable region gene segments and the variable recombination which may occur during such joining, is the production of a primary antibody repertoire. Generally, each B-cell which has differentiated to this stage, produces a single primary repertoire antibody. During this differentiation process, cellular events occur which suppress the functional rearrangement of gene segments other than those contained within the functionally rearranged Ig gene. The process by which diploid B-cells maintain such mono-specificity is termed allelic exclusion.

The Secondary Repertoire

B-cell clones expressing immunoglobulins from within the set of sequences comprising the primary repertoire are immediately available to respond to foreign antigens. Because of the limited diversity generated by simple VJ and VDJ joining, the antibodies produced by the so-called primary response are of relatively low affinity. Two different types of B-cells make up this initial response: precursors of primary antibody-forming cells and precursors of secondary repertoire B-cells (Linton et al., *Cell* 59:1049–1059 (1989)). The first type of B-cell matures into IgM-secreting plasma cells in response to certain antigens. The other B-cells respond to initial exposure to antigen by entering a T-cell dependent maturation pathway.

During the T-cell dependent maturation of antigen stimulated B-cell clones, the structure of the antibody molecule on the cell surface changes in two ways: the constant region switches to a non-IgM subtype and the sequence of the variable region can be modified by multiple single amino acid substitutions to produce a higher affinity antibody molecule.

As previously indicated, each variable region of a heavy or light Ig chain contains an antigen binding domain. It has been determined by amino acid and nucleic acid sequencing that somatic mutation during the secondary response occurs throughout the V region including the three complementary determining regions (CDR1, CDR2 and CDR3) also referred to as hypervariable regions 1, 2 and 3 (Kabat et al. *Sequences of Proteins of Immunological Interest* (1991) U.S. Department of Health and Human Services, Washington, D.C., incorporated herein by reference. The CDR1 and CDR2 are located within the variable gene segment whereas the CDR3 is largely the result of recombination between V and J gene segments or V, D and J gene segments. Those portions of the variable region which do not consist of CDR1, 2 or 3 are commonly referred to as framework regions designated FR1, FR2, FR3 and FR4. See FIG. 1. During hypermutation, the rearranged DNA is mutated to give rise to new clones with altered Ig molecules. Those clones with higher affinities for the foreign antigen are selectively expanded by helper T-cells, giving rise to affinity maturation of the expressed antibody. Clonal selection typically results in expression of clones containing new mutation within the CDR1, 2 and/or 3 regions. However, mutations outside these regions also occur which influence the specificity and affinity of the antigen binding domain.

Transgenic Non-Human Animals Capable of Producing Heterologous Antibody

Transgenic non-human animals in one aspect of the invention are produced by introducing at least one of the immunoglobulin transgenes of the invention (discussed hereinafter) into a zygote or early embryo of a non-human animal. The non-human animals which are used in the invention generally comprise any mammal which is capable of rearranging immunoglobulin gene segments to produce a primary antibody response. Such nonhuman transgenic animals may include, for example, transgenic pigs, transgenic rats, transgenic rabbits, transgenic cattle, and other transgenic animal species, particularly mammalian species, known in the art. A particularly preferred non-human animal is the mouse or other members of the rodent family.

However, the invention is not limited to the use of mice. Rather, any non-human mammal which is capable of mounting a primary and secondary antibody response may be used. Such animals include non-human primates, such as chimpanzee, bovine, ovine, and porcine species, other members of the rodent family, e.g. rat, as well as rabbit and guinea pig. Particular preferred animals are mouse, rat, rabbit and guinea pig, most preferably mouse.

In one embodiment of the invention, various gene segments from the human genome are used in heavy and light chain transgenes in an unrearranged form. In this embodiment, such transgenes are introduced into mice. The unrearranged gene segments of the light and/or heavy chain transgene have DNA sequences unique to the human species which are distinguishable from the endogenous immunoglobulin gene segments in the mouse genome. They may be readily detected in unrearranged form in the germ line and somatic cells not consisting of B-cells and in rearranged form in B-cells.

In an alternate embodiment of the invention, the transgenes comprise rearranged heavy and/or light immunoglobulin transgenes. Specific segments of such transgenes corresponding to functionally rearranged VDJ or VJ segments, contain immunoglobulin DNA sequences which are also clearly distinguishable from the endogenous immunoglobulin gene segments in the mouse.

Such differences in DNA sequence are also reflected in the amino acid sequence encoded by such human immunoglobulin transgenes as compared to those encoded by mouse B-cells. Thus, human immunoglobulin amino acid sequences may be detected in the transgenic non-human animals of the invention with antibodies specific for immunoglobulin epitopes encoded by human immunoglobulin gene segments.

Transgenic B-cells containing unrearranged transgenes from human or other species functionally recombine the appropriate gene segments to form functionally rearranged light and heavy chain variable regions. It will be readily apparent that the antibody encoded by such rearranged transgenes has a DNA and/or amino acid sequence which is heterologous to that normally encountered in the nonhuman animal used to practice the invention.

Unrearranged Transgenes

As used herein, an "unrearranged immunoglobulin heavy chain transgene" comprises DNA encoding at least one variable gene segment, one diversity gene segment, one joining gene segment and one constant region gene segment. Each of the gene segments of said heavy chain transgene are derived from, or has a sequence corresponding to, DNA encoding immunoglobulin heavy chain gene segments from a species not consisting of the non-human animal into which said transgene is introduced. Similarly, as used herein, an "unrearranged immunoglobulin light chain transgene" comprises DNA encoding at least one variable gene segment, one joining gene segment and at least one constant region gene segment wherein each gene segment of said light chain transgene is derived from, or has a sequence corresponding to, DNA encoding immunoglobulin light chain gene segments from a species not consisting of the non-human animal into which said light chain transgene is introduced.

Such heavy and light chain transgenes in this aspect of the invention contain the above-identified gene segments in an unrearranged form. Thus, interposed between the V, D and J segments in the heavy chain transgene and between the V and J segments on the light chain transgene are appropriate recombination signal sequences (RSS's). In addition, such transgenes also include appropriate RNA splicing signals to join a constant region gene segment with the VJ or VDJ rearranged variable region.

In order to facilitate isotype switching within a heavy chain transgene containing more than one C region gene segment, e.g. Cµ and Cγ1 from the human genome, as explained below "switch regions" are incorporated upstream from each of the constant region gene segments and downstream from the variable region gene segments to permit recombination between such constant regions to allow for immunoglobulin class switching, e.g. from IgM to IgG. Such heavy and light immunoglobulin transgenes also contain transcription control sequences including promoter regions situated upstream from the variable region gene segments which typically contain TATA motifs. A promoter region can be defined approximately as a DNA sequence that, when operably linked to a downstream sequence, can produce transcription of the downstream sequence. Promoters may require the presence of additional linked cis-acting sequences in order to produce efficient transcription. In addition, other sequences that participate in the transcription of sterile transcripts are preferably included. Examples of sequences that participate in expression of sterile transcripts can be found in the published literature, including Rothman et al., *Intl. Immunol.* 2:621–627 (1990); Reid et al., *Proc. Natl. Acad. Sci. USA* 86:840–844 (1989); Stavnezer et al., *Proc. Natl. Acad. Sci. USA* 85:7704–7708 (1988); and Mills et al., *Nucl. Acids Res.* 18:7305–7316 (1991), each of which is incorporated herein by reference. These sequences typically include about at least 50 bp immediately upstream of a switch region, preferably about at least 200 bp upstream of a switch region; and more preferably about at least 200–1000 bp or more upstream of a switch region. Suitable sequences occur immediately upstream of the human $S_{\gamma 1}$, $S_{\gamma 2}$, $S_{\gamma 3}$, $S_{\gamma 4}$, $S_{\alpha 1}$, $S_{\alpha 2}$, and $S_\epsilon$ switch regions; the sequences immediately upstream of the human $S_{\gamma 1}$, and $S_{\gamma 3}$ switch regions can be used to advantage, with generally preferred. Alternatively, or in combination, murine Ig switch sequences may be used; it may frequently be advantageous to employ Ig switch sequences of the same species as the transgenic non-human animal. Furthermore, interferon (IFN) inducible transcriptional regulatory elements, such as IFN-inducible enhancers, are preferably included immediately upstream of transgene switch sequences.

In addition to promoters, other regulatory sequences which function primarily in B-lineage cells are used. Thus, for example, a light chain enhancer sequence situated preferably between the J and constant region gene segments on the light chain transgene is used to enhance transgene expression, thereby facilitating allelic exclusion. In the case of the heavy chain transgene, regulatory enhancers and also employed. Such regulatory sequences are used to maximize the transcription and translation of the transgene so as to induce allelic exclusion and to provide relatively high levels of transgene expression.

Although the foregoing promoter and enhancer regulatory control sequences have been generically described, such regulatory sequences may be heterologous to the nonhuman animal being derived from the genomic DNA from which the heterologous transgene immunoglobulin gene segments are obtained. Alternately, such regulatory gene segments are derived from the corresponding regulatory sequences in the genome of the non-human animal, or closely related species, which contains the heavy and light transgene.

In the preferred embodiments, gene segments are derived from human beings. The transgenic non-human animals harboring such heavy and light transgenes are capable of mounting an Ig-mediated immune response to a specific antigen administered to such an animal. B-cells are produced within such an animal which are capable of producing heterologous human antibody. After immortalization, and the selection for an appropriate monoclonal antibody (Mab), e.g. a hybridoma, a source of therapeutic human monoclonal antibody is provided. Such human Mabs have significantly reduced immunogenicity when therapeutically administered to humans.

Although the preferred embodiments disclose the construction of heavy and light transgenes containing human gene segments, the invention is not so limited. In this regard, it is to be understood that the teachings described herein may be readily adapted to utilize immunoglobulin gene segments from a species other than human beings. For example, in addition to the therapeutic treatment of humans with the antibodies of the invention, therapeutic antibodies encoded by appropriate gene segments may be utilized to generate monoclonal antibodies for use in the veterinary sciences.

Rearranged Transgenes

In an alternative embodiment, transgenic nonhuman animals contain functionally at least one rearranged heterologous heavy chain immunoglobulin transgene in the germline of the transgenic animal. Such animals contain primary repertoire B-cells that express such rearranged heavy transgenes. Such B-cells preferably are capable of undergoing somatic mutation when contacted with an antigen to form a heterologous antibody having high affinity and specificity for the antigen. Said rearranged transgenes will contain at least two $C_H$ genes and the associated sequences required for isotype switching.

The invention also includes transgenic animals containing germ line cells having heavy and light transgenes wherein one of the said transgenes contains rearranged gene segments with the other containing unrearranged gene segments. In such animals, the heavy chain transgenes shall have at least two $C_H$ genes and the associated sequences required for isotype switching.

The invention further includes methods for generating a synthetic variable region gene segment repertoire to be used in the transgenes of the invention. The method comprises generating a population of immunoglobulin V segment DNAs wherein each of the V segment DNAs encodes an immunoglobulin V segment and contains at each end a cleavage recognition site of a restriction endonuclease. The population of immunoglobulin V segment DNAs is thereafter concatenated to form the synthetic immunoglobulin V segment repertoire. Such synthetic variable region heavy chain transgenes shall have at least two $C_H$ genes and the associated sequences required for isotype switching.

Isotype Switching

In the development of a B lymphocyte, the cell initially produces IgM with a binding specificity determined by the productively rearranged $V_H$ and $V_L$ regions. Subsequently, each B cell and its progeny cells synthesize antibodies with the same L and H chain V regions, but they may switch the isotype of the H chain.

The use of $\mu$ or $\delta$ constant regions is largely determined by alternate splicing, permitting IgM and IgD to be coexpressed in a single cell. The other heavy chain isotypes ($\gamma$, $\alpha$, and $\epsilon$) are only expressed natively after a gene rearrangement event deletes the $C\mu$ and $C\delta$ exons. This gene rearrangement process, termed isotype switching, typically occurs by recombination between so called switch segments located immediately upstream of each heavy chain gene (except $\delta$). The individual switch segments are between 2 and 10 kb in length, and consist primarily of short repeated sequences. The exact point of recombination differs for individual class switching events. Investigations which have used solution hybridization kinetics or Southern blotting with cDNA-derived $C_H$ probes have confirmed that switching can be associated with loss of $C_H$ sequences from the cell.

The switch (S) region of the $\mu$ gene, $S_\mu$, is located about 1 to 2 kb 5' to the coding sequence and is composed of numerous tandem repeats of sequences of the form $(GAGCT)_n(GGGGT)$, where n is usually 2 to 5 but can range as high as 17. (See T. Nikaido et al. Nature 292:845–848 (1981))

Similar internally repetitive switch sequences spanning several kilobases have been found 5' of the other $C_H$ genes. The $S_\alpha$ region has been sequenced and found to consist of tandemly repeated 80-bp homology units, whereas murine $S_{\gamma 2a}$, $S_{\gamma 2b}$, and $S_{\gamma 3}$ all contain repeated 49-bp homology units very similar to each other. (See, P. Szurek et al., J. Immunol 135:620–626 (1985) and T. Nikaido et al., J. Biol. Chem. 257:7322–7329 (1982), which are incorporated herein by reference.) All the sequenced S regions include numerous occurrences of the pentamers GAGCT and GGGGT that are the basic repeated elements of the $S_\mu$ gene (T. Nikaido et al., J. Biol. Chem. 257:7322–7329 (1982) which is incorporated herein by reference); in the other S regions these pentamers are not precisely tandemly repeated as in $S_\mu$, but instead are embedded in larger repeat units. The $S_{\gamma 1}$ region has an additional higher-order structure: two direct repeat sequences flank each of two clusters of 49-bp tandem repeats. (See M. R. Mowatt et al., J. Immunol. 136:2674–2683 (1986), which is incorporated herein by reference).

Switch regions of human H chain genes have been found to be very similar to their mouse homologs. Indeed, similarity between pairs of human and mouse clones 5' to the $C_H$ genes has been found to be confined to the S regions, a fact that confirms the biological significance of these regions.

A switch recombination between $\mu$ and $\alpha$ genes produces a composite $S_\mu$–$S_\alpha$ sequence. Typically, there is no specific site, either in $S_\mu$ or in any other S region, where the recombination always occurs.

Generally, unlike the enzymatic machinery of V-J recombination, the switch machinery can apparently accommodate different alignments of the repeated homologous regions of germline S precursors and then join the sequences at different positions within the alignment. (See, T. H. Rabbits et al., NucleicAcids Res. 9:4509–4524 (1981) and J. Ravetch et al., Proc. Natl. Acad. Sci. USA 77:6734–6738 (1980), which are incorporated herein by reference.)

The exact details of the mechanism(s) of selective activation of switching to a particular isotype are unknown. Although exogenous influences such as lymphokines and cytokines might upregulate isotype-specific recombinases, it is also possible that the same enzymatic machinery catalyzes switches to all isotypes and that specificity lies in targeting this machinery to specific switch regions.

The T-cell-derived lymphokines IL-4 and $IFN_\gamma$ have been shown to specifically promote the expression of certain isotypes: in the mouse, IL-4 decreases IgM, IgG2a, IgG2b, and IgG3 expression and increases IgE and IgG1 expression; while IFN$_\gamma$ selectively stimulates IgG2a expression and antagonizes the IL-4-induced increase in IgE and IgG1 expression (Coffman et al., *J. Immunol.* 136: 949 (1986) and Snapper et al., *Science* 236: 944 (1987), which are incorporated herein by reference). A combination of IL-4 and IL-5 promotes IgA expression (Coffman et al., *J. Immunol.* 139: 3685 (1987), which is incorporated herein by reference).

Most of the experiments implicating T-cell effects on switching have not ruled out the possibility that the observed increase in cells with particular switch recombinations might reflect selection of preswitched or precommitted cells; but the most likely explanation is that the lymphokines actually promote switch recombination.

Induction of class switching appears to be associated with sterile transcripts that initiate upstream of the switch segments (Lutzker et al., *Mol. Cell. Biol.* 8:1849 (1988); Stavnezer et al., *Proc. Natl. Acad. Sci. USA* 85:7704 (1988); Esser and Radbruch, *EMBO J.* 8:483 (1989); Berton et al., *Proc. Natl. Acad. Sci. USA* 86:2829 (1989); Rothman et al., *Int. Immunol.* 2:621 (1990), each of which is incorporated by reference). For example, the observed induction of the γ1 sterile transcript by IL-4 and inhibition by IFN-γ correlates with the observation that IL-4 promotes class switching to γ1 in B-cells in culture, while IFN-γ inhibits γ1 expression. Therefore, the inclusion of regulatory sequences that affect the transcription of sterile transcripts may also affect the rate of isotype switching. For example, increasing the transcription of a particular sterile transcript typically can be expected to enhance the frequency of isotype switch recombination involving adjacent switch sequences.

For these reasons, it is preferable that transgenes incorporate transcriptional regulatory sequences within about 1–2 kb upstream of each switch region that is to be utilized for isotype switching. These transcriptional regulatory sequences preferably include a promoter and an enhancer element, and more preferably include the 5' flanking (i.e., upstream) region that is naturally associated (i.e., occurs in germline configuration) with a switch region. This 5' flanking region is typically about at least 50 nucleotides in length, preferably about at least 200 nucleotides in length, and more preferably at least 500–1000 nucleotides.

Although a 5' flanking sequence from one switch region can be operably linked to a different switch region for transgene construction (e.g., a 5' flanking sequence from the human S$_{\gamma 1}$ switch can be grafted immediately upstream of the S$_{\alpha 1}$ switch; a murine S$_{\gamma 1}$ flanking region can be grafted adjacent to a human γ1 switch sequence; or the murine S$_{\gamma 1}$ switch can be grafted onto the human γ1 coding region), in some embodiments it is preferred that each switch region incorporated in the transgene construct have the 5' flanking region that occurs immediately upstream in the naturally occurring germline configuration.

Monoclonal Antibodies

Monoclonal antibodies can be obtained by various techniques familiar to those skilled in the art. Briefly, spleen cells from an animal immunized with a desired antigen are immortalized, commonly by fusion with a myeloma cell (see, Kohler and Milstein, *Eur. J. Immunol.*, 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Various techniques useful in these arts are discussed, for example, in Harlow and Lane, *Antibodies: A Laboratory Manual*, Cold Spring Harbor, N.Y. (1988) including: immunization of animals to produce immunoglobulins; production of monoclonal antibodies; labeling immunoglobulins for use as probes; immunoaffinity purification; and immunoassays.

The Transgenic Primary Repertoire

A. The Human Immunoglobulin Loci

An important requirement for transgene function is the generation of a primary antibody repertoire that is diverse enough to trigger a secondary immune response for a wide range of antigens. The rearranged heavy chain gene consists of a signal peptide exon, a variable region exon and a tandem array of multi-domain constant region regions, each of which is encoded by several exons. Each of the constant region genes encode the constant portion of a different class of immunoglobulins. During B-cell development, V region proximal constant regions are deleted leading to the expression of new heavy chain classes. For each heavy chain class, alternative patterns of RNA splicing give rise to both transmembrane and secreted immunoglobulins.

The human heavy chain locus is estimated to consist of approximately 200 V gene segments (current data supports the existence of about 50–100 V gene segments) spanning 2 Mb, approximately 30 D gene segments spanning about 40 kb, six J segments clustered within a 3 kb span, and nine constant region gene segments spread out over approximately 300 kb. The entire locus spans approximately 2.5 Mb of the distal portion of the long arm of chromosome 14.

B. Gene Fragment Transgenes

1. Heavy Chain Transgene

In a preferred embodiment, immunoglobulin heavy and light chain transgenes comprise unrearranged genomic DNA from humans. In the case of the heavy chain, a preferred transgene comprises a NotI fragment having a length between 670 to 830 kb. The length of this fragment is ambiguous because the 3' restriction site has not been accurately mapped. It is known, however, to reside between the α1 and ψα gene segments. This fragment contains members of all six of the known V$_H$ families, the D and J gene segments, as well as the μ, δ, γ3, γ1 and α1 constant regions (Berman et al., *EMBO J.* 7:727–738 (1988), which is incorporated herein by reference). A transgenic mouse line containing this transgene correctly expresses a heavy chain class required for B-cell development (IgM) and at least one switched heavy chain class (IgG$_1$), in conjunction with a sufficiently large repertoire of variable regions to trigger a secondary response for most antigens.

2. Light Chain Transgene

A genomic fragment containing all of the necessary gene segments and regulatory sequences from a human light chain locus may be similarly constructed. Such transgenes are constructed as described in the Examples and in copending application, entitled "Transgenic Non-Human Animals Capable of Producing Heterologous Antibodies," filed Aug. 29, 1990, under U.S. Ser. No. 07/574,748.

C. Transgenes Generated Intracellularly by In Vivo Recombination

It is not necessary to isolate the all or part of the heavy chain locus on a single DNA fragment. Thus, for example, the 670–830 kb NotI fragment from the human immunoglobulin heavy chain locus may be formed in vivo in the non-human animal during transgenesis. Such in vivo transgene construction is produced by introducing two or more overlapping DNA fragments into an embryonic nucleus of the non-human animal. The overlapping portions of the DNA fragments have DNA sequences which are substantially homologous. Upon exposure to the recombinases contained within the embryonic nucleus, the overlapping DNA fragments homologously recombined in proper orientation to form the 670–830 kb NotI heavy chain fragment.

In vivo transgene construction can be used to form any number of immunoglobulin transgenes which because of their size are otherwise difficult, or impossible, to make or manipulate by present technology. Thus, in vivo transgene construction is useful to generate immunoglobulin transgenes which are larger than DNA fragments which may be manipulated by YAC vectors (Murray and Szostak, Nature 305:189–193 (1983)). Such in vivo transgene construction may be used to introduce into a non-human animal substantially the entire immunoglobulin loci from a species not consisting of the transgenic non-human animal.

In addition to forming genomic immunoglobulin transgenes, in vivo homologous recombination may also be utilized to form "mini-locus" transgenes as described in the Examples.

In the preferred embodiments utilizing in vivo transgene construction, each overlapping DNA fragment preferably has an overlapping substantially homologous DNA sequence between the end portion of one DNA fragment and the end portion of a second DNA fragment. Such overlapping portions of the DNA fragments preferably comprise about 500 bp to about 2000 bp, most preferably 1.0 kb to 2.0 kb. Homologous recombination of overlapping DNA fragments to form transgenes in vivo is further described in commonly assigned U.S. patent application entitled "Intracellular Generation of DNA by Homologous Recombination of DNA Fragments" filed Aug. 29, 1990, under U.S. Ser. No. 07/574,747.

D. Minilocus Transgenes

As used herein, the term "immunoglobulin minilocus" refers to a DNA sequence (which may be within a longer sequence), usually of less than about 150 kb, typically between about 25 and 100 kb, containing at least one each of the following: a functional variable (V) gene segment, a functional joining (J) region segment, at least one functional constant (C) region gene segment, and—if it is a heavy chain minilocus—a functional diversity (D) region segment, such that said DNA sequence contains at least one substantial discontinuity (e.g., a deletion, usually of at least about 2 to 5 kb, preferably 10–25 kb or more, relative to the homologous genomic DNA sequence). A light chain minilocus transgene will be at least 25 kb in length, typically 50 to 60 kb. A heavy chain transgene will typically be about 70 to 80 kb in length, preferably at least about 60 kb with two constant regions operably linked to switch regions. Furthermore, the individual elements of the minilocus are preferably in the germline configuration and capable of undergoing gene rearrangement in the pre-B cell of a transgenic animal so as to express functional antibody molecules with diverse antigen specificities encoded entirely by the elements of the minilocus. Further, a heavy chain minilocus comprising at least two $C_H$ genes and the requisite switching sequences is typically capable of undergoing isotype switching, so that functional antibody molecules of different immunoglobulin classes will be generated. Such isotype switching may occur in vivo in B-cells residing within the transgenic nonhuman animal, or may occur in cultured cells of the B-cell lineage which have been explanted from the transgenic nonhuman animal.

In an alternate preferred embodiment, immunoglobulin heavy chain transgenes comprise one or more of each of the $V_H$, D, and $J_H$ gene segments and two or more of the $C_H$ genes. At least one of each appropriate type gene segment is incorporated into the minilocus transgene. With regard to the $C_H$ segments for the heavy chain transgene, it is preferred that the transgene contain at least one μ gene segment and at least one other constant region gene segment, more preferably a γ gene segment, and most preferably γ3 or γ1. This preference is to allow for class switching between IgM and IgG forms of the encoded immunoglobulin and the production of a secretable form of high affinity non-IgM immunoglobulin. Other constant region gene segments may also be used such as those which encode for the production of IgD, IgA and IgE.

Those skilled in the art will also construct transgenes wherein the order of occurrence of heavy chain $C_H$ genes will be different from the naturally-occurring spatial order found in the germline of the species serving as the donor of the $C_H$ genes.

Additionally, those skilled in the art can select $C_H$ genes from more than one individual of a species (e.g., allogeneic $C_H$ genes) and incorporate said genes in the transgene as supernumerary $C_H$ genes capable of undergoing isotype switching; the resultant transgenic nonhuman animal may then, in some embodiments, make antibodies of various classes including all of the allotypes represented in the species from which the transgene $C_H$ genes were obtained.

Still further, those skilled in the art can select $C_H$ genes from different species to incorporate into the transgene. Functional switch sequences are included with each $C_H$ gene, although the switch sequences used are not necessarily those which occur naturally adjacent to the $C_H$ gene. Interspecies $C_H$ gene combinations will produce a transgenic nonhuman animal which may produce antibodies of various classes corresponding to $C_H$ genes from various species. Transgenic nonhuman animals containing interspecies $C_H$ transgenes may serve as the source of B-cells for constructing hybridomas to produce monoclonals for veterinary uses.

The heavy chain J region segments in the human comprise six functional J segments and three pseudo genes clustered in a 3 kb stretch of DNA. Given its relatively compact size and the ability to isolate these segments together with the μ gene and the 5' portion of the δ gene on a single 23 kb SFiI/SpeI fragment (Sado et al., Biochem. Biophys. Res. Comm. 154:264271 (1988), which is incorporated herein by reference), it is preferred that all of the J region gene segments be used in the mini-locus construct. Since this fragment spans the region between the μ and δ genes, it is likely to contain all of the 3' cis-linked regulatory elements required for μ expression. Furthermore, because this fragment includes the entire J region, it contains the heavy chain enhancer and the μ switch region (Mills et al., Nature 306:809 (1983); Yancopoulos and Alt, Ann. Rev. Immunol. 4:339–368 (1986), which are incorporated herein by reference). It also contains the transcription start sites which trigger VDJ joining to form primary repertoire B-cells (Yancopoulos and Alt, Cell 40:271–281 (1985), which is incorporated herein by reference). Alternatively, a 36 kb BssHII/SpeI1 fragment, which includes part on the D region, may be used in place of the 23 kb SfiI/SpeI1 fragment. The use of such a fragment increases the amount of 5' flanking sequence to facilitate efficient D-to-J joining.

Figure 4:
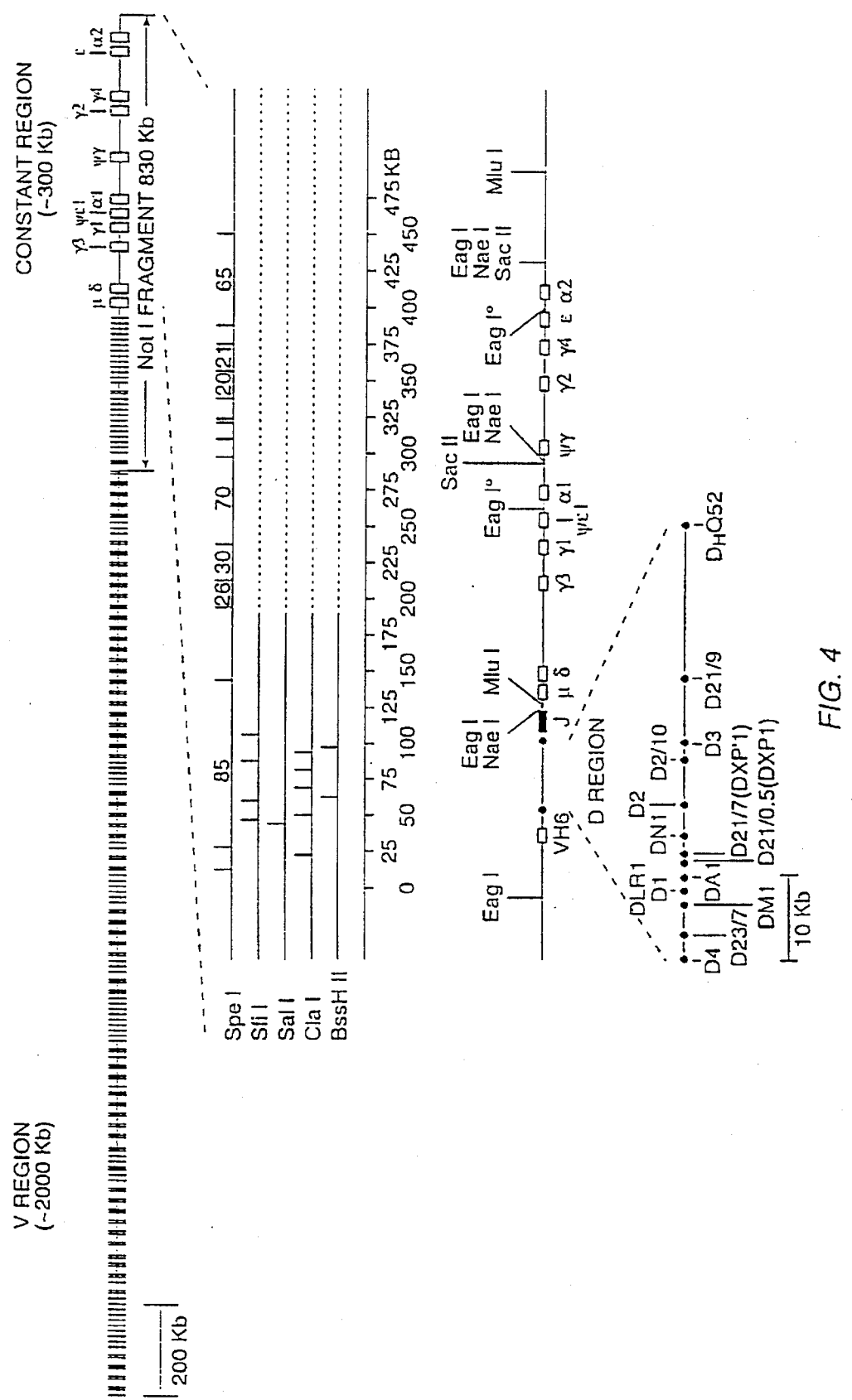
FIG. 4 depicts the human heavy chain locus.
Figure 5:
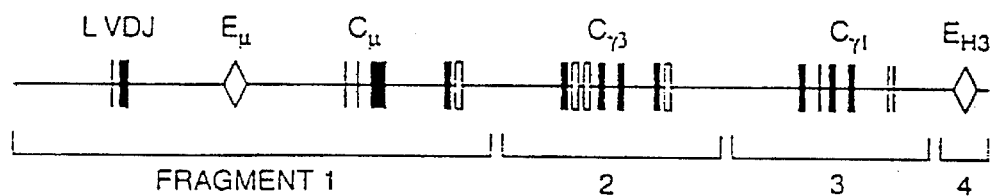
FIG. 5 depicts a transgene construct containing a rearranged IgM gene ligated to a 25 kb fragment that contains human γ3 and γ1 constant regions followed by a 700 bp fragment containing the rat chain 3' enhancer sequence.
Figure 6:
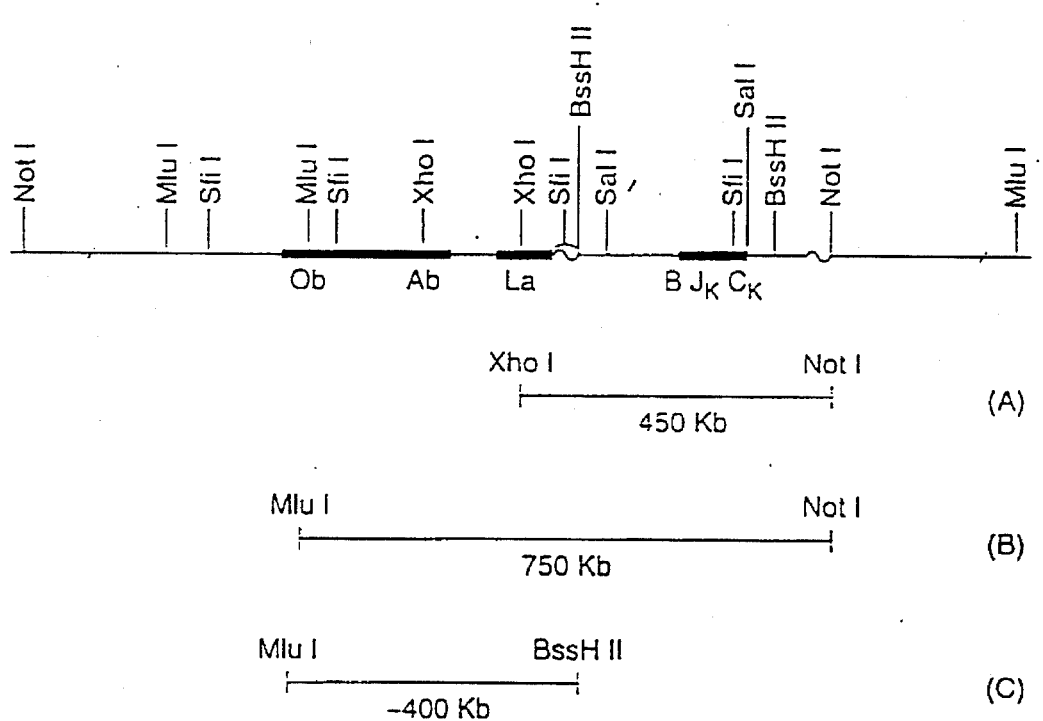
FIG. 6 is a restriction map of the human κ chain locus depicting the fragments to be used to form a light chain transgene by way of in vivo homologous recombination.
Figure 7:
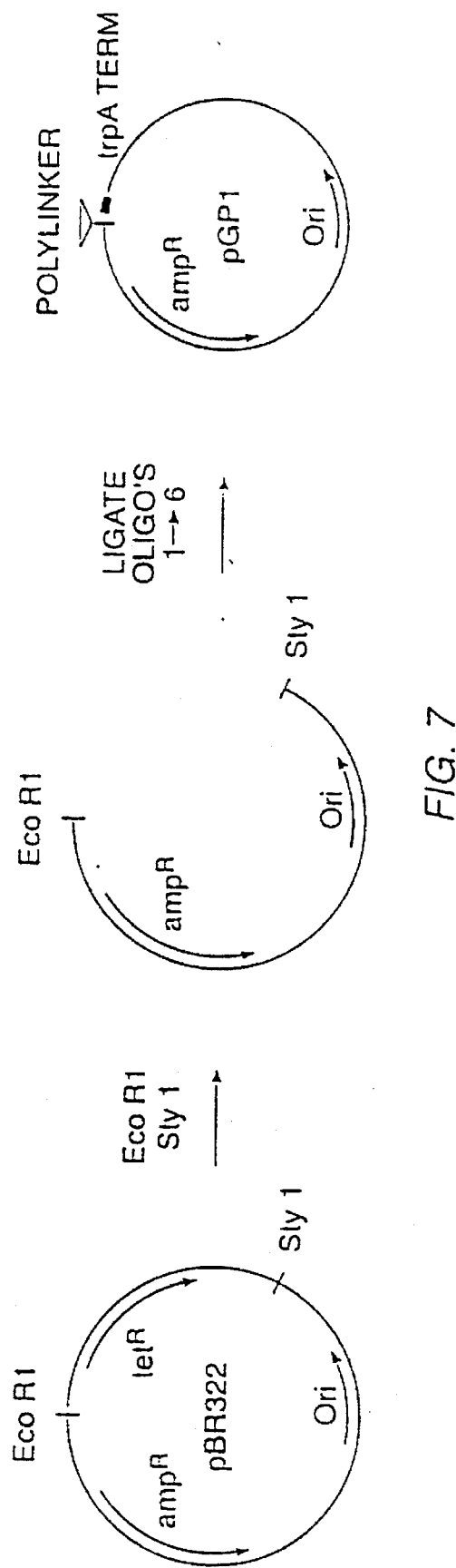
FIG. 7 depicts the construction of pGP1.

The human D region consists of 4 homologous 9 kb subregions, linked in tandem (Siebenlist, et al. (1981), Nature, 294, 631–635). Each subregion contains up to 10 individual D segments. Some of these segments have been mapped and are shown in FIG. 4. Two different strategies are used to generate a mini-locus D region. The first strategy involves using only those D segments located in a short contiguous stretch of DNA that includes one or two of the repeated D subregions. A candidate is a single 15 kb fragment that contains 12 individual D segments. This piece of DNA consists of 2 contiguous EcoRI fragments and has been completely sequenced (Ichihara, et al. (1988), *EMBO J.*, 7, 4141–4150). Twelve D segments should be sufficient for a primary repertoire. However, given the dispersed nature of the D region, an alternative strategy is to ligate together several non-contiguous D-segment containing fragments, to produce a smaller piece of DNA with a greater number of segments. Additional D-segment genes can be identified, for example, by the presence of characteristic flanking nonamer and heptamer sequences, supra, and by reference to the literature.

At least one, and preferably more than one V gene segment is used to construct the heavy chain minilocus transgene. Rearranged or unrearranged V segments with or without flanking sequences can be isolated as described in copending applications, U.S. Ser. No. 07/574,748 filed Aug. 29, 1990, PCT/US91/06185 filed Aug. 28, 1991, and U.S. Ser. No. 07/810,279 filed Dec. 17, 1991, each of which is incorporated herein by reference.

Rearranged or unrearranged V segments, D segments, J segments, and C genes, with or without flanking sequences, can be isolated as described in copending applications U.S. Ser. No. 07/574,748 filed Aug. 29, 1990 and PCT/US91/06185 filed Aug. 28, 1991.

A minilocus light chain transgene may be similarly constructed from the human λ or κ immunoglobulin locus. Thus, for example, an immunoglobulin heavy chain minilocus transgene construct, e.g., of about 75 kb, encoding V, D, J and constant region sequences can be formed from a plurality of DNA fragments, with each sequence being substantially homologous to human gene sequences. Preferably, the sequences are operably linked to transcription regulatory sequences and are capable of undergoing rearrangement. With two or more appropriately placed constant region sequences (e.g., μ and γ) and switch regions, switch recombination also occurs. An exemplary light chain transgene construct can be formed similarly from a plurality of DNA fragments, substantially homologous to human DNA and capable of undergoing rearrangement, as described in copending application, U.S. Ser. No. 07/574,748 filed Aug. 29, 1990.

E. Transgene Constructs Capable of Isotype Switching

Ideally, transgene constructs that are intended to undergo class switching should include all of the cis-acting sequences necessary to regulate sterile transcripts. Naturally occurring switch regions and upstream promoters and regulatory sequences (e.g., IFN-inducible elements) are preferred cis-acting sequences that are included in transgene constructs capable of isotype switching. About at least 50 basepairs, preferably about at least 200 basepairs, and more preferably at least 500 to 1000 basepairs or more of sequence immediately upstream of a switch region, preferably a human γ1 switch region, should be operably linked to a switch sequence, preferably a human γ1 switch sequence. Further, switch regions can be linked upstream of (and adjacent to) $C_H$ genes that do not naturally occur next to the particular switch region. For example, but not for limitation, a human $\gamma_1$ switch region may be linked upstream from a human $\alpha_2$ $C_H$ gene, or a murine $\gamma_1$ switch may be linked to a human $C_H$ gene.

An alternative method for obtaining non-classical isotype switching (e.g., δ-associated deletion) in transgenic mice involves the inclusion of the 400 bp direct repeat sequences (σμ and εμ) that flank the human μ gene (Yasui et al., *Eur. J. Immunol.* 19:1399 (1989)). Homologous recombination between these two sequences deletes the μ gene in IgD-only B-cells. Heavy chain transgenes can be represented by the following formulaic description:

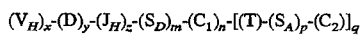

where:

$V_H$ is a heavy chain variable region gene segment,

D is a heavy chain D (diversity) region gene segment, $J_H$ is a heavy chain J (joining) region gene segment, $S_D$ is a donor region segment capable of participating in a recombination event with the $S_a$ acceptor region segments such that isotype switching occurs, $C_1$ is a heavy chain constant region gene segment encoding an isotype utilized in for B cell development (e.g., μ or δ), T is a cis-acting transcriptional regulatory region segment containing at least a promoter, $S_A$ is an acceptor region segment capable of participating in a recombination event with selected $S_D$ donor region segments, such that isotype switching occurs, $C_2$ is a heavy chain constant region gene segment encoding an isotype other than μ (e.g., $\gamma_1$, $\gamma_2$, $\gamma_3$, $\gamma_4$, $\alpha_1$, $\alpha_2$, ε).

x, y, z, m, n, p, and q are integers. x is 1–100, n is 0–10, y is 1–50, p is 1–10, z is 1–50, q is 0–50, m is 0–10. Typically, when the transgene is capable of isotype switching, q must be at least 1, m is at least 1, n is at least 1, and m is greater than or equal to n.

$V_H$, D, $J_H$, $S_D$, $C_1$, T, $S_A$, and $C_2$ segments may be selected from various species, preferably mammalian species, and more preferably from human and murine germline DNA.

$V_H$ segments may be selected from various species, but are preferably selected from $V_H$ segments that occur naturally in the human germline, such as $V_{H251}$. Typically about 2 $V_H$ gene segments are included, preferably about 4 $V_H$ segments are included, and most preferably at least about 10 $V_H$ segments are included.

At least one D segment is typically included, although at least 10 D segments are preferably included, and some embodiments include more than ten D segments. Some preferred embodiments include human D segments.

Typically at least one $J_H$ segment is incorporated in the transgene, although it is preferable to include about six $J_H$ segments, and some preferred embodiments include more than about six $J_H$ segments. Some preferred embodiments include human $J_H$ segments, and further preferred embodiments include six human $J_H$ segments and no nonhuman $J_H$ segments.

$S_D$ segments are donor regions capable of participating in recombination events with the $S_A$ segment of the transgene. For classical isotype switching, $S_D$ and $S_A$ are switch regions such as $S_\mu$, $S_{\gamma 1}$, $S_{\gamma 2}$, $S_{\gamma 3}$, $S_{\gamma 4}$, $S_\alpha$, $S_{\alpha 2}$, and $S_\epsilon$. Preferably the switch regions are murine or human, more preferably $S_D$ is a human or murine $S_\mu$ and $S_A$ is a human or murine $S_{\gamma 1}$. For nonclassical isotype switching (δ-associated deletion), $S_D$ and $S_A$ are preferably the 400 basepair direct repeat sequences that flank the human μ gene.

$C_1$ segments are typically μ or δ genes, preferably a μ gene, and more preferably a human or murine μ gene.

T segments typically include 5' flanking sequences that are adjacent to naturally occurring (i.e., germline) switch regions. T segments typically at least about at least 50 nucleotides in length, preferably about at least 200 nucleotides in length, and more preferably at least 500–1000 nucleotides in length. Preferably T segments are 5' flanking sequences that occur immediately upstream of human or murine switch regions in a germline configuration. It is also evident to those of skill in the art that T segments may comprise cis-acting transcriptional regulatory sequences that do not occur naturally in an animal germline (e.g., viral enhancers and promoters such as those found in SV40, adenovirus, and other viruses that infect eukaryotic cells).

$C_2$ segments are typically a $\gamma_1$, $\gamma_2$, $\gamma_3$, $\gamma_4$, $\alpha_1$, $\alpha_2$, or $\epsilon$ $C_H$ gene, preferably a human $C_H$ gene of these isotypes, and more preferably a human $\gamma_1$ or $\gamma_3$ gene. Murine $\gamma_{2a}$ and $\gamma_{2b}$ may also be used, as may downstream (i.e., switched) isotype genes form various species. Where the heavy chain transgene contains an immunoglobulin heavy chain minilocus, the total length of the transgene will be typically 150 kilo basepairs or less.

In general, the transgene will be other than a native heavy chain Ig locus. Thus, for example, deletion of unnecessary regions or substitutions with corresponding regions from other species will be present.

F. Methods for Determining Functional Isotype Switching in Ig Transgenes

The occurrence of isotype switching in a transgenic nonhuman animal may be identified by any method known to those in the art. Preferred embodiments include the following, employed either singly or in combination:

1. detection of mRNA transcripts that contain a sequence homologous to at least one transgene downstream $C_H$ gene other than $\delta$ and an adjacent sequence homologous to a transgene $V_H$-$D_H$-$J_H$ rearranged gene; such detection may be by Northern hybridization, $S_1$ nuclease protection assays, PCR amplification, cDNA cloning, or other methods;

2. detection in the serum of the transgenic animal, or in supernatants of cultures of hybridoma cells made from B-cells of the transgenic animal, of immunoglobulin proteins encoded by downstream $C_H$ genes, where such proteins can also be shown by immunochemical methods to comprise a functional variable region;

3. detection, in DNA from B-cells of the transgenic animal or in genomic DNA from hybridoma cells, of DNA rearrangements consistent with the occurrence of isotype switching in the transgene, such detection may be accomplished by Southern blot hybridization, PCR amplification, genomic cloning, or other method; or 4. identification of other indicia of isotype switching, such as production of sterile transcripts, production of characteristic enzymes involved in switching (e.g., "switch recombinase"), or other manifestations that may be detected, measured, or observed by contemporary techniques.

Because each transgenic line may represent a different site of integration of the transgene, and a potentially different tandem array of transgene inserts, and because each different configuration of transgene and flanking DNA sequences can affect gene expression, it is preferable to identify and use lines of mice that express high levels of human immunoglobulins, particularly of the IgG isotype, and contain the least number of copies of the transgene. Single copy transgenics minimize the potential problem of incomplete allelic expression. Transgenes are typically integrated into host chromosomal DNA, most usually into germline DNA and propagated by subsequent breeding of germline transgenic breeding stock animals. However, other vectors and transgenic methods known in the present art or subsequently developed may be substituted as appropriate and as desired by a practitioner.

G. Functional Disruption of Endogenous Immunoglobulin Loci

The expression of successfully rearranged immunoglobulin heavy and light transgenes is expected to have a dominant effect by suppressing the rearrangement of the endogenous immunoglobulin genes in the transgenic nonhuman animal. However, another way to generate a nonhuman that is devoid of endogenous antibodies is by mutating the endogenous immunoglobulin loci. Using embryonic stem cell technology and homologous recombination, the endogenous immunoglobulin repertoire can be readily eliminated. The following describes the functional description of the mouse immunoglobulin loci. The vectors and methods disclosed, however, can be readily adapted for use in other non-human animals.

Briefly, this technology involves the inactivation of a gene, by homologous recombination, in a pluripotent cell line that is capable of differentiating into germ cell tissue. A DNA construct that contains an altered, copy of a mouse immunoglobulin gene is introduced into the nuclei of embryonic stem cells. In a portion of the cells, the introduced DNA recombines with the endogenous copy of the mouse gene, replacing it with the altered copy. Cells containing the newly engineered genetic lesion are injected into a host mouse embryo, which is reimplanted into a recipient female. Some of these embryos develop into chimeric mice that possess germ cells entirely derived from the mutant cell line. Therefore, by breeding the chimeric mice it is possible to obtain a new line of mice containing the introduced genetic lesion (reviewed by Capecchi (1989), *Science*, 244, 1288–1292).

Because the mouse $\lambda$ locus contributes to only 5% of the immunoglobulins, inactivation of the heavy chain and/or $\kappa$-light chain loci is sufficient. There are three ways to disrupt each of these loci, deletion of the J region, deletion of the J-C intron enhancer, and disruption of constant region coding sequences by the introduction of a stop codon. The last option is the most straightforward, in terms of DNA construct design. Elimination of the $\mu$ gene disrupts B-cell maturation thereby preventing class switching to any of the functional heavy chain segments. The strategy for knocking out these loci is outlined below.

To disrupt the mouse $\mu$ and $\kappa$ genes, targeting vectors are used based on the design employed by Jaenisch and co-workers (Zijlstra, et al. (1989), *Nature*, 342, 435–438) for the successful disruption of the mouse $\beta$2-microglobulin gene. The neomycin resistance gene (neo), from the plasmid pMCIneo is inserted into the coding region of the target gene. The pMCIneo insert uses a hybrid viral promoter/enhancer sequence to drive neo expression. This promoter is active in embryonic stem cells. Therefore, neo can be used as a selectable marker for integration of the knock-out construct. The HSV thymidine kinase (tk) gene is added to the end of the construct as a negative selection marker against random insertion events (Zijlstra, et al., supra.).

A preferred strategy for disrupting the heavy chain locus is the elimination of the J region. This region is fairly compact in the mouse, spanning only 1.3 kb. To construct a gene targeting vector, a 15 kb KpnI fragment containing all of the secreted A constant region exons from mouse genomic library is isolated. The 1.3 kb J region is replaced with the 1.1 kb insert from pMCIneo. The HSV tk gene is then added to the 5' end of the KpnI fragment. Correct integration of this construct, via homologous recombination, will result in the replacement of the mouse $J_H$ region with the neogene. Recombinants are screened by PCR, using a primer based on the neogene and a primer homologous to mouse sequences 5' of the KpnI site in the D region.

Alternatively, the heavy-chain locus is knocked out by disrupting the coding region of the µ gene. This approach involves the same 15 kb KpnI fragment used in the previous approach. The 1.1 kb insert from pMCIneo is inserted at a unique BamHI site in exon II, and the HSV tk gene added to the 3' KpnI end. Double crossover events on either side of the neo insert, that eliminate the tk gene, are then selected for. These are detected from pools of selected clones by PCR amplification. One of the PCR primers is derived from neo sequences and the other from mouse sequences outside of the targeting vector. The functional disruption of the mouse immunoglobulin loci is presented in the Examples.

G. Suppressing Expression of Endogenous Immunoglobulin Loci

In addition to functional disruption of endogenous Ig loci, an alternative method for preventing the expression of an endogenous Ig locus is suppression. Suppression of endogenous Ig genes may be accomplished with antisense RNA produced from one or more integrated transgenes, by antisense oligonucleotides, and/or by administration of antisera specific for one or more endogenous Ig chains.

Antisense Polynucleotides

Antisense RNA transgenes can be employed to partially or totally knock-out expression of specific genes (Pepin et al. (1991) *Nature* 355: 725; Helene., C. and Toulme, J. (1990) *Biochimica Biophys. Acta* 1049: 99; Stout, J. and Caskey, T. (1990) *Somat. Cell Mol. Genet.* 16: 369; Munir et al. (1990) *Somat. Cell Mol. Genet.* 16: 383, each of which is incorporated herein by reference).

"Antisense polynucleotides" are polynucleotides that: (1) are complementary to all or part of a reference sequence, such as a sequence of an endogenous Ig $C_H$ or $C_L$ region, and (2) which specifically hybridize to a complementary target sequence, such as a chromosomal gene locus or a Ig mRNA. Such complementary antisense polynucleotides may include nucleotide substitutions, additions, deletions, or transpositions, so long as specific hybridization to the relevant target sequence is retained as a functional property of the polynucleotide. Complementary antisense polynucleotides include soluble antisense RNA or DNA oligonucleotides which can hybridize specifically to individual mRNA species and prevent transcription and/or RNA processing of the mRNA species and/or translation of the encoded polypeptide (Ching et al., *Proc. Natl. Acad. Sci. U.S.A.* 86:10006–10010 (1989); Broder et al., *Ann. Int. Med.* 113:604–618 (1990); Loreau et al., *FEBS Letters* 274:53–56 (1990); Holcenberg et al., WO91/11535; U.S. Ser. No. 07/530,165 ("New human CRIPTO gene"); WO91/09865; WO91/04753; WO90/13641; and EP 386563, each of which is incorporated herein by reference). An antisense sequence is a polynucleotide sequence that is complementary to at least one immunoglobulin gene sequence of at least about 15 contiguous nucleotides in length, typically at least 20 to 30 nucleotides in length, and preferably more than about 30 nucleotides in length. However, in some embodiments, antisense sequences may have substitutions, additions, or deletions as compared to the complementary immunoglobulin gene sequence, so long as specific hybridization is retained as a property of the antisense polynucleotide. Generally, an antisense sequence is complementary to an endogenous immunoglobulin gene sequence that encodes, or has the potential to encode after DNA rearrangement, an immunoglobulin chain. In some cases, sense sequences corresponding to an immunoglobulin gene sequence may function to suppress expression, particularly by interfering with transcription.

The antisense polynucleotides therefore inhibit production of the encoded polypeptide(s). In this regard, antisense polynucleotides that inhibit transcription and/or translation of one or more endogenous Ig loci can alter the capacity and/or specificity of a non-human animal to produce immunoglobulin chains encoded by endogenous Ig loci.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual, or a transgenic non-human animal. Alternatively, the antisense polynucleotides may comprise soluble oligonucleotides that are administered to the external milieu, either in culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties, alternatively phosphorothiolates or O-methylribonucleotides may be used, and chimeric oligonucleotides may also be used (Dagle et al. (1990) *Nucleic Acids Res.* 18: 4751). For some applications, antisense oligonucleotides may comprise polyamide nucleic acids (Nielsen et al. (1991) *Science* 254: 1497). For general methods relating to antisense polynucleotides, see *Antisense RNA and DNA*, (1988), D. A. Melton, Ed., Cold Spring Harbor Laboratory, Cold Spring Harbor, N.Y.).

Antisense polynucleotides complementary to one or more sequences are employed to inhibit transcription, RNA processing, and/or translation of the cognate mRNA species and thereby effect a reduction in the amount of the respective encoded polypeptide. Such antisense polynucleotides can provide a therapeutic function by inhibiting the formation of one or more endogenous Ig chains in vivo.

Whether as soluble antisense oligonucleotides or as antisense RNA transcribed from an antisense transgene, the antisense polynucleotides of this invention are selected so as to hybridize preferentially to endogenous Ig sequences at physiological conditions in vivo. Most typically, the selected antisense polynucleotides will not appreciably hybridize to heterologous Ig sequences encoded by a heavy or light chain transgene of the invention (i.e., the antisense oligonucleotides will not inhibit transgene Ig expression by more than about 25 to 35 percent).

Antiserum Suppression

Partial or complete suppression of endogenous Ig chain expression can be produced by injecting mice with antisera against one or more endogenous Ig chains (Weiss et al. (1984) *Proc. Natl. Acad. Sci. (U.S.A.)* 81 211, which is incorporated herein by reference). Antisera are selected so as to react specifically with one or more endogenous Ig chains but to have minimal or no cross-reactivity with heterologous Ig chains encoded by an Ig transgene of the invention. Thus, administration of selected antisera according to a schedule as typified by that of Weiss et al. op.cit. will suppress endogenous Ig chain expression but permits expression of heterologous Ig chain(s) encoded by a transgene of the present invention.

Complete Endogenous Ig Locus Inactivation

In certain embodiments, it is desirable to effect complete inactivation of the endogenous Ig loci so that hybrid immunoglobulin chains comprising a human variable region and a non-human (e.g., murine) constant region cannot be formed (e.g., by trans-switching between the transgene and endogenous Ig sequences). Knockout mice bearing endogenous heavy chain alleles with are functionally disrupted in the $J_H$ region only frequently exhibit trans-switching, typically wherein a rearranged human variable region (VDJ) encoded by a transgene is expressed as a fusion protein linked to an endogenous murine constant region, although other trans-switched junctions are possible. To overcome this potential problem, it is generally desirable to completely inactivate the endogenous heavy chain locus by any of various methods, including but not limited to the following: (1) functionally disrupting and/or deleting by homologous recombination at least one and preferably all of the endogenous heavy chain constant region genes, (2) mutating at least one and preferably all of the endogenous heavy chain constant region genes to encode a termination codon (or frameshift) to produce a truncated or frameshifted product (if trans-switched), and other methods and strategies apparent to those of skill in the art. Deletion of a substantial portion or all of the heavy chain constant region genes may be accomplished by various methods, including sequential deletion by homologous recombination targeting vectors, especially of the "hit-and-run" type and the like. Similarly, functional disruption and/or deletion of at least one endogenous light chain locus (e.g., κ) to ablate endogenous light chain constant region genes is often preferable.

Specific Preferred Embodiments

A preferred embodiment of the invention is an animal containing at least one, typically 2–10, and sometimes 25–50 or more copies of the transgene described in Example 12 (e.g., pHC1 or pHC2) bred with an animal containing a single copy of a light chain transgene described in Examples 5, 6, 8, or 14, and the offspring bred with the $J_H$ deleted animal described in Example 10. Animals are bred to homozygosity for each of these three traits. Such animals have the following genotype: a single copy (per haploid set of chromosomes) of a human heavy chain unrearranged mini-locus (described in Example 12), a single copy (per haploid set of chromosomes) of a rearranged human κ light chain construct (described in Example 14), and a deletion at each endogenous mouse heavy chain locus that removes all of the functional $J_H$ segments (described in Example 10). Such animals are bred with mice that are homozygous for the deletion of the $J_H$ segments (Examples 10) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Example 9 and 12. Furthermore, a substantial fraction of the B cells will be monospecific with regards to the human or mouse light chains because expression of the single copy of the rearranged human κ light chain gene will allelically and isotypically exclude the rearrangement of the endogenous mouse κ and λ chain genes in a significant fraction of B-cells.

The transgenic mouse of the preferred embodiment will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. Of course, the IgG to IgM ratio will be much lower in the immature mouse. In general, greater than about 10%, preferably 40 to 80% of the spleen and lymph node B cells express exclusively human IgG protein.

The repertoire will ideally approximate that shown in a non-transgenic mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, including, but not limited to: pigeon cytochrome C, chicken lysozyme, pokeweed mitogen, bovine serum albumin, keyhole limpit hemocyanin, influenza hemagglutinin, staphylococcus protein A, sperm whale myoglobin, influenza neuraminidase, and lambda repressor protein. Some of the immunoglobulins will exhibit an affinity for preselected antigens of at least about $10^7 M^{-1}$, preferably $10^8 M^{-1}$ to $10^9 M^{-1}$ or greater.

Thus, prior to rearrangement of a transgene containing various heavy or light chain gene segments, such gene segments may be readily identified, e.g. by hybridization or DNA sequencing, as being from a species of organism other than the transgenic animal.

Although the foregoing describes a preferred embodiment of the transgenic animal of the invention, other embodiments are defined by the disclosure herein and more particularly by the transgenes described in the Examples. Four categories of transgenic animal may be defined:

I. Transgenic animals containing an unrearranged heavy and rearranged light immunoglobulin transgene.

II. Transgenic animals containing an unrearranged heavy and unrearranged light immunoglobulin transgene III. Transgenic animal containing rearranged heavy and an unrearranged light immunoglobulin transgene, and IV. Transgenic animals containing rearranged heavy and rearranged light immunoglobulin transgenes.

Of these categories of transgenic animal, the preferred order of preference is as follows II>I>III>IV where the endogenous light chain genes (or at least the κ gene) have been knocked out by homologous recombination (or other method) and I>II>III>IV where the endogenous light chain genes have not been knocked out and must be dominated by allelic exclusion.

EXPERIMENTAL EXAMPLES

Methods and Materials

Transgenic mice are derived according to Hogan, et al., "Manipulating the Mouse Embryo: A Laboratory Manual", Cold Spring Harbor Laboratory, which is incorporated herein by reference.

Embryonic stem cells are manipulated according to published procedures (Teratocarcinomas and embryonic stem cells: a practical approach, E. J. Robertson, ed., IRL Press, Washington, D.C., 1987; Zjilstra et al., *Nature* 342:435–438 (1989); and Schwartzberg et al., *Science* 246:799–803 (1989), each of which is incorporated herein by reference).

DNA cloning procedures are carried out according to J. Sambrook, et al. in Molecular Cloning: A Laboratory Manual, 2d ed., 1989, Cold Spring Harbor Laboratory Press, Cold Spring Harbor, N.Y., which is incorporated herein by reference.

Oligonucleotides are synthesized on an Applied Bio Systems oligonucleotide synthesizer according to specifications provided by the manufacturer.

Hybridoma cells and antibodies are manipulated according to "Antibodies: A Laboratory Manual", Ed Harlow and David Lane, Cold Spring Harbor Laboratory (1988), which is incorporated herein by reference.

EXAMPLE 1

Genomic Heavy Chain Human Ig Transgene

This Example describes the cloning and microinjection of a human genomic heavy chain immunoglobulin transgene which is microinjected into a murine zygote.

Nuclei are isolated from fresh human placental tissue as described by Marzluff et al., "Transcription and Translation: A Practical Approach", B. D. Hammes and S. J. Higgins, eds., pp. 89–129, IRL Press, Oxford (1985)). The isolated nuclei (or PBS washed human spermatocytes) are embedded in a low melting point agarose matrix and lysed with EDTA and proteinase κ to expose high molecular weight DNA, which is then digested in the agarose with the restriction enzyme NotI as described by M. Finney in Current Protocols in Molecular Biology (F. Ausubel, et al., eds. John Wiley & Sons, Supp. 4, 1988, Section 2.5.1).

The NotI digested DNA is then fractionated by pulsed field gel electrophoresis as described by Anand et al., Nucl. Acids Res. 17:3425–3433 (1989). Fractions enriched for the NotI fragment are assayed by Southern hybridization to detect one or more of the sequences encoded by this fragment. Such sequences include the heavy chain D segments, J segments, μ and γ1 constant regions together with representatives of all 6 VH families (although this fragment is identified as 670 kb fragment from HeLa cells by Berman et al. (1988), supra., we have found it to be as 830 kb fragment from human placental an sperm DNA). Those fractions containing this NotI fragment (see FIG. 4) are pooled and cloned into the NotI site of the vector pYACNN in Yeast cells. Plasmid pYACNN is prepared by digestion of pYAC-4 Neo (Cook et al., Nucleic Acids Res. 16: 11817 (1988)) with EcoRI and ligation in the presence of the oligonucleotide 5' - AAT TGC GGC CGC - 3'.

YAC clones containing the heavy chain NotI fragment are isolated as described by Brownstein et al., Science 244:1348–1351 (1989), and Green et al., Proc. Natl. Acad. Sci. USA 87:1213–1217 (1990), which are incorporated herein by reference. The cloned NotI insert is isolated from high molecular weight yeast DNA by pulse field gel electrophoresis as described by M. Finney, op cit. The DNA is condensed by the addition of 1 mM spermine and microinjected directly into the nucleus of single cell embryos previously described.

EXAMPLE 2

Genomic κ Light Chain Human Ig Transgene Formed by In Vivo Homologous Recombination A map of the human κ light chain has been described in Lorenz et al., Nucl. Acids Res. 15:9667–9677 (1987), which is incorporated herein by reference.

A 450 kb XhoI to NotI fragment that includes all of $C_\kappa$, the 3' enhancer, all J segments, and at least five different V segments is isolated and microinjected into the nucleus of single cell embryos as described in Example 1.

EXAMPLE 3

Genomic κ Light Chain Human Ig Transgene Formed by In Vivo Homologous Recombination A 750 kb MluI to NotI fragment that includes all of the above plus at least 20 more V segments is isolated as described in Example 1 and digested with BssHII to produce a fragment of about 400 kb.

The 450 kb XhoI to NotI fragment plus the approximately 400 kb MluI to BssHII fragment have sequence overlap defined by the BssHII and XhoI restriction sites. Homologous recombination of these two fragments upon microinjection of a mouse zygote results in a transgene containing at least an additional 15-20 V segments over that found in the 450 kb XhoI/NotI fragment (Example 2).

EXAMPLE 4

Construction of Heavy Chain Mini-Locus

Figure 9:
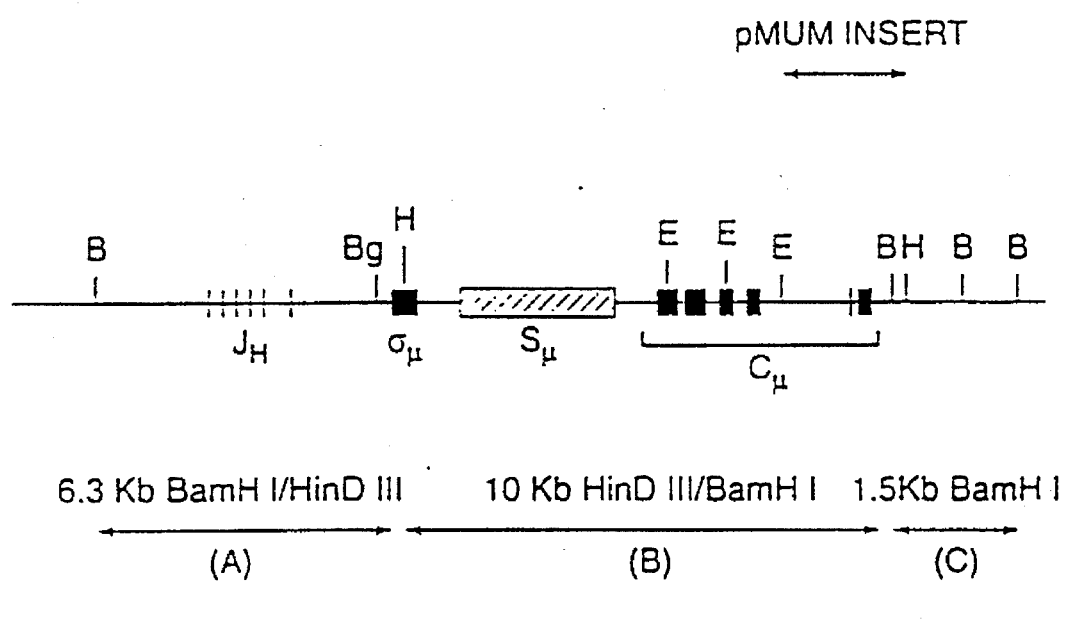
FIG. 9 depicts the fragments used to construct a human heavy chain transgene of the invention.

A. Construction of pGP1 and pGP2 pBR322 is digested with EcoRI and StyI and ligated with the following oligonucleotides to generate pGP1 which contains a 147 base pair insert containing the restriction sites shown in FIG. 8. The general overlapping of these oligos is also shown in FIG. 9.

The oligonucleotides are:

| oligo-1 | 5' - CTT GAG | CCC | GCC | TAA | TGA | GCG | GGC | TTT |
|---------|--------------|-----|-----|-----|-----|-----|-----|-----|
|         | TTT TTG      | CAT | ACT | GCG | GCC | - 3' |     |     |
| oligo-2 | 5' - GCA ATG | GCC | TGG | ATC | CAT | GGC | GCG | CTA |
|         | GCA TCG      | ATA | TCT | AGA | GCT | CGA | GCA | - 3' |
| oligo-3 | 5' - TGC AGA | TCT | GAA | TTC | CCG | GGT | ACC | AAG |
|         | CTT ACG      | CGT | ACT | AGT | GCG | GCC | GCT | - 3' |
| oligo-4 | 5' - AAT TAG | CGG | CCG | CAC | TAG | TAC | GCG | TAA |
|         | GCT TGG      | TAC | CCG | GGA | ATT | - 3' |     |     |
| oligo-5 | 5' - CAG ATC | TGC | ATG | CTC | GAG | CTC | TAG | ATA |
|         | TCG ATG      | CTA | GCG | CGC | CAT | GGA | TCC | - 3' |
| oligo-6 | 5' - AGG CCA | TTG | CGG | CCG | CAG | TAT | GCA | AAA |
|         | AAA AGC      | CCG | CTC | ATT | AGG | CGG | GCT | - 3' |

This plasmid contains a large polylinker flanked by rare cutting NotI sites for building large inserts that can be isolated from vector sequences for microinjection. The plasmid is based on pBR322 which is relatively low copy compared to the pUC based plasmids (pGP1 retains the pBR322 copy number control region near the origin of replication). Low copy number reduces the potential toxicity of insert sequences. In addition, pGP1 contains a strong transcription terminator sequence derived from trpA (Christie et al., *Proc. Natl. Acad. Sci. USA* 78:4180 (1981)) inserted between the ampicillin resistance gene and the polylinker. This further reduces the toxicity associated with certain inserts by preventing readthrough transcription coming from the ampicillin promoters.

Plasmid pGP2 is derived from pGP1 to introduce an additional restriction site (SfiI) in the polylinker. pGP1 is digested with MluI and SpeI to cut the recognition sequences in the polylinker portion of the plasmid.

The following adapter oligonucleotides are ligated to the thus digested pGP1 to form pGP2.

5' CGC GTG GCC GCA ATG GCC A 3'
5' CTA GTG GCC ATT GCG GCC A 3' pGP2 is identical to pGP1 except that it contains an additional Sfi I site located between the MluI and SpeI sites. This allows inserts to be completely excised with SfiI as well as with NotI.

B. Construction of pRE3 (Rat Enhancer 3')

An enhancer sequence located downstream of the rat constant region is included in the heavy chain constructs.

The heavy chain region 3' enhancer described by Petterson et al., *Nature* 344:165–168 (1990), which is incorporated herein by reference) is isolated and cloned. The rat IGH 3' enhancer sequence is PCR amplified by using the following oligonucleotides:

5' CAG GAT CCA GAT ATC AGT ACC TGA AAC AGG GCT TGC 3'
5' GAG CAT GCA CAG GAC CTG GAG CAC ACA CAG CCT TCC 3'

The thus formed double stranded DNA encoding the 3' enhancer is cut with BamHI and SphI and clone into BamHI/SphI cut pGP2 to yield pRE3 (rat enhancer 3').

C. Cloning of Human J-μ Region

A substantial portion of this region is cloned by combining two or more fragments isolated from phage lambda inserts. See FIG. 9.

A 6.3 kb BamHI/HindIII fragment that includes all human J segments (Matsuda et al., *EMBO J.*, 7:1047–1051 (1988); Ravetech et al.m *Cell*, 27:583–591 (1981), which are incorporated herein by reference) is isolated from human genomic DNA library using the oligonucleotide GGA CTG TGT CCC TGT GTG ATG CTT TTG ATG TCT GGG GCC AAG.

An adjacent 10 kb HindIII/BamII fragment that contains enhancer, switch and constant region coding exons (Yasui et al., *Eur. J. Immunol.* 19:1399–1403 (1989)) is similarly isolated using the oligonucleotide:

CAC CAA GTT GAC CTG CCT GGT CAC AGA CCT GAC CAC CTA TGA

An adjacent 3' 1.5 kb BamHI fragment is similarly isolated using clone pMUM insert as probe (pMUM is 4 kb EcoRI/HindIII fragment isolated from human genomic DNA library with oligonucleotide:

CCT GTG GAC CAC CGC CTC CAC CTT CAT CGT CCT CTT CCT CCT mu membrane exon 1) and cloned into pUC19.

pGP1 is digested with BamHI and BglII followed by treatment with calf intestinal alkaline phosphatase.

Fragments (a) and (b) from FIG. 9 are cloned in the digested pGP1. A clone is then isolated which is oriented such that 5' BamHI site is destroyed by BamHI/Bgl fusion. It is identified as pMU (see FIG. 10). pMU is digested with BamHI and fragment (c) from FIG. 9 is inserted. The orientation is checked with HindIII digest. The resultant plasmid pHIG1 (FIG. 10) contains an 18 kb insert encoding J and Cμ segments.

Figure 14:
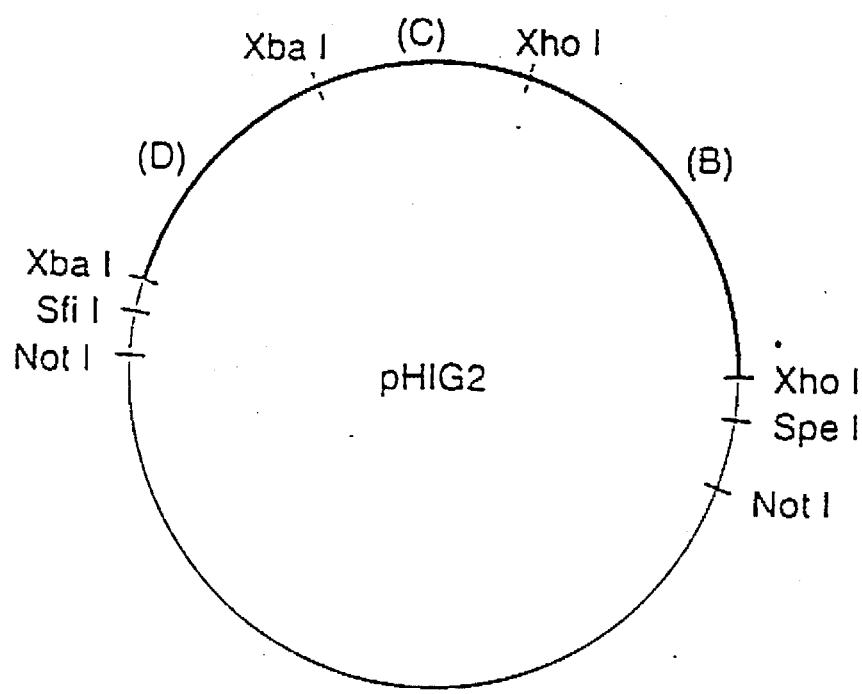
FIG. 14 depicts the construction of pHIG2 (D segment containing plasmid).
Figure 15:
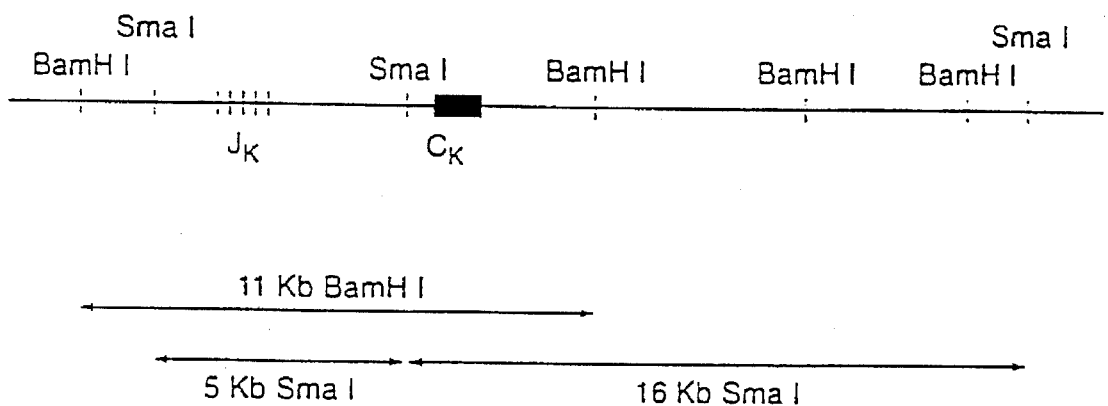
FIG. 15 depicts the fragments covering the human Jκ and human Cκ gene segments used in constructing a transgene of the invention.

D. Cloning of Cμ Region pGP1 is digested with BamHI and HindIII is followed by treatment with calf intestinal alkaline phosphatase (FIG. 14). The so treated fragment (b) of FIG. 14 and fragment (c) of FIG. 14 are cloned into the BamHI/HindIII cut pGP1. Proper orientation of fragment (c) is checked by HindIII digestion to form pCON1 containing a 12 kb insert encoding the Cμ region.

Whereas pHIG1 contains J segments, switch and μ sequences in its 18 kb insert with an SfiI 3' site and a SpeI 5' site in a polylinker flanked by NotI sites, will be used for rearranged VDJ segments. pCON1 is identical except that it lacks the J region and contains only a 12 kb insert. The use of pCON1 in the construction of fragment containing rearranged VDJ segments will be described hereinafter.

E. Cloning of γ-1 Constant Region (pREG2)

Figure 16:
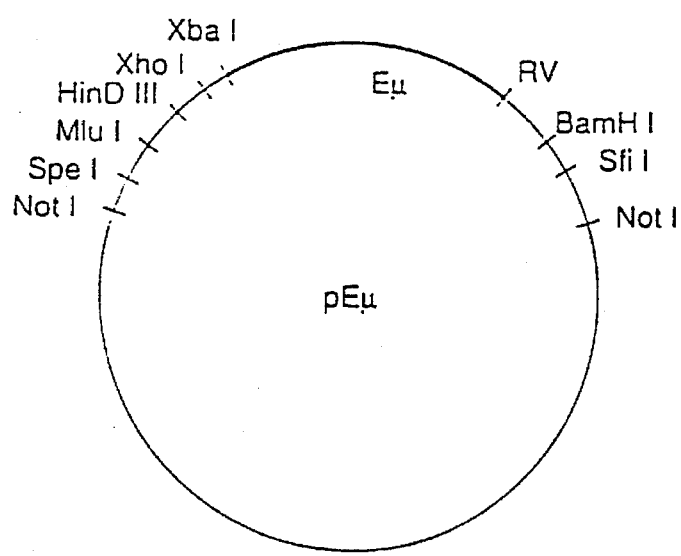
FIG. 16 depicts the structure of pEµ.
Figure 18A:
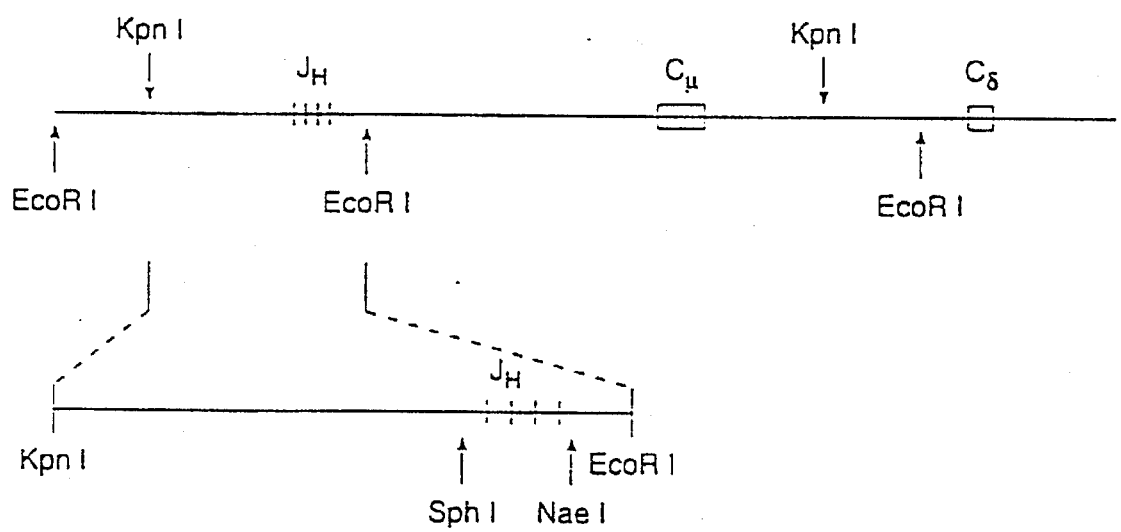
FIGS. 18A through 18D depict the construction of a positive-negative selection vector for functionally disrupting the endogenous heavy chain immunoglobulin locus of mouse.
Figure 18B:
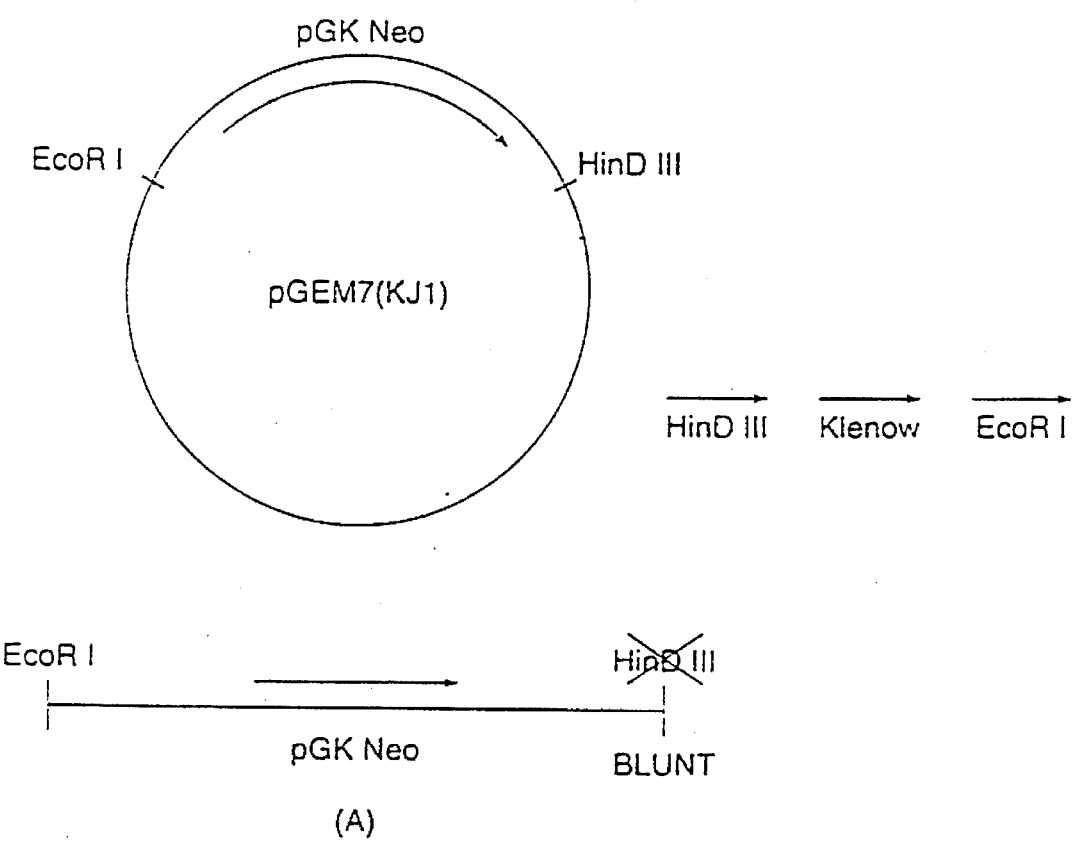
Figure 18C:
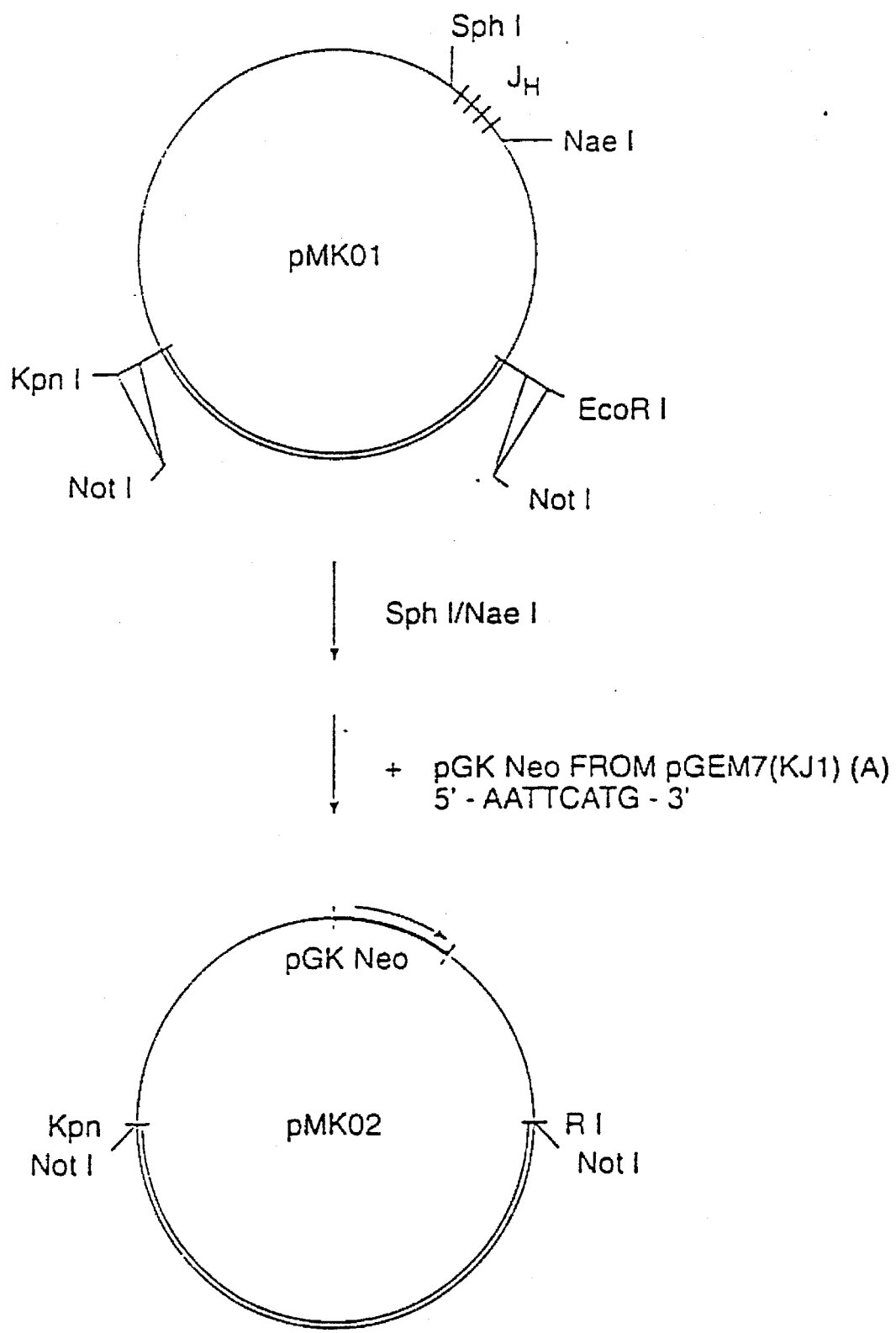
Figure 18D:
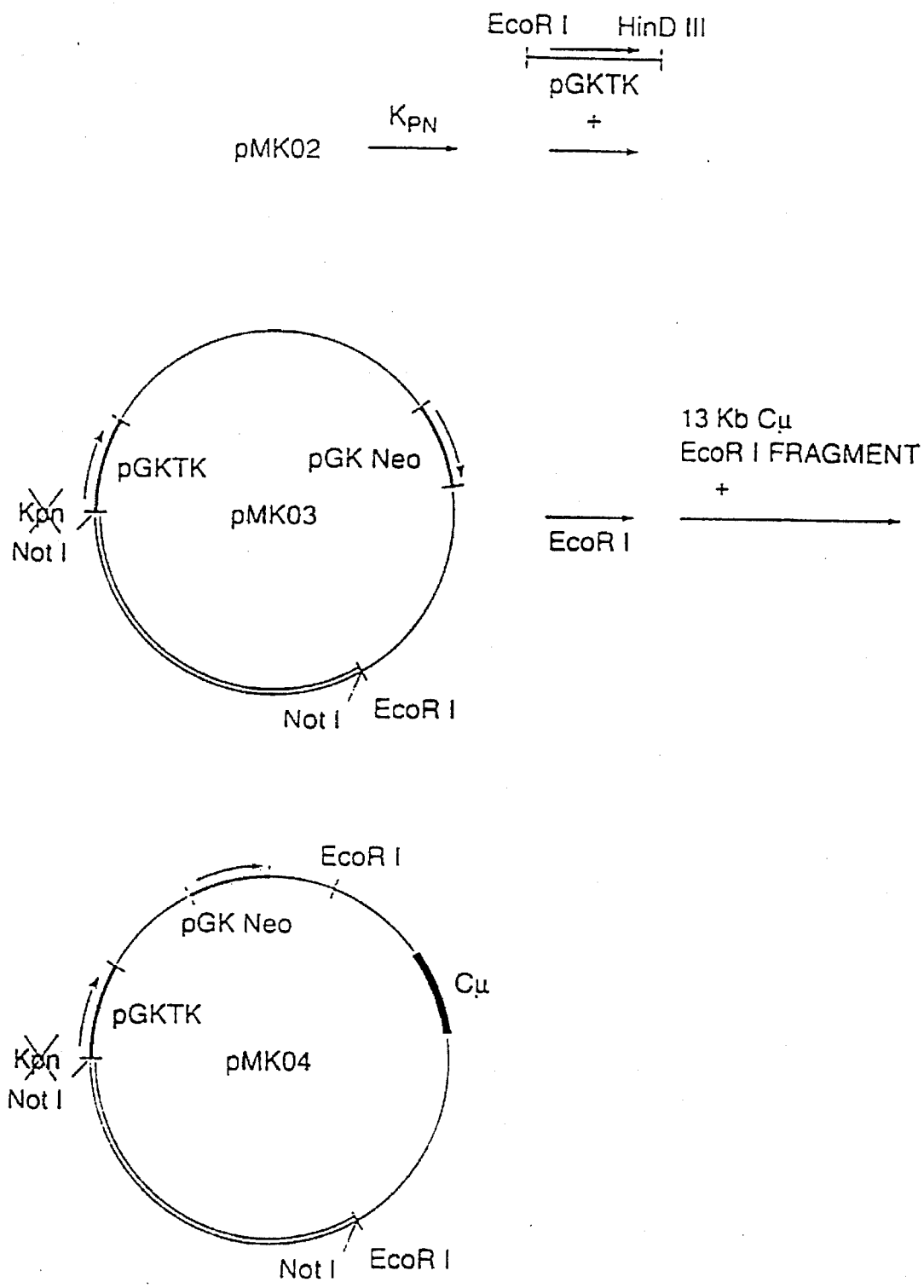
Figure 19A:
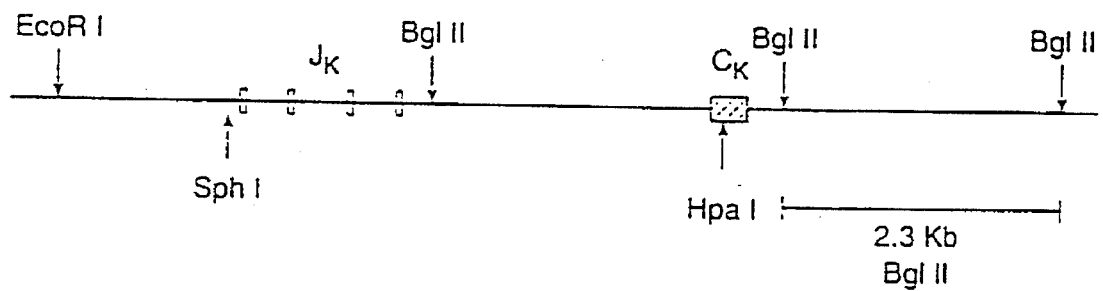
Figure 19B:
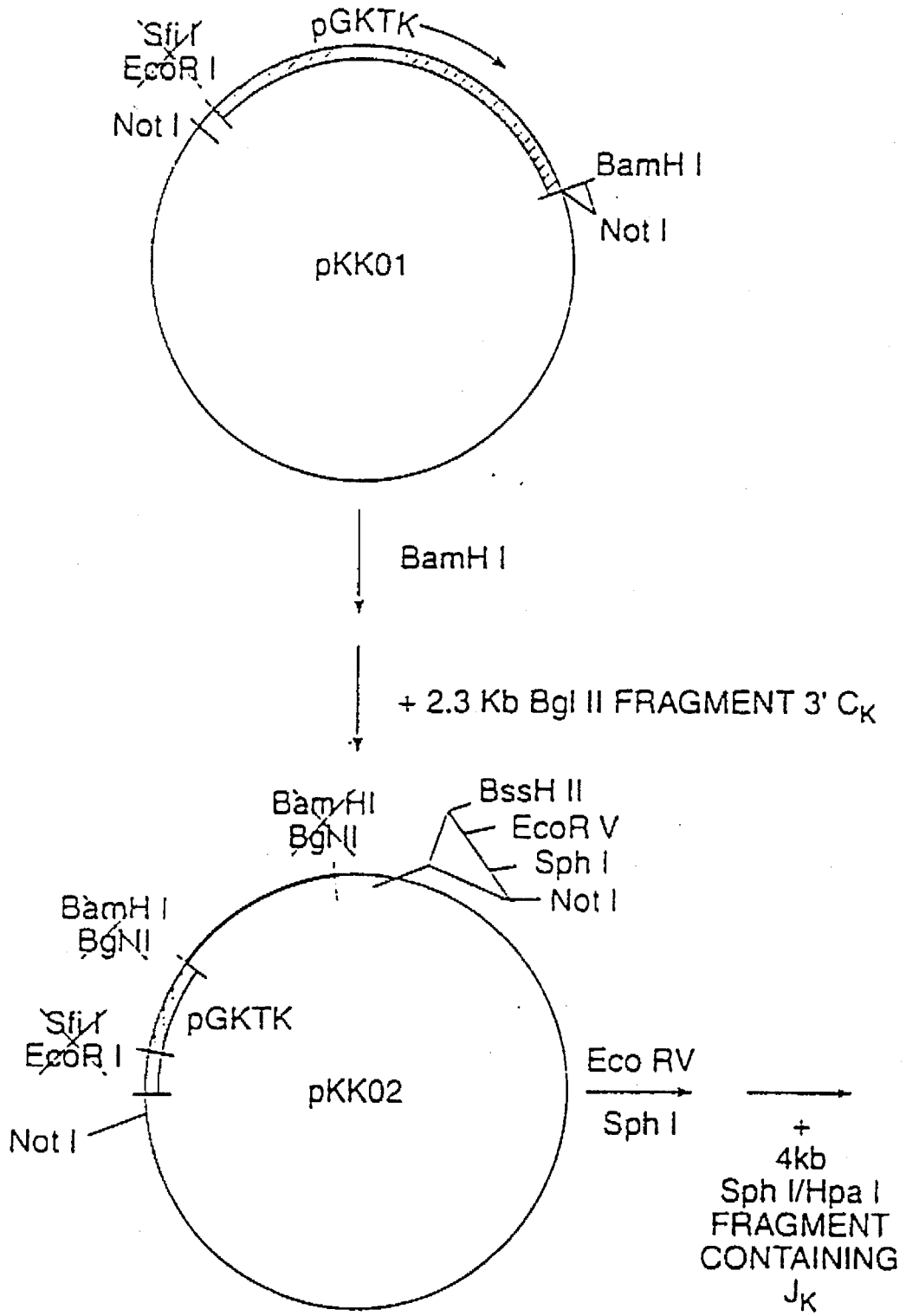

The cloning of the human γ-1 region is depicted in FIG. 16.

Yamamura et al., *Proc. Natl. Acad. Sci. USA* 83:2152–2156 (1986) reported the expression of membrane bound human γ-1 from a transgene construct that had been partially deleted on integration. Their results indicate that the 3' BamHI site delineates a sequence that includes the transmembrane rearranged and switched copy of the gamma gene with a V-C intron of less than 5 kb. Therefore, in the unrearranged, unswitched gene, the entire switch region is included in a sequence beginning less than 5 kb from the 5' end of the first γ-1 constant exon. Therefore it is included in the 5' 5.3 kb HindIII fragment (Ellison et al., *Nucleic Acids Res.* 10:4071–4079 (1982), which is incorporated herein by reference). Takahashi et al., *Cell* 29: 671–679 (1982), which is incorporated herein by reference, also reports that this fragment contains the switch sequence, and this fragment together with the 7.7 kb HindIII to BamHI fragment must include all of the sequences we need for the transgene construct. An intronic sequence is a nucleotide sequence of at least 15 contiguous nucleotides that occurs in an intron of a specified gene.

Phage clones containing the γ-1 region are identified and isolated using the following oligonucleotide which is specific for the third exon of γ-I (CH3).

5' TGA GCC ACG AAG ACC CTG AGG TCA AGT TCA ACT GGT ACG TGG 3'

Figure 11:
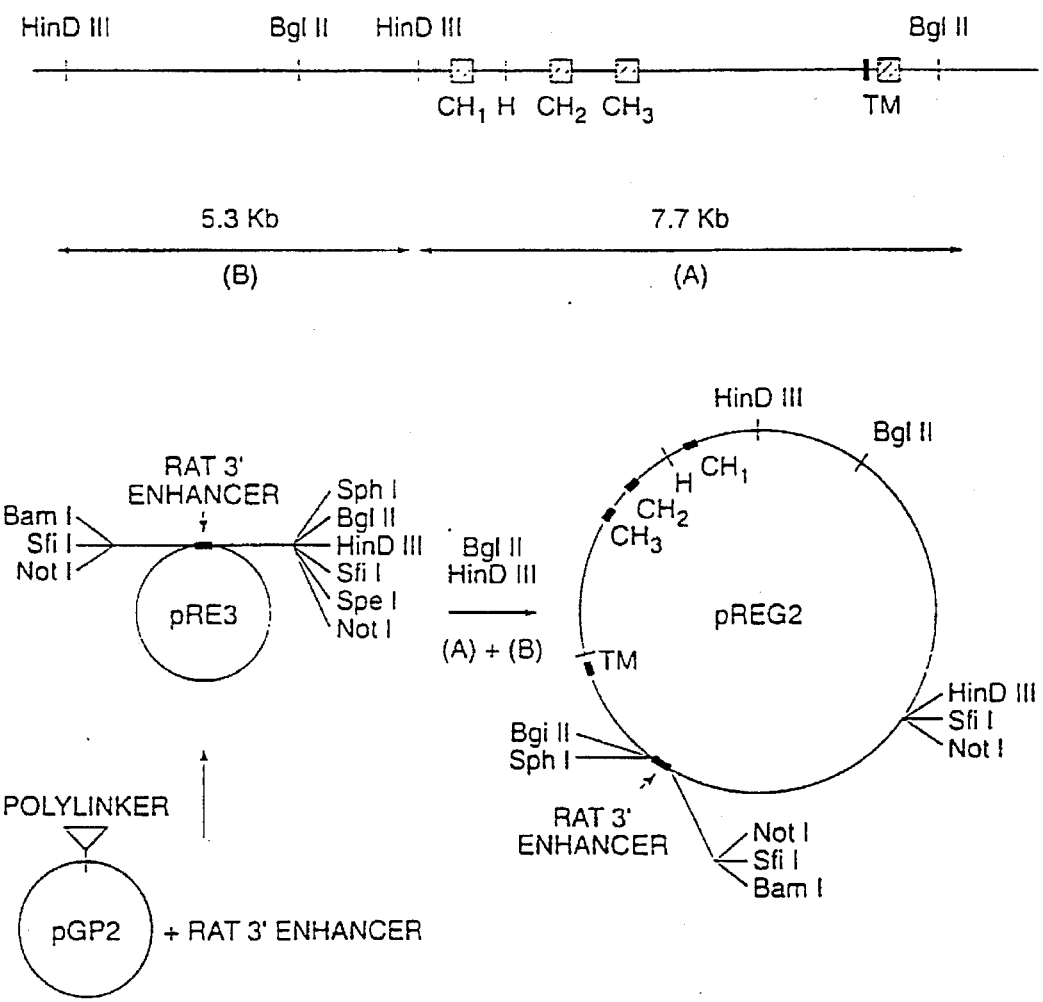
FIG. 11 depicts the human Cγ1 fragments which are inserted into pRE3 (rat enhancer 3') to form pREG2.

A 7.7 kb HindIII to BglII fragment (fragment (a) in FIG. 11) is cloned into HindIII/BglII cut pRE3 to form pREG1. The upstream 5.3 kb HindIII fragment (fragment (b) in FIG. 11) is cloned into HindIII digested pREG1 to form pREG2. Correct orientation is confirmed by BamHI/SpeI digestion.

F. Combining Cγ and Cμ

Figure 10:
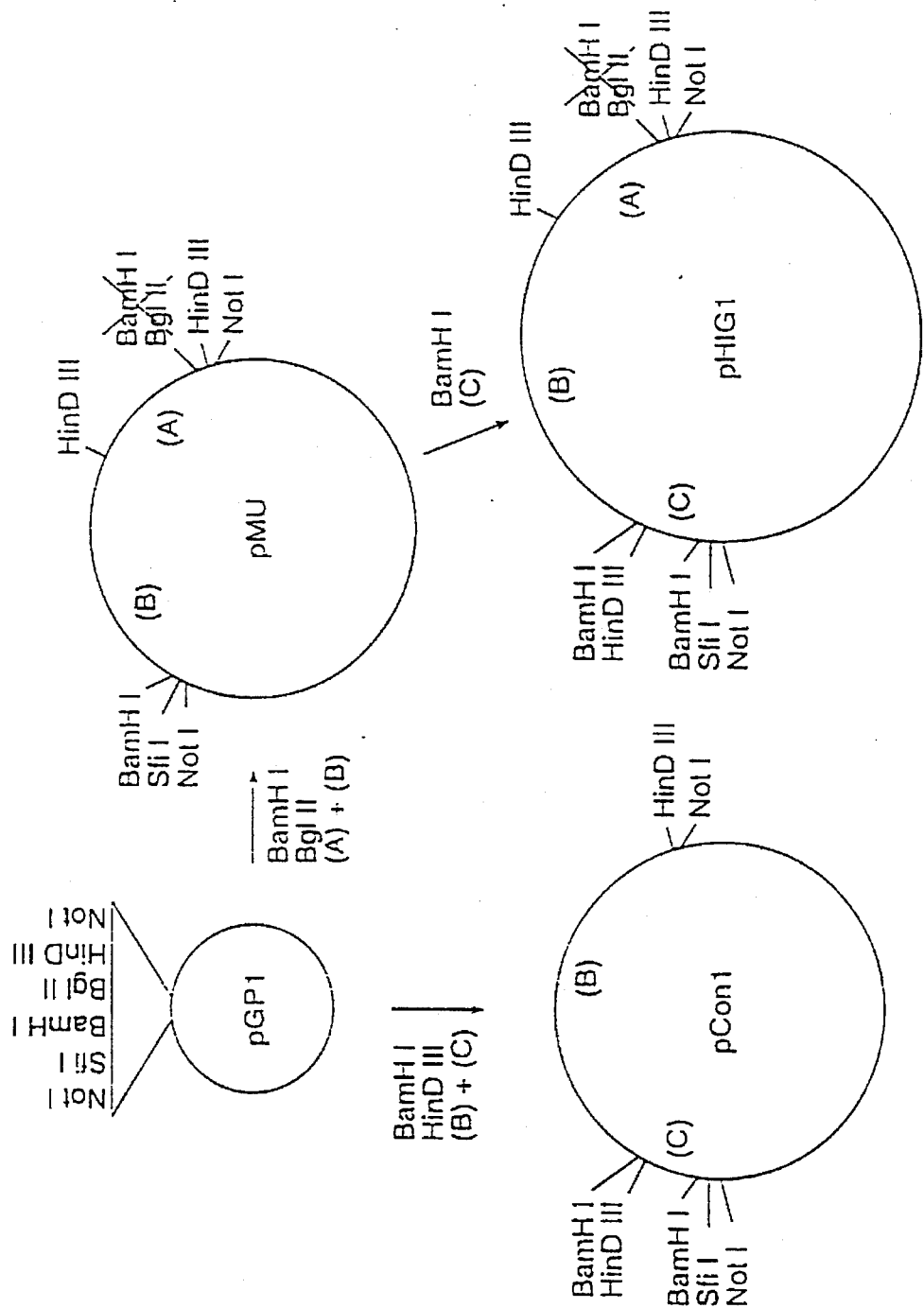
FIG. 10 depicts the construction of pHIG1 and pCON1.

The previously described plasmid pHIG1 contains human J segments and the Cμ constant region exons. To provide a transgene containing the Cμ constant region gene segments, pHIG1 was digested with SfiI (FIG. 10). The plasmid pREG2 was also digested with SfiI to produce a 13.5 kb insert containing human Cγ exons and the rat 3' enhancer sequence. These sequences were combined to produce the plasmid pHIG3' (FIG. 12) containing the human J segments, the human Cμ constant region, the human Cγ1 constant region and the rat 3' enhancer contained on a 31.5 kb insert.

A second plasmid encoding human Cμ and human Cγ1 without J segments is constructed by digesting pCON1 with SfiI and combining that with the SfiI fragment containing the human Cγ region and the rat 3' enhancer by digesting pREG2 with SfiI. The resultant plasmid, pCON (FIG. 12) contains a 26 kb NotI/SpeI insert containing human Cμ, human γ1 and the rat 3' enhancer sequence.

G. Cloning of D Segment

Figure 13:
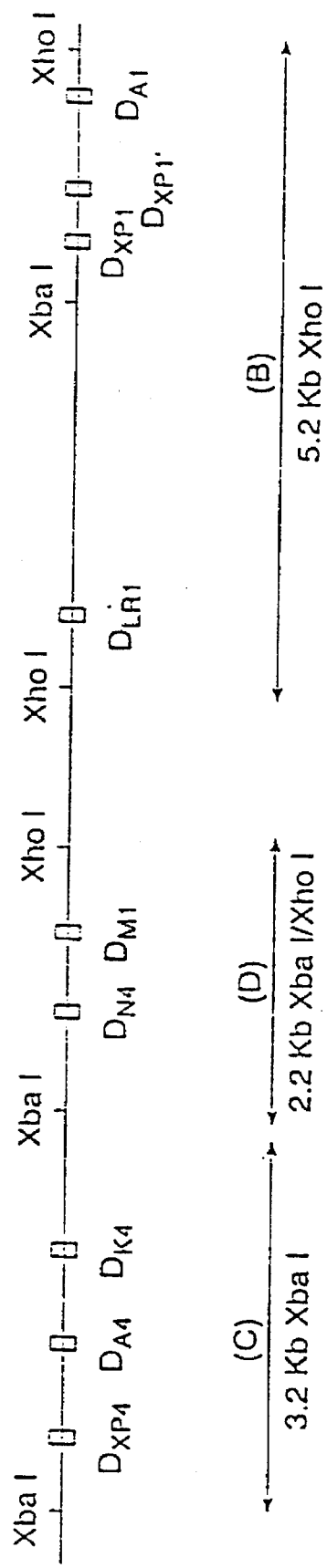
FIG. 13 depicts the fragment containing human D region segments used in construction of the transgenes of the invention.

The strategy for cloning the human D segments is depicted in FIG. 13. Phage clones from the human genomic library containing D segments are identified and isolated using probes specific for diversity region sequences (Ichihara et al., *EMBO J.* 7:4141–4150 (1988)). The following oligonucleotides are used:

DXP1: 5' - TGG TAT TAC TAT GGT TCG GGG AGT TAT TAT AAC CAC AGT GTC - 3'

DXP4: 5' - GCC TGA AAT GGA GCC TCA GGG CAC AGT GGG CAC GGA CAC TGT - 3'

DN4: 5' - GCA GGG AGG ACA TGT TTA GGA TCT GAG GCC GCA CCT GAC ACC - 3'

A 5.2 kb XhoI fragment (fragment (b) in FIG. 13) containing DLR1, DXP1, DXP'1, and DA1 is isolated from a phage clone identified with oligo DXP1.

A 3.2 kb XbaI fragment (fragment (c) in FIG. 13) containing DXP4, DA4 and DK4 is isolated from a phage clone identified with oligo DXP4.

Fragments (b), (c) and (d) from FIG. 13 are combined and cloned into the XbaI/XhoI site of pGP1 to form pHIG2 which contains a 10.6 kb insert.

This cloning is performed sequentially. First, the 5.2 kb fragment (b) in FIG. 13 and the 2.2 kb fragment (d) of FIG. 13 are treated with calf intestinal alkaline phosphatase and cloned into pGP1 digested with XhoI and XbaI. The resultant clones are screened with the 5.2 and 2.2 kb insert. Half of those clones testing positive with the 5.2 and 2.2 kb inserts have the 5.2 kb insert in the proper orientation as determined by BamHI digestion. The 3.2 kb XbaI fragment from FIG. 13 is then cloned into this intermediate plasmid containing fragments (b) and (d) to form pHIG2. This plasmid contains diversity segments cloned into the polylinker with a unique 5' SfiI site and unique 3' SpeI site. The entire polylinker is flanked by NotI sites.

H. Construction of Heavy Chain Minilocus

The following describes the construction of a human heavy chain mini-locus which contain one or more V segments.

An unrearranged V segment corresponding to that identified as the V segment contained in the hybridoma of Newkirk et al., *J. Clin. Invest.* 81:1511–1518 (1988), which is incorporated herein by reference, is isolated using the following oligonucleotide:

5' - GAT CCT GGT TTA GTT AAA GAG GAT TTT ATT CAC CCC TGT GTC - 3'

A restriction map of the unrearranged V segment is determined to identify unique restriction sites which provide upon digestion a DNA fragment having a length approximately 2 kb containing the unrearranged V segment together with 5' and 3' flanking sequences. The 5' prime sequences will include promoter and other regulatory sequences whereas the 3' flanking sequence provides recombination sequences necessary for V-DJ joining. This approximately 3.0 kb V segment insert is cloned into the polylinker of pGB2 to form pVH1.

pVH1 is digested with SfiI and the resultant fragment is cloned into the SfiI site of pHIG2 to form a pHIG5'. Since pHIG2 contains D segments only, the resultant pHIG5' plasmid contains a single V segment together with D segments. The size of the insert contained in pHIG5 is 10.6 kb plus the size of the V segment insert.

The insert from pHIG5 is excised by digestion with NotI and SpeI and isolated. pHIG3' which contains J, Cμ and cγ1 segments is digested with SpeI and NotI and the 3' kb fragment containing such sequences and the rat 3' enhancer sequence is isolated. These two fragments are combined and ligated into NotI digested pGP1 to produce pHIG which contains insert encoding a V segment, nine D segments, six functional J segments, Cμ, Cγ and the rat 3' enhancer. The size of this insert is approximately 43 kb plus the size of the V segment insert.

I. Construction of Heavy Chain Minilocus by Homologous Recombination

As indicated in the previous section, the insert of pHIG is approximately 43 to 45 kb when a single V segment is employed. This insert size is at or near the limit of that which may be readily cloned into plasmid vectors. In order to provide for the use of a greater number of V segments, the following describes in vivo homologous recombination of overlapping DNA fragments which upon homologous recombination within a zygote or ES cell form a transgene containing the rat 3' enhancer sequence, the human Cμ, the human Cγ1, human J segments, human D segments and a multiplicity of human V segments.

A 6.3 kb BamHI/HindIII fragment containing human J segments (see fragment (a) in FIG. 9) is cloned into MluI/SpeI digested pHIG5' using the following adapters:

5' GAT CCA AGC AGT 3'
5' CTA GAC TGC TTG 3'
5' CGC GTC GAA CTA 3'
5' AGC TTA GTT CGA 3'

The resultant is plasmid designated pHIG5'O (overlap). The insert contained in this plasmid contains human V, D and J segments. When the single V segment from pVH1 is used, the size of this insert is approximately 17 kb plus 2 kb. This insert is isolated and combined with the insert from pHIG3' which contains the human J, Cμ, γ1 and rat 3' enhancer sequences. Both inserts contain human J segments which provide for approximately 6.3 kb of overlap between the two DNA fragments. When coinjected into the mouse zygote, in vivo homologous recombination occurs generating a transgene equivalent to the insert contained in pHIG.

This approach provides for the addition of a multiplicity of V segments into the transgene formed in vivo. For example, instead of incorporating a single V segment into pHIG5', a multiplicity of V segments contained on (1) isolated genomic DNA, (2) ligated DNA derived from genomic DNA, or (3) DNA encoding a synthetic V segment repertoire is cloned into pHIG2 at the SfiI site to generate pHIG5' $V_N$. The J segments fragment (a) of FIG. 9 is then cloned into pHIG5' $V_N$ and the insert isolated. This insert now contains a multiplicity of V segments and J segments which overlap with the J segments contained on the insert isolated from pHIG3'. When cointroduced into the nucleus of a mouse zygote, homologous recombination occurs to generate in vivo the transgene encoding multiple V segments and multiple J segments, multiple D segments, the Cμ region, the Cγ1 region (all from human) and the rat 3' enhancer sequence.

EXAMPLE 5

Construction of Light Chain Minilocus

A. Construction of pEµ1

The construction of pEµ1 is depicted in FIG. 16. The mouse heavy chain enhancer is isolated on the XbaI to EcoRI 678 bp fragment (Banerji et al., *Cell* 33:729–740 (1983)) from phage clones using oligo:

5' GAA TGG GAG TGA GGC TCT CTC ATA CCC TAT TCA GAA CTG ACT 3'

This Eµ fragment is cloned into EcoRV/XbaI digested pGP1 by blunt end filling in EcoRI site. The resultant plasmid is designated pEmu1.

B. Construction of κ Light Chain Minilocus

The κ construct contains at least one human V$_κ$ segment, all five human J$_κ$ segments, the human J-C$_κ$ enhancer, human κ constant region exon, and, ideally, the human 3' κ enhancer (Meyer et al., *EMBO J.* 8:1959–1964 (1989)). The κ enhancer in mouse is 9 kb downstream from C$_κ$. However, it is as yet unidentified in the human. In addition, the construct contains a copy of the mouse heavy chain J-Cµ enhancers.

The minilocus is constructed from four component fragments:

(a) A 16 kb SmaI fragment that contains the human C$_κ$ exon and the 3' human enhancer by analogy with the mouse locus;

(b) A 5' adjacent 5 kb SmaI fragment, which contains all five J segments;

(c) The mouse heavy chain intronic enhancer isolated from pEµ1 (this sequence is included to induce expression of the light chain construct as early as possible in B-cell development. Because the heavy chain genes are transcribed earlier than the light chain genes, this heavy chain enhancer is presumably active at an earlier stage than the intronic κ enhancer); and (d) A fragment containing one or more V segments.

The preparation of this construct is as follows. Human placental DNA is digested with SmaI and fractionated on agarose gel by electrophoresis. Similarly, human placental DNA is digested with BamHI and fractionated by electrophoresis. The 16 kb fraction is isolated from the SmaI digested gel and the 11 kb region is similarly isolated from the gel containing DNA digested with BamHI.

The 16 kb SmaI fraction is cloned into Lambda FIX II (Stratagene, La Jolla, Calif.) which has been digested with XhoI, treated with klenow fragment DNA polymerase to fill in the XhoI restriction digest product. Ligation of the 16 kb SmaI fraction destroys the SmaI sites and lases XhoI sites intact.

The 11 kb BamHI fraction is cloned into λ EMBL3 (Strategene, La Jolla, Calif.) which is digested with BamHI prior to cloning.

Clones from each library were probed with the Cκ specific oligo:

5' GAA CTG TGG CTG CAC CAT CTG TCT TCA TCT TCC CGC CAT CTG 3'

A 16 kb XhoI insert that was subcloned into the XhoI cut pEµ1 so that Cκ is adjacent to the SmaI site. The resultant plasmid was designated pKap1.

Figure 20:
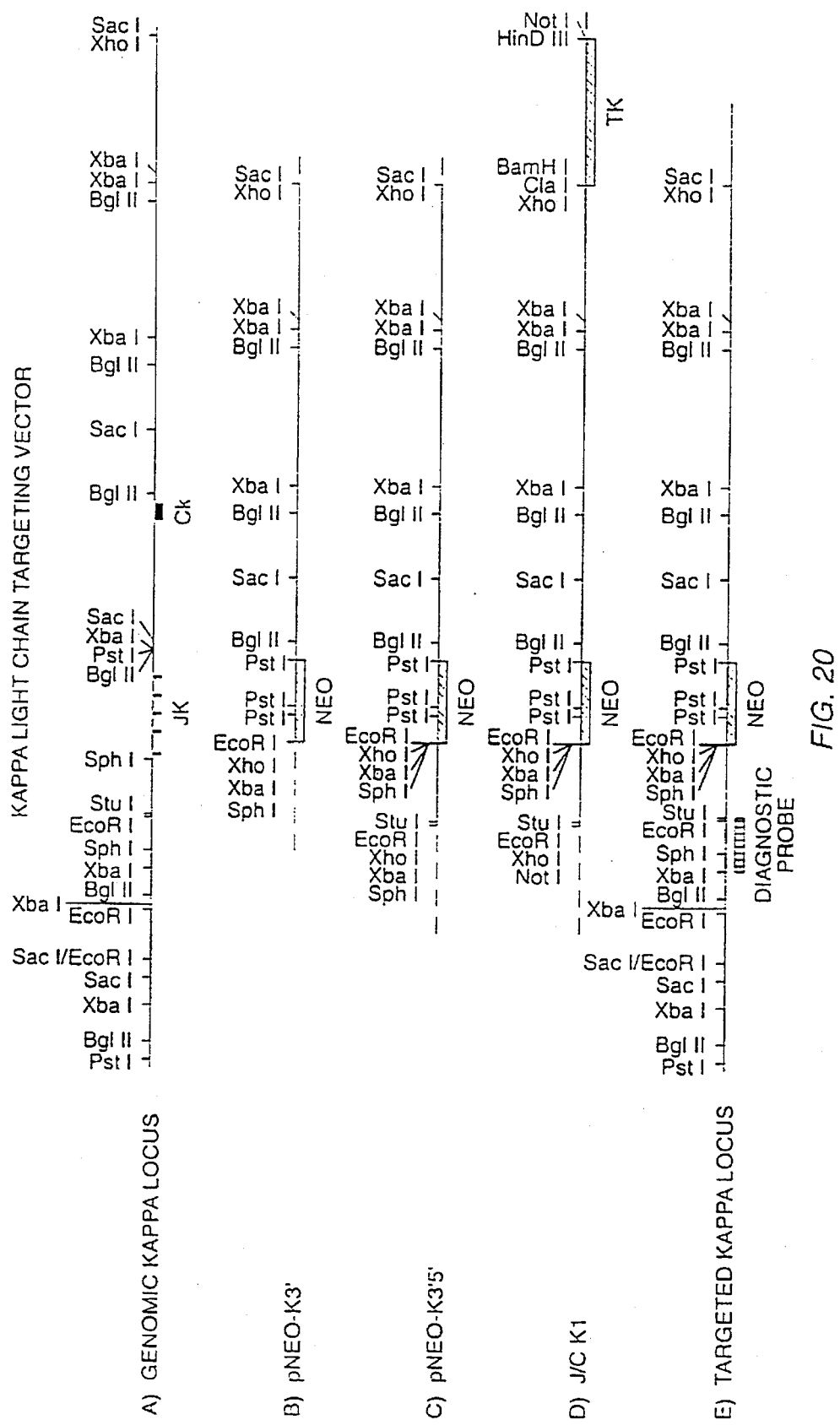
FIGS. 20 a through e depict the structure of a kappa light chain targeting vector.

The above Cκ specific oligonucleotide is used to probe the λ EMBL3/BamHI library to identify an 11 kb clone. A 5 kb SmaI fragment (fragment (b) in FIG. 20) is subcloned and subsequently inserted into pKap1 digested with SmaI. Those plasmids containing the correct orientation of J segments, Cκ and the Eµ enhancer are designated pKap2.

One or more Vκ segments are thereafter subcloned into the MluI site of pKap2 to yield the plasmid pKapH which encodes the human Vκ segments, the human Jκ segments, the human Cκ segments and the human Eµ enhancer. This insert is excised by digesting pKapH with NotI and purified by agarose gel electrophoresis. The thus purified insert is microinjected into the pronucleus of a mouse zygote as previously described.

C. Construction of κ Light Chain Minilocus by In Vivo Homologous Recombination The 11 kb BamHI fragment is cloned into BamHI digested pGP1 such that the 3' end is toward the SfiI site. The resultant plasmid is designated pKAPint. One or more Vκ segments is inserted into the polylinker between the BamHI and SpeI sites in pKAPint to form pKapHV. The insert of pKapHV is excised by digestion with NotI and purified. The insert from pKap2 is excised by digestion with NotI and purified. Each of these fragments contain regions of homology in that the fragment from pKapHV contains a 5 kb sequence of DNA that include the J$_κ$ segments which is substantially homologous to the 5 kb SmaI fragment contained in the insert obtained from pKap2. As such, these inserts are capable of homologously recombining when microinjected into a mouse zygote to form a transgene encoding V$_κ$, J$_κ$ and C$_κ$.

EXAMPLE 6

Isolation of Genomic Clones Corresponding to Rearranged and Expressed Copies of Immunoglobulin κ Light Chain Genes This example describes the cloning of immunoglobulin κ light chain genes from cultured cells that express an immunoglobulin of interest. Such cells may contain multiple alleles of a given immunoglobulin gene. For example, a hybridoma might contain four copies of the κ light chain gene, two copies from the fusion partner cell line and two copies from the original B-cell expressing the immunoglobulin of interest. Of these four copies, only one encodes the immunoglobulin of interest, despite the fact that several of them may be rearranged. The procedure described in this example allows for the selective cloning of the expressed copy of the κ light chain.

A. Double Stranded cDNA

Cells from human hybridoma, or lymphoma, or other cell line that synthesizes either cell surface or secreted or both forms of IgM with a κ light chain are used for the isolation of polyA+ RNA. The RNA is then used for the synthesis of oligo dT primed cDNA using the enzyme reverse transcriptase. The single stranded cDNA is then isolated and G residues are added to the 3' end using the enzyme polynucleotide terminal transferase. The Gtailed single-stranded cDNA is then purified and used as template for second strand synthesis (catalyzed by the enzyme DNA polymerase) using the following oligonucleotide as a primer:

5' - GAG GTA CAC TGA CAT ACT GGC ATG CCC CCC CCC CCC - 3'

The double stranded cDNA is isolated and used for determining the nucleotide sequence of the 5' end of mRNAs encoding the heavy and light chains of the expressed immunoglobulin molecule. Genomic clones of these expressed genes are then isolated. The procedure for cloning the expressed light chain gene is outlined in part B below.

B. Light Chain

The double stranded cDNA described in part A is denatured and used as a template for a third round of DNA synthesis using the following oligonucleotide primer:

5' - GTA CGC CAT ATC AGC TGG ATG AAG TCA TCA GAT GGC GGG AAG ATG AAG ACA GAT GGT GCA - 3'

This primer contains sequences specific for the constant portion of the κ light chain message (TCA TCA GAT GGC GGG AAG ATG AAG ACA GAT GGT GCA) as well as unique sequences that can be used as a primer for the PCR amplification of the newly synthesized DNA strand (GTA CGC CAT ATC AGC TGG ATG AAG). The sequence is amplified by PCR using the following two oligonucleotide primers:

5' - GAG GTA CAC TGA CAT ACT GGC ATG -3'
5' - GTA CGC CAT ATC AGC TGG ATG AAG -3'

The PCR amplified sequence is then purified by gel electrophoresis and used as template for dideoxy sequencing reactions using the following oligonucleotide as a primer:

5' - GAG GTA CAC TGA CAT ACT GGC ATG -3'

The first 42 nucleotides of sequence will then be used to synthesize a unique probe for isolating the gene from which immunoglobulin message was transcribed. This synthetic 42 nucleotide segment of DNA will be referred to below as o-kappa.

A Southern blot of DNA, isolated from the Ig expressing cell line and digested individually and in pairwise combinations with several different restriction endonucleases including SmaI, is then probed with the 32-P labelled unique oligonucleotide o-kappa. A unique restriction endonuclease site is identified upstream of the rearranged V segment.

DNA from the Ig expressing cell line is then cut with SmaI and second enzyme (or BamHI or KpnI if there is SmaI site inside V segment). Any resulting non-blunted ends are treated with the enzyme T4 DNA polymerase to give blunt ended DNA molecules. Then add restriction site encoding linkers (BamHI, EcoRI or XhoI depending on what site does not exist in fragment) and cut with the corresponding linker enzyme to give DNA fragments with BamHI, EcoRI or XhoI ends. The DNA is then size fractionated by agarose gel electrophoresis, and the fraction including the DNA fragment covering the expressed V segment is cloned into lambda EMBL3 or Lambda FIX (Stratagene, La Jolla, Calif.). V segment containing clones are isolated using the unique probe o-kappa. DNA is isolated from positive clones and subcloned into the polylinker of pKap1. The resulting clone is called pRKL.

EXAMPLE 7

Isolation of Genomic Clones Corresponding to Rearranged Expressed Copies of Immunoglobulin Heavy Chain μ Genes This example describes the cloning of immunoglobulin heavy chain μ genes from cultured cells of expressed and immunoglobulin of interest. The procedure described in this example allows for the selective cloning of the expressed copy of a μ heavy chain gene.

Double-stranded cDNA is prepared and isolated as described herein before. The double-stranded cDNA is denatured and used as a template for a third round of DNA synthesis using the following oligonucleotide primer:

5'-GTA CGC CAT ATC AGC TGG ATG AAG ACA GGA GAC GAG GGG GAA AAG GGT TGG GGC GGA TGC-3'

This primer contains sequences specific for the constant portion of the μ heavy chain message (ACA GGA GAC GAG GGG GAAAAG GGT TGG GGC GGA TGC) as well as unique sequences that can be used as a primer for the PCR amplification of the newly synthesized DNA strand (GTA CGC CAT ATC AGC TGG ATG AAG). The sequence is amplified by PCR using the following two oligonucleotide primers:

5'-GAG GTA CAC TGA CAT ACT GGC ATG-3'
5'-GTA CTC CAT ATC AGC TGG ATG AAG-3'

The PCR amplified sequence is then purified by gel electrophoresis and used as template for dideoxy sequencing reactions using the following oligonucleotide as a primer:

5'-GAG GTA CAC TGA CAT ACT GGC ATG-3'

The first 42 nucleotides of sequence are then used to synthesize a unique probe for isolating the gene from which immunoglobulin message was transcribed. This synthetic 42 nucleotide segment of DNA will be referred to below as o-mu.

A Southern blot of DNA, isolated from the Ig expressing cell line and digested individually and in pairwise combinations with several different restriction endonucleases including MluI (MluI is a rare cutting enzyme that cleaves between the J segment and mu CH1), is then probed with the 32-P labelled unique oligonucleotide o-mu. A unique restriction endonuclease site is identified upstream of the rearranged V segment.

DNA from the Ig expressing cell line is then cut with MluI and second enzyme. MluI or SpeI adapter linkers are then ligated onto the ends and cut to convert the upstream site to MluI or SpeI. The DNA is then size fractionated by agarose gel electrophoresis, and the fraction including the DNA fragment covering the expressed V segment is cloned directly into the plasmid pGPI. V segment containing clones are isolated using the unique probe o-mu, and the insert is subcloned into MluI or MluI/SpeI cut plasmid pCON2. The resulting plasmid is called pRMGH.

EXAMPLE 8

Construction of Human κ Miniloci Transgenes Light Chain Minilocus

A human genomic DNA phage library was screened with kappa light chain specific oligonucleotide probes and isolated clones spanning the $J_\kappa$-C region. A 5.7 kb ClaI/XhoI fragment containing $J_\kappa 1$ together with a 13 kb XhoI fragment containing $J_\kappa 2$–5 and $C_\kappa$ into pGP1d was cloned and used to create the plasmid pKcor. This plasmid contains $J_\kappa 1$–5, the kappa intronic enhancer and $C_\kappa$ together with 4.5 kb of 5' and 9 kb of 3' flanking sequences. It also has a unique 5' XhoI site for cloning $V_\kappa$ segments and a unique 3' SalI site for inserting additional cis-acting regulatory sequences.

V kappa genes

A human genomic DNA phage library was screened with $V_\kappa$ light chain specific oligonucleotide probes and isolated clones containing human $V_\kappa$ segments. Functional V segments were identified by DNA sequence analysis. These clones contain TATA boxes, open reading frames encoding leader and variable peptides (including 2 cysteine residues), splice sequences, and recombination heptamer-12 bp spacer-nonamer sequences. Three of the clones were mapped and sequenced. Two of the clones, 65.5 and 65.8 appear to be functional, they contain TATA boxes, open reading frames encoding leader and variable peptides (including 2 cysteine residues), splice sequences, and recombination heptamer-12 bp spacer-nonamer sequences. The third clone, 65.4, appears to encode a $V_\kappa I$ pseudogene as it contains a non-canonical recombination heptamer.

One of the functional clones, Vk 65-8, which encodes a VkIII family gene, was used to build a light chain minilocus construct.

pKC1

Figure 32:
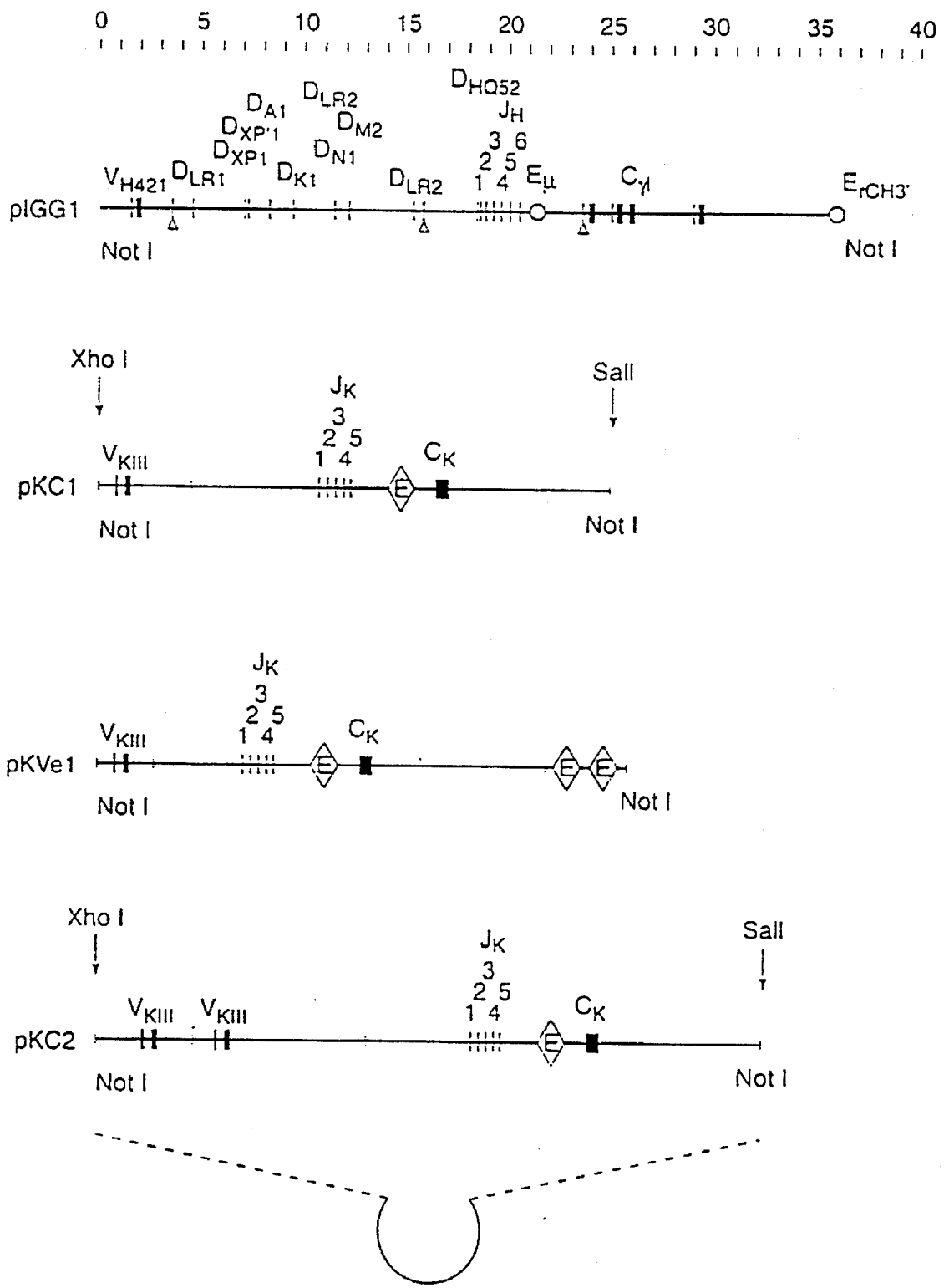
FIG. 32 is a schematic representation of the heavy chain minilocus construct pIGG1 and the κ light chain minilocus construct pKC1, pKVe1, and pKC2.

The kappa light chain minilocus transgene pKC1 (FIG. 32) was generated by inserting a 7.5 kb XhoI/SalI fragment containing $V_\kappa$ 65.8 into the 5' XhoI site of pKcor. The transgene insert was isolated by digestion with NotI prior to injection.

The purified insert was microinjected into the pronuclei of fertilized (C57BL/6 x CBA)F2 mouse embryos and transferred the surviving embryos into pseudopregnant females as described by Hogan et al. (in Methods of Manipulating the Mouse Embryo, 1986, Cold Spring Harbor Laboratory, New York). Mice that developed from injected embryos were analyzed for the presence of transgene sequences by Southern blot analysis of tail DNA. Transgene copy number was estimated by band intensity relative to control standards containing known quantities of cloned DNA. Serum was isolated from these animals and assayed for the presence of transgene encoded human Ig kappa protein by ELISA as described by Harlow and Lane (in Antibodies: A Laboratory Manual, 1988, Cold Spring Harbor Laboratory, New York). Microtiter plate wells were coated with mouse monoclonal antibodies specific for human Ig kappa (clone 6E1, #0173, AMAC, Inc., Westbrook, Me.), human IgM (Clone AF6, #0285, AMAC, Inc., Westbrook, Me.) and human IgG1 (clone JL512, #0280, AMAC, Inc., Westbrook, Me.). Serum samples were serially diluted into the wells and the presence of specific immunoglobulins detected with affinity isolated alkaline phosphatase conjugated goat anti-human Ig (polyvalent) that had been pre-adsorbed to minimize cross-reactivity with mouse immunoglobulins.

Figure 35:
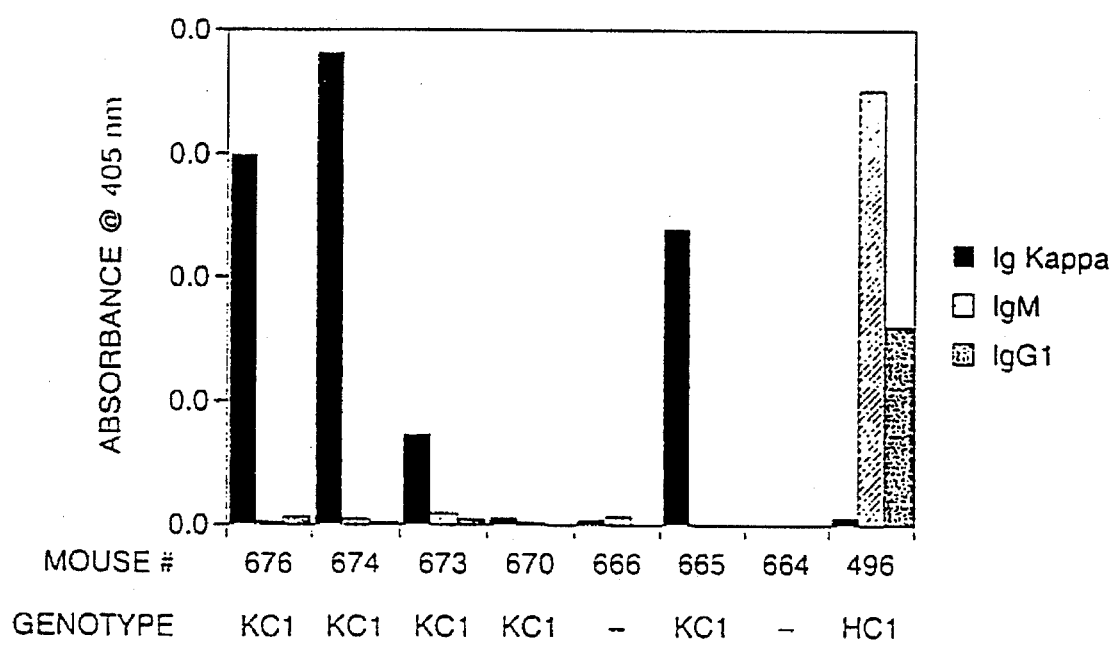
FIG. 35 depicts the results of an ELISA assay of serum from 8 transgenic mice.

FIG. 35 shows the results of an ELISA assay of serum from 8 mice (I.D. #676, 674, 673, 670, 666, 665, 664, and 496). The first seven of these mice developed from embryos that were injected with the pKC1 transgene insert and the eighth mouse is derived from a mouse generated by microinjection of the pHC1 transgene (described previously). Two of the seven mice from KC1 injected embryos (I.D.#'s 666 and 664) did not contain the transgene insert as assayed by DAN Southern blot analysis, and five of the mice (I.D.#'s 676, 674, 673, 670, and 665) contained the transgene. All but one of the KC1 transgene positive animals express detectable levels of human Ig kappa protein, and the single non-expressing animal appears to be a genetic mosaic on the basis of DNA Southern blot analysis. The pHC1 positive transgenic mouse expresses human IgM and IgG1 but not Ig kappa, demonstrating the specificity of the reagents used in the assay.

pKC2

The kappa light chain minilocus transgene pKC2 was generated by inserting an 8 kb XhoI/SalI fragment containing $V_\kappa$ 65.5 into the 5' XhoI site of pKC1. The resulting transgene insert, which contains two $V_\kappa$ segments, was isolated prior to microinjection by digestion with NotI.

pKVe2

This construct is identical to pKC1 except that it includes 1.2 kb of additional sequence 5' of $J_\kappa$ and is missing 4.5 kb of sequence 3' of $V_\kappa$ 65.8. In additional it contains a 0.9 kb XbaI fragment containing the mouse heavy chain J-m intronic enhancer (Banerji et al., *Cell* 33:729–740 (1983)) together with a 1.4 kb MluI HindIII fragment containing the human heavy chain J-m intronic enhancer (Hayday et al., *Nature* 307:334–340 (1984)) inserted downstream. This construct tests the feasibility of initiating early rearrangement of the light chain minilocus to effect allelic and isotypic exclusion. Analogous constructs can be generated with different enhancers, i.e., the mouse or rat 3' kappa or heavy chain enhancer (Meyer and Neuberger, *EMBO J.* 8:1959–1964 (1989); Petterson et al. *Nature* 344:165–168 (1990), which are incorporated herein by reference).

Rearranged Light Chain Transgenes

Figure 33:
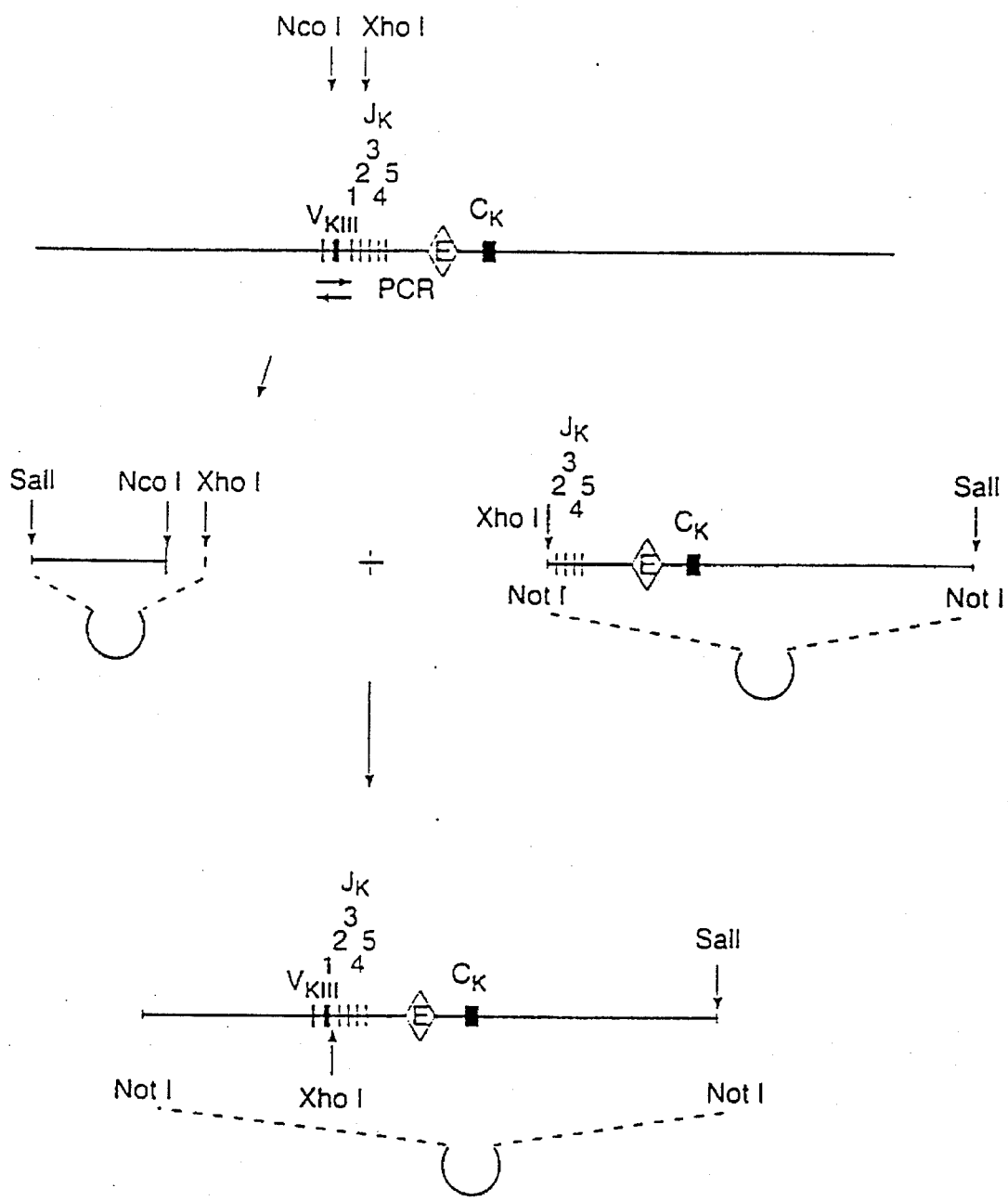
FIG. 33 depicts a scheme to reconstruct functionally rearranged light chain genes.

A kappa light chain expression cassette was designed to reconstruct functionally rearranged light chain genes that have been amplified by PCR from human B-cell DNA. The scheme is outlined in FIG. 33. PCR amplified light chain genes are cloned into the vector pK5nx that includes 3.7 kb of 5' flanking sequences isolated from the kappa light chain gene 65.5. The VJ segment fused to the 5' transcriptional sequences are then cloned into the unique XhoI site of the vector pK31s that includes $J_\kappa 2$–4, the $J_\kappa$ intronic enhancer, $C_\kappa$, and 9 kb of downstream sequences. The resulting plasmid contains a reconstructed functionally rearranged kappa light chain transgene that can be excised with NotI for microinjection into embryos. The plasmids also contain unique SalI sites at the 3' end for the insertion of additional cis-acting regulatory sequences.

Two synthetic oligonucleotides (o-130, o-131) were used to amplify rearranged kappa light chain genes from human spleen genomic DNA. Oligonucleotide o-131 (gga ccc aga (g,c)gg aac cat gga a(g,a)(g,a,t,c)) is complementary to the 5' region of $V_\kappa III$ family light chain genes and overlaps the first ATC of the leader sequence. Oligonucleotide o-130 (gtg caa tca att ctc gag ttt gac tac aga c) is complementary to a sequence approximately 150 bp 3' of $J_\kappa 1$ and includes an XhoI site. These two oligonucleotides amplify a 0.7 kb DNA fragment from human spleen DNA corresponding to rearranged $V_\kappa III$ genes joined to $J_\kappa 1$ segments. The PCR amplified DNA was digested with NcoI and XhoI and cloned individual PCR products into the plasmid pNN03. The DNA sequence of 5 clones was determined and identified two with functional VJ joints (open reading frames). Additional functionally rearranged light chain clones are collected. The functionally rearranged clones can be individually cloned into light chain expression cassette described above (FIG. 33). Transgenic mice generated with the rearranged light chain constructs can be bred with heavy chain minilocus transgenics to produce a strain of mice that express a spectrum of fully human antibodies in which all of the diversity of the primary repertoire is contributed by the heavy chain. One source of light chain diversity can be from somatic mutation. Because not all light chains will be equivalent with respect to their ability to combine with a variety of different heavy chains, different strains of mice, each containing different light chain constructs can be generated and tested. The advantage of this scheme, as opposed to the use of unrearranged light chain miniloci, is the increased light chain allelic and isotypic exclusion that comes from having the light chain ready to pair with a heavy chain as soon as heavy chain VDJ joining occurs. This combination can result in an increased frequency of B-cells expressing fully human antibodies, and thus it can facilitate the isolation of human Ig expressing hybridomas.

NotI inserts of plasmids pIGM1, pHC1, pIGG1, pKC1, and pKC2 were isolated away from vector sequences by agarose gel electrophoresis. The purified inserts were microinjected into the pronuclei of fertilized (C57BL/6 x CBA)F2 mouse embryos and transferred the surviving embryos into pseudopregnant females as described by Hogan et al. (Hogan et al., *Methods of Manipulating the Mouse Embryo*, Cold Spring Harbor Laboratory, N.Y. (1986)).

EXAMPLE 9

Inactivation of the Mouse Kappa Light Chain Gene by Homologous Recombination

This example describes the inactivation of the mouse endogenous kappa locus by homologous recombination in embryonic stem (ES) cells followed by introduction of the mutated gene into the mouse germ line by injection of targeted ES cells bearing an inactivated kappa allele into early mouse embryos (blastocysts).

The strategy is to delete $J_K$ and $C_K$ by homologous recombination with a vector containing DNA sequences homologous to the mouse kappa locus in which a 4.5 kb segment of the locus, spanning the $J_K$ gene and $C_K$ segments, is deleted and replaced by the selectable marker neo.

Construction of the kappa targeting vector

The plasmid pGEM7 (KJ1) contains the neomycin resistance gene (neo), used for drug selection of transfected ES cells, under the transcriptional control of the mouse phosphoglycerate kinase (pgk) promoter (XbaI/TaqI fragment; Adra et al., *Gene* 60:65–74 (1987)) in the cloning vector pGEM-7Zf(+). The plasmid also includes a heterologous polyadenylation site for the neo gene, derived from the 3' region of the mouse pgk gene (PvuII/HindIII. fragment; Boer et al., *Biochemical Genetics*, 28:299–308 (1990)). This plasmid was used as the starting point for construction of the kappa targeting vector. The first step was to insert sequences homologous to the kappa locus 3' of the neo expression cassette.

Mouse kappa chain sequences (FIG. 20a) were isolated from a genomic phage library derived from liver DNA using oligonucleotide probes specific for the $C_K$ locus:
5'-GGC TGA TGC TGC ACC AAC TGT ATC CAT CTT CCC ACC ATC CAG-3'
and for the Jк5 gene segment:
5'-CTC ACG TTC GGT GCT GGG ACC AAG CTG GAG CTG AAA CGT AAG-3'.

An 8 kb BglII/SacI fragment extending 3' of the mouse $C_K$ segment was isolated from a positive phage clone in two pieces, as a 1.2 kb BglII/SacI fragment and a 6.8 kb SacI fragment, and subcloned into BglII/SacI digested pGEM7 (KJ1) to generate the plasmid pNEO-K3' (FIG. 20b).

A 1.2 kb EcoRI/SphI fragment extending 5' of the $J_K$ region was also isolated from a positive phage clone. An SphI/XbaI/BglII/EcoRI adaptor was ligated to the SphI site of this fragment, and the resulting EcoRI fragment was ligated into EcoRI digested pNEO-K3', in the same 5' to 3' orientation as the neo gene and the downstream 3' kappa sequences, to generate pNEO-K5'3' (FIG. 20c).

The Herpes Simplex Virus (HSV) thymidine kinase (TK) gene was then included in the construct in order to allow for enrichment of ES clones bearing homologous recombinants, as described by Mansour et al., *Nature* 336:348–352 (1988), which is incorporated herein by reference. The HSV TK cassette was obtained from the plasmid pGEM7 (TK), which contains the structural sequences for the HSV TK gene bracketed by the mouse pgk promoter and polyadenylation sequences as described above for pGEM7 (KJ1). The EcoRI site of pGEM7 (TK) was modified to a BamHI site and the TK cassette was then excised as a BamHI/HindIII fragment and subcloned into pGP1b to generate pGP1b-TK. This plasmid was linearized at the XhoI site and the XhoI fragment from pNEO-K5'3', containing the neo gene flanked by genomic sequences from 5' of $J_K$ and 3' of $C_K$, was inserted into pGP1b-TK to generate the targeting vector J/C KI (FIG. 20d). The putative structure of the genomic kappa locus following homologous recombination with J/C K1 is shown in FIG. 20e.

Generation and analysis of ES cells with targeted inactivation of a kappa allele The ES cells used were the AB-1 line grown on mitotically inactive SNL76/7 cell feeder layers (McMahon and Bradley, *Cell* 62:1073–1085 (1990)) essentially as described (Robertson, E. J. (1987) in *Teratocarcinomas and Embryonic Stem Cells: A Practical Approach*. E. J. Robertson, ed. (Oxford: IRL Press), p. 71–112). Other suitable ES lines include, but are not limited to, the E14 line (Hooper et al. (1987) *Nature* 326: 292–295), the D3 line (Doetschman et al. (1985) *J. Embryol. Exp. Morph*. 87: 27–45), and the CCE line (Robertson et al. (1986) *Nature* 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal).

The pluripotence of any given ES cell line can vary with time in culture and the care with which it has been handled. The only definitive assay for pluripotence is to determine whether the specific population of ES cells to be used for targeting can give rise to chimeras capable of germline transmission of the ES genome. For this reason, prior to gene targeting, a portion of the parental population of AB-1 cells is injected into C57Bl/6J blastocysts to ascertain whether the cells are capable of generating chimeric mice with extensive ES cell contribution and whether the majority of these chimeras can transmit the ES genome to progeny.

The kappa chain inactivation vector J/C K1 was digested with NotI and electroporated into AB-1 cells by the methods described (Hasty et al., *Nature*, 350:243–246 (1991)). Electroporated cells were plated onto 100 mm dishes at a density of $1-2 \times 10^6$ cells/dish. After 24 hours, G418 (200 µg/ml of active component) and FIAU (0.5 µM) were added to the medium, and drug-resistant clones were allowed to develop over 10–11 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described (Laird et al., *Nucl. Acids Res*. 19:4293 (1991)) digested with XbaI and probed with the 800 bp EcoRI/XbaI fragment indicated in FIG. 20e as probe A. This probe detects a 3.7 kb XbaI fragment in the wild type locus, and a diagnostic 1.8 kb band in a locus which has homologously recombined with the targeting vector (see FIGS. 20a and e). Of 901 G418 and FIAU resistant clones screened by Southern blot analysis, 7 displayed the 1.8 kb XbaI band indicative of a homologous recombination into one of the kappa genes. These 7 clones were further digested with the enzymes BglII, SacI, and PstI to verify that the vector integrated homologously into one of the kappa genes. When probed with the diagnostic 800 bp EcoRI/XbaI fragment (probe A), BglII, SacI, and PstI digests of wild type DNA produce fragments of 4.1, 5.4, and 7 kb, respectively, whereas the presence of a targeted kappa allele would be indicated by fragments of 2.4, 7.5, and 5.7 kb, respectively (see FIGS. 20a and e). All 7 positive clones detected by the XbaI digest showed the expected BglII, SacI, and PstI restriction fragments diagnostic of a homologous recombination at the kappa light chain. In addition, Southern blot analysis of an NsiI digest of the targeted clones using a neo specific probe (probe B, FIG. 20e) generated only the predicted fragment of 4.2 kb, demonstrating that the clones each contained only a single copy of the targeting vector.

Generation of mice bearing the inactivated kappa chain

Five of the targeted ES clones described in the previous section were thawed and injected into C57Bl/6J blastocysts as described (Bradley, A. (1987) in *Teratocarcinomas and Embryonic Stem Cells: A Practical Approach*. E. J. Robertson, ed. (Oxford: IRL Press), p. 113–151) and transferred into the uteri of pseudopregnant females to generate chimeric mice resulting from a mixture of cells derived from the input ES cells and the host blastocyst. The extent of ES cell contribution to the chimeras can be visually estimated by the amount of agouti coat coloration, derived from the ES cell line, on the black C57Bl/6J background. Approximately half of the offspring resulting from blastocyst injection of the targeted clones were chimeric (i.e., showed agouti as well as black pigmentation) and of these, the majority showed extensive (70 percent or greater) ES cell contribution to coat pigmentation. The AB1 ES cells are an XY cell line and a majority of these high percentage chimeras were male due to sex conversion of female embryos colonized by male ES cells. Male chimeras derived from 4 of the 5 targeted clones were bred with C57BL/6J females and the offspring monitored for the presence of the dominant agouti coat color indicative of germline transmission of the ES genome. Chimeras from two of these clones consistently generated agouti offspring. Since only one copy of the kappa locus was targeted in the injected ES clones, each agouti pup had a 50 percent chance of inheriting the mutated locus. Screening for the targeted gene was carried out by Southern blot analysis of Bgl II-digested DNA from tail biopsies, using the probe utilized in identifying targeted ES clones (probe A, FIG. 20e). As expected, approximately 50 percent of the agouti offspring showed a hybridizing Bgl II band of 2.4 kb in addition to the wild-type band of 4.1 kb, demonstrating the germline transmission of the targeted kappa locus.

In order to generate mice homozygous for the mutation, heterozygotes were bred together and the kappa genotype of the offspring determined as described above. As expected, three genotypes were derived from the heterozygote matings: wild-type mice bearing two copies of a normal kappa locus, heterozygotes carrying one targeted copy of the kappa gene and one NT kappa gene, and mice homozygous for the kappa mutation. The deletion of kappa sequences from these latter mice was verified by hybridization of the Southern blots with a probe specific for $J_K$ (probe C, FIG. 20a). Whereas hybridization of the $J_K$ probe was observed to DNA samples from heterozygous and wild-type siblings, no hybridizing signal was present in the homozygotes, attesting to the generation of a novel mouse strain in which both copies of the kappa locus have been inactivated by deletion as a result of targeted mutation.

EXAMPLE 10

Inactivation of the Mouse Heavy Chain Gene by Homologous Recombination

This example describes the inactivation of the endogenous murine immunoglobulin heavy chain locus by homologous recombination in embryonic stem (ES) cells. The strategy is to delete the endogenous heavy chain J segments by homologous recombination with a vector containing heavy chain sequences from which the $J_H$ region has been deleted and replaced by the gene for the selectable marker neo.

Construction of a heavy chain targeting vector

Mouse heavy chain sequences containing the $J_H$ region (FIG. 21a) were isolated from a genomic phage library derived from the D3 ES cell line (Gossler et al., *Proc. Natl. Acad. Sci. U.S.A.* 83:9065–9069 (1986)) using a $J_H4$ specific oligonucleotide probe:

5'-ACT ATG CTA TGG ACT ACT GGG GTC AAG GAA CCT CAG TCA CCG-3'

A 3.5 kb genomic SacI/StuI fragment, spanning the $J_H$ region, was isolated from a positive phage clone and subcloned into SacI/SmaI digested pUC18. The resulting plasmid was designated pUC18 $J_H$. The neomycin resistance gene (neo), used for drug selection of transfected ES cells, was derived from a repaired version of the plasmid pGEM7 (KJ1). A report in the literature (Yenofsky et al. (1990) *Proc. Natl. Acad. Sci. (U.S.A.)* 87: 3435–3439) documents a point mutation the neo coding sequences of several commonly used expression vectors, including the construct pMC1neo (Thomas and Cappechi (1987) *Cell* 51: 503–512) which served as the source of the neo gene used in pGEM7 (KJ1). This mutation reduces the activity of the neo gene product and was repaired by replacing a restriction fragment encompassing the mutation with the corresponding sequence from a wild-type neo clone. The HindIII site in the prepared pGEM7 (KJ1) was converted to a SalI site by addition of a synthetic adaptor, and the neo expression cassette excised by digestion with XbaI/SalI. The ends of the neo fragment were then blunted by treatment with the Klenow form of DNA polI, and the neo fragment was subcloned into the NaeI site of pUC18 $J_H$, generating the plasmid pUC18 $J_H$-neo (FIG. 21b).

Further construction of the targeting vector was carried out in a derivative of the plasmid pGP1b. pGP1b was digested with the restriction enzyme NotI and ligated with the following oligonucleotide as an adaptor:

5'-GGC CGC TCG ACG ATA GCC TCG AGG CTA TAA ATC TAG AAG AAT TCC AGC AAA GCT TTG GC-3'

The resulting plasmid, called pGMT, was used to build the mouse immunoglobulin heavy chain targeting construct.

The Herpes Simplex Virus (HSV) thymidine kinase (TK) gene was included in the construct in order to allow for enrichment of ES clones bearing homologous recombinants, as described by Mansour et al. (*Nature* 336, 348–352 (1988)). The HSV TK gene was obtained from the plasmid pGEM7 (TK) by digestion with EcoRI and HindIII. The TK DNA fragment was subcloned between the EcoRI and HindIII sites of pGMT, creating the plasmid pGMT-TK (FIG. 21c).

To provide an extensive region of homology to the target sequence, a 5.9 kb genomic XbaI/XhoI fragment, situated 5' of the $J_H$ region, was derived from a positive genomic phage clone by limit digestion of the DNA with XhoI, and partial digestion with XbaI. As noted in FIG. 21a, this XbaI site is not present in genomic DNA, but is rather derived from phage sequences immediately flanking the cloned genomic heavy chain insert in the positive phage clone. The fragment was subcloned into XbaI/XhoI digested pGMT-TK, to generate the plasmid pGMT-TK-$J_H5'$ (FIG. 21d).

The final step in the construction involved the excision from pUC18 $J_H$-neo of the 2.8 kb EcoRI fragment which contained the neo gene and flanking genomic sequences 3' of $J_H$. This fragment was blunted by Klenow polymerase and subcloned into the similarly blunted XhoI site of pGMT-TK-$J_H5'$. The resulting construct, $J_H$KO1 (FIG. 21e), contains 6.9 kb of genomic sequences flanking the $J_H$ locus, with a 2.3 kb deletion spanning the $J_H$ region into which has been inserted the neo gene. FIG. 21f shows the structure of an endogenous heavy chain gene after homologous recombination with the targeting construct.

EXAMPLE 11

Generation and analysis of targeted ES cells

AB-1 ES cells (McMahon and Bradley, Cell 62:1073–1085 (1990)) were grown on mitotically inactive SNL76/7 cell feeder layers essentially as described (Robertson, E. J. (1987) Teratocarcinomas and Embryonic Stem Cells: A Practical Approach. E. J. Robertson, ed. (Oxford: IRL Press), pp. 71–112). As described in the previous example, prior to electroporation of ES cells with the targeting construct $J_H$KO1, the pluripotency of the ES cells was determined by generation of AB-1 derived chimeras which were shown capable of germline transmission of the ES genome.

The heavy chain inactivation vector $J_H$KO1 was digested with NotI and electroporated into AB-1 cells by the methods described (Hasty et al., Nature 350:243–246 (1991)). Electroporated cells were plated into 100 mm dishes at a density of 1–2×10$^6$ cells/dish. After 24 hours, G418 (200 mg/ml of active component) and FIAU (0.5 mM) were added to the medium, and drug-resistant clones were allowed to develop over 8–10 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described (Laird et al. (1991) Nucleic Acids Res. 19: 4293), digested with StuI and probed with the 500 bp EcoRI/StuI fragment designated as probe A in FIG. 21f. This probe detects a StuI fragment of 4.7 kb in the wild-type locus, whereas a 3 kb band is diagnostic of homologous recombination of endogenous sequences with the targeting vector (see FIGS. 21a and f). Of 525 G418 and FIAU doubly-resistant clones screened by Southern blot hybridization, 12 were found to contain the 3 kb fragment diagnostic of recombination with the targeting vector. That these clones represent the expected targeted events at the $J_H$ locus (as shown in FIG. 21f) was confirmed by further digestion with HindIII, SpeI and HpaI. Hybridization of probe A (see FIG. 21f) to Southern blots of HindIII, SpeI, and HpaI digested DNA produces bands of 2.3 kb, >10 kb, and >10 kb, respectively, for the wild-type locus (see FIG. 21a), whereas bands of 5.3 kb, 3.8 kb, and 1.9 kb, respectively, are expected for the targeted heavy chain locus (see FIG. 21f). All 12 positive clones detected by the StuI digest showed the predicted HindIII, SpeI, and HpaI bands diagnostic of a targeted $J_H$ gene. In addition, Southern blot analysis of a StuI digest of all 12 clones using a neo-specific probe (probe B, FIG. 21f) generated only the predicted fragment of 3 kb, demonstrating that the clones each contained only a single copy of the targeting vector.

Generation of mice carrying the $J_H$ deletion

Three of the targeted ES clones described in the previous section were thawed and injected into C57BL/6J blastocysts as described (Bradley, A. (1987) in Teratocarcinomas and Embryonic Stem Cells: A Practical Approach, E. J. Robertson, ed. (Oxford: IRL Press), p.113–151) and transferred into the uteri of pseudopregnant females. The extent of ES cell contribution to the chimera was visually estimated from the amount of agouti coat coloration, derived from the ES cell line, on the black C57BL/6J background. Half of the offspring resulting from blastocyst injection of two of the targeted clones were chimeric (i.e., showed agouti as well as black pigmentation); the third targeted clone did not generate any chimeric animals. The majority of the chimeras showed significant (approximately 50 percent or greater) ES cell contribution to coat pigmentation. Since the AB-1 ES cells are an XY cell line, most of the chimeras were male, due to sex conversion of female embryos colonized by male ES cells. Males chimeras were bred with C57BL/6J females and the offspring monitored for the presence of the dominant agouti coat color indicative of germline transmission of the ES genome. Chimeras from both of the clones consistently generated agouti offspring. Since only one copy of the heavy chain locus was targeted in the injected ES clones, each agouti pup had a 50 percent chance of inheriting the mutated locus. Screening for the targeted gene was carried out by Southern blot analysis of StuI-digested DNA from tail biopsies, using the probe utilized in identifying targeted ES clones (probe A, FIG. 21f). As expected, approximately 50 percent of the agouti offspring showed a hybridizing StuI band of approximately 3 kb in addition to the wild-type band of 4.7 kb, demonstrating germline transmission of the targeted $J_H$ gene segment.

In order to generate mice homozygous for the mutation, heterozygotes were bred together and the heavy chain genotype of the offspring determined as described above. As expected, three genotypes were derived from the heterozygote matings: wild-type mice bearing two copies of the normal $J_H$ locus, heterozygotes caring one targeted copy of the gene and one normal copy, and mice homozygous for the $J_H$ mutation. The absence of $J_H$ sequences from these latter mice was verified by hybridization of the Southern blots of StuI-digested DNA with a probe specific for $J_H$ (probe C, FIG. 21a). Whereas hybridization of the $J_H$ probe to a 4.7 kb fragment in DNA samples from heterozygous and wild-type siblings was observed, no signal was present in samples from the $J_H$-mutant homozygotes, attesting to the generation of a novel mouse strain in which both copies of the heavy chain gene have been mutated by deletion of the $J_H$ sequences.

EXAMPLE 12

Heavy Chain Minilocus Transgene

A. Construction of plasmid vectors for cloning large DNA sequences 1. pGP1a

The plasmid pBR322 was digested with EcoRI and StyI and ligated with the following oligonucleotides:

oligo-42 5'-caa gag ccc gcc taa tga gcg ggc ttt ttt ttg cat act gcg gcc gct-3' oligo-43 5'-aat tag cgg ccg cag tat gca aaa aaa agc ccg ctc att agg cgg gct-3'

The resulting plasmid, pGP1a, is designed for cloning very large DNA constructs that can be excised by the rare cutting restriction enzyme NotI. It contains a NotI restriction site downstream (relative to the ampicillin resistance gene, AmpR) of a strong transcription termination signal derived from the trpA gene (Christie et al., Proc. Natl. Acad. Sci. USA 78:4180 (1981)). This termination signal reduces the potential toxicity of coding sequences inserted into the NotI site by eliminating readthrough transcription from the AmpR gene. In addition, this plasmid is low copy relative to the pUC plasmids because it retains the pBR322 copy number control region. The low copy number further reduces the potential toxicity of insert sequences and reduces the selection against large inserts due to DNA replication. The vectors pGP1b, pGP1c, pGP1d, and pGP1f are derived from pGP1a and contain different polylinker cloning sites. The polylinker sequences are given below pGP1a

```
                        Not I
                       GCGGCCGC
``` pGP1b

```
        Not I    XhoI       Cla I         BamHI       HindIII   NotI
     GCggccgcctcgagatcactatcgattaattaaggatccagcagtaagcttgcGGCCGC
``` pGI1c

```
        NotI    SmaI    XhoI    SalI    HindIII       BamHI   SacII   NotI
     GCggccgcatcccgggtctcgaggtcgacaagctttcgaggatccgcGGCCGC
``` pGP1d

```
        NotI    SalI    HindIII    ClaI    BamHI   XhoI    NotI
     GCggccgctgtcgacaagcttatcgatggatcctcgagtgcGGCCGC
``` pGP1f

```
        NotI    SalI    HindIII    EcoRI    ClaI        KpnI    BamHI   XhoI       NotI
     GCggccgctgtcgacaagcttcgaattcagatcgatgtggtacctggatcctcgagtgcGGCCGC
```

Each of these plasmids can be used for the construction of large transgene inserts that are excisable with NotI so that the transgene DNA can be purified away from vector sequences prior to microinjection.

2. pGP1b pGP1a was digested with NotI and ligated with the following oligonucleotides:

oligo-47 5'-ggc cgc aag ctt act gct gga tcc tta att aat cga tag tga tct cga ggc-3' oligo-48 5'-ggc cgc ctc gag atc act atc gat taa tta agg atc cag cag taa gct tgc-3'

The resulting plasmid, pGP1b, contains a short polylinker region flanked by NotI sites. This facilitates the construction of large inserts that can be excised by NotI digestion.

3. pGPe

The following oligonucleotides:

oligo-44 5'-ctc cag gat cca gat atc agt acc tga aac agg gct tgc-3' oligo-45 5'-ctc gag cat gca cag gac ctg gag cac aca cag cct tcc-3' were used to amplify the immunoglobulin heavy chain 3' enhancer (S. Petterson, et al., Nature 344:165–168 (1990)) from rat liver DNA by the polymerase chain reaction technique.

Figure 22:
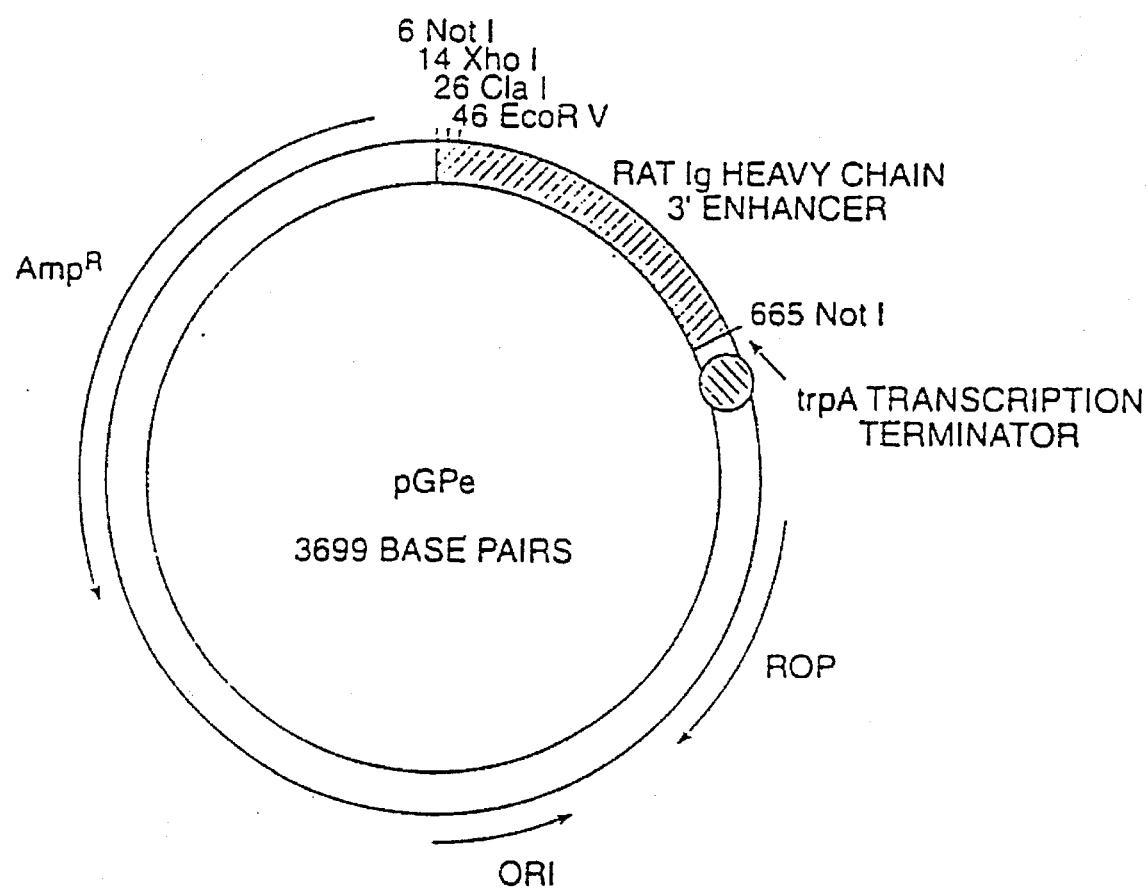
FIG. 22 depicts the map of vector pGPe.

The amplified product was digested with BamHI and SphI and cloned into BamHI/SphI digested pNNO3 (pNNO3 is a pUC derived plasmid that contains a polylinker with the following restriction sites, listed in order: NotI, BamHI, NcoI, ClaI, EcoRV, XbaI, SacI, XhoI, SphI, PstI, BglII, EcoRI, SmaI, KpnI, HindIII, and NotI). The resulting plasmid, pRE3, was digested with BamHI and HindIII, and the insert containing the rat Ig heavy chain 3' enhancer cloned into BamHI/HindIII digested pGP1b. The resulting plasmid, pGPe (FIG. 22 and Table 1), contains several unique restriction sites into which sequences can be cloned and subsequently excised together with the 3' enhancer by NotI digestion.

TABLE 1

Sequence of vector pGPe.

```
AATTAGCggccgcctcgagatcactatcgattaattaaggatccagatatcagtacctgaaacagggcttgctcacaaca
tctctctctctgtctctctgtctctgtgtgtgtgtctctctctgtctctgtctctctctgtctctctgtctctgtgtgtg
tctctctctgtctctctctctgtctctctgtctctctgtctgtctctgtctctgtctctgtctctctctctctctctctc
tctctctctctctctcacacacacacacacacacacacacacacacctgccgagtgactcactctgtgcagggttggccc
tcggggcacatgcaaatggatgtttgttccatgcagaaaaacatgtttctcattctctgagccaaaaatagcatcaatga
ttcccccaccctgcagctgcaggttcaccccacctggccaggttgaccagctttggggatggggctggggttccatgac
ccctaacggtgacattgaattcagtgttttcccatttatcgacactgctggaatctgaccctaggagggaatgacaggag
ataggcaaggtccaaacaccccagggaagtgggagagacaggaaggctgtgtgtgctccaggtcctgtgcatgctgcaga
tctgaattcccgggtaccaagcttgcGGCCGCAGTATGCAAAAAAAAGCCCGCTCATTAGGCGGGCTCTTGGCAGAACAT
ATCCATCGCGTCCGCCATCTCCAGCAGCCGCACGCGGCGCATCTCGGGCAGCGTTGGGTCCTGGCCACGGGTGCGCATGA
TCGTGCTCCTGTCGTTGAGGACCCGGCTAGGCTGGCGGGGTTGCCTTACTGGTTAGCAGAATGAATCACCGATACGCGAG
```

TABLE 1-continued

Sequence of vector pGPe.

```
CGAACGTGAAGCGACTGCTGCTGCAAAACGTCTGCGACCTGAGCAACAACATGAATGGTCTTCGGTTTCCGTGTTTCGTA
AAGTCTGGAAACGCGGAAGTCAGCGCCCTGCACCATTATGTTCCGGATCTGCATCGCAGGATGCTGCTGGCTACCCTGTG
GAACACCTACATCTGTATTAACGAAGCGCTGGCATTGACCCTGAGTGATTTTTCTCTGGTCCCGCCGCATCCATACCGCC
AGTTGTTTACCCTCACAACGTTCCAGTAACCGGGCATGTTCATCATCAGTAACCCGTATCGTGAGCATCCTCTCTCGTTT
CATCGGTATCATTACCCCCATGAACAGAAATTCCCCCTTACACGGAGGCATCAAGTGACCAAACAGGAAAAAACCGCCCT
TAACATGGCCCGCTTTATCAGAAGCCAGACATTAACGCTTCTGGAGAAACTCAACGAGCTGGACGCGGATGAACAGGCAG
ACATCTGTGAATCGCTTCACGACCACGCTGATGAGCTTTACCGCAGCTGCCTCGCGCGTTTCGGTGATGACGGTGAAAAC
CTCTGACACATGCAGCTCCCGGAGACGGTCACAGCTTGTCTGTAAGCGGATGCCGGGAGCAGACAAGCCCGTCAGGGCGC
GTCAGCGGGTGTTGGCGGGTGTCGGGGCGCAGCCATGACCCAGTCACGTAGCGATAGCGGAGTGTATACTGGCTTAACTA
TGCGGCATCAGAGCAGATTGTACTGAGAGTGCACCATATGCGGTGTGAAATACCGCACAGATGCGTAAGGAGAAAATACC
GCATCAGGCGCTCTTCCGCTTCCTCGCTCACTGACTCGCTGCGCTCGGTCGTTCGGCTGCGGCGAGCGGTATCAGCTCAC
TCAAAGGCGGTAATACGGTTATCCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCTGACGAGCATCACAAAAATCGACGCT
CAAGTCAGAGGTGGCGAAACCCGACAGGACTATAAAGATACCAGGCGTTTCCCCCTGGAAGCTCCCTCGTGCGCTCTCCT
GTTCCGACCCTGCCGCTTACCGGATACCTGTCCGCCTTTCTCCCTTCGGGAAGCGTGGCGCTTTCTCATAGCTCACGCTG
TAGGTATCTCAGTTCGGTGTAGGTCGTTCGCTCCAAGCTGGGCTGTGTGCACGAACCCCCCGTTCAGCCCGACCGCTGCG
CCTTATCCGGTAACTATCGTCTTGAGTCCAACCCGGTAAGACACGACTTATCGCCACTGGCAGCAGCCACTGGTAACAGG
ATTAGCAGAGCGAGGTATGTAGGCGGTGCTACAGAGTTCTTGAAGTGGTGGCCTAACTACGGCTACACTAGAAGGACAGT
ATTTGGTATCTGCGCTCTGCTGAAGCCAGTTACCTTCGGAAAAAGAGTTGGTAGCTCTTGATCCGGCAAACAAACCACCG
CTGGTAGCGGTGGTTTTTTTGTTTGCAAGCAGCAGATTACGCGCAGAAAAAAAGGATCTCAAGAAGATCCTTTGATCTTT
TCTACGGGGTCTGACGCTCAGTGGAACGAAAACTCACGTTAAGGGATTTTGGTCATGAGATTATCAAAAAGGATCTTCAC
CTAGATCCTTTTAAATTAAAAATGAAGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCTGACTCCCCGTCGTGTAGATA
ACTACGATACGGGAGGGCTTACCATCTGGCCCCAGTGCTGCAATGATACCGCGAGACCCACGCTCACCGGCTCCAGATTT
ATCAGCAATAAACCAGCCAGCCGGAAGGGCCGAGCGCAGAAGTGGTCCTGCAACTTTATCCGCCTCCATCCAGTCTATTA
ATTGTTGCCGGGAAGCTAGAGTAAGTAGTTCGCCAGTTAATAGTTTGCGCAACGTTGTTGCCATTGCTGCAGGCATCGTG
GTGTCACGCTCGTCGTTTGGTATGGCTTCATTCAGCTCCGGTTCCCAACGATCAAGGCGAGTTACATGATCCCCCATGTT
GTGCAAAAAAGCGGTTAGCTCCTTCGGTCCTCCGATCGTTGTCAGAAGTAAGTTGGCCGCAGTGTTATCACTCATGGTTA
TGGCAGCACTGCATAATTCTCTTACTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAACACGGGATAATACCGCGCCACATAGCAGAAC
TTTAAAAGTGCTCATCATTGGAAAACGTTCTTCGGGGCGAAAACTCTCAAGGATCTTACCGCTGTTGAGATCCAGTTCGA
TGTAACCCACTCGTGCACCCAACTGATCTTGACGATCTTTTACTTTCACCAGCGTTTCTGGGTGAGCAAAAACAGGAAGG
CAAAATGCCGCAAAAAAGGGAATAAGGGCGACACGGAAATGTTGAATACTCATACTCTTCCTTTTTCAATATTATTGAAG
CATTTATCAGGGTTATTGTCTCATGAGCGGATACATATTTGAATGTATTTAGAAAAATAAACAAATAGGGGTTCCGCGCA
CATTTCCCCGAAAAGTGCCACCTGACGTCTAAGAAACCATTATTATCATGACATTAACCTATAAAAATAGGCGTATCACG
AGGCCCTTTCGTCTTCAAG
```

B. Construction of IgM expressing minilocus transgene, pIGM1

1. Isolation of J-μ constant region clones and construction of pJM1

A human placental genomic DNA library cloned into the phage vector λEMBL3/SP6/T7 (Clonetech Laboratories, Inc., Palo Alto, Calif.) was screened with the human heavy chain J region specific oligonucleotide:

oligo-1 5'-gga ctg tgt ccc tgt gtg atg ctt ttg atg tct ggg gcc aag-3' and the phage clone λ1.3 isolated. A 6 kb HindIII/KpnI fragment from this clone, containing all six J segments as well as D segment DHQ52 and the heavy chain J-μ intronic enhancer, was isolated. The same library was screened with the human μ specific oligonucleotide:

oligo-2 5'-cac caa gtt gac ctg cct ggt cac aga cct gac cac cta tga-3' and the phage clone λ2.1 isolated. A 10.5 kb HindIII/XhoI fragment, containing the μ switch region and all of the μ constant region exons, was isolated from this clone. These two fragments were ligated together with KpnI/XhoI digested pNN03 to obtain the plasmid pJM1.

2. pJM2

Figure 23:
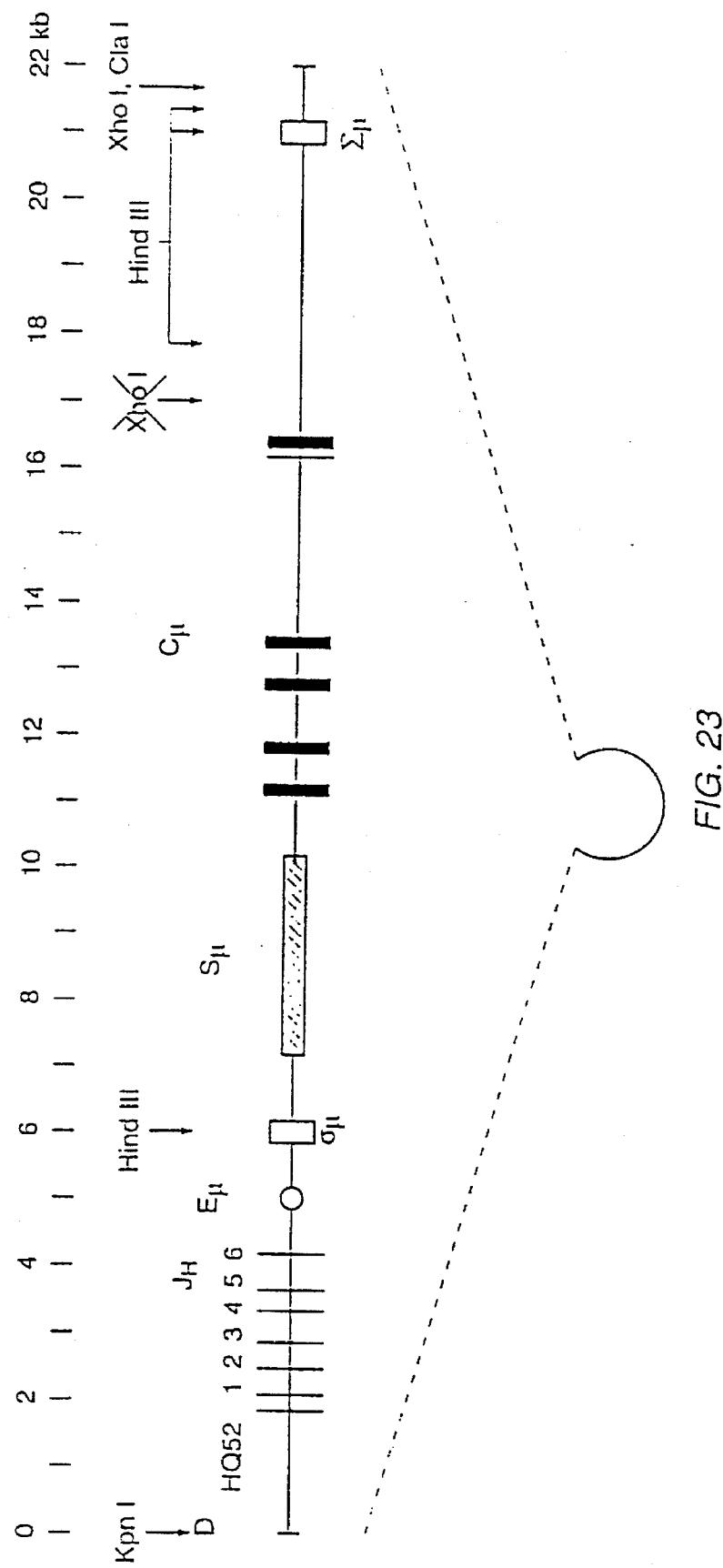
FIG. 23 depicts the structure of vector pJM2.

A 4 kb XhoI fragment was isolated from phage clone λ2.1 that contains sequences immediately downstream of the sequences in pJM1, including the so called Σμ element involved in δ-associated deleteon of the μ in certain IgD expressing B-cells (Yasui et al., *Eur. J. Immunol.* 19:1399 (1989), which is incorporated herein by reference). This fragment was treated with the Klenow fragment of DNA polymerase I and ligated to XhoI cut, Klenow treated, pJM1. The resulting plasmid, pJM2 (FIG. 23), had lost the internal XhoI site but retained the 3' XhoI site due to incomplete reaction by the Klenow enzyme. pJM2 contains the entire human J region, the heavy chain J-μ intronic enhancer, the μ switch region and all of the μ constant region exons, as well as the two 0.4 kb direct repeats, σμ and Σμ, involved in δ-associated deletion of the μ gene.

3. Isolation of D region clones and construction of pDH1

The following human D region specific oligonucleotide:

oligo-4 5'-tgg tat tac tat ggt tcg ggg agt tat tat aac cac agt gtc-3' was used to screen the human placenta genomic library for D region clones. Phage clones λ4.1 and λ4.3 were isolated. A 5.5 kb XhoI fragment, that includes the D elements $D_{K1}$, $D_{N1}$, and $D_{M2}$ (Ichihara et al., *EMBO J.* 7:4141 (1988)), was isolated from phage clone λ4.1. An adjacent upstream 5.2 kb XhoI fragment, that includes the D elements $D_{LR1}$, $D_{XP1}$, $D_{XP'1}$, and $D_{A1}$, was isolated from phage clone λ4.3. Each of these D region XhoI fragments were cloned into the SalI site of the plasmid vector pSP72 (Promega, Madison, Wis.) so as to destroy the XhoI site linking the two sequences. The upstream fragment was then excised with XhoI and SmaI, and the downstream fragment with EcoRV and XhoI. The resulting isolated fragments were ligated together with SalI digested pSP72 to give the plasmid pDH1. pDH1 contains a 10.6 kb insert that includes at least 7 D segments and can be excised with XhoI (5') and EcoRV (3').

4. pCOR1

Figure 24:
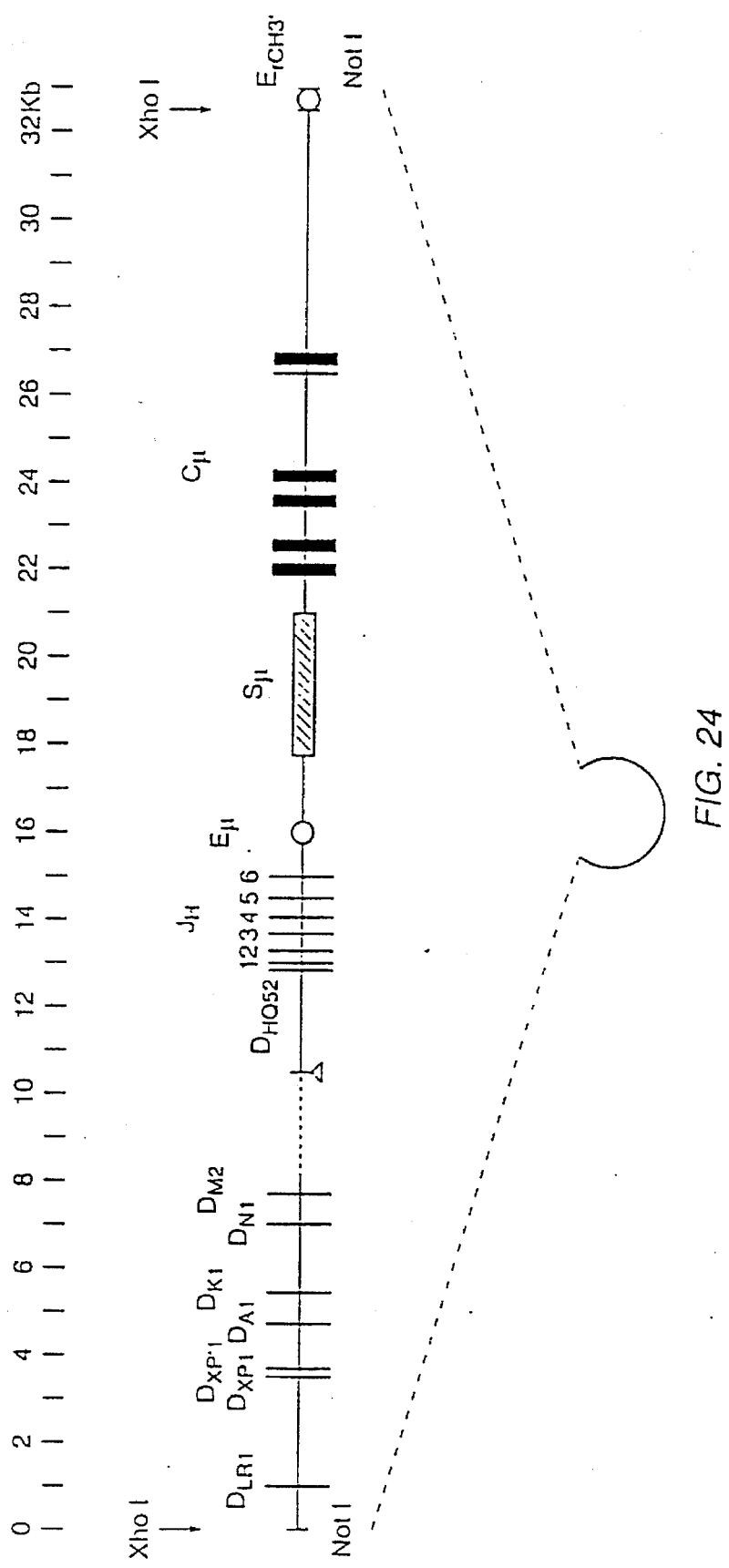
FIG. 24 depicts the structure of vector pCOR1.

The plasmid pJM2 was digested with Asp718 (an isoschizomer of KpnI) and the overhang filled in with the Klenow fragment of DNA polymerase I. The resulting DNA was then digested with ClaI and the insert isolated. This insert was ligated to the XhoI/EcoRV insert of pDH1 and XhoI/ClaI digested pGPe to generate pCOR1 (FIG. 24).

5. pVH251

A 10.3 kb genomic HindIII fragment containing the two human heavy chain variable region segments $V_H251$ and $V_H105$ (Humphries et al., *Nature* 331:446 (1988), which is incorporated herein by reference) was subcloned into pSP72 to give the plasmid pVH251.

6. pIGM1

Figure 25:
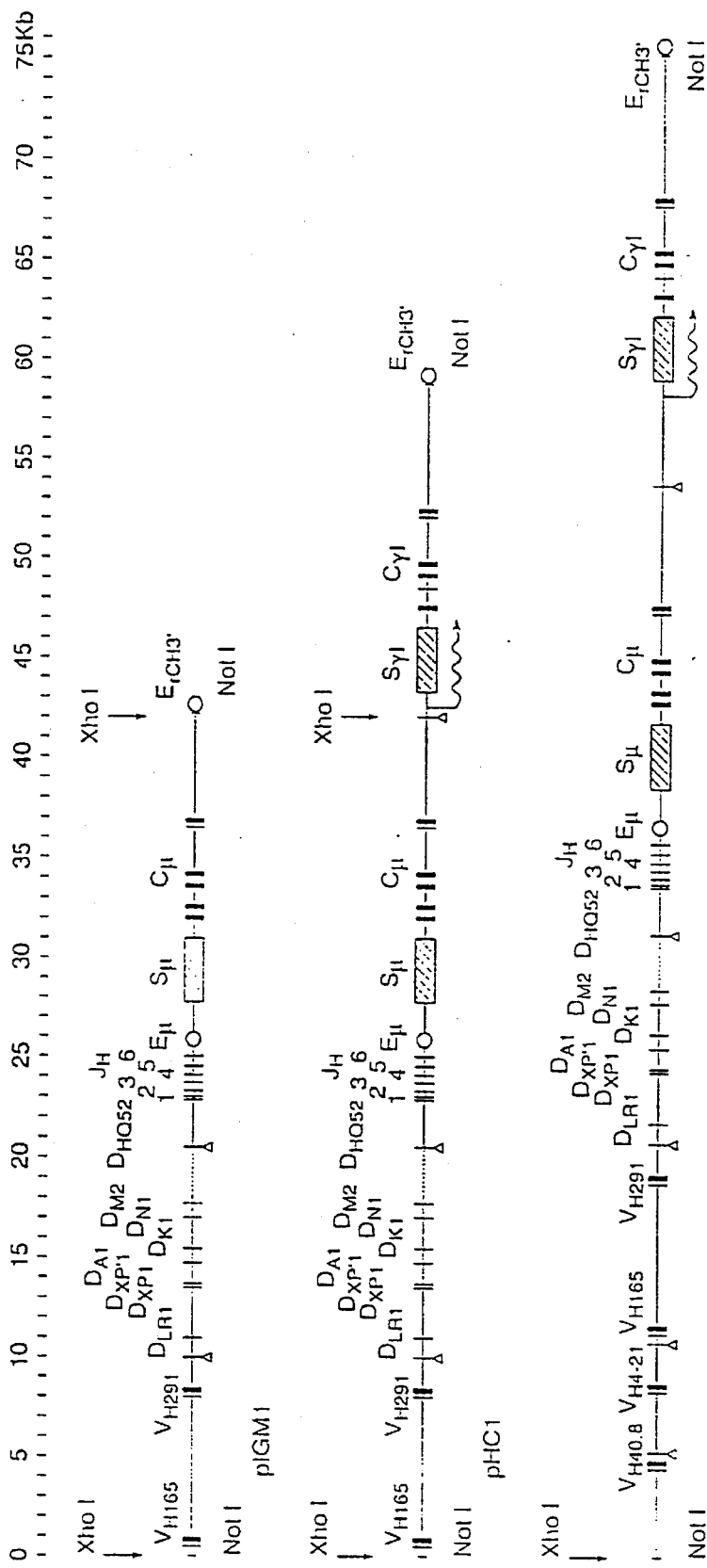
FIG. 25 depicts the transgene constructs for pIGM1, pHC1 and pHC2.

The plasmid pCOR1 was partially digested with XhoI and the isolated XhoI/SalI insert of pVH251 cloned into the upstream XhoI site to generate the plasmid pIGM1 (FIG. 25). pIGM1 contains 2 functional human variable region segments, at least 8 human D segments all 6 human $J_H$ segments, the human J-μ enhancer, the human σμ element, the human μ switch region, all of the human μ coding exons, and the human Σμ element, together with the rat heavy chain 3' enhancer, such that all of these sequence elements can be isolated on a single fragment, away from vector sequences, by digestion with NotI and microinjected into mouse embryo pronuclei to generate transgenic animals.

C. Construction of IgM and IgG expressing minilocus transgene, pHC1

1. Isolation of γ constant region clones

The following oligonucleotide, specific for human Ig g constant region genes:

oligo-29 5'-cag cag gtg cac acc caa tgc cca tga gcc cag aca ctg gac-3' was used to screen the human genomic library. Phage clones λ29.4 and λ29.5 were isolated. A 4 kb HindIII fragment of phage clone λ29.4, containing a γ switch region, was used to probe a human placenta genomic DNA library cloned into the phage vector lambda FIX™ II (Stratagene, La Jolla, Calif.). Phage clone λSg1.13 was isolated. To determine the subclass of the different γ clones, dideoxy sequencing reactions were carried out using subclones of each of the three phage clones as templates and the following oligonucleotide as a primer:

oligo-67 5'-tga gcc cag aca ctg gac-3'

Phage clones λ29.5 and λSγ1.13 were both determined to be of the γ1 subclass.

2. pγe1

A 7.8 kb HindIII fragment of phage clone λ29.5, containing the γ1 coding region was cloned into pUC18. The resulting plasmid, pLT1, was digested with XhoI, Klenow treated, and religated to destroy the internal XhoI site. The resulting clone, pLT1xk, was digested with HindIII and the insert isolated and cloned into pSP72 to generate the plasmid clone pLT1xks. Digestion of pLT1xks at a polylinker XhoI site and a human sequence derived BamHI site generates a 7.6 kb fragment containing the γ1 constant region coding exons. This 7.6 kb XhoI/BamHI fragment was cloned together with an adjacent downstream 4.5 kb BamHI fragment from phage clone λ29.5 into XhoI/BamHI digested pGPe to generate the plasmid clone pγe1. pγe1 contains all of the γ1 constant region coding exons, together with 5 kb of downstream sequences, linked to the rat heavy chain 3' enhancer.

3. pγe2

Figure 26:
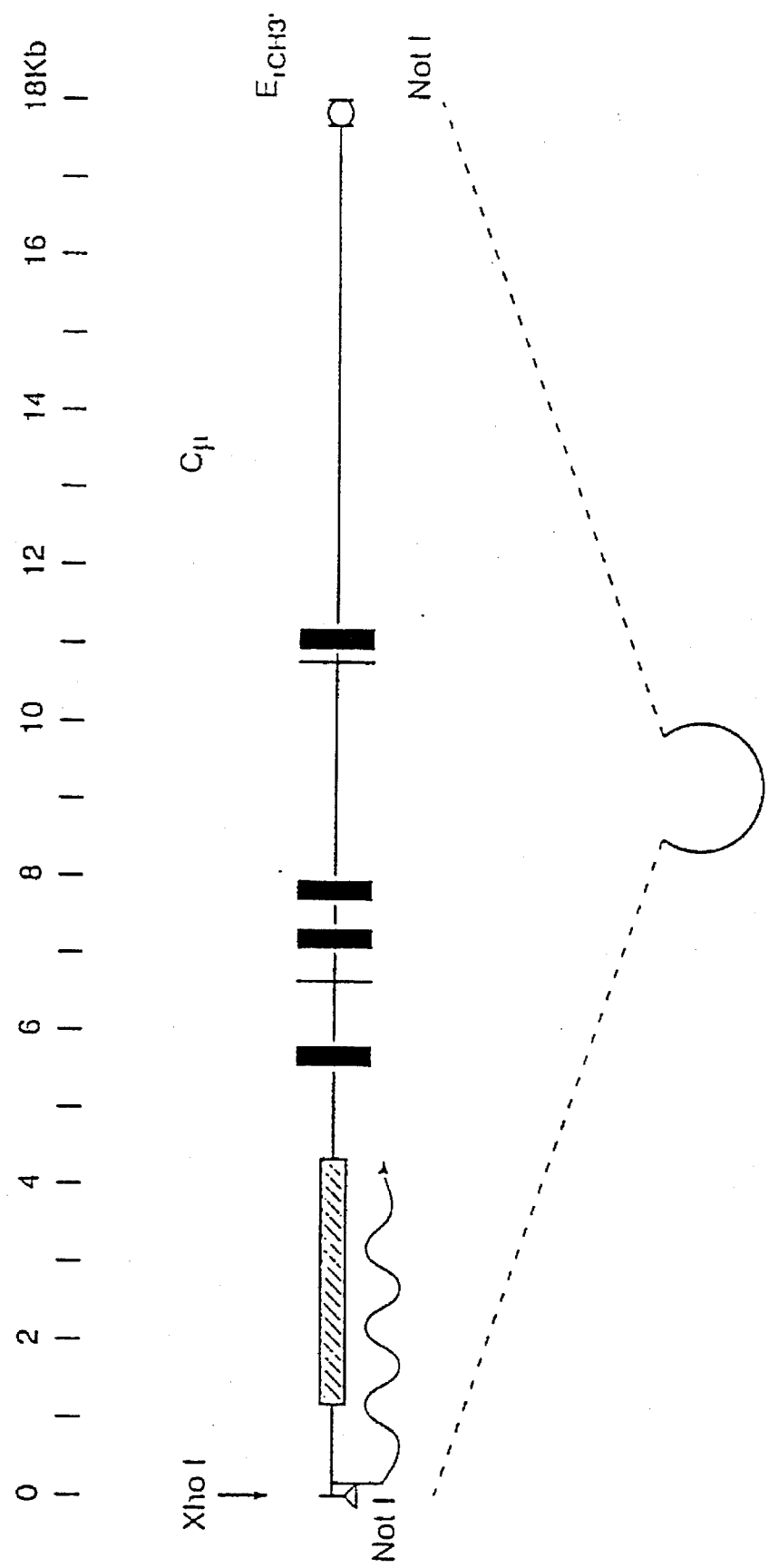
FIG. 26 depicts the structure of pγe2.

A 5.3 kb HindIII fragment containing the γ1 switch region and the first exon of the pre-switch sterile transcript (P. Sideras et al. (1989) *International Immunol.* 1, 631) was isolated from phage clone λSγ1.13 and cloned into pSP72 with the polylinker XhoI site adjacent to the 5' end of the insert, to generate the plasmid clone pSγ1s. The XhoI/SalI insert of pSγ1s was cloned into XhoI digested pγe1 to generate the plasmid clone pγe2 (FIG. 26). pγe2 contains all of the γ1 constant region coding exons, and the upstream switch region and sterile transcript exons, together with 5 kb of downstream sequences, linked to the rat heavy chain 3' enhancer. This clone contains a unique XhoI site at the 5' end of the insert. The entire insert, together with the XhoI site and the 3' rat enhancer can be excised from vector sequences by digestion with NotI.

4. pHC1

The plasmid pIGM1 was digested with XhoI and the 43 kb insert isolated and cloned into XhoI digested pge2 to generate the plasmid pHC1 (FIG. 25). pHC1 contains 2 functional human variable region segments, at least 8 human D segments all 6 human $J_H$ segments, the human J-μ enhancer, the human σμ element, the human μ switch region, all of the human μ coding exons, the human Σμ element, and the human γ1 constant region, including the associated switch region and sterile transcript associated exons, together with the rat heavy chain 3' enhancer, such that all of these sequence elements can be isolated on a single fragment, away from vector sequences, by digestion with NotI and microinjected into mouse embryo pronuclei to generate transgenic animals.

D. Construction of IgM and IgG expressing minilocus transgene, pHC2

1. Isolation of human heavy chain V region gene VH49.8

The human placental genomic DNA library lambda, FIX™ II, Stratagene, La Jolla, Calif.) was screened with the following human VH1 family specific oligonucleotide:

oligo-49 5'-gtt aaa gag gat ttt att cac ccc tgt gtc ctc tcc aca ggt gtc-3'

Phage clone λ49.8 was isolated and a 6.1 kb XbaI fragment containing the variable segment VH49.8 sub-cloned into pNN03 (such that the polylinker ClaI site is downstream of VH49.8 and the polylinker XhoI site is upstream) to generate the plasmid pVH49.8. An 800 bp region of this insert was sequenced, and VH49.8 found to have an open reading frame and intact splicing and recombination signals, thus indicating that the gene is functional (Table 2).

TABLE 2

Sequence of human $V_HI$ family gene $V_H$ 49.8

| | | | | | | |
|---|---|---|---|---|---|---|
| TTCCTCAGGC | AGGATTTAGG | GCTTGGTCTC | TCAGCATCCC | ACACTTGTAC | | 50 |
| AGCTGATGTG | GCATCTGTGT | TTTCTTTCTC | ATCCTAGATC | AAGCTTTGAG | | 100 |
| CTGTGAAATA | CCCTGCCTCA | TGAATATGCA | AATAATCTGA | GGTCTTCTGA | | 150 |
| GATAAATATA | GATATATTGG | TGCCCTGAGA | GCATCACATA | ACAACCAGAT | | 200 |
| TCCTCCTCTA | AAGAAGCCCC | TGGGAGCACA | GCTCATCACC | ATGGACTGGA MetAspTrpT | | 250 |
| CCTGGAGGTT hrTrpArgPh agtcctaagg | CCTCTTTGTG eLeuPheVal ctgaggaagg | GTGGCAGCAG ValAlaAlaA gatcctggtt | CTACAGgtaa laThr tagttaaaga | ggggcttcct ggattttatt | | 300 350 |
| caccctgtg | tcctctccac | agGTGTCCAG GlyValGln | TCCCAGGTCC SerGlnValG | AGCTGGTGCA lnLeuValGl | | 400 |
| GTCTGGGGCT nSerGlyAla | GAGGTGAAGA GluValLysL | AGCCTGGGTC ysProGlySe | CTCGGTGAAG rSerValLys | GTCTCCTGCA ValSerCysL | | 450 |
| AGGCTTCTGG ysAlaSerGl | AGGCACCTTC yGlyThrPhe | AGCAGCTATG SerSerTyrA | CTATCAGCTG laIleSerTr | GGTGCGACAG pValArgGln | | 500 |
| GCCCCTGGAC AlaProGlyG | AAGGGCTTGA lnGlyLeuGl | GTGGATGGGA uTrpMetGly | AGGATCATCC ArgIleIleP | CTATCCTTGG roIleLeuGl | | 550 |
| TATAGCAAAC yIleAlaAsn | TACGCACAGA TyrAlaGlnL | AGTTCCAGGG ysPheGlnGl | CAGAGTCACG yArgValThr | ATTACCGCGG IleThrAlaA | | 600 |
| ACAAATCCAC spLysSerTh | GAGCACAGCC rSerThrAla | TACATGGAGC TyrMetGluL | TGAGCAGCCT euSerSerLe | GAGATCTGAG uArgSerGlu | | 650 |
| GACACGGCCG AspThrAlaV | TGTATTACTG alTyrTyrCy | TGCGAGAGAC sAlaArg | ACAGTG TGAA | AACCCACATC | | 700 |
| CTGAGAGTG T CAGAAACC CT | | GAGGGAGAAG | GCAGCTGTGC | CGGGCTGAGG | | 750 |
| AGATGACAGG | GTTTATTAGG | TTTSSGGCTG | TTTACAAAAT | GGGTTATATA | | 800 |
| TTTGAGAAAA | AA | | | | | 812 |

2. pV2

A 4 kb XbaI genomic fragment containing the human $V_HIV$ family gene $V_H$4-21 (Sanz et al., EMBO J., 8:3741 (1989)), subcloned into the plasmid pUC12, was excised with SmaI and HindIII, and treated with the Klenow fragment of polymerase I. The blunt ended fragment was then cloned into ClaI digested, Klenow treated, pVH49.8. The resulting plasmid, pV2, contains the human heavy chain gene VH49.8 linked upstream of VH4-21 in the same orientation, with a unique SalI site at the 3' end of the insert and a unique XhoI site at the 5' end.

3. pSγ1-5'

A 0.7 kb XbaI/HindIII fragment (representing sequences immediately upstream of, and adjacent to, the 5.3 kb γ1 switch region containing fragment in the plasmid pγe2) together with the neighboring upstream 3.1 kb XbaI fragment were isolated from the phage clone λSg1.13 and cloned into HindIII/XbaI digested pUC18 vector. The resulting plasmid, pSγ1-5', contains a 3.8 kb insert representing sequences upstream of the initiation site of the sterile transcript found in B-cells prior to switching to the γ1 isotype (P. Sideras et al., *International Immunol.* 1:631 (1989)). Because the transcript is implicated in the initiation of isotype switching, and upstream cis-acting sequences are often important for transcription regulation, these sequences are included in transgene constructs to promote correct expression of the sterile transcript and the associated switch recombination.

4. pVGE1

The pSγ1-5' insert was excised with SmaI and HindIII, treated with Klenow enzyme, and ligated with the following oligonucleotide linker:

5'-ccg gtc gac cgg-3'

Figure 27:
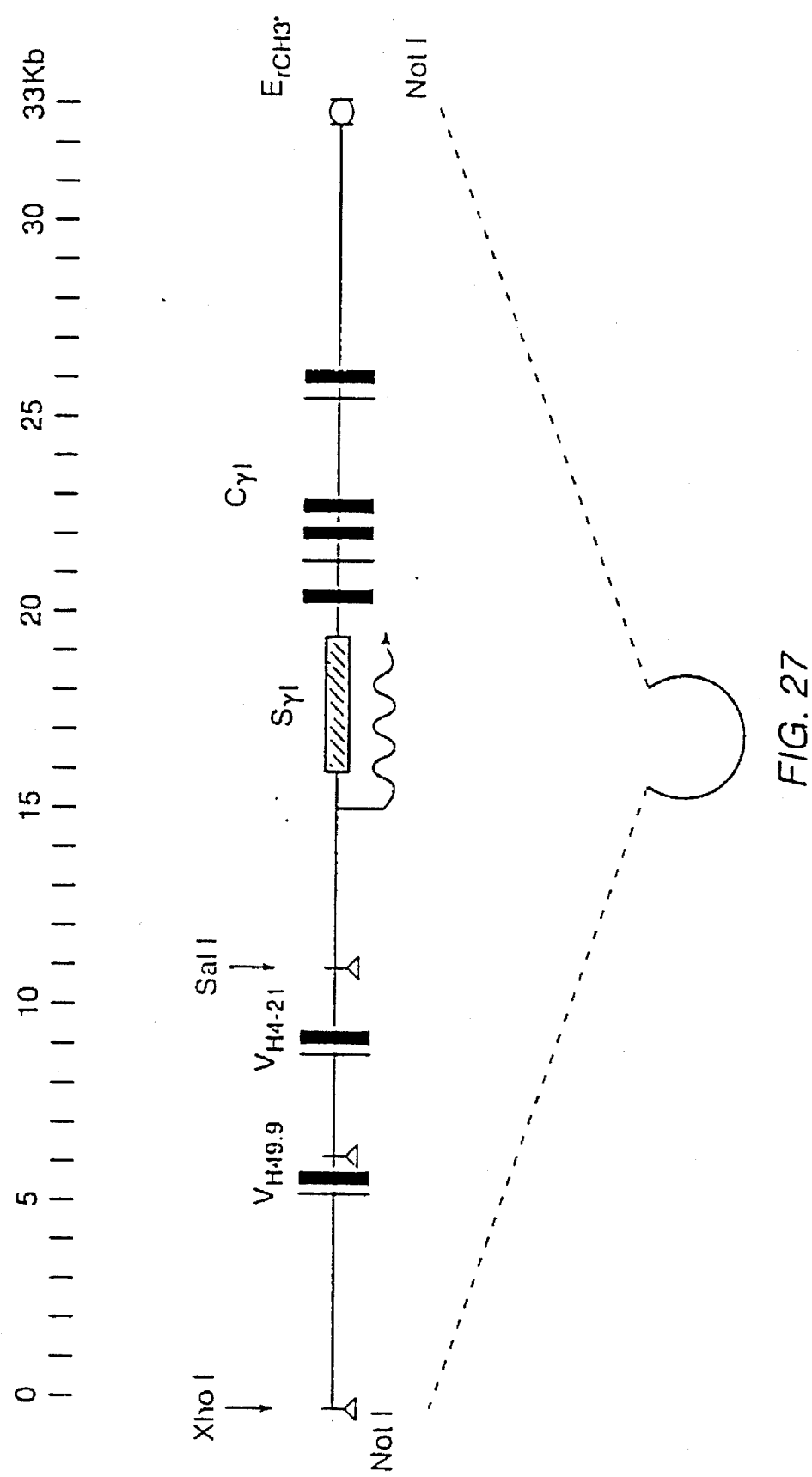
FIG. 27 depicts the structure of pVGE1.

The ligation product was digested with SalI and ligated to SalI digested pV2. The resulting plasmid, pVP, contains 3.8 kb of γ1 switch 5' flanking sequences linked downstream of the two human variable gene segments VH49.8 and VH4-21 (see Table 2). The pVP insert is isolated by partial digestion with SalI and complete digestion with XhoI, followed by purification of the 15 kb fragment on an agarose gel. The insert is then cloned into the XhoI site of pγe2 to generate the plasmid clone pVGE1 (FIG. 27). pVGE1 contains two human heavy chain variable gene segments upstream of the human γ1 constant gene and associated switch region. A unique SalI site between the variable and constant regions can be used to clone in D, J, and μ gene segments. The rat heavy chain 3' enhancer is linked to the 3' end of the γ1 gene and the entire insert is flanked by NotI sites.

5. pHC2

The plasmid clone pVGE1 is digested with SalI and the XhoI insert of pIGM1 is cloned into it. The resulting clone, pHC2 (FIG. 25), contains 4 functional human variable region segments, at least 8 human D segments all 6 human $J_H$ segments, the human J-m enhancer, the human σμ element, the human μ switch region, all of the human μ coding exons, the human Σμ element, and the human γ1 constant region, including the associated switch region and sterile transcript associated exons, together with 4 kb flanking sequences upstream of the sterile transcript initiation site. These human sequences are linked to the rat heavy chain 3' enhancer, such that all of the sequence elements can be isolated on a single fragment, away from vector sequences, by digestion with NotI and microinjected into mouse embryo pronuclei to generate transgenic animals. A unique XhoI site at the 5' end of the insert can be used to clone in additional human variable gene segments to further expand the recombinational diversity of this heavy chain minilocus.

E. Transgenic mice

Figure 28:
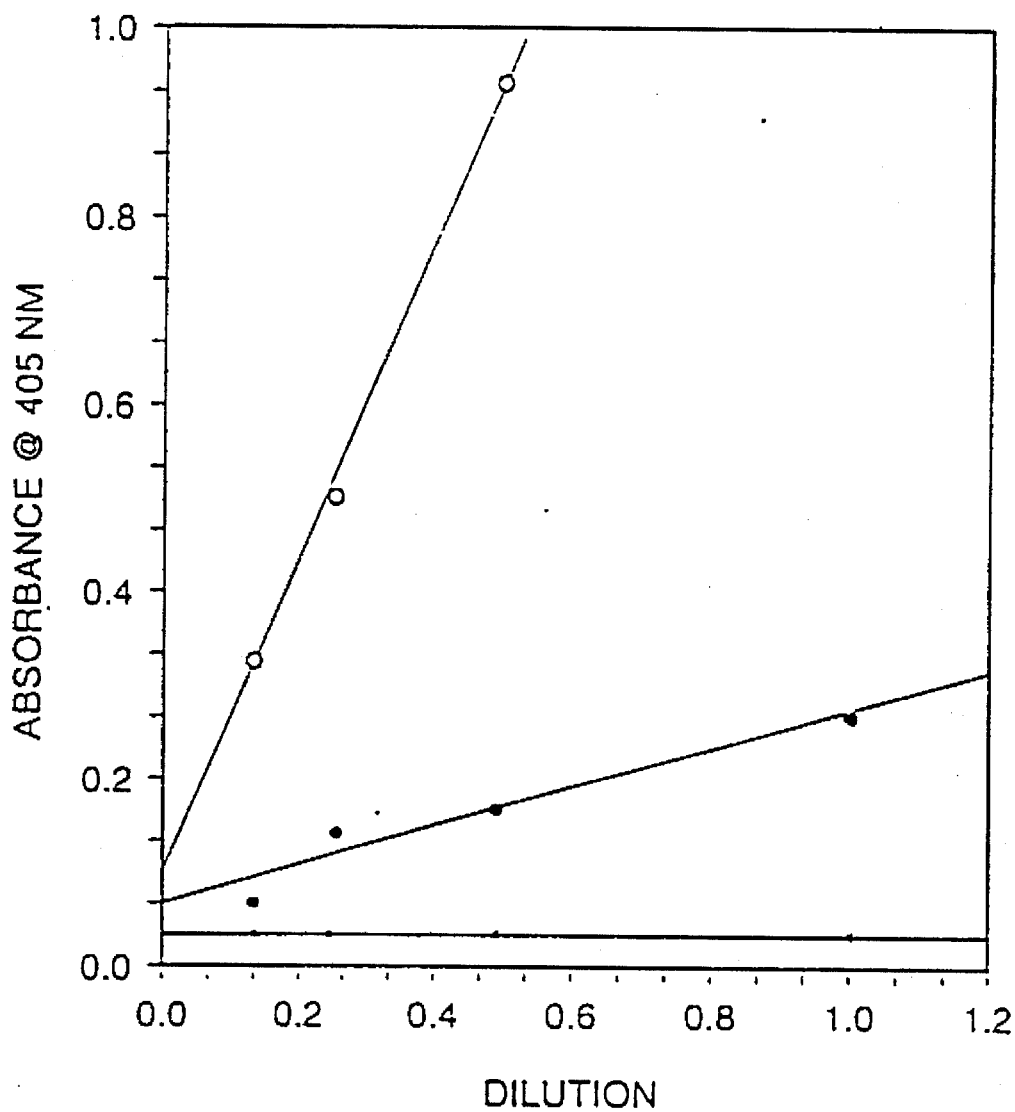
FIG. 28 depicts the assay results of human Ig expression in a pHC1 transgenic mouse.
Figure 29:
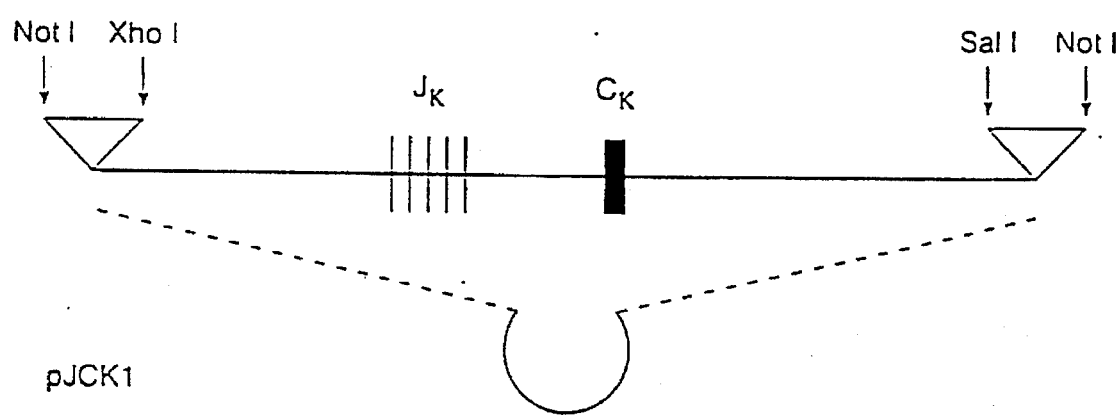
FIG. 29 depicts the structure of pJCK1.
Figure 30:
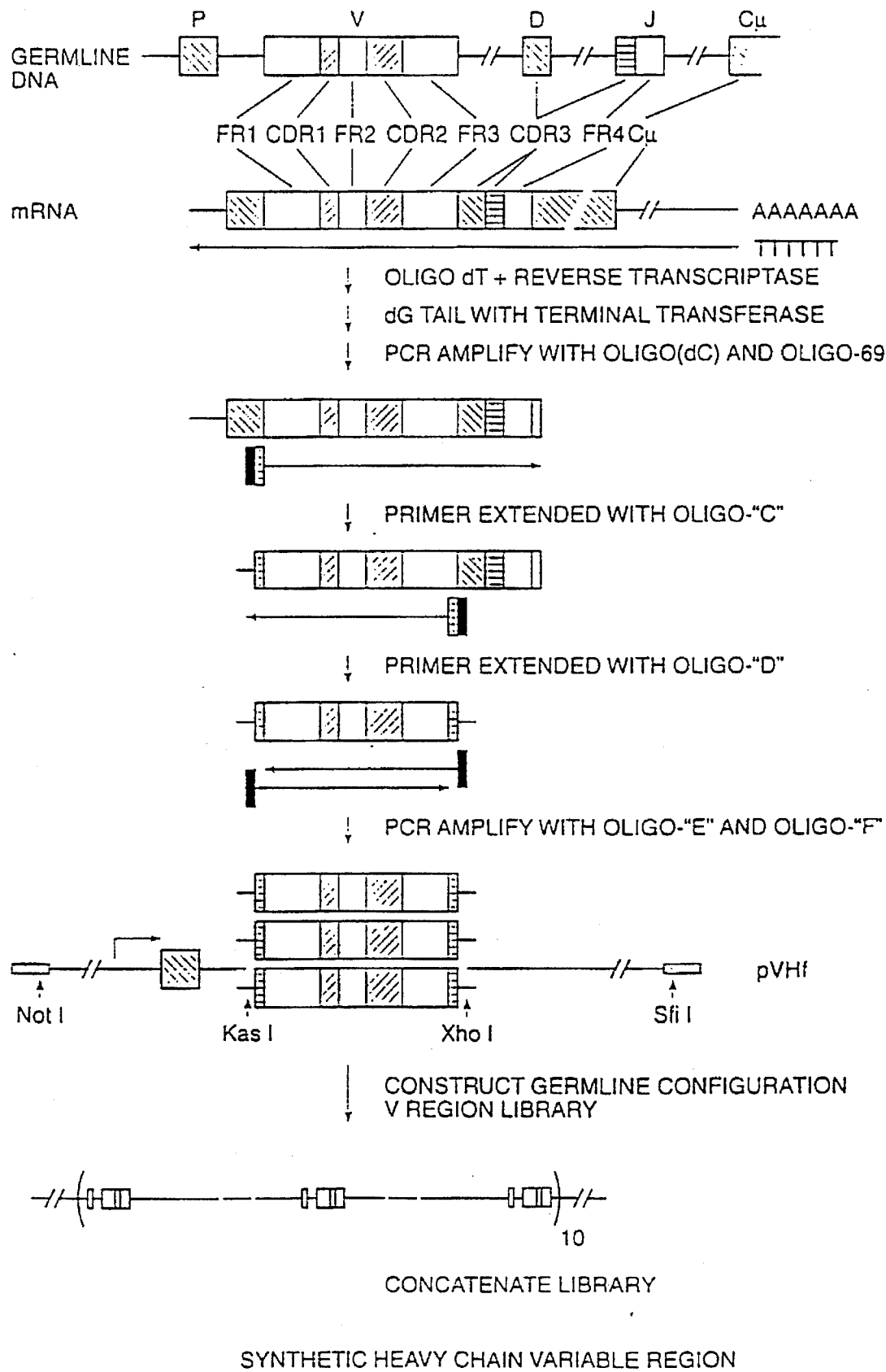
FIG. 30 depicts the construction of a synthetic heavy chain variable region.
Figure 31:
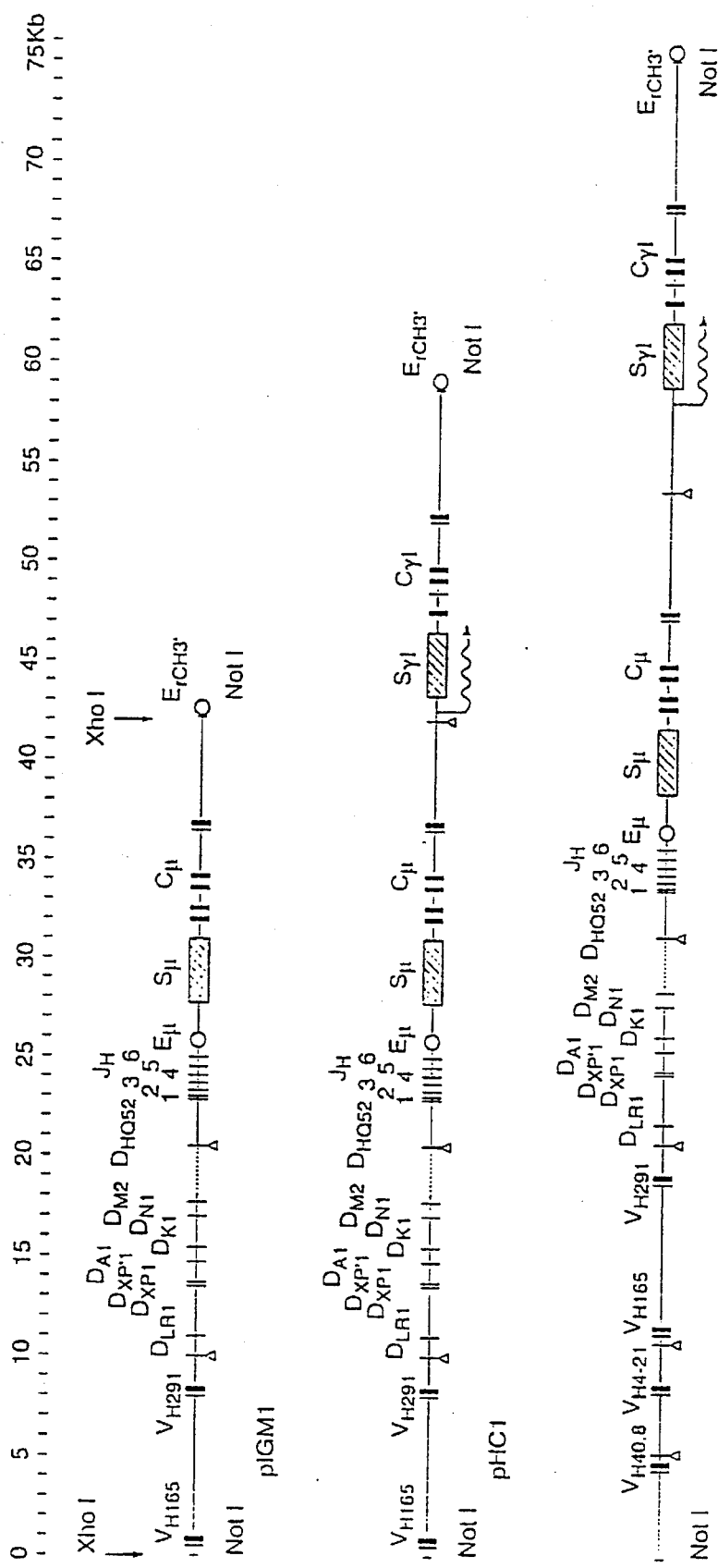
FIG. 31 is a schematic representation of the heavy chain minilocus constructs pIGM$_1$, pHC1, and pHC2.

The NotI inserts of plasmids pIGM1 and pHC1 were isolated from vector sequences by agarose gel electrophoresis. The purified inserts were microinjected into the pronuclei of fertilized (C57BL/6 x CBA)F2 mouse embryos and transferred the surviving embryos into pseudopregnant females as described by Hogan et al. (B. Hogan, F. Costantini, and E. Lacy, Methods of Manipulating the Mouse Embryo, 1986, Cold Spring Harbor Laboratory, New York). Mice that developed from injected embryos were analyzed for the presence of transgene sequences by Southern blot analysis of tail DNA. Transgene copy number was estimated by band intensity relative to control standards containing known quantities of cloned DNA. At 3 to 8 weeks of age, serum was isolated from these animals and assayed for the presence of transgene encoded human IgM and IgG1 by ELISA as described by Harlow and Lane (E. Harlow and D. Lane. Antibodies: A Laboratory Manual, 1988, Cold Spring Harbor Laboratory, New York). Microtiter plate wells were coated with mouse monoclonal antibodies specific for human IgM (clone AF6, #0285, AMAC, Inc. Westbrook, Me.) and human IgG1 (clone JL512, #0280, AMAC, Inc. Westbrook, Me.). Serum samples were serially diluted into the wells and the presence of specific immunoglobulins detected with affinity isolated alkaline phosphatase conjugated goat anti-human Ig (polyvalent) that had been pre-adsorbed to minimize cross-reactivity with mouse immunoglobulins. Table 3 and FIG. 28 show the results of an ELISA assay for the presence of human IgM and IgG1 in the serum of two animals that developed from embryos injected with the transgene insert of plasmid pHC1. All of the control non-transgenic mice tested negative for expression of human IgM and IgG1 by this assay. Mice from two lines containing the pIGM1 NotI insert (lines #6 and 15) express human IgM but not human IgG1. We tested mice from 6 lines that contain the pHC1 insert and found that 4 of the lines (lines #26, 38, 57 and 122) express both human IgM and human IgG1, while mice from two of the lines (lines #19 and 21) do not express detectable levels of human immunoglobulins. The pHC1 transgenic mice that did not express human immunoglobulins were so-called $G_o$ mice that developed directly from microinjected embryos and may have been mosaic for the presence of the transgene. Southern blot analysis indicates that many of these mice contain one or fewer copies of the transgene per cell. The detection of human IgM in the serum of pIGM1 transgenics, and human IgM and IgG1 in pHC1 transgenics, provides evidence that the transgene sequences function correctly in directing VDJ joining, transcription, and isotype switching. One of the animals (#18) was negative for the transgene by Southern blot analysis, and showed no detectable levels of human IgM or IgG1. The second animal (#38) contained approximately 5 copies of the transgene, as assayed by Southern blotting, and showed detectable levels of both human IgM and IgG1. The results of ELISA assays for 11 animals that developed from transgene injected embryos is summarized in the table below (Table 3).

TABLE 3

Detection of human IgM and IgG1 in the serum of transgenic animals by ELISA assay

| animal # | injected transgene | approximate transgene copies per cell | human IgM | human IgG1 |
|---|---|---|---|---|
| 6 | pIGM1 | 1 | ++ | − |
| 7 | pIGM1 | 0 | − | − |
| 9 | pIGM1 | 0 | − | − |
| 10 | pIGM1 | 0 | − | − |
| 12 | pIGM1 | 0 | − | − |
| 15 | pIGM1 | 10 | ++ | − |
| 18 | pHC1 | 0 | − | − |
| 19 | pHC1 | 1 | − | − |
| 21 | pHC1 | <1 | − | − |
| 26 | pHC1 | 2 | ++ | + |
| 38 | pHC1 | 5 | ++ | + |

Table 3 shows a correlation between the presence of integrated transgene DNA and the presence of transgene encoded immunoglobulins in the serum. Two of the animals that were found to contain the pHC1 transgene did not express detectable levels of human immunoglobulins. These were both low copy animals and may not have contained complete copies of the transgenes, or the animals may have been genetic mosaics (indicated by the <1 copy per cell estimated for animal #21), and the transgene containing cells may not have populated the hematopoietic lineage. Alternatively, the transgenes may have integrated into genomic locations that are not conducive to their expression.

The detection of human IgM in the serum of pIGM1 transgenics, and human IgM and IgG1 in pHC1 transgenics, indicates that the transgene sequences function correctly in directing VDJ joining, transcription, and isotype switching.

F. cDNA clones

To assess the functionality of the pHC1 transgene in VDJ joining and class switching, as well the participation of the transgene encoded human B-cell receptor in B-cell development and allelic exclusion, the structure of immunoglobulin cDNA clones derived from transgenic mouse spleen mRNA were examined. The overall diversity of the transgene encoded heavy chains, focusing on D and J segment usage, N region addition, CDR3 length distribution, and the frequency of joints resulting in functional mRNA molecules was examined. Transcripts encoding IgM and IgG incorporating VH105 and VH251 were examined.

Figure 34:
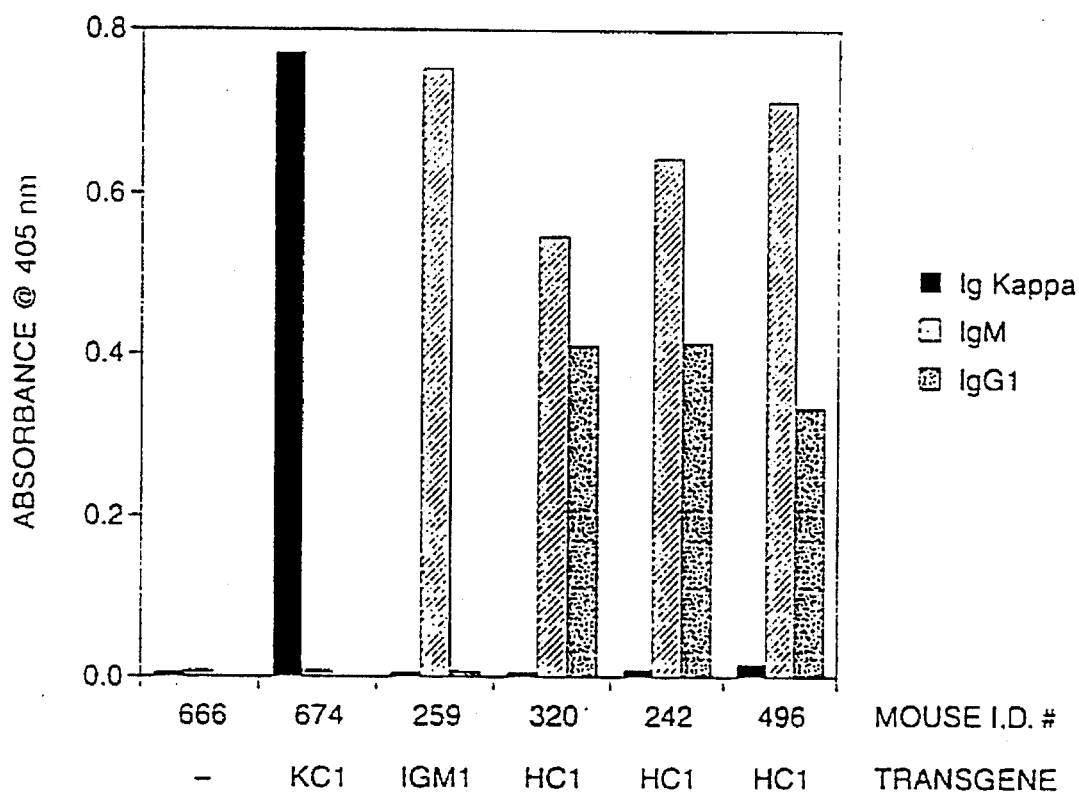
FIG. 34 depicts serum ELISA results

Polyadenylated RNA was isolated from an eleven week old male second generation line-57 pHC1 transgenic mouse. This RNA was used to synthesize oligo-dT primed single stranded cDNA. The resulting cDNA was then used as template for four individual PCR amplifications using the following four synthetic oligonucleotides as primers: VH251 specific oligo-149, cta gct cga gtc caa gga gtc tgt gcc gag gtg cag ctg (g,a,t,c); VH105 specific o-150, gtt gct cga gtg aaa ggt gtc cag tgt gag gtg cag ctg (g,a,t,c); human gamma1 specific oligo-151, ggc gct cga gtt cca cga cac cgt cac cgg ttc; and human mu specific oligo-152, cct gct cga ggc agc caa cgg cca cgc tgc tcg. Reaction 1 used primers o-149 and o-151 to amplify VH251-gamma1 transcripts, reaction 2 used o-149 and o-152 to amplify VH251-mu transcripts, reaction 3 used o-150 and o-151 to amplify VH105-gamma1 transcripts, and reaction 4 used o-150 and o-152 to amplify VH105-mu transcripts. The resulting 0.5 kb PCR products were isolated from an agarose gel; the μ transcript products were more abundant than the γ transcript products, consistent with the corresponding ELISA data (FIG. 34). The PCR products were digested with XhoI and cloned into the plasmid pNN03. Double-stranded plasmid DNA was isolated from minipreps of nine clones from each of the four PCR amplifications and dideoxy sequencing reactions were performed. Two of the clones turned out to be deletions containing no D or J segments. These could not have been derived from normal RNA splicing products and are likely to have originated from deletions introduced during PCR amplification. One of the DNA samples turned out to be a mixture of two individual clones, and three additional clones did not produce readable DNA sequence (presumably because the DNA samples were not clean enough). The DNA sequences of the VDJ joints from the remaining 30 clones are compiled in Table 4. Each of the sequences are unique, indicating that no single pathway of gene rearrangement, or single clone of transgene expressing B-cells is dominant. The fact that no two sequences are alike is also an indication of the large diversity of immunoglobulins that can be expressed from a compact minilocus containing only 2 V segments, 10 D segments, and 6 J segments. Both of the V segments, all six of the J segments, and 7 of the 10 D segments that are included in the transgene are used in VDJ joints. In addition, both constant region genes (mu and gamma1) are incorporated into transcripts. The VH105 primer turned out not to be specific for VH105 in the reactions performed. Therefore many of the clones from reactions 3 and 4 contained VH251 transcripts. Additionally, clones isolated from ligated reaction 3 PCR product turned out to encode IgM rather than IgG; however this may reflect contamination with PCR product from reaction 4 as the DNA was isolated on the same gel. An analogous experiment, in which immunoglobulin heavy chain sequences were amplified from adult human peripheral blood lymphocytes (PBL), and the DNA sequence of the VDJ joints determined, was recently reported by Yamada et al. (*J. Exp. Med.* 173:395–407 (1991), which is incorporated herein by reference). We compared the data from human PBL with our data from the pHC1 transgenic mouse.

TABLE 4

| # | | V | n-D-n | J | C |
|---|---|---|---|---|---|
| 1 | VH251 DHQ52J3 η | TACTGTGCGAGA | CGGCTAACTGGGTTGAT | GCTTTTGATATCTGGGGCCAAGGGACAAATGGTCACCGTCTCTTCAG | CCTCCACCAAG |
| 2 | VH251 DN1 J4 η | TACTGTGCGAGA | CACCGTATAGCAGCAGTGG | CTTTGACTACTGGGGCCAGGGAACCCTGGTCACCGTCTCCTCAG | CCTCCACCAAG |
| 3 | VH251 D? J6 η | TACTGTGCGAGA | T | CCTCCACCAAG |
| 4 | VH251 DXP'1 J6 η | TACTGTGCGAGA | CATTACGATATTTGACTGGTC | ATTACTACTACTACGGTATGGACGTCTGGGGCCAAGGGACCACGGTCACCGTCTCCTCAG | CCTCCACCAAG |
| 5 | VH251 DXP'1 J4 η | TACTGTGCGAGA | CGGAGGTACTATGGTTCGGGGGAGTTATTATAACGT | CTACTACTACTACGGTATGGACGTCTGGGGCCAAGGGAACCCTGGTCACCGTCTCCTCAG | CCTCCACCAAG |
| 6 | VH251 D? J3 η | TACTGTGCGAGA | CGGGGGGTGTCTGAT | CTTGACTACTGGGGCCAGGGAACCCTGGTCACCGTCTCCTCAG | CCTCCACCAAG |
| 7 | VH251 DHQ52J3 μ | TACTGTGCGAGA | GCAACTGGC | GCTTTTGATATCTGGGGCCAAGGGACAAATGGTCACCGTCTCCTCAG | CCTCCACCAAG |
| 8 | VH251 DHQ52J6 μ | TACTGTGCGAGA | TCGGCTAACTGGGGATC | GCTTTTGATATCTGGGGCCAAGGGACAAATGGTCACCGTCTCCTCAG | GGAGTGCATCC |
| 9 | VH251 — J1 μ | TACTGTGCGAGA | | CTACTACTACTACGGTATGGACGTCTGGGGCCAAGGGAACCCTGGTCACCGTCTCCTCAG | GGAGTGCATCC |
| 10 | VH251 DLR2 J4 μ | TACTGTGCGAGA | CACGTAGCTAACTCT | TACTTCCAGCACTGGGGCCAGGGAACCCTGGTCACCGTCTCCTCAG | GGAGTGCATCC |
| 11 | VH251 DXP'1 J4 μ | TACTGTGCGAGA | CAAATTACTATGGTTCGGGGGAGTTCC | TTTGACTACTGGGGCCAGGGAACCCTGGTCACCGTCTCCTCAG | GGAGTGCATCC |
| 12 | VH251 D? J1 μ | TACTGTGCGAGA | C | CTTGACTACTGGGGCCAGGGAACCCTGGTCACCGTCTCCTCAG | GGAGTGCATCC |
| 13 | VH251 DHQ52J6 μ | TACTGTGCGAGA | CAAACTGGGG | AATACTTCCAGCACTGGGGCCAGGGAACCCTGGTCACCGTCTCCTCAG | GGAGTGCATCC |
| 14 | VH251 DXP'1 J6 μ | TACTGTGCGAGA | CATTACTATGGTTCGGGGGAGTTATG | ACTACTACTACTACGGTATGGACGTCTGGGGCCAAGGGAACCCTGGTCACCGTCTCCTCAG | GGAGTGCATCC |
| 15 | VH251 DXP'1 J4 μ | TACTGTGCGAGA | CAGGGAG | ACTACTACTACGGTATGGACGTCTGGGGCCAAGGGAACCCTGGTCACCGTCTCCTCAG | GGAGTGCATCC |
| 16 | VH105 DXP'1 J5 μ | TACTGTGCGAGA | TTCTGGGAG | TGGGGCCAGGGAACCCTGGTCACCGTCTCCTCAG | CCTCCACCAAG |
| 17 | VH251 DXP'1 J4 η | TACTGTGCGAGA | CGGAGGTACTATGGTTCGGGAGGTATTATAACGT | ACTGGTTCGACCCCTGGGGCCAGGGAACCCTGGTCACCGTCTCCTCAG | CCTCCACCAAG |
| 18 | VH251 DHQ52J4 η | TACTGTGCGAGA | CAAACCTGGGAGGA | CTTTGACTACTGGGGCCAGGGAACCCTGGTCACCGTCTCCTCAG | CCTCCACCAAG |
| 19 | VH251 DK1 J6 η | TACTGTGCGAGA | GGATATAGTGGCTACGATA | GACTACTGGGGCCAGGGAACCCTGGTCACCGTCTCCTCAG | CCTCCACCAAG |
| 20 | VH251 DHQ52J4 μ | TACTGTGCGAGA | CAAACTGGGGAG | ACTACTACGGTATGGACGTCTGGGGCCAAGGGAACCCTGGTCACCGTCTCCTCAG | CCTCCACCAAG |
| 21 | VH251 DK1 J2 η | TACTGTGCGAGA | TATAGTGGCTACGATTAC | ACTACTTTGACTCCGATCTCTGGGGCCAAGGGAACCCTGGTCACCGTCTCCTCAG | CCTCCACCAAG |
| 22 | VH251 DIR2 J6 η | TACTGTGCGAGA | GCATCCCTCCCTCCTTTG | CTACTGGTACTACGGTATGGACGTCTGGGGCCAAGGGAACCCTGGTCACCGTCTCCTCAG | CCTCCACCAAG |
| 23 | VH251 DIR2 J4 μ | TACTGTGCGAGA | CGGGGTGGGG | ACTACTACGGTATGGACGTCTGGGGCCAAGGGAACCCTGGTCACCGTCTCCTCAG | GGAGTGCATCC |
| 24 | VH105 D? J6 μ | TACTGTGTG | CCGGTCGAAACT | TTTGACTACTGGGGCCAGGGAACCCTGGTCACCGTCTCCTCAG | GGAGTGCATCC |
| 25 | VH251 DXP'1 J4 η | TACTGTGCGAGA | GATATTTGACTGGTTAACG | TTACTACTACTACTACGGTATGGACGTCTGGGGCCAAGGGAACCCTGGTCACCGTCTCCTCAG | GGAGTGCATCC |
| 26 | VH251 DN1 J3 μ | TACTGTGCGAGA | CATTGGTATAGCAGCAGCTGGTAC | TGACTACTGGGGCCAGGGAACCCTGGTCACCGTCTCCTCAG | GGAGTGCATCC |
| 27 | VH105 DHQ52J3 μ | TACTGTGCGAGA | TCAACTGGGGTTG | TGCTTTTGATATCTGGGGCCAAGGGACAAATGGTCACCGTCTCCTCAG | GGAGTGCATCC |
| 28 | VH251 DN1 J4 μ | TACTGTGCG | GAAAATAGCAGCAGCTGCC | ATGCTTTTGATATCTGGGGCCAAGGGACAAATGGTCACCGTCTCCTCAG | GGAGTGCATCC |
| 29 | VH105 DN1 J4 μ | TACTGTGTG | TGTATAGCAGCAGCTGGTAAAGGAAACGG | CTACTTTGACTACTGGGGCCAGGGAACCCTGGTCACCGTCTCCTCAG | GGAGTGCATCC |
| 30 | VH251 DHQ52J4 μ | TACTGTGCGAGA | CAAAACTGGGG | TGACTACTGGGGCCAGGGAACCCTGGTCACCGTCTCCTCAG | GGAGTGCATCC |

G. J segment choice

Table 5 compared the distribution of J segments incorporated into pHC1 transgene encoded transcripts to J segments found in adult human PBL immunoglobulin transcripts. The distribution profiles are very similar, J4 is the dominant segment in both systems, followed by J6. J2 is the least common segment in human PBL and the transgenic animal.

TABLE 5

J. Segment Choice

| J. Segment | Percent Usage (±3%) | |
|---|---|---|
| | HC1 transgenic | Human PBL |
| J1 | 7 | 1 |
| J2 | 3 | <1 |
| J3 | 17 | 9 |
| J4 | 44 | 53 |
| J5 | 3 | 15 |
| J6 | 26 | 22 |
| | 100% | 100% |

H. D segment choice

49% (40 of 82) of the clones analyzed by Yamada et al. incorporated D segments that are included in the pHC1 transgene. An additional 11 clones contained sequences that were not assigned by the authors to any of the known D segments. Two of these 11 unassigned clones appear to be derived from an inversion of the DIR2 segments which is included in the pHC1 construct. This mechanism, which was predicted by Ichihara et al. (*EMBO J.* 7:4141 (1988)) and observed by Sanz (*J. Immunol.* 147:1720–1729 (1991)), was not considered by Yamada et al. (*J. Exp. Med.* 173:395–407 (1991)). Table 5 is a comparison of the D segment distribution for the pHC1 transgenic mouse and that observed for human PBL transcripts by Yamada et al. The data of Yamada et al. was recompiled to include DIR2 use, and to exclude D segments that are not in the pHC1 transgene. Table 6 demonstrates that the distribution of D segment incorporation is very similar in the transgenic mouse and in human PBL. The two dominant human D segments, DXP'1 and DN1, are also found with high frequency in the transgenic mouse. The most dramatic dissimilarity between the two distributions is the high frequency of DHQ52 in the transgenic mouse as compared to the human. The high frequency of DHQ52 is reminiscent of the D segment distribution in the human fetal liver. Sanz has observed that 14% of the heavy chain transcripts contained DHQ52 sequences. If D segments not found in pHC1 are excluded from the analysis, 31% of the fetal transcripts analyzed by Sanz contain DHQ52. This is comparable to the 27% that we observe in the pHC1 transgenic mouse.

TABLE 6

D Segment Choice

| D. Segment | Percent Usage (±3%) | |
|---|---|---|
| | HC1 transgenic | Human PBL |
| DLR1 | <1 | <1 |
| DXP1 | 3 | 6 |
| DXP'1 | 25 | 19 |
| DA1 | <1 | 12 |
| DK1 | 7 | 12 |
| DN1 | 12 | 22 |
| DIR2 | 7 | 4 |
| DM2 | <1 | 2 |
| DLR2 | 3 | 4 |
| DHQ52 | 26 | 2 |
| ? | 17 | 17 |
| | 100% | 100% |

I. Functionality of VDJ joints

Table 7 shows the predicted amino acid sequences of the VDJ regions from 30 clones that were analyzed from the pHC1 transgenic. The translated sequences indicate that 23 of the 30 VDJ joints (77%) are in-frame with respect to the variable and J segments.

TABLE 7

Functionality of V-D-J Joints

| | | | | | FR3 | CDR3 | FR4 |
|---|---|---|---|---|---|---|---|
| 1 | VH251 | DHQ52 | J3 | γ1 | YCAR | RLTGVDAFDI | WGQGTMVTVSSASTK |
| 2 | VH251 | DN1 | J4 | γ1 | YCAR | HRIAAAGFDY | WGQGTLVTVSSASTK |
| 3 | VH251 | D? | J6 | γ1 | YCAR | YYYYYYGMDV | WGQGTTVTVSSASTK |
| 4 | VH251 | DXP'1 | J6 | γ1 | YCAR | HYDILTGPTTTTVWTSGAKGPRSPSPQPPP | |
| 5 | VH251 | DXP'1 | J4 | γ1 | YCAR | RRYYGSGSYYNVFDY | WGQGTLVTVSSASTK |
| 6 | VH251 | D? | J3 | γ1 | YCAR | RGVSDAFDI | WGQGTMVTVSSASTK |
| 7 | VH251 | DHQ52 | J3 | μ | YCAR | ATGAFDI | WGQGTMVTVSSGSAS |
| 8 | VH251 | DHQ52 | J6 | μ | YCAR | SANWGSYYYYGMDV | WGQGTTVTVSSGSAS |
| 9 | VH251 | — | J1 | μ | YCAR | YFQH | WGQGTLVTVSSGSAS |
| 10 | VH251 | DLR2 | J4 | μ | YCAR | HVANSFDY | WGQGTLVTVSSGSAS |
| 11 | VH251 | DXP'1 | J4 | μ | YCAR | QITMVRGVPFDY | WGQGTLVTVSSGSAS |
| 12 | VH251 | D? | J1 | μ | YCAR | QYFQH | WGQGTLVTVSSGSAS |
| 13 | VH251 | DHQ52 | J6 | μ | YCAR | QTGDYYYYGMDV | WGQGTTVTVSSGSAS |
| 14 | VH251 | DXP'1 | J6 | μ | YCAR | HYYGSGSYDYYYYGMDV | WGQGTTVTVSSGSAS |
| 15 | VH251 | DXP'1 | J4 | γ1 | YCVR | QGVGPGNPGHRLLSLHQ | |
| 16 | VH105 | DXP'1 | J5 | μ | YCAR | FWETGSTPGAREPWSPSPQGVH | |
| 17 | VH251 | DXP'1 | J4 | γ1 | YCAR | RRYYGSGSYYNVFDY | WGQGTLVTVSSASTK |
| 18 | VH251 | DHQ52 | J4 | γ1 | YCAR | QTWGGDY | WGQGTLVTVSSASTK |
| 19 | VH251 | DK1 | J6 | γ1 | YCAR | GYSGYDNYYYGIHV | WGQGTTVTVSSASTK |

TABLE 7-continued

Functionality of V-D-J Joints

| | | | | | FR3 | CDR3 | FR4 |
|---|---|---|---|---|---|---|---|
| 20 | VH251 | DHQ52 | J4 | μ | YCAR | QTGEDYFDY | WGQGTLVTVSSGSAS |
| 21 | VH251 | DK1 | J2 | γ1 | YCAR | YSGYDYLLVLRSLGPWHPGHCLLSLHR | |
| 22 | VH251 | DIR2 | J6 | γ1 | YCAR | ASLPSFDYYGMDV | WGQGTTVTVSSASTK |
| 23 | VH251 | DIR2 | J4 | μ | YCAR | RGGGLTTGAREPWSPSPQGVH | |
| 24 | VH105 | D? | J6 | μ | YCVP | VETLLLLLRYGRLGPRDHGHRLLRECI | |
| 25 | VH105 | DXP1 | J4 | μ | YCVR | DILTGXRDY | WGQGTLVTVSSGSAS |
| 26 | VH251 | DN1 | J3 | μ | YCAR | HGIAAAGTAFDI | WGQGTMVTVSSGSAS |
| 27 | VH105 | DHQ52 | J3 | μ | YCVR | STGVDAFDI | WGQGTMVTVSSGSAS |
| 28 | VH251 | DN1 | J4 | μ | YCAE | IAAAALLXLLGPGNPGHRLLRECI | |
| 29 | VH105 | DN1 | J4 | μ | YCVC | IAAAGKGNGY | WGQGTLVTVSSGSAS |
| 30 | VH251 | DHQ52 | J4 | μ | YCAR | QNWGDY | WGQGTLVTVSSGSAS |

J. CDR3 length distribution

Table 8 compared the length of the CDR3 peptides from transcripts with in-frame VDJ joints in the pHC1 transgenic mouse to those in human PBL. Again the human PBL data comes from Yamada et al. The profiles are similar with the transgenic profile skewed slightly toward smaller CDR3 peptides than observed from human PBL. The average length of CDR3 in the transgenic mouse is 10.3 amino acids. This is substantially the same as the average size reported for authentic human CDR3 peptides by Sanz (*J. Immunol.* 147:1720–1729 (1991)).

TABLE 8

CDR3 Length Distribution

| | Percent Occurrence (±3%) | |
|---|---|---|
| #amino acids in CDR3 | HC1 transgenic | Human PBL |
| 3–8 | 26 | 14 |
| 9–12 | 48 | 41 |
| 13–18 | 26 | 37 |
| 19–23 | <1 | 7 |
| >23 | <1 | 1 |
| | 100% | 100% |

EXAMPLE 13

Rearranged Heavy Chain Transgenes

A. Isolation of Rearranged Human Heavy Chain VDJ segments.

Two human leukocyte genomic DNA libraries cloned into the phage vector λEMBL3/SP6/T7 (Clonetech Laboratories, Inc., Palo Alto, Calif.) are screened with a 1 kb PacI/HindIII fragment of λ1.3 containing the human heavy chain J-μ intronic enhancer. Positive clones are tested for hybridization with a mixture of the following $V_H$ specific oligonucleotides:

oligo-7 5'-tca gtg aag gtt tcc tgc aag gca tct gga tac acc ttc acc-3' oligo-8 5'-tcc ctg aga ctc tcc tgt gca gcc tct gga ttc acc ttc agt-3'

Clones that hybridized with both V and J-μ probes are isolated and the DNA sequence of the rearranged VDJ segment determined.

B. Construction of rearranged human heavy chain transgenes

Fragments containing functional VJ segments (open reading frame and splice signals) are subcloned into the plasmid vector pSP72 such that the plasmid derived XhoI site is adjacent to the 5' end of the insert sequence. A subclone containing a functional VDJ segment is digested with XhoI and PacI (PacI, a rare-cutting enzyme, recognizes a site near the J-m intronic enhancer), and the insert cloned into XhoI/PacI digested pHC2 to generate a transgene construct with a functional VDJ segment, the J-μ intronic enhancer, the μ switch element, the μ constant region coding exons, and the γ1 constant region, including the sterile transcript associated sequences, the γ1 switch, and the coding exons. This transgene construct is excised with NotI and microinjected into the pronuclei of mouse embryos to generate transgenic animals as described above.

EXAMPLE 14

Light Chain Transgenes

A. Construction of Plasmid vectors

1. Plasmid vector pGP1c

Plasmid vector pGP1a is digested with NotI and the following oligonucleotides ligated in:

oligo-81 5'-ggc cgc atc ccg ggt ctc gag gtc gac aag ctt tcg agg atc cgc-3' oligo-82 5'-ggc cgc gga tcc tcg aaa gct tgt cga cct cga gac ccg gga tgc-3'

The resulting plasmid, pGP1c, contains a polylinker with XmaI, XhoI, SalI, HindIII, and BamHI restriction sites flanked by NotI sites.

2. Plasmid vector pGP1d

Plasmid vector pGP1a is digested with NotI and the following oligonucleotides ligated in:

oligo-87 5'-ggc cgc tgt cga caa gct tat cga tgg atc ctc gag tgc-3' oligo-88 5'-ggc cgc act cga gga tcc atc gat aag ctt gtc gac agc-3'

The resulting plasmid, pGP1d, contains a polylinker with SalI, HindIII, ClaI, BamHI, and XhoI restriction sites flanked by NotI sites.

B. Isolation of $J_κ$ and $C_κ$ clones

A human placental genomic DNA library cloned into the phage vector λEMBL3/SP6/T7 (Clonetech Laboratories, Inc., Palo Alto, Calif.) was screened with the human kappa light chain J region specific oligonucleotide:

oligo-36 5'-cac ctt cgg cca agg gac acg act gga gat taa acg taa gca-3' and the phage clones 136.2 and 136.5 isolated. A 7.4 kb XhoI fragment that includes the $J_κ1$ segment was isolated from 136.2 and subcloned into the plasmid pNN03 to generate the plasmid clone p36.2. A neighboring 13 kb XhoI fragment that includes Jk segments 2 through 5 together with the $C_κ$ gene segment was isolated from phage clone 136.5 and subcloned into the plasmid pNN03 to generate the plasmid clone p36.5. Together these two clones span the region beginning 7.2 kb upstream of $J_\kappa 1$ and ending 9 kb downstream of $C_\kappa$.

C. Construction of rearranged light chain transgenes 1. pCK1, a $C_\kappa$ vector for expressing rearranged variable segments The 13 kb XhoI insert of plasmid clone p36.5 containing the $C_\kappa$ gene, together with 9 kb of downstream sequences, is cloned into the SalI site of plasmid vector pGP1c with the 5' end of the insert adjacent to the plasmid XhoI site. The resulting clone, pCK1 can accept cloned fragments containing rearranged $VJ_\kappa$ segments into the unique 5' XhoI site. The transgene can then be excised with NotI and purified from vector sequences by gel electrophoresis. The resulting transgene construct will contain the human J-$C_\kappa$ intronic enhancer and may contain the human $3'_\kappa$ enhancer.

2. pCK2, a $C_\kappa$ vector with heavy chain enhancers for expressing rearranged variable segments A 0.9 kb XbaI fragment of mouse genomic DNA containing the mouse heavy chain J-μ intronic enhancer (J. Banerji et al., Cell 33:729–740 (1983)) was subcloned into pUC18 to generate the plasmid pJH22.1. This plasmid was linearized with SphI and the ends filled in with Klenow enzyme. The Klenow treated DNA was then digested with HindIII and a 1.4 kb MluI/HindIII fragment of phage clone λ1.3 (previous example), containing the human heavy chain J-μ intronic enhancer (Hayday et al., Nature 307:334–340 (1984)), to it. The resulting plasmid, pMHE1, consists of the mouse and human heavy chain J-μ intronic enhancers ligated together into pUC18 such that they are excised on a single BamHI/HindIII fragment. This 2.3 kb fragment is isolated and cloned into pGP1c to generate pMHE2. pMHE2 is digested with SalI and the 13 kb XhoI insert of p36.5 cloned in. The resulting plasmid, pCK2, is identical to pCK1, except that the mouse and human heavy chain J-μ intronic enhancers are fused to the 3' end of the transgene insert. To modulate expression of the final transgene, analogous constructs can be generated with different enhancers, i.e. the mouse or rat 3' kappa or heavy chain enhancer (Meyer and Neuberger, EMBO J., 8:1959–1964 (1989); Petterson et al., Nature, 344:165–168 (1990)).

3. Isolation of rearranged kappa light chain variable segments

Two human leukocyte genomic DNA libraries cloned into the phage vector λEMBL3/SP6/T7 (Clonetech Laboratories, Inc., Palo Alto, Calif.) were screened with the human kappa light chain J region containing 3.5 kb XhoI/SmaI fragment of p36.5. Positive clones were tested for hybridization with the following $V_\kappa$ specific oligonucleotide:

oligo-65 5'-agg ttc agt ggc agt ggg tct ggg aca gac ttc act ctc acc atc agc-3'

Clones that hybridized with both V and J probes are isolated and the DNA sequence of the rearranged $VJ_\kappa$ segment determined.

4. Generation of transgenic mice containing rearranged human light chain constructs.

Fragments containing functional VJ segments (open reading frame and splice signals) are subcloned into the unique XhoI sites of vectors pCK1 and pCK2 to generate rearranged kappa light chain transgenes. The transgene constructs are isolated from vector sequences by digestion with NotI. Agarose gel purified insert is microinjected into mouse embryo pronuclei to generate transgenic animals. Animals expressing human kappa chain are bred with heavy chain minilocus containing transgenic animals to generate mice expressing fully human antibodies.

Because not all $VJ_\kappa$ combinations may be capable of forming stable heavy-light chain complexes with a broad spectrum of different heavy chain VDJ combinations, several different light chain transgene constructs are generated, each using a different rearranged VJk clone, and transgenic mice that result from these constructs are bred with heavy chain minilocus transgene expressing mice. Peripheral blood, spleen, and lymph node lymphocytes are isolated from double transgenic (both heavy and light chain constructs) animals, stained with fluorescent antibodies specific for human and mouse heavy and light chain immunoglobulins (Pharmingen, San Diego, Calif.) and analyzed by flow cytometry using a FACScan analyzer (Becton Dickinson, San Jose, Calif.). Rearranged light chain transgenes constructs that result in the highest level of human heavy/light chain complexes on the surface of the highest number of B cells, and do not adversely affect the immune cell compartment (as assayed by flow cytometric analysis with B and T cell subset specific antibodies), are selected for the generation of human monoclonal antibodies.

D. Construction of unrearranged light chain minilocus transgenes 1. pJCK1, a $J_\kappa$, $C_\kappa$ containing vector for constructing minilocus transgenes The 13 kb $C_\kappa$ containing XhoI insert of p36.5 is treated with Klenow enzyme and cloned into HindIII digested, Klenow-treated, plasmid pGP1d. A plasmid clone is selected such that the 5' end of the insert is adjacent to the vector derived ClaI site. The resulting plasmid, p36.5-1d, is digested with ClaI and Klenow-treated. The $J_\kappa 1$ containing 7.4 kb XhoI insert of p36.2 is then Klenow-treated and cloned into the ClaI, Klenow-treated p36.5-1d. A clone is selected in which the p36.2 insert is in the same orientation as the p36.5 insert. This clone, pJCK1 (FIG. 34), contains the entire human $J_\kappa$ region and $C_\kappa$, together with 7.2 kb of upstream sequences and 9 kb of downstream sequences. The insert also contains the human J-$C_\kappa$ intronic enhancer and may contain a human $3'_\kappa$ enhancer. The insert is flanked by a unique 3' SalI site for the purpose of cloning additional 3' flanking sequences such as heavy chain or light chain enhancers. A unique XhoI site is located at the 5' end of the insert for the purpose of cloning in unrearranged $V_\kappa$ gene segments. The unique SalI and XhoI sites are in turn flanked by NotI sites that are used to isolate the completed transgene construct away from vector sequences.

2. Isolation of unrearranged $V_\kappa$ gene segments and generation of transgenic animals expressing human Ig light chain protein The $V_\kappa$ specific oligonucleotide, oligo-65 (discussed above), is used to probe a human placental genomic DNA library cloned into the phage vector lEMBL3/SP6/T7 (Clonetech Laboratories, Inc., Palo Alto, Calif.). Variable gene segments from the resulting clones are sequenced, and clones that appear functional are selected. Criteria for judging functionality include: open reading frames, intact splice acceptor and donor sequences, and intact recombination sequence. DNA fragments containing selected variable gene segments are cloned into the unique XhoI site of plasmid pJCK1 to generate minilocus constructs. The resulting clones are digested with NotI and the inserts isolated and injected into mouse embryo pronuclei to generate transgenic animals. The transgenes of these animals will undergo V to J joining in developing B-cells. Animals expressing human kappa chain are bred with heavy chain minilocus containing transgenic animals to generate mice expressing fully human antibodies.

EXAMPLE 15

Genomic Heavy Chain Human Ig Transgene

This Example describes the cloning of a human genomic heavy chain immunoglobulin transgene which is then introduced into the murine germline via microinjection into zygotes or integration in ES cells.

Nuclei are isolated from fresh human placental tissue as described by Marzluff, W. F., et al. (1985), *Transcription and Translation: A Practical Approach*, B. D. Hammes and S. J. Higgins, eds., pp. 89–129, IRL Press, Oxford). The isolated nuclei (or PBS washed human spermatocytes) are embedded in 0.5% low melting point agarose blocks and lysed with 1 mg/ml proteinase K in 500 mM EDTA, 1% SDS for nuclei, or with 1 mg/ml proteinase K in 500 mM EDTA, 1% SDS, 10 mM DTT for spermatocytes at 50° C. for 18 hours. The proteinase K is inactivated by incubating the blocks in 40 µg/ml PMSF in TE for 30 minutes at 50° C., and then washing extensively with TE. The DNA is then digested in the agarose with the restriction enzyme NotI as described by M. Finney in *Current Protocols in Molecular Biology* (F. Ausubel et al., eds. John Wiley & Sons, Supp. 4, 1988, e.g., Section 2.5.1).

The NotI digested DNA is then fractionated by pulsed field gel electrophoresis as described by Anand et al., *Nuc. Acids Res.* 17:3425–3433 (1989). Fractions enriched for the NotI fragment are assayed by Southern hybridization to detect one or more of the sequences encoded by this fragment. Such sequences include the heavy chain D segments, J segments, and γ1 constant regions together with representatives of all 6 $V_H$ families (although this fragment is identified as 670 kb fragment from HeLa cells by Berman et al. (1988), supra., we have found it to be an 830 kb fragment from human placental and sperm DNA). Those fractions containing this NotI fragment are ligated into the NotI cloning site of the vector pYACNN as described (McCormick et al., *Technique* 2:65–71 (1990)). Plasmid pYACNN is prepared by digestion of pYACneo (Clontech) with EcoRI and ligation in the presence of the oligonucleotide 5'-AAT TGC GGC CGC-3'.

YAC clones containing the heavy chain NotI fragment are isolated as described by Traver et al., *Proc. Natl. Acad. Sci. USA*, 86:5898–5902 (1989). The cloned NotI insert is isolated from high molecular weight yeast DNA by pulse field gel electrophoresis as described by M. Finney, op. cit. The DNA is condensed by the addition of 1 mM spermine and microinjected directly into the nucleus of single cell embryos previously described. Alternatively, the DNA is isolated by pulsed field gel electrophoresis and introduced into ES cells by lipofection (Gnirke et al., *EMBO J.* 10:1629–1634 (1991)), or the YAC is introduced into ES cells by spheroplast fusion.

EXAMPLE 16

Discontinuous Genomic Heavy Chain Ig Transgene

An 85 kb SpeI fragment of human genomic DNA, containing $V_H6$, D segments, J segments, the µ constant region and part of the γ constant region, has been isolated by YAC cloning essentially as described in Example 1. A YAC carrying a fragment from the germline variable region, such as a 570 kb NotI fragment upstream of the 670–830 kb NotI fragment described above containing multiple copies of $V_1$ through $V_5$, is isolated as described. (Berman et al. (1988), supra. detected two 570 kb NotI fragments, each containing multiple V segments.) The two fragments are coinjected into the nucleus of a mouse single cell embryo as described in Example 1.

Typically, coinjection of two different DNA fragments result in the integration of both fragments at the same insertion site within the chromosome. Therefore, approximately 50% of the resulting transgenic animals that contain at least one copy of each of the two fragments will have the V segment fragment inserted upstream of the constant region containing fragment. Of these animals, about 50% will carry out V to DJ joining by DNA inversion and about 50% by deletion, depending on the orientation of the 570 kb NotI fragment relative to the position of the 85 kb SpeI fragment. DNA is isolated from resultant transgenic animals and those animals found to be containing both transgenes by Southern blot hybridization (specifically, those animals containing both multiple human V segments and human constant region genes) are tested for their ability to express human immunoglobulin molecules in accordance with standard techniques.

EXAMPLE 17

Identification of functionally rearranged variable region sequences in transgenic B cells An antigen of interest is used to immunize (see Harlow and Lane, *Antibodies: A Laboratory Manual*, Cold Spring Harbor, N.Y. (1988)) a mouse with the following genetic traits: homozygosity at the endogenous having chain locus for a deletion of $J_H$ (Examples 10); hemizygous for a single copy of unrearranged human heavy chain minilocus transgene (examples 5 and 14); and hemizygous for a single copy of a rearranged human kappa light chain transgene (Examples 6 and 14).

Following the schedule of immunization, the spleen is removed, and spleen cells used to generate hybridomas. Cells from an individual hybridoma clone that secretes antibodies reactive with the antigen of interest are used to prepare genomic DNA. A sample of the genomic DNA is digested with several different restriction enzymes that recognize unique six base pair sequences, and fractionated on an agarose gel. Southern blot hybridization is used to identify two DNA fragments in the 2–10 kb range, one of which contains the single copy of the rearranged human heavy chain VDJ sequences and one of which contains the single copy of the rearranged human light chain VJ sequence. These two fragments are size fractionated on agarose gel and cloned directly into pUC18. The cloned inserts are then subcloned respectively into heavy and light chain expression cassettes that contain constant region sequences.

The plasmid clone pγe1 (Example 12) is used as a heavy chain expression cassette and rearranged VDJ sequences are cloned into the XhoI site. The plasmid clone pCK1 is used as a light chain expression cassette and rearranged VJ sequences are cloned into the XhoI site. The resulting clones are used together to transfect $SP_O$ cells to produce antibodies that react with the antigen of interest (Co. et al., *Proc. Natl. Acad. Sci.* USA 88:2869 (1991), which is incorporated herein by reference).

Alternatively, mRNA is isolated from the cloned hybridoma cells described above, and used to synthesize cDNA. The expressed human heavy and light chain VDJ and VJ sequence are then amplified by PCR and cloned (Larrick et al., *Biol. Technology*, 7:934–938 (1989)). After the nucleotide sequence of these clones has been determined, oligonucleotides are synthesized that encode the same polypeptides, and synthetic expression vectors generated as described by Queen et al., *Proc. Natl. Acad. Sci. USA*, 84:5454–5458 (1989).

Immunization of Transgenic Animals with Complex Antigens

The following experiment demonstrates that transgenic animals can be successfully immunized with complex antigens such as those on human red blood cells and respond with kinetics that are similar to the response kinetics observed in normal mice.

Blood cells generally are suitable immunogens and comprise many different types of antigens on the surface of red and white blood cells.

Immunization with human blood

Tubes of human blood from a single donor were collected and used to immunize transgenic mice having functionally disrupted endogenous heavy chain loci ($J_HD$) and harboring a human heavy chain minigene construct (HC1); these mice are designated as line 112. Blood was washed and resuspended in 50 mls Hanks' and diluted to $1\times10^8$ cells/ml 0.2 mls ($2\times10^7$ cells) were then injected interperitoneally using a 28 gauge needle and 1 cc syringe. This immunization protocol was repeated approximately weekly for 6 weeks. Serum titers were monitored by taking blood from retro-orbital bleeds and collecting serum and later testing for specific antibody. A pre-immune bleed was also taken as a control. On the very last immunization, three days before these animals were sacrificed for serum and for hybridomas, a single immunization of $1\times10^7$ cells was given intravenously through the tail to enhance the production of hybridomas.

TABLE 9

| | Animals | | | |
|---|---|---|---|---|
| Mouse ID | Line | Sex | HC1-112 | JHD |
| 1 | 2343 | 112 | M | + | ++ |
| 2 | 2344 | 112 | M | - | + |
| 3 | 2345 | 112 | F | - | + |
| 4 | 2346 | 112 | F | - | ++ |
| 5 | 2347 | 112 | F | - | ++ |
| 6 | 2348 | 112 | F | + | ++ |
| 7 | 2349 | 112 | F | - | + |

Mice # 2343 and 2348 have a desired phenotype: human heavy chain mini-gene transgenic on heavy chain knock-out background.

Generation of Hybridomas

Hybridomas were generated by fusing mouse spleen cells of approximately 16 week-old transgenic mice (Table 9) that had been immunized as described (supra) to a fusion partner consisting of the non-secreting HAT-sensitive myeloma cell line, X63 Ag8.653. Hybridoma clones were cultivated and hybridoma supernatants containing immunoglobulins having specific binding affinity for blood cell antigens were identified, for example, by flow cytometry.

Flow cytometry

Serum and hybridoma supernatants were tested using flow cytometry. Red blood cells from the donor were washed 4× in Hanks' balanced salt solution and 50,000 cells were placed in 1.1 ml polypropylene microtubes. Cells were incubated with antisera or supernatant from the hybridomas for 30 minutes on ice in staining media (1× RPMI 1640 media without phenol red or biotin (Irvine Scientific) 3% newborn calf serum, 0.1% Na azide). Controls consisted of littermate mice with other genotypes. Cells were then washed by centrifugation at 4° C. in Sorvall RT600B for 5-10 minutes at 1000 rpm. Cells were washed two times and then antibody detected on the cell surface with a fluorescent developing reagent. Two monoclonal reagents were used to test. One was a FITC-labeled mouse anti-human µ heavy chain antibody (Pharmagen, San Diego, Calif.) and the other was a PE-labeled rat anti-mouse kappa light chain (Becton-Dickenson, San Jose, Calif.). Both of these reagents gave similar results. Whole blood (red blood cells and white blood cells) and white blood cells alone were used as target cells. Both sets gave positive results.

Serum of transgenic mice and littermate controls was incubated with either red blood cells from the donor, or white blood cells from another individual, washed and then developed with anti-human IgM FITC labeled antibody and analyzed in a flow cytometer. Results showed that serum from mice that are transgenic for the human mini-gene locus (mice 2343 and 2348) show human IgM reactivity whereas all littermate animals (2344, 2345, 2346, 2347) do not. Normal mouse serum (NS) and phosphate buffer saline (PBS) were used as negative controls. Red blood cells were ungated and white blood cells were gated to include only lymphocytes. Lines are drawn on the x and y axis to provide a reference. Flow cytometry was performed on 100 supernatants from fusion 2348. Four supernatants showed positive reactivity for blood cell antigens.

EXAMPLE 18

Reduction of Endogenous Mouse Immunoglobulin Expression by Antisense RNA

A. Vector for Expression of Antisense Ig Sequences

1. Construction of the cloning vector pGP1h

The vector pGP1b (referred to in a previous example) is digested with XhoI and BamHI and ligated with the following oligonucleotides:

5'-gat cct cga gac cag gta cca gat ctt gtg aat tcg-3'
5'-tcg acg aat tca caa gat ctg gta cct ggt ctc gag-3' to generate the plasmid pGP1h. This plasmid contains a polylinker that includes the following restriction sites: NotI, EcoRI, BglII, Asp718, XhoI, BamHI, HindIII, NotI.

Construction of pBCE1.

A 0.8 kb XbaI/BglII fragment of pVH251 (referred to in a previous example), that includes the promoter leader sequence exon, first intron, and part of the second exon of the human VH-V family immunoglobulin variable gene segment, was inserted into XbaI/BglII digested vector pNN03 to generate the plasmid pVH251.

The 2.2 kb BamHI/EcoRI DNA fragment that includes the coding exons of the human growth hormone gene (hGH; Seeburg, (1982) DNA 1:239–249) is cloned into BglII/EcoRI digested pGH1h. The resulting plasmid is digested with BamHI and the BamHI/BglII of pVH251N is inserted in the same orientation as the hGH gene to generate the plasmid pVhgh.

A 0.9 kb XbaI fragment of mouse genomic DNA containing the mouse heavy chain J-µ intronic enhancer (Banerji et al., (1983) Cell 33:729-740) was subcloned into pUC18 to generate the plasmid pJH22.1. This plasmid was linearized with SphI and the ends filled in with klenow enzyme. The klenow treated DNA was then digested with HindIII and a 1.4 kb MluI(klenow)/HindIII fragment of phage clone λ1.3 (previous example), containing the human heavy chain J-µ intronic enhancer (Hayday et al., (1984) Nature 307:334–340), to it. The resulting plasmid, pMHE1, consists of the mouse and human heavy chain J-µ intron enhancers ligated together into pUC18 such that they can be excised on a single BamHI/HindIII fragment.

Figure 36:
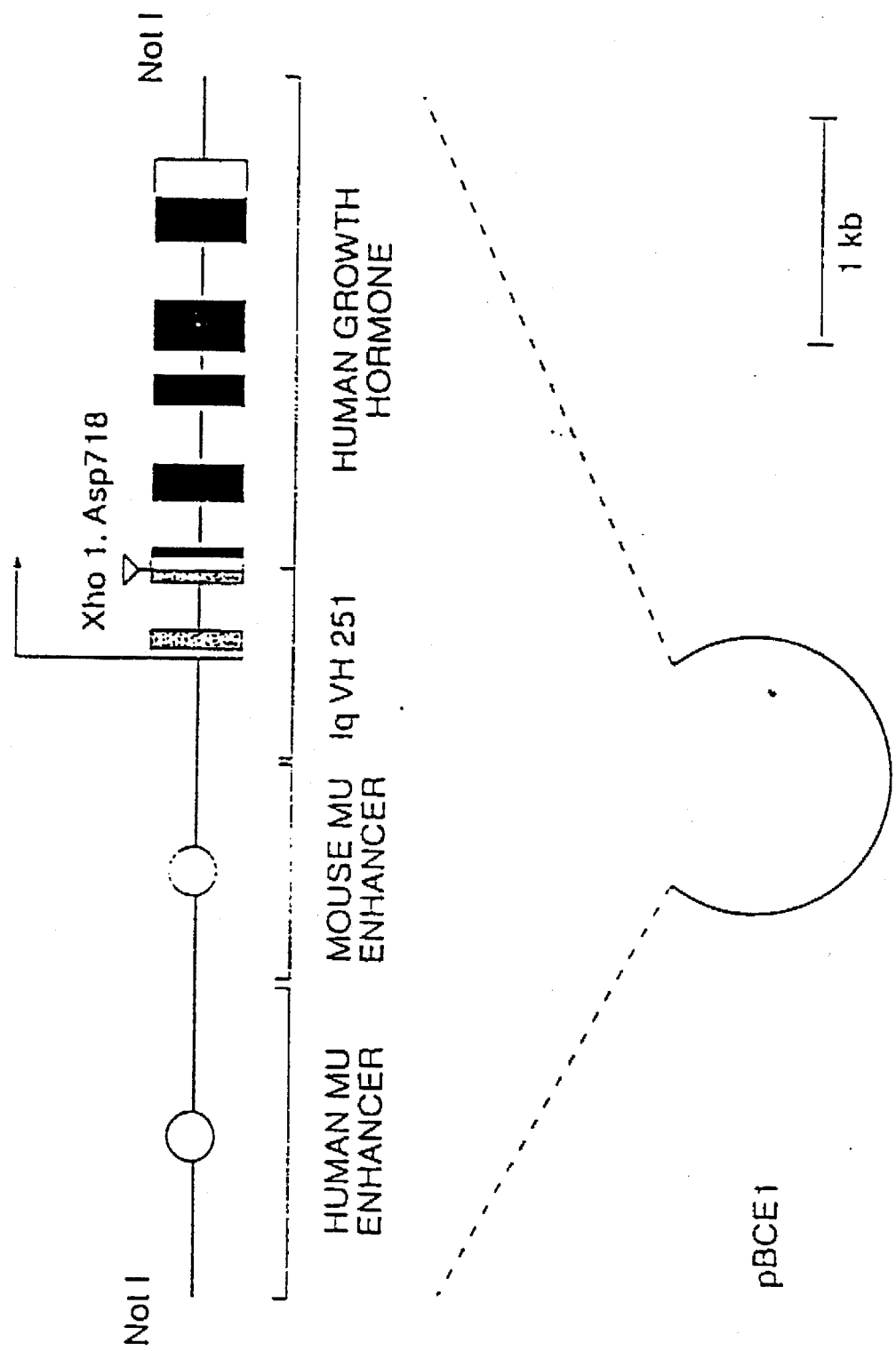
FIG. 36 is a schematic representation of plasmid pBCE1.

The BamHI/HindIII fragment of pMHE1 is cloned into BamHI/HindIII cut pVhgh to generate the B-cell expression vector pBCE1. This vector, depicted in FIG. 36, contains unique XhoI and Asp718 cloning sites into which antisense DNA fragments can be cloned. The expression of these antisense sequences is driven by the upstream heavy chain promoter-enhancer combination the downstream hGH gene sequences provide polyadenylation sequences in addition to intron sequences that promote the expression of transgene constructs. Antisense transgene constructs generated from pBCE1 can be separated from vector sequences by digestion with NotI.

B. An IgM antisense transgene construct.

The following two oligonucleotides:

5'-cgc ggt acc gag agt cag tcc ttc cca aat gtc-3'
5'-cgc ctc gag aca gct gga atg ggc aca tgc aga-3' are used as primers for the amplification of mouse IgM constant region sequences by polymerase chain reaction (PCR) using mouse spleen cDNA as a substrate. The resulting 0.3 kb PCR product is digested with Asp718 and XhoI and cloned into Asp718/XhoI digested pBCE1 to generate the antisense transgene construct pMAS1. The purified NotI insert of pMAS1 is microinjected into the pronuclei of half day mouse embryos—alone or in combination with one or more other transgene constructs—to generate transgenic mice. This construct expresses an RNA transcript in B-cells that hybridizes with mouse IgM mRNA, thus down-regulating the expression of mouse IgM protein. Double transgenic mice containing pMAS1 and a human heavy chain transgene minilocus such as pHC1 (generated either by coinjection of both constructs or by breeding of singly transgenic mice) will express the human transgene encoded Ig receptor on a higher percentage of B-cell than mice transgenic for the human heavy chain minilocus alone. The ratio of human to mouse Ig receptor expressing cells is due in part to competition between the two populations for factors and cells that promoter B-cell differentiation and expansion. Because the Ig receptor plays a key role in B-cell development, mouse Ig receptor expressing B-cells that express reduced levels of IgM on their surface (due to mouse Ig specific antisense down-regulation) during B-cell development will not compete as well as cells that express the human receptor.

C. An IgKappa antisense transgene construct.

The following two oligonucleotides:

5'-cgc ggt acc gct gat gct gca cca act gta tcc-3'
5'-cgc ctc gag cta aca ctc att cct gtt gaa gct-3' are used as primers for the amplification of mouse IgKappa constant region sequences by polymerase chain reaction (PCR) using mouse spleen cDNA as a substrate. The resulting 0.3 kb PCR product is digested with Asp718 and XhoI and cloned into Asp718/XhoI digested pBCE1 to generate the antisense transgene construct pKAS1. The purified NotI insert of pKAS1 is microinjected into the pronuclei of half day mouse embryos—alone or in combination with one or more other transgene constructs—to generate transgenic mice. This construct expresses an RNA transcript in B-cells that hybridizes with mouse IgK mRNA, thus down-regulating the expression of mouse IgK protein as described above for pMAS1.

EXAMPLE 19

This example demonstrates the successful immunization and immune response in a transgenic mouse of the present invention.

Immunization of Mice

Keyhole limpet hemocyanin conjugated with greater than 400 dinitrophenyl groups per molecule (Calbiochem, La Jolla, Calif.) (KLH-DNP) was alum precipitated according to a previously published method (Practical Immunology, L. Hudson and F. C. Hay, Blackwell Scientific (Pubs.), p. 9, 1980). Four hundred µg of alum precipitated KLH-DNP along with 100 µg dimethyldioctadecyl Ammonium Bromide in 100 µL of phosphate buffered saline (PBS) was injected intraperitoneally into each mouse. Serum samples were collected six days later by retro-orbital sinus bleeding.

Analysis of Human Antibody Reactivity in Serum

Antibody reactivity and specificity were assessed using an indirect enzyme-linked immunosorbent assay (ELISA). Several target antigens were tested to analyze antibody induction by the immunogen. Keyhole limpet hemocyanin (Calbiochem) was used to identify reactivity against the protein component, bovine serum albumin-DNP for reactivity against the hapten and/or modified amino groups, and KLH-DNP for reactivity against the total immunogen. Human antibody binding to antigen was detected by enzyme conjugates specific for IgM and IgG sub-classes with no cross reactivity to mouse immunoglobulin. Briefly, PVC microtiter plates were coated with antigen drying overnight at 37° C. of 5 µg/mL protein in PBS. Serum samples diluted in PBS, 5% chicken serum, 0.5% Tween-20 were incubated in the wells for 1 hour at room temperature, followed by anti-human IgG Fc and IgG F(ab')-horseradish peroxidase or anti-human IgM Fc-horseradish peroxidase in the same diluent. After 1 hour at room temperature enzyme activity was assessed by addition of ABTS substrate (Sigma, St. Louis, Mo.) and read after 30 minutes at 415–490 nm.

Human Heavy Chain Participation in Immune Response in Transgenic Mice

Figure 37A:
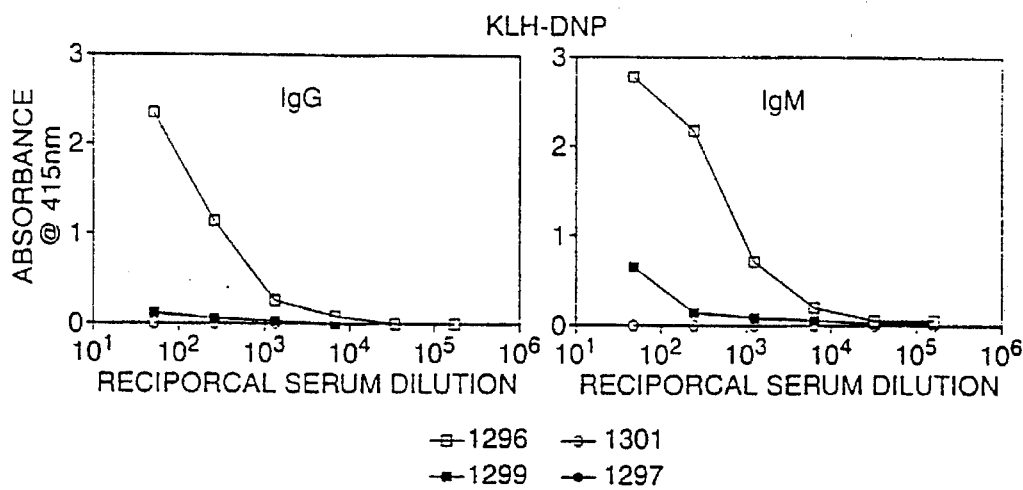
FIG. 37 depicts the immune response of transgenic mice of the present invention against KLH-DNP, by measuring IgG and IgM levels specific for KLH-DNP (37A), KLH (37B) and BSA-DNP (37C).
Figure 37B:
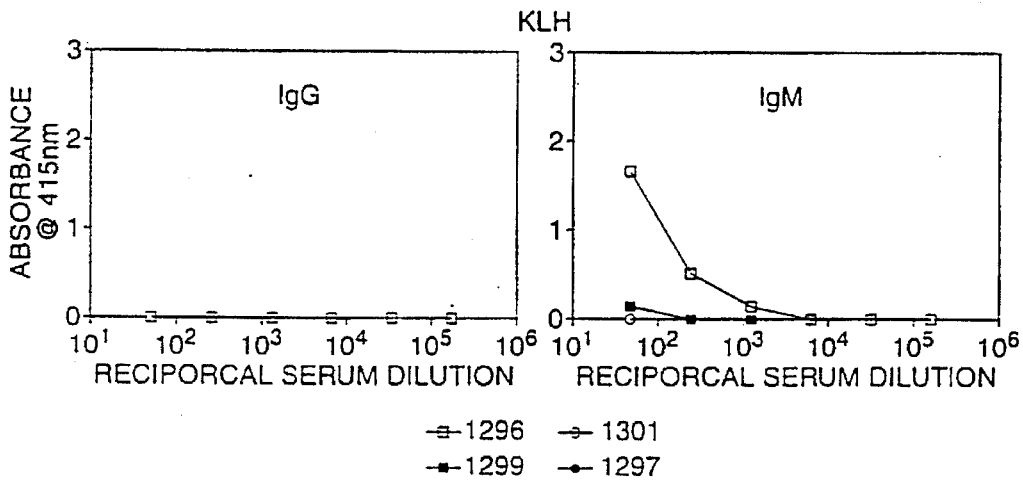
Figure 37C:
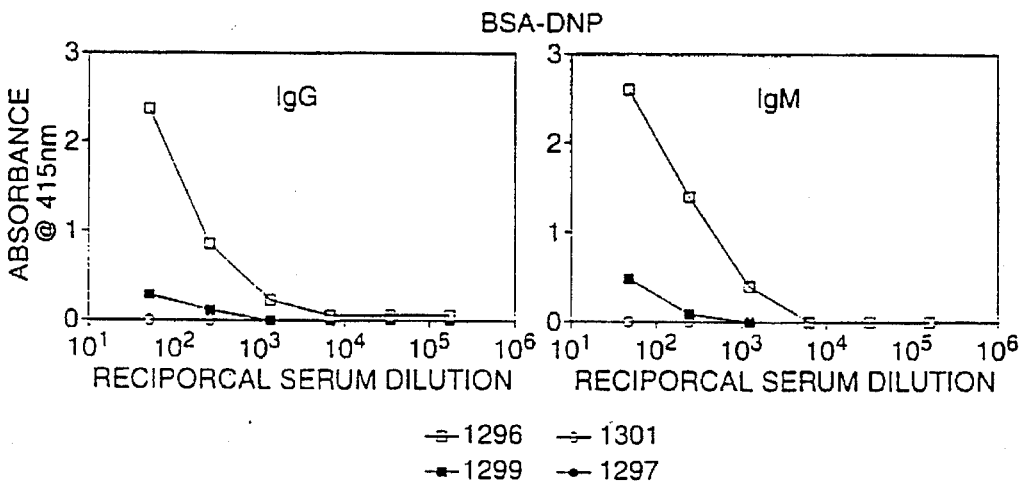

FIG. 37 illustrates the response of three mouse littermates to immunization with KLH-DNP. Mouse number 1296 carried the human IgM and IgG unrearranged transgene and was homozygous for mouse Ig heavy chain knockout. Mouse number 1299 carried the transgene on a non-knockout background, while mouse 1301 inherited neither of these sets of genes. Mouse 1297, another littermate, carried the human transgene and was hemizygous with respect to mouse heavy chain knockout. It was included as a non-immunized control.

The results demonstrate that both human IgG and IgM responses were developed to the hapten in the context of conjugation to protein. Human IgM also developed to the KLH molecule, but no significant levels of human IgG were present at this time point. In pre-immunization serum samples from the same mice, titers of human antibodies to the same target antigens were insignificant.

EXAMPLE 20

This example demonstrates the successful immunization with a human antigen and immune response in a transgenic mouse of the present invention, and provides data demonstrating that nonrandom somatic mutation occurs in the variable region sequences of the human transgene.

Demonstration of antibody responses comprising human immunoglobulin heavy chains against a human glycoprotein antigen Transgenic mice used for the experiment were homozygous for functionally disrupted murine immunoglobulin heavy chain loci produced by introduction of a transgene at the joining (J) region (supra) resulting in the absence of functional endogenous (murine) heavy chain production. The transgenic mice also harbored at least one complete unrearranged human heavy chain mini-locus transgene, (HC1, supra), which included a single functional $V_H$ gene ($V_H251$), human µ constant region gene, and human γ1 constant region gene. Transgenic mice shown to express human immunoglobulin transgene products (supra) were selected for immunization with a human antigen to demonstrate the capacity of the transgenic mice to make an immune response against a human antigen immunization. Three mice of the HC1-26 line and three mice of the HC1-57 line (supra) were injected with human antigen.

One hundred μg of purified human carcinoembryonic antigen (CEA) insolubilized on alum was injected in complete Freund's adjuvant on Day 0, followed by further weekly injections of alum-precipitated CEA in incomplete Freund's adjuvant on Days 7, 14, 21, and 28. Serum samples were collected by retro-orbital bleeding on each day prior to injection of CEA. Equal volumes of serum were pooled from each of the three mice in each group for analysis.

Figure 38:
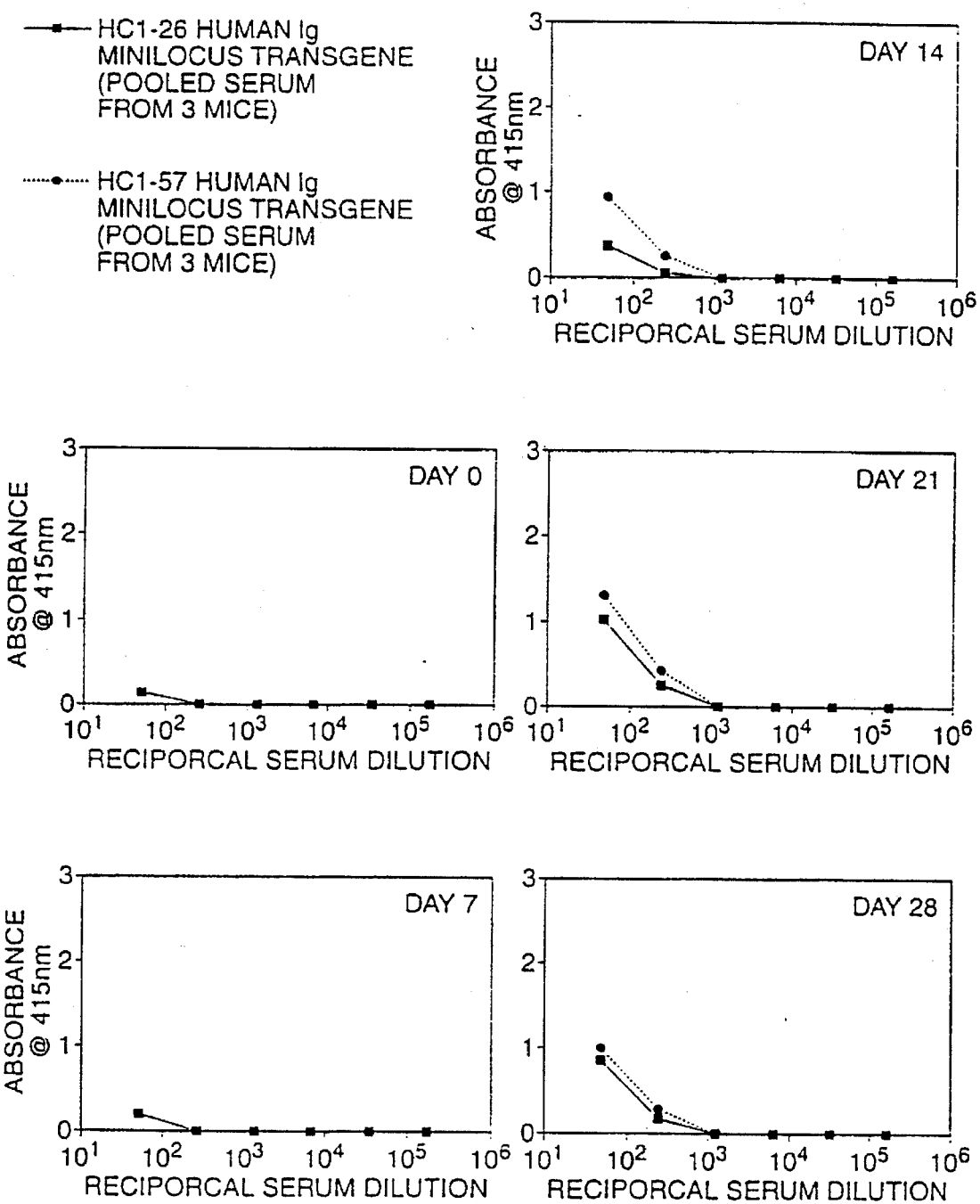
FIG. 38 shows ELISA data demonstrating the presence of antibodies that bind human carcinoembryonic antigen (CEA) and comprise human µ chains; each panel shows reciprocal serial dilutions from pooled serum samples obtained from mice on the indicated day following immunization.
Figure 39:
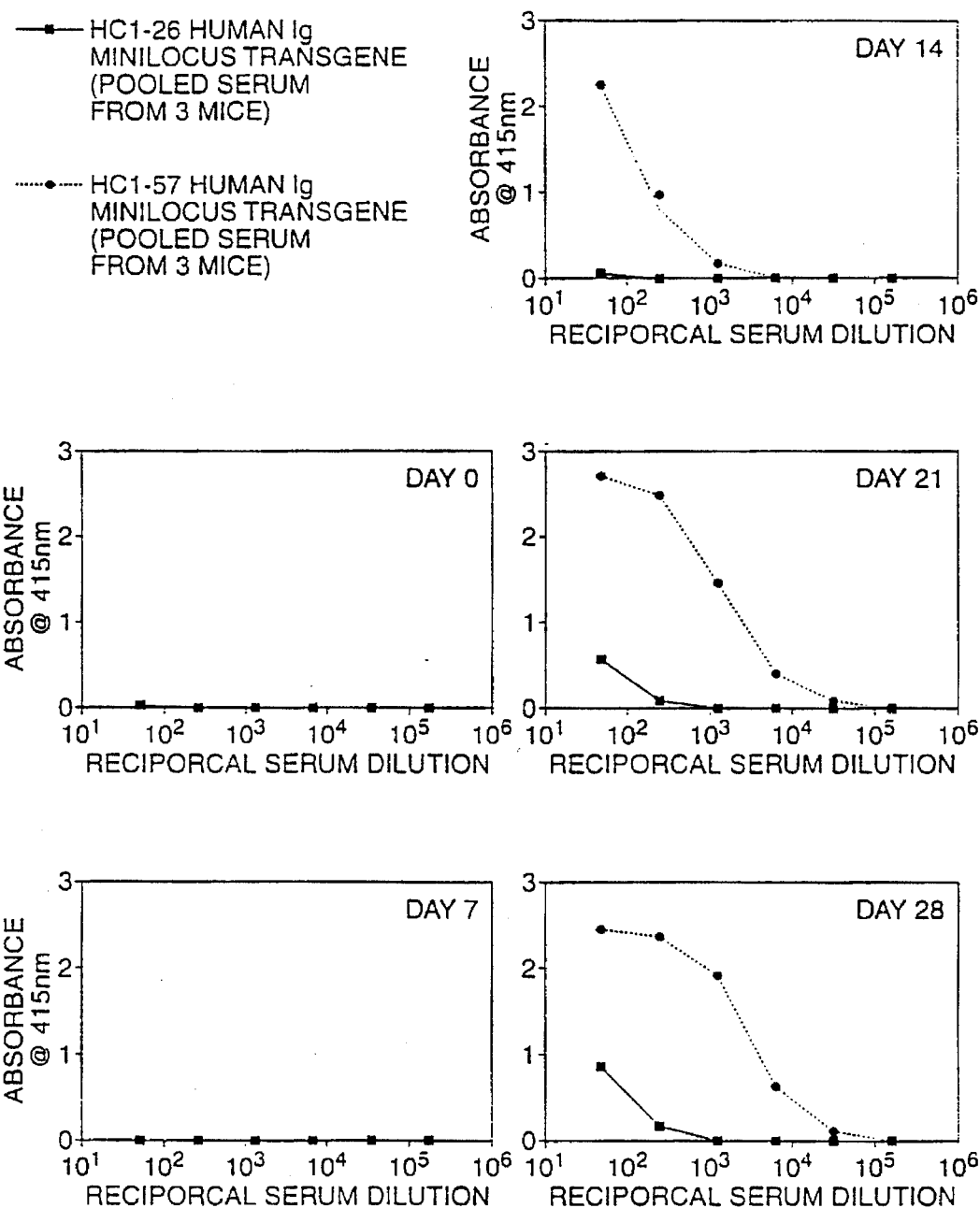
FIG. 39 shows ELISA data demonstrating the presence of antibodies that bind human carcinoembryonic antigen (CEA) and comprise human γ chains; each panel shows reciprocal serial dilutions from pooled serum samples obtained from mice on the indicated day following immunization.

Titres of human μ chain-containing immunoglobulin and human γ chain-containing immunoglobulin which bound to human CEA immobilized on microtitre wells were determined by ELISA assay. Results of the ELISA assays for human μ chain-containing immunoglobulins and human γ chain-containing immunoglobulins are shown in FIGS. 38 and 39, respectively. Significant human μ chain Ig titres were detected for both lines by Day 7 and were observed to rise until about Day 21. For human γ chain Ig, significant titres were delayed, being evident first for line HC1-57 at Day 14, and later for line HC1-26 at Day 21. Titres for human γ chain Ig continued to show an increase over time during the course of the experiment. The observed human μ chain Ig response, followed by a plateau, combined with a later geveloping γ chain response which continues to rise is characteristic of the pattern seen with affinity maturation. Analysis of Day 21 samples showed lack of reactivity to an unrelated antigen, keyhole limpet hemocyanin (KLC), indicating that the antibody response was directed against CEA in a specific manner.

These data indicate that animals transgenic for human unrearranged immunoglobulin gene loci: (1) can respond to a human antigen (e.g., the human glycoprotein, CEA), (2) can undergo isotype switching ("class switching") as exemplified by the observed μ to γ class switch, and (3) exhibit characteristics of affinity maturation in their humoral immune responses. In general, these data indicate: (1) the human Ig transgenic mice have the ability to induce heterologous antibody production in response to a defined antigen, (2) the capacity of a single transgene heavy chain variable region to respond to a defined antigen, (3) response kinetics over a time period typical of primary and secondary response development, (4) class switching of a transgene-encoded humoral immune response from IgM to IgG, and (5) the capacity of transgenic animal to produce human-sequence antibodies against a human antigen.

Demonstration of somatic mutation in a human heavy chain transgene minilocus.

Line HC1-57 transgenic mice, containing multiple copies of the HC1 transgene, were bred with immunoglobulin heavy chain deletion mice to obtain mice that contain the HC1 transgene and contain disruptions at both alleles of the endogenous mouse heavy chain (supra). These mice express human mu and gammal heavy chains together with mouse kappa and lambda light chains (supra). One of these mice was hyperimmunized against human carcinoembryonic antigen by repeated intraperitoneal injections over the course of 1.5 months. This mouse was sacrificed and lymphoid cells isolated from the spleen, inguinal and mesenteric lymph nodes, and peyers patches. The cells were combined and total RNA isolated. First strand cDNA was synthesized from the RNA and used as a template for PCR amplification with the following 2 oligonucleotide primers:

149 5'-cta gct cga gtc caa gga gtc tgt gcc gag gtg cag ctg (g/a/t/c)-3'

151 5'-ggc gct cga gtt cca cga cac cgt cac cgg ttc-3'

Figure 40:
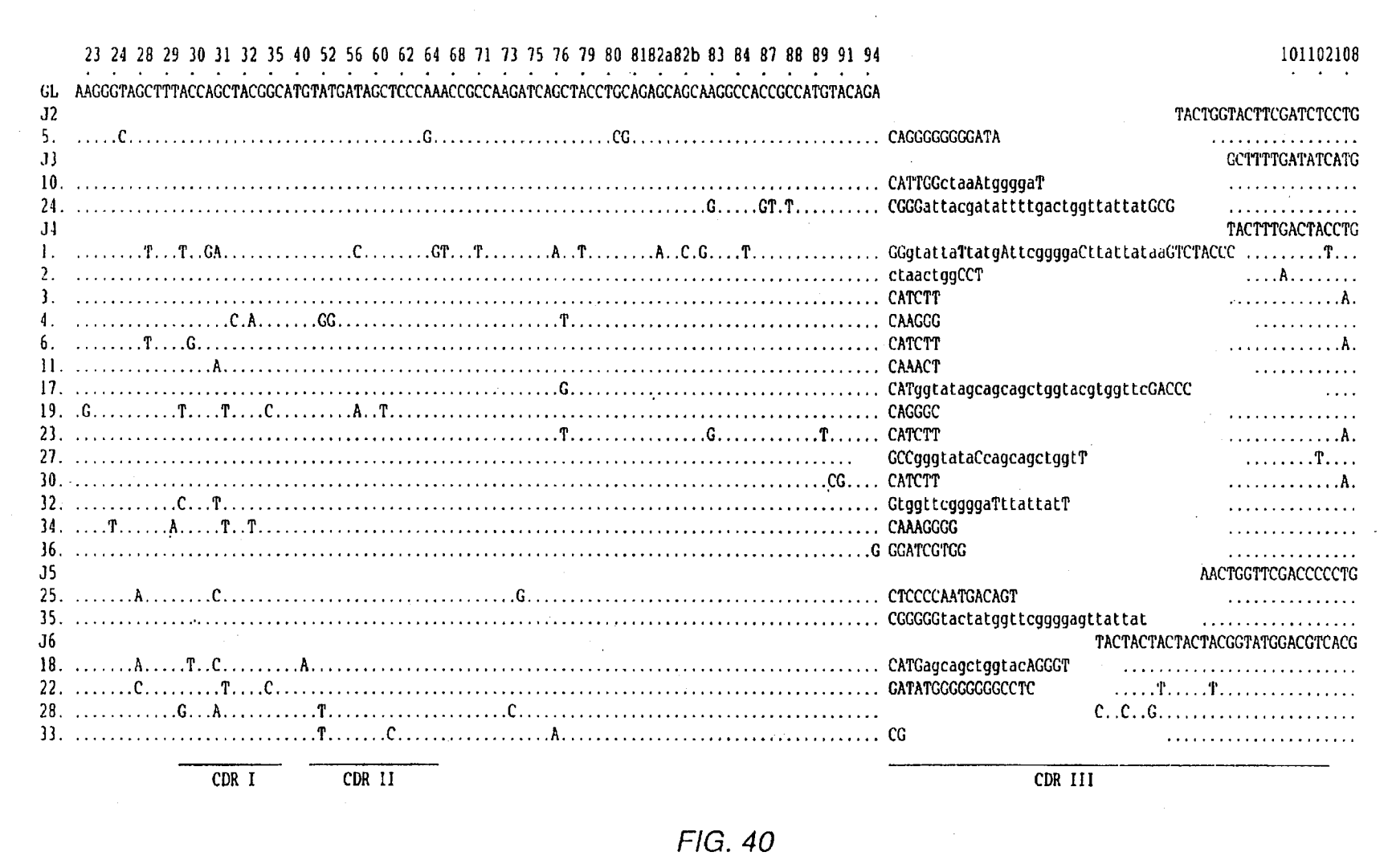

These primers specifically amplify VH251/gammal cDNA sequences. The amplified sequences were digested with XhoI and cloned into the vector pNN03. DNA sequence from the inserts of 23 random clones is shown in FIG. 40; sequence variations from germline sequence are indicated, dots indicate sequence is identical to germline. Comparison of the cDNA sequences with the germline sequence of the VH251 transgene reveals that 3 of the clones are completely unmutated, while the other 20 clones contain somatic mutations. One of the 3 non-mutated sequences is derived from an out-of-frame VDJ joint. Observed somatic mutations at specific positions of occur at similar frequencies and in similar distribution patterns to those observed in human lymphocytes (Cai et al. (1992) *J. Exp. Med.* 176: 1073, incorporated herein by reference). The overall frequency of somatic mutations is approximately 1%; however, the frequency goes up to about 5% within CDR1, indicating selection for amino acid changes that affect antigen binding. This demonstrates antigen driven affinity maturation of the human heavy chain sequences.

EXAMPLE 21

This example demonstrates the successful formation of a transgene by co-introduction of two separate polynucleotides which recombine to form a complete human light chain minilocus transgene.

Generation of an unrearranged light chain minilocus transgene by co-injection of two overlapping DNA fragments 1. Isolation of unrearranged functional $V_\kappa$ gene segments vk65.3, vk65.5, vk65.8 and vk65.15

The $V_\kappa$ specific oligonucleotide, oligo-65 (5'-agg ttc agt ggc agt ggg tct ggg aca gac ttc act ctc acc atc agc-3'), was used to probe a human placental genomic DNA library cloned into the phage vector λEMBL3/SP6/T7 (Clonetech Laboratories, Inc., Palo Alto, Calif.). DNA fragments containing $V_\kappa$ segments from positive phage clones were subcloned into plasmid vectors. Variable gene segments from the resulting clones are sequenced, and clones that appear functional were selected. Criteria for judging functionality include: open reading frames, intact splice acceptor and donor sequences, and intact recombination sequence. DNA sequences of 4 functional $V_\kappa$ gene segments (vk65.3, vk65.5, vk65.8, and vk65.15) from 4 different plasmid clones isolated by this procedure are shown in FIGS. 41–44. The four plasmid clones, p65.3f, p65.5gl, p65.8, and p65.15f, are described below.

(1 a) p65.3f

A 3 kb Xba fragment of phage clone λ65.3 was subcloned into pUC19 so that the vector derived SalI site was proximal to the 3' end of the insert and the vector derived BamHI site 5'. The 3 kb BamHI/SalI insert of this clone was subcloned into pGP1f to generate p65.3f.

(1 b) p65.5g1

A 6.8 kb EcoRI fragment of phage clone λ65.5 was subcloned into pGP1f so that the vector derived XhoI site is proximal to the 5' end of the insert and the vector derived SalI site 3'. The resulting plasmid is designated p65.5g1.

(1 c) p65.8

A 6.5 kb HindIII fragment of phage clone λ65.8 was cloned into pSP72 to generate p65.8.

(1 d) p65.15f

A 10 kb EcoRI fragment of phage clone λ65.16 was subcloned into pUC18 to generate the plasmid p65.15.3. The $V_\kappa$ gene segment within the plasmid insert was mapped to a 4.6 kb EcoRI/HindIII subfragment, which was cloned into pGP1f. The resulting clone, p65.15f, has unique XhoI and SalI sites located at the respective 5' and 3' ends of the insert.

2. pKV4

The XhoI/SalI insert of p65.8 was cloned into the XhoI site of p65.15f to generate the plasmid pKV2. The XhoI/SalI insert of p65.5g1 was cloned into the XhoI site of pKV2 to generate pKV3. The XhoI/SalI insert of pKV3 was cloned into the XhoI site of p65.3f to generate the plasmid pKV4. This plasmid contains a single 21 kb XhoI/SalI insert that includes 4 functional $V_\kappa$ gene segments. The entire insert can also be excised with NotI.

3. pKC1B (3 a) pKcor

Two XhoI fragments derived from human genomic DNA phage λ clones were subcloned into plasmid vectors. The first, a 13 kb $J_\kappa 2$-$J_\kappa 5$/$C_\kappa$ containing fragment, was treated with Klenow enzyme and cloned into HindIII digested, Klenow treated, plasmid pGP1d. A plasmid clone (pK-31) was selected such that the 5' end of the insert is adjacent to the vector derived ClaI site. The second XhoI fragment, a 7.4 kb piece of DNA containing $J_\kappa 1$ was cloned into XhoI/SalI-digested pSP72, such that the 3' insert XhoI site was destroyed by ligation to the vector SalI site. The resulting clone, p36.2s, includes an insert derived ClaI site 4.5 kb upstream of $J_\kappa 1$ and a polylinker derived ClaI site downstream in place of the naturally occurring XhoI site between $J_\kappa 1$ and $J_\kappa 2$. This clone was digested with ClaI to release a 4.7 kb fragment which was cloned into ClaI digested pK-31 in the correct 5' to 3' orientation to generate a plasmid containing all 5 human $J_\kappa$ segments, the human intronic enhancer human $C_\kappa$, 4.5 kb of 5' flanking sequence, and 9 kb of 3' flanking sequence. This plasmid, pKcor, includes unique flanking XhoI and SalI sites on the respective 5' and 3' sides of the insert.

(3 b) pKcorB

A 4 kb BamHI fragment containing the human 3' kappa enhancer (Judde, J.-G. and Max, E. E. (1992) *Mol. Cell. Biol.* 12: 5206, incorporated herein by reference) was cloned into pGP1f such that the 5' end is proximal to the vector XhoI site. The resulting plasmid, p24Bf, was cut with XhoI and the 17.7 kb XhoI/SalI fragment of pKcor cloned into it in the same orientation as the enhancer fragment. The resulting plasmid, pKcorB, includes unique XhoI and SalI sites at the 5' and 3' ends of the insert respectively.

(3 c) pKC1B

The XhoI/SalI insert of pKcorB was cloned into the SalI site of p65.3f to generate the light-chain minilocus-transgene plasmid pKC1B. This plasmid includes a single functional human $V_\kappa$ segment, all 5 human $J_\kappa$ segments, the human intronic enhancer, human $C_\kappa$, and the human 3' kappa enhancer. The entire 25 kb insert can be isolated by NotI digestion.

4. Co4

Figure 45:
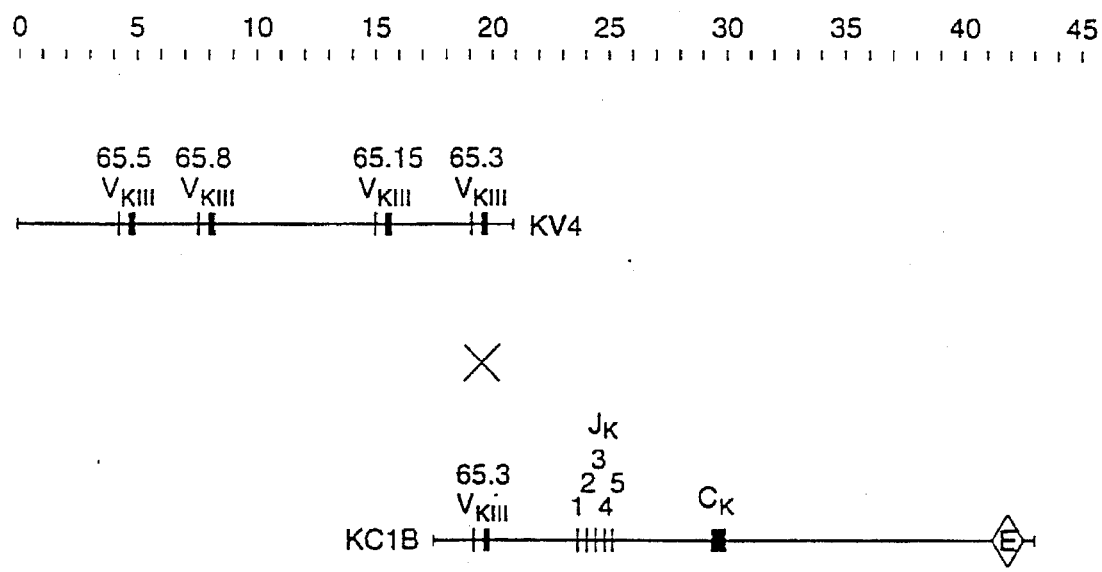
FIG. 45 shows formation of a light chain minilocus by homologous recombination between two overlapping fragments which were co-injected.

The two NotI inserts from plasmids pKV4 and pKC1B were mixed at a concentration of 2.5 μg/ml each in micro-injection buffer, and co-injected into the pronuclei of half day mouse embryos as described in previous examples. Resulting transgenic animals contain transgene inserts (designated Co4, product of the recombination shown in FIG. 45) in which the two fragments co-integrated. The 3' 3 kb of the pKV4 insert and the 5'3 kb of the pKC1B insert are identical. Some of the integration events will represent homologous recombinations between the two fragments over the 3 kb of shared sequence. The Co4 locus will direct the expression of a repertoire of human sequence light chains in a transgenic mouse.

EXAMPLE 22

This example demonstrates the successful production of a murine hybridoma clone secreting a monoclonal antibody reactive with a specific immunogen, wherein the monoclonal antibody comprises a human immunoglobulin chain encoded by a human Ig transgene.

Generation of Monoclonal Antibodies Incorporating Human Heavy Chain Transgene Product 1. Immunization of Mouse Harboring Human Heavy Chain Transgene A mouse containing a human heavy chain encoding transgene and homozygous for knockout (i.e., functional disruption) of the endogenous heavy chain locus (see, EXAMPLE 20, supra) was immunized with purified human CEA, and spleen cells were subsequently harvested after a suitable immune response period. The murine spleen cells were fused with mouse myeloma cells to generate hybridomas using conventional techniques (see, Kohler and Milstein, *Eur. J. Immunol.*, 6:511–519 (1976); Harlow and Lane, *Antibodies: A Laboratory Manual*, Cold Spring Harbor, N.Y. (1988)). The mouse used for immunization contained a human unrearranged heavy chain minilocus transgene which comprised a single functional $V_H$ gene ($V_{H251}$), human D and J segments, human μ constant region, and human γ1 constant region genes. The transgenic line from which it originated was designated HC1-57 (supra).

One hundred μg of purified human carcinoembryonic antigen (CEA) (Cyrstal Chem., Chicago, Ill. or Scripps Labs, San Diego, Calif.) insolubilized on alum was injected in complete Freund's adjuvant on Day 0, followed by further weekly injections of alum-precipitated CEA in incomplete Freund's adjuvant on Days 7, 14, 21, and 28. An additional 20 μg of soluble CEA was administered intravenously on Day 83, followed by 50 μg alum-precipitated CEA in incomplete Freund's adjuvant on Day 92. Human heavy chain responses to CEA were confirmed in serum samples prior to fusion of spleen cells with myleoma cells. The animal was sacrificed on Day 95, the spleen removed and fused with P3X63-Ag8.653 mouse myeloma cells (ATCC CRL 1580, American Type Culture Collection, Rockville, Md.) using polyethylene glycol. Two weeks later, supernates from fusion wells were screened for the presence of antibodies specifically reactive with CEA, and which contained human heavy chain μ or γ constant region epitopes by ELISA. Briefly, purified human CEA was coated onto PVC microtitre plates at 2.5 μg/ml, and incubate with culture supernate diluted 1:4 or 1:5 in PBS, 0.5% Tween-20, 5% chicken serum. Plates were washed, followed by addition of horseradish peroxidase-conjugated goat antiserum specific for human IgG Fc or rabbit antiserum specific for human IgMFc5Mu (Jackson ImmunoResearch, West Grove, Pa.). Presence of conjugate bound to captured antibody was determined, after further washing, by the addition of ABTS substrate. Two independent fusion wells were found to contain antibody with substantial binding to CEA. After cloning, both hybridomas were found to be positive for the presence of human μ chain and murine κ chain by ELISA. No mouse IgG or IgM were detected using similar assays.

Subcloning of the two independent parent hybridomas resulted in two clones, designated 92-09A-4F7-A5-2 and 92-09A-1D7-1-7-1. Both lines were deposited with the ATCC Patent Culture Depository under the Budapest Treaty and were assigned ATCC Designation HB 11307 and HB 11308, respectively. Culture supernatants from these cell lines were assessed for specificity by testing for reactivity to several purified target proteins using ELISA. As shown in FIG. 46, ELISA assays for determining the reactivity of the monoclonal antibodies to various antigens demonstrate that only CEA and the CEA-related antigen NCA-2 show significant reactivity, indicating the development of a restricted reactivity for the variable regions of the heterohybrid immunoglobulin molecules.

EXAMPLE 23

This example demonstrates that a rearranged human VDJ gene encoded by a human Ig minilocus transgene may be transcribed as a transcript which includes an endogenous Ig constant region gene, for example by the mechanism of trans-switching, to encode a chimeric human/mouse Ig chain.

Identification of Trans-Switch Transcripts Encoding Chimeric Human-Mouse Heavy Chains RNA was isolated from a hyperimmunized HC1 line 57 transgenic mouse homozygous for the endogenous heavy chain J segment deletion (supra). cDNA was synthesized according to Taylor et al. (1993) *Nucleic Acids Res.* 20: 6287, incorporated herein by reference, and amplified by PCR using the following two primers:

o-149 (human $V_{H251}$):
5'-CTA GCT CGA GTC CAA GGA GTC TGT GCC GAG GTG CAG CTG (G,A,T,C)-3' o-249 (mouse gamma):
5'-GGC GCT CGA GCT GGA CAG GG(A/C) TCC A(G/T)A GTT CCA-3'

Oligonucleotide o-149 is specific for the HC1-encoded variable gene segment $V_{H251}$, while o-249 hybridizes to both mouse and human gamma sequences with the following order of specificities:
mouse γ1=mouse γ2b=mouse γ3>mouse γ2a>>human γ1.

DNA sequences from 10 randomly chosen clones generated from the PCR products was determined and is shown in FIG. 47. Two clones comprised human VDJ and mouse γ1; four clones comprised human VDJ and mouse γ2b; and four clones comprised human VDJ and mouse γ3. These results indicate that in a fraction of the transgenic B cells, the transgene-encoded human VDJ recombined into the endogenous murine heavy chain locus by class switching or an analogous recombination.

EXAMPLE 24

This example describes a method for screening a pool of hybridomas to discriminate clones which encode chimeric human/mouse Ig chains from clones which encode and express a human Ig chain. For example, in a pool of hybridoma clones made from a transgenic mouse comprising a human Ig heavy chain transgene and homozygous for a J region-disrupted endogenous heavy chain locus, hybridoma clones encoding trans-switched human VDJ-murine constant region heavy chains may be identified and separated from hybridoma clones expressing human VDJ-human constant region heavy chains.

Sceening Hybridomas to Eliminate Chimeric Ig Chains

The screening process involves two stages, which may be conducted singly or optionally in combination: (1) a preliminary ELISA-based screen, and (2) a secondary molecular characterization of candidate hybridomas. Preferably, a preliminary ELISA-based screen is used for initial identification of candidate hybridomas which express a human VDJ region and a human constant region.

Hybridomas that show positive reactivity with the antigen (e.g., the immunogen used to elicit the antibody response in the transgenic mouse) are tested using a panel of monoclonal antibodies that specifically react with mouse μ, γ, κ, and λ, and human μ, γ, and κ. Only hybridomas that are positive for human heavy and light chains, as well as negative for mouse chains, are identified as candidate hybridomas that express human immunoglobulin chains. Thus, candidate hybridomas are shown to have reactivity with specific antigen and to possess epitopes characteristic of a human constant region.

RNA is isolated from candidate hybridomas and used to synthesize first strand cDNA. The first strand cDNA is then ligated to a unique single-stranded oligonucleotide of predetermined sequence (oligo-X) using RNA ligase (which ligates single-stranded DNA). The ligated cDNA is then amplified in two reactions by PCR using two sets of oligonucleotide primers. Set H (heavy chain) includes an oligo that specifically anneals to either human μ or human γ1 (depending on the results of the ELISA) and an oligo that anneals to the oligo-X sequence. This prevents bias against detection of particular V segments, including mouse V segments that may have trans-rearranged into the human minilocus. A second set of primers, Set L (light chain), includes an oligo that specifically anneals to human κ and an oligo that anneals specifically to oligo-X. The PCR products are molecularly cloned and the DNA sequence of several are determined to ascertain whether the hybridoma is producing a unique human antibody on the basis of sequence comparison to human and murine Ig sequences.

EXAMPLE 25

This example demonstrates production of a transgenic mouse harboring a human light chain (κ) minilocus.

Human κ Minilocus transgenic mice KC1

A 13 kb XhoI Jκ2-Kκ containing fragment from a phage clone (isolated from a human genomic DNA phage library by hybridization to a κ specific oligonucleotide, e.g., supra) was treated with Klenow enzyme and cloned into the Klenow treated HindIII site of pGP1d to produce pK-31. This destroyed the insert XhoI sites and positioned the unique polylinker derived XhoI site at the 5' end next to $J_\kappa 2$. A unique polylinker derived ClaI site is located between this XhoI site and the inset sequences, while a unique polylinker derived SalI site is located at the 3' end of the insert. A 7.5 kb XhoI fragment, containing $J_\kappa 1$ and upstream sequences, was also isolated from a human genomic DNA phage clone (isolated from a human genomic DNA phage library by hybridization to a κ specific oligonucleotide, e.g. supra). This 7.5 kb XhoI fragment was cloned into the SalI site of pSP72 (Promega, Madison, Wis.), thus destroying both XhoI sites and positioning a polylinker ClaI site 3' of $J_\kappa 1$. Digestion of the resulting clone with ClaI released a 4.7 kb fragment containing Jk1 and 4.5 kb of upstream sequences. This 4.7 kb fragment was cloned into the ClaI site of pK-31 to create pKcor. The remaining unique 5' XhoI site is derived from polylinker sequences. A 6.5 kb XhoI/SalI DNA fragment containing the unrearranged human $V_\kappa III$ gene segment 65.8 (plasmid p65.8, EXAMPLE 21) was cloned into the XhoI site of pKcor to generate the plasmid pKC1. The NotI insert of pKC1 was microinjected into ½ day mouse embryos to generate transgenic mice. Two independent pKC1 derived transgenic lines were established and used to breed mice containing both heavy and light chain miniloci. These lines, KC1-673 and KC1-674, were estimated by Southern blot hybridization to contain integrations of approximately 1 and 10–20 copies of the transgenes respectively.

KC1e

The plasmid pMHE1 (EXAMPLES 13 and 18) was digested with BamHI and HindIII to excise the 2.3 kb insert containing both the mouse and human heavy chain J-μ intronic enhancers. This fragment was Klenow treated, ligated to SalI linkers (New England Biolabs, Beverly, Mass.), and cloned into the unique 3' SalI site of pKC1 to generate the plasmid pKC1e. The NotI insert of pKC1e was microinjected into ½ day mouse embryos to generate transgenic mice. Four independent pKC1e derived transgenic lines were established and used to breed mice containing both heavy and light chain miniloci. These lines, KC1e-1399, KC1e-1403, KC1e-1527, and KC1e-1536, were estimated by Southern blot hybridization to contain integrations of approximately 20–50, 5–10, 1–5, and 3–5 copies of the transgene, respectively.

pKC2

A 6.8 kb XhoI/SalI DNA fragment containing the unrearranged human V$_\kappa$III gene segment 65.5 (plasmid p65.5g1, EXAMPLE 21) was cloned into the unique 5' XhoI site of pKC1 to generate the plasmid pKC2. This minilocus transgene contains two different functional V$_\kappa$III gene segments. The NotI insert of pKC2 was microinjected into ½ day mouse embryos to generate transgenic mice. Five independent pKC2 derived transgenic lines were established and used to breed mice containing both heavy and light chain miniloci. These lines, KC2-1573, pKC2-1579, pKC2-1588, pKC2-1608, and pKC2-1610, were estimated by Southern blot hybridization to contain integrations of approximately 1–5, 10–50, 1–5, 50–100, and 5–20 copies of the transgene, respectively.

EXAMPLE 26

This example shows that transgenic mice bearing the human κ transgene can make an antigen-induced antibody response forming antibodies comprising a functional human κ chain.

Antibody Responses Associated with Human Ig κ Light Chain

A transgenic mouse containing the HC1-57 human heavy chain and KC1e human κ transgenes was immunized with purified human soluble CD4 (a human glycoprotein antigen). Twenty μg of purified human CD4 (NEN Research products, Westwood, Mass.) insolublized by conjugation to polystyrene latex particles (Polysciences, Warrington, Pa.) was injected intraperitoneally in saline with dimethyldioctadecyl ammonium bromide (Calbiochem, San Diego, Calif.) on Day 0, followed by further injections on Day 20 and Day 34.

Retro-orbital bleeds were taken on Days 25 and 40, and screened for the presence of antibodies to CD4, containing human IgM or human IgG heavy chain by ELISA. Briefly, purified human CD4 was coated onto PVC microtitre plates at 2.5 μg/ml and incubated with culture supernate diluted 1:4/1:5 in PBS, 0.5% Tween-20, 5% chicken serum. Plates were washed, followed by addition of horseradish peroxidase-conjugated goat antiserum specific for human IgG Fc or rabbit antiserum specific for human IgM Fc5Mu (Jackson ImmunoResearch, Westr Grove, Pa.). Presence of conjugate bound to captured antibody was determined after further washing by addition of ABTS substrate. Human μ reactive with antigen was detected in both bleeds, while there was essentially undetectable γ reactivity. The Day 40 sample was also tested for antigen-reactive human κ chain using the same assay with goat anti-human κ peroxidase conjugate (Sigma, St. Louis, Mo.). CD4-binding κ reactivity was detected at this time point. The assay results are shown in FIG. 48.

The foregoing description of the preferred embodiments of the present invention has been presented for purposes of illustration and description. They are not intended to be exhaustive or to limit the invention to the precise form disclosed, and many modifications and variations are possible in light of the above teaching.

All publications and patent applications herein are incorporated by reference to the same extent as if each individual publication or patent application was specifically and individually indicated to be incorporated by reference.

Although the present invention has been described in some detail by way of illustration for purposes of clarity of understanding, it will be apparent that certain changes and modifications may be practiced within the scope of the claims.

---

What is claimed is:

1. A method for obtaining secondary repertoire, somatically mutated human immunoglobulin V gene segments encoding immunoglobin V regions reactive with a pre-selected antigen the method comprising: antigenically stimulating a transgenic mouse with said pre-selected antigen said transgenic mouse having one or more transgenes containing DNA segments from unrearranged human immunoglobulin heavy and kappa light chain gene loci incorporated its germline DNA, said transgene or transgenes comprising a plurality of human V kappa gene segments, a plurality of human J kappa gene segments, a human kappa constant region gene segment, a plurality of human VH gene segments, a plurality of human DH gene segments, a plurality of human JH gene segments, a human mu switch segment, and a human mu constant region gene segment, wherein a first subset of B lymphocytes of said transgenic mouse produce IgM immunoglobulin molecules encoded by functional rearrangement of said immunoglobulin heavy and kappa light chain gene loci, said functionally rearranged immunoglobulin genes having variable region sequences including FR1, CDR1, FR2, CDR2, and FR3 portions from said human V kappa or VH gene segments of said unrearranged gene loci, and wherein a second subset of B lymphocytes of said transgenic mouse produce non-IgM immunoglobulin molecules encoded by somatically mutated immunoglobulin heavy and kappa light chain gene loci, said somatically mutated immunoglobulin heavy and kappa light chin gene loci having variable region sequences including FR1, CDR1, FR2, CDR2, and FR3 portions of somatically mutated DNA sequences from said human V kappa or VH gene segments of said first subset; and obtaining said somatically mutated human immunoglobulin V gene segments by (1) collecting somatically mutated V gene segments from said second subset of B lymphocytes or (2) immortalizing said second subset of B lymphocytes and then collecting somatically mutated V gene segments from said lymphocytes, wherein one or more of the somatically mutated V gene segments encode immunoglobulin V regions reactive with the preselected antigen.

2. The method of claim 1, wherein said J kappa and kappa constant region gene segments are contained within a BamHI DNA fragment of about 11 kb.

3. The method of claim 1, wherein said plurality of human DH gene segments includes DLR1, DXP1, DXP'1, and DA1 gene segments contained within an XhoI DNA fragment of about 5.2 kb.

4. The method of claim 1, wherein said JH gene, mu switch, and mu constant region gene segments are contained within a BamHI DNA fragment of about 16.3 kb.

5. The method of claim 1, wherein at least one of the transgenes includes the human VH251 gene segment.

6. The method of claim 1, wherein the VH gene segments include the sequence
5'-GAT CCT GGT TTA GTT AAA GAG GAT TTT ATT C&C CCC TGT GTC-3' (Seq. ID NO:27).

7. The method of claim 1, wherein the second subset of B lymphocytes express γ isotype immunoglobulin chains.

8. The method of claim 7, wherein the γ isotype is $\gamma_1$ or $\gamma_3$.

9. The method of claim 1, further comprising the step of expressing one or more collected V region gene segments in a host cell.

10. The method of claim 9, further comprising the step of purifying protein encoded by the expressed V region gene segment.

11. The method of claim 10, wherein the V region gene segment is linked to a human immunoglobulin constant region.

12. The method of claim 11, wherein at least one of the transgenes further comprises a human γ gene segment.

13. The method of claim 12, wherein the constant region is a γ isotype.

14. The method of claim 13, wherein the γ isotype is a human $\gamma_1$ isotype or a human $\gamma_3$ isotype.

15. A method for obtaining secondary repertoire V regions reactive with a preselected antigen, said V regions encoded by somatically mutated human immunoglobulin V gene segments, the method comprising:

antigenically stimulating a transgenic mouse with said pre-selected antigen, said transgenic mouse having one or more transgenes containing DNA segments from unrearranged human immunoglobulin heavy and kappa light chain gene loci incorporated into its germline DNA, said transgene or transgenes comprising a plurality of human V kappa gene segments, a plurality of human J kappa gene segments, a human kappa constant region gene segment, a plurality of human VH gene segments, a plurality of human DH gene segments, a plurality of human JH gene segments, a human mu switch segment, and a human mu constant region gene segment, wherein a subset of B lymphocytes of said transgenic mouse produce IgM immunoglobulin molecules encoded by functional rearrangement of said immunoglobulin heavy and kappa light chain gene loci, said functionally rearranged immunoglobulin genes having variable region sequences including FR1, CDR1, FR2, CDR2, and FR3 portions from said human V kappa or VH gene segments of said unrearranged gene loci, and wherein a second subset of B lymphocytes of said transgenic mouse produce non-IgM immunoglobulin molecules encoded by somatically mutated immunoglobulin heavy and kappa light chain gene loci, said somatically mutated immunoglobulin heavy and kappa light chain gene loci having variable region sequences including FR1, CDR1, FR2, CDR2, and FR3 portions of somatically mutated DNA sequences from said human V kappa or VH gene segments; and obtaining said secondary repertoire V regions reactive with said preselected antigen, by (1) collecting said somatically mutated immunoglobulin V gene segments from said second subset of B lymphocytes, and expressing collected V region gene segments in a host cell, or (2) immortalizing cells of said second subset of B lymphocytes and collecting said secondary repertoire V regions.

16. The method of claim 15 wherein at least one of the transgenes includes the human VH251 gene segment.

17. The method of claim 15, wherein the VH gene segments include the sequence 5'-GAT CCT GGT TTA GTT AAA GAG GAT TTT ATT CAC CCC TGT GTC-3' (Seq. ID NO:27).

18. The method of claim 15, wherein the V region gene segment is linked to a human immunoglobulin constant region.

19. The method of claim 18, wherein at least one of the transgenes further comprises a human γ gene segment.

20. The method of claim 19, wherein the constant region is a γ isotype.

21. The method of claim 20, wherein the γ isotype is a human $\gamma_1$ isotype or a human $\gamma_3$ isotype.

* * * * *